United States Patent
Allen et al.

(10) Patent No.: US 11,307,139 B2
(45) Date of Patent: Apr. 19, 2022

(54) NON-DESTRUCTIVE ASSAY FOR SOYBEAN SEEDS USING NEAR INFRARED ANALYSIS

(71) Applicant: PIONEER HI-BRED INTERNATIONAL, INC., Johnston, IA (US)

(72) Inventors: Ross M Allen, Des Moines, IA (US); John D Everard, Grimes, IA (US); Min Ren, Johnston, IA (US)

(73) Assignee: PIONEER HI-BRED INTERNATIONAL, INC.

( * ) Notice: Subject to any disclaimer, the term of this patent is extended or adjusted under 35 U.S.C. 154(b) by 344 days.

(21) Appl. No.: 16/490,261

(22) PCT Filed: Feb. 26, 2018

(86) PCT No.: PCT/US2018/019683
§ 371 (c)(1),
(2) Date: Aug. 30, 2019

(87) PCT Pub. No.: WO2018/160485
PCT Pub. Date: Sep. 7, 2018

(65) Prior Publication Data
US 2019/0383733 A1   Dec. 19, 2019

Related U.S. Application Data

(60) Provisional application No. 62/466,575, filed on Mar. 3, 2017.

(51) Int. Cl.
| | |
|---|---|
| *G01N 21/84* | (2006.01) |
| *G01N 21/359* | (2014.01) |
| *B07C 5/342* | (2006.01) |
| *C12N 15/82* | (2006.01) |
| *G01N 21/3563* | (2014.01) |
| *G01N 33/02* | (2006.01) |

(52) U.S. Cl.
CPC ......... *G01N 21/359* (2013.01); *B07C 5/3425* (2013.01); *C12N 15/8245* (2013.01); *C12N 15/8247* (2013.01); *G01N 21/3563* (2013.01); *G01N 21/84* (2013.01); *G01N 33/025* (2013.01); *G01N 2021/8466* (2013.01)

(58) Field of Classification Search
CPC .... G01N 21/359; G01N 21/84; G01N 33/025; G01N 33/10; G01N 21/3563; B07C 5/3425; C12N 15/8245; C12N 15/8247
See application file for complete search history.

(56) References Cited

U.S. PATENT DOCUMENTS

| | | | | |
|---|---|---|---|---|
| 4,752,689 | A * | 6/1988 | Satake | G01N 21/4738 250/339.07 |
| 6,646,264 | B1 * | 11/2003 | Modiano | G01N 21/359 250/339.07 |
| 7,600,642 | B2 * | 10/2009 | Deppermann | B07C 5/36 209/552 |
| 9,227,230 | B2 * | 1/2016 | Bensley-Bromilow | A01D 45/30 |
| 9,387,518 | B2 * | 7/2016 | Deppermann | B07C 5/3425 |

FOREIGN PATENT DOCUMENTS

CN    109211784 A * 1/2019 ............. G01J 3/108

OTHER PUBLICATIONS

Hollung, Kristin et al.: "Evaluation of Nonstarch Polysaccharides and Oligosaccharide Content of Different Soybean Varieties (*Glycine max*) by Near-Infrared Spectroscopy and Proteomics", J. Agric. Food Chem., Oct. 14, 2005 (Oct. 14, 2005), vol. 53, pp. 9112-9121 (Year: 2005).*
Hollung, Kristin; et al.: "Evaluation of Nonstarch Polysaccharides and Oligosaccharide Content of Different Soybean Varieties (*Glycine max*) by Near-Infrared Spectroscopy and Proteomics", J. Agric. Food Chem., Oct. 14, 2005 (Oct. 14, 2005), vol. 53, pp. 9112-9121.
Poysa, V.; et al.: "Stability of soybean seed composition and its effect on soymilk and tofu yield and quality", Food Research International, 2002, vol. 35, No. 4, pp. 337-345.
International Search Report and Written Opinion, International Application No. PCT/US2018/019683, dated May 2, 2018.

* cited by examiner

*Primary Examiner* — Patrick H Mackey

(57) ABSTRACT

Disclosed are methods and systems for spectral imaging of soybean samples to accurately and non-destructively measure the amount of sucrosyl-oligosaccharide in the soybean samples. Populations containing modified and unmodified soybean seeds and having varying amounts of sucrosyl-oligosaccharides, oil or protein can be sorted and separated and further used in soybean processing or breeding.

20 Claims, No Drawings

Specification includes a Sequence Listing.

SEQUENCE LISTING

```
<160> NUMBER OF SEQ ID NOS: 12

<210> SEQ ID NO 1
<211> LENGTH: 17719
<212> TYPE: DNA
<213> ORGANISM: Artificial Sequence
<220> FEATURE:
<223> OTHER INFORMATION: synthesized DNA of PHP48070
<220> FEATURE:
<221> NAME/KEY: misc_feature
<222> LOCATION: (12906)..(12906)
<223> OTHER INFORMATION: n is a, c, g, or t

<400> SEQUENCE: 1
cgcgccggaa ttaattaggt aatttcacgc gccggatcct taattaagtc tagagtcgac      60
tgtttaattc tagtggccgg cccagctgat gatcccggtg aagttcctat tccgaagttc     120
ctattctcca gaaagtatag gaacttcact agagcttgcg gccgctcgag ttctatagtg     180
tcacctaaat cgtatgtgta tgatacataa ggttatgtat taattgtagc cgcgttctaa     240
cgacaatatg tccatatggt gcactctcag tacaatctgc tctgatgccg catagttaag     300
ccagccccga cacccgccaa cacccgctga cgcgccctga cgggcttgtc tgctcccggc     360
atccgcttac agacaagctg tgaccgtctc cgggagctgc atgtgtcaga ggttttcacc     420
```

```
gtcatcaccg aaacgcgcga gacgaaaggg cctcgtgata cgcctatttt tataggttaa    480
tgtcatgacc aaaatccctt aacgtgagtt tcgttccac tgagcgtcag accccgtaga     540
aaagatcaaa ggatcttctt gagatccttt ttttctgcgc gtaatctgct gcttgcaaac    600
aaaaaaacca ccgctaccag cggtggtttg tttgccggat caagagctac caactctttt    660
tccgaaggta actggcttca gcagagcgca gataccaaat actgtccttc tagtgtagcc    720
gtagttaggc caccacttca agaactctgt agcaccgcct acatacctcg ctctgctaat    780
cctgttacca gtggctgctg ccagtggcga taagtcgtgt cttaccgggt tggactcaag    840
acgatagtta ccggataagg cgcagcggtc gggctgaacg gggggttcgt gcacacagcc    900
cagcttggag cgaacgacct acaccgaact gagataccta cagcgtgagc attgagaaag    960
cgccacgctt cccgaaggga gaaggcggac aggtatccg gtaagcggca gggtcggaac     1020
aggagagcgc acgagggagc ttccaggggg aaacgcctgg tatctttata gtcctgtcgg    1080
gtttcgccac ctctgacttg agcgtcgatt tttgtgatgc tcgtcagggg gcggagcct     1140 atggaaaaac gccagcaacg cggccttttt acggttcctg ccttttgct ggccttttgc     1200 tcacatgttc tttcctgcgt tatcccctga ttctgtggat aaccgtatta ccgcctttga    1260
gtgagctgat accgctcgcc gcagccgaac gaccgagcgc agcgagtcag tgagcgagga    1320
agcggaagag cgcccaatac gcaaaccgcc tctccccgcg cgttggccga ttcattaatg    1380
caggttgatc agatctcgat cccgcgaaat taatacgact cactataggg agaccacaac    1440
ggtttccctc tagaaataat tttgtttaac tttaagaagg agatataccc atggaaaagc    1500
ctgaactcac cgcgacgtct gtcgagaagt ttctgatcga aaagttcgac agcgtctccg    1560
acctgatgca gctctcggag ggcgaagaat ctcgtgcttt cagcttcgat gtaggagggc    1620
gtggatatgt cctgcgggta aatagctgcg ccgatggttt ctacaaagat cgttatgttt    1680
atcggcactt tgcatcggcc gcgctcccga ttccggaagt gcttgacatt ggggaattca    1740
gcgagagcct gacctattgc atctcccgcc gtgcacaggg tgtcacgttg caagacctgc    1800
ctgaaaccga actgcccgct gttctgcagc cggtcgcgga ggctatggat gcgatcgctg    1860
cggccgatct tagccagacg agcggggttcg gcccattcgg accgcaagga atcggtcaat    1920
acactacatg gcgtgatttc atatgcgcga ttgctgatcc ccatgtgtat cactggcaaa    1980
ctgtgatgga cgacaccgtc agtgcgtccg tcgcgcaggc tctcgatgag ctgatgcttt    2040
gggccgagga ctgccccgaa gtccggcacc tcgtgcacgc ggatttcggc tccaacaatg    2100
tcctgacgga caatggccgc ataacagcgg tcattgactg gagcgaggcg atgttcgggg    2160
attcccaata cgaggtcgcc aacatcttct tctggaggcc gtggttggct tgtatggagc    2220
agcagacgcg ctacttcgag cggaggcatc cggagcttgc aggatcgccg cggctccggg    2280
cgtatatgct ccgcattggt cttgaccaac tctatcagag cttggttgac ggcaatttcg    2340
atgatgcagc ttgggcgcag gtcgatgcg acgcaatcgt ccgatccgga gccgggactg    2400
tcgggcgtac acaaatcgcc cgcagaagcg cggccgtctg gaccgatggc tgtgtagaag    2460
tactcgccga tagtggaaac cgacgcccca gcactcgtcc gagggcaaag gaatagtgag    2520
gtacagcttg gatcgatccg gctgctaaca aagcccgaaa ggaagctgag ttggctgctg    2580
ccaccgctga gcaataacta gcataacccc ttggggcctc taaacgggtc ttgaggggtt    2640
ttttgctgaa aggaggaact atatccggat gatcgtcgag gcctcacgtg ttaacaagct    2700
tgcatgccgg tttaaacagt cgaggtcgac ggtatcgata agcttgttaa cagaagttcc    2760
tattccgaag ttcctattct ctagaaagta taggaacttc caccacacaa cacaatggcg    2820
```

```
gccaccgctt ccagaaccac ccgattctct tcttcctctt cacacccac cttccccaaa      2880 cgcattacta gatccaccct ccctctctct catcaaaccc tcaccaaacc caaccacgct      2940
ctcaaaatca aatgttccat ctccaaaccc cccacggcgg cgcccttcac caaggaagcg      3000
ccgaccacgg agcccttcgt gtcacggttc gcctccggcg aacctcgcaa gggcgcggac      3060
atccttgtgg aggcgctgga gaggcagggc gtgacgacgg tgttcgcgta ccccggcggt      3120
gcgtcgatgg agatccacca ggcgctcacg cgctccgccg ccatccgcaa cgtgctcccg      3180
cgccacgagc agggcggcgt cttcgccgcc gaaggctacg cgcgttcctc cggcctcccc      3240
ggcgtctgca ttgccacctc cggccccggc gccaccaacc tcgtgagcgg cctcgccgac      3300
gctttaatgg acagcgtccc agtcgtcgcc atcaccggcc aggtcgcccg ccggatgatc      3360
ggcaccgacg ccttccaaga aaccccgatc gtggaggtga gcagatccat cacgaagcac      3420
aactacctca tcctcgacgt cgacgacatc ccccgcgtcg tcgccgaggc tttcttcgtc      3480
gccacctccg gccgccccgg tccggtcctc atcgacattc ccaaagacgt tcagcagcaa      3540
ctcgccgtgc ctaattggga cgagcccgtt aacctccccg gttacctcgc caggctgccc      3600 aggcccccccg ccgaggccca attggaacac attgtcagac tcatcatgga ggcccaaaag      3660
cccgttctct acgtcggcgg tggcagtttg aattccagtg ctgaattgag gcgctttgtt      3720
gaactcactg gtattcccgt tgctagcact ttaatgggtc ttggaacttt tcctattggt      3780
gatgaatatt cccttcagat gctgggtatg catggtactg tttatgctaa ctatgctgtt      3840
gacaatagtg atttgttgct tgcctttggg gtaaggtttg atgaccgtgt tactgggaag      3900
cttgaggctt ttgctagtag ggctaagatt gttcacattg atattgattc tgccgagatt      3960
gggaagaaca agcaggcgca cgtgtcggtt tgcgcggatt tgaagttggc cttgaaggga      4020
attaatatga tttggagga gaaaggagtg gagggtaagt ttgatcttgg aggttggaga      4080
gaagagatta atgtgcagaa acacaagttt ccattgggtt acaagacatt ccaggacgcg      4140
atttctccgc agcatgctat cgaggttctt gatgagttga ctaatggaga tgctattgtt      4200
agtactgggg ttgggcagca tcaaatgtgg gctgcgcagt tttacaagta caagagaccg      4260
aggcagtggt tgacctcagg gggtcttgga gccatgggtt ttggattgcc tgcggctatt      4320
ggtgctgctg ttgctaaccc tgggctgtt gtggttgaca ttgatgggga tggtagtttc      4380
atcatgaatg ttcaggagtt ggccactata agagtggaga atctcccagt taagatattg      4440
ttgttgaaca atcagcattt gggtatggtg gttcagtggg aggataggtt ctacaagtcc      4500
aatagagctc acacctatct tggagatccg tctagcgaga gcgagatatt cccaaacatg      4560
ctcaagtttg ctgatgcttg tgggataccg gcagcgcgag tgacgaagaa ggaagagctt      4620
agagcggcaa ttcagagaat gttggacacc cctggcccct accttcttga tgtcattgtg      4680
ccccatcagg agcatgtgtt gccgatgatt cccagtaatg gatccttcaa ggatgtgata      4740
actgagggtg atggtagaac gaggtactga ctagctagtc agttaaccta gacttgtcca      4800
tcttctggat tggccaactt aattaatgta tgaaataaaa ggatgcacac atagtgacat      4860
gctaatcact ataatgtggg catcaaagtt gtgtgttatg tgtaaattact agttatctga      4920 ataaaagaga aagagatcat ccatatttct tatcctaaat gaatgtcacg tgtctttata      4980
attctttgat gaaccagatg catttcatta accaaatcca tatacatata aatattaatc      5040
atatataatt aatatcaatt gggttagcaa aacaaatcta gtctaggtgt gttttgcccc      5100
caagcttatc gataccgtcg gcgcggggta cgttagctga ttaagtcagc atgcgcggcc      5160
```

```
ggcgtatgaa ctaaaatgca tgtaggtgta agagctcatg gagagcatgg aatattgtat      5220
ccgaccatgt aacagtataa taactgagct ccatctcact tcttctatga ataaacaaag      5280
gatgttatga tatattaaca ctctatctat gcaccttatt gttctatgat aaatttcctc      5340
ttattattat aaatcatctg aatcgtgacg gcttatggaa tgcttcaaat agtacaaaaa      5400
caaatgtgta ctataagact ttctaaacaa ttctaacctt agcattgtga acgagacata      5460
agtgttaaga agacataaca attataatgg aagaagtttg tctccattta tatattatat      5520
attacccact tatgtattat attaggatgt taaggagaca taacaattat aaagagagaa      5580
gtttgtatcc atttatatat tatatactac ccatttatat attatactta tccacttatt      5640
taatgtcttt ataaggtttg atccatgata tttctaatat tttagttgat atgtatatga      5700
aaaggtacta tttgaactct cttactctgt ataaaggttg gatcatcctt aaagtgggtc      5760
tatttaattt tattgcttct tacagataaa aaaaaaatta tgagttggtt tgataaaata      5820
ttgaaggatt taaataataa ataaataaca tataatatat gtatataaat ttattataat      5880
ataacattta tctataaaaa agtaaatatt gtcataaatc tatacaatcg tttagccttg      5940
ctggaacgaa tctcaattat ttaaacgaga gtaaacatat ttgactttt  ggttatttaa      6000 caaattatta tttaacacta tatgaaattt tttttttat  cagcaaagaa taaaattaaa      6060
ttaagaagga caatggtgtc ccaatcctta tacaaccaac ttccacaaga aagtcaagtc      6120
agagacaaca aaaaaacaag caaaggaaat ttttaattt  gagttgtctt gtttgctgca      6180
taatttatgc agtaaaacac tacacataac cctttagca  gtagagcaat ggttgaccgt      6240
gtgcttagct tcttttattt tatttttta  tcagcaaaga ataaataaaa taaaatgaga      6300
cacttcaggg atgtttcaac aggtacccat  cacttaagtg gcgcgccgtc gacggatccg      6360
tacgatccat gccttcatt  tgccgcttat taattaattt ggtaacagtc cgtactaatc       6420
agttacttat ccttccccca tcataattaa tcttggtagt ctcgaatgcc acaacactga      6480
ctagtctctt ggatcataag aaaaagccaa ggaacaaaag aagacaaaac acaatgagag      6540
tatcctttgc atagcaatgt ctaagttcat aaaattcaaa caaaaacgca atcacacaca      6600
gtggacatca cttatccact agctgatcag gatcgccgcg tcaagaaaaa aaaactggac      6660
cccaaaagcc atgcacaaca acacgtactc acaaggtgt  caatcgagca gcccaaaaca      6720
ttcaccaact caacccatca tgagccctca catttgttgt ttctaaccca acctcaaact      6780
cgtattctct tccgccacct cattttttgtt tatttcaaca cccgtcaaac tgcatgccac      6840
cccgtggcca aatgtccatg catgttaaca agacctatga ctataaatag ctgcaatctc      6900
ggcccaggtt ttcatcatca agaaccagtt caatatccta gtacaccgta ttaaagaatt      6960
taagatatac tgcggccgcg cgagaaactt tgtatgggca tggttatttc tcacttctca      7020
ccctccttta ctttcttatg ctaaatcctc cttcccctat atctccaccc tcaacccctt      7080
tttctcatta taacttttgg tgcctagatg gtgtgtgtgt gtgcgcgcga gagatctgag      7140
ctcaattttc ctctctcaag tcctggtcat gctttgaggg aaaaggggttg aggaacttat      7200 gcatcttata tctctccacc tccaggattt taagccctag ttactcaacc cttttccctc      7260
agaatatggc aattcaggct tttaattgct ttcatttggt accatcactt gcaagatttc      7320
agagtacaag gtgaacacac acatcttcct cttcatcaat tctctagttt catccttatc      7380
ttttcattca cggtaactct cactacccct tttcatctta aagttatac  cggggggtgtg     7440 atgttgatga gtgtaaatta aatatatgtg atctctttct ctggaaaaat tttcagtgtg      7500
atatacataa taatctctta atctagagat tttatggctt tgttatatat aagcggcgca      7560
```

```
agggcgaatt ctgcagatat ccatcacact tgggccgctt ctagctagct agggtttggg    7620
tagtgagtgt aataaagttg caaagttttt ggttaggtta cgttttgacc ttattattat    7680
agttcaaagg gaaacattaa ttaaggggga ttatgaaggt ggatgatgcc tgattggatt    7740
gaggatctta ctgggtgaat tgagctgctt agctatggat cccacagttc tacccatcaa    7800
taagtgcttt tgtggtagtc ttgtggcttc catatctggg gagcttcatt tgcctttata    7860
gtattaacct tcttccaatc cagcatcatc caccacccett ctcttctttt ctctcataat    7920
aatttaaatt tgttatagac tctaaacttt aaatgttttt tttgaagttt ttccgttttt    7980
ctcttttgcc atgatcccgt tcttgctgtg gagtaacctt gtccgaggta tgtgcatgat    8040
tagatccata cttaatttgt gtgcatcacg aaggtgaggt tgaaatgaac tttgcttttt    8100
tgacctttta ggaaagttct tttgttgcag taatcaattt taattagttt taattgacac    8160
tattactttt attgtcatct ttgttagttt tattgttgaa ttgagtgcat atttcctagg    8220
aaattctctt acctaacatt ttttatacag atctatgctc ttggctcttg cccttactct    8280
tggccttgtg ttggttattt gtctacatat ttattgactg gtcgatgaga catgtcacaa    8340
ttcttgggct tatttgttgg tctaataaaa ggagtgctta ttgaaagatc aagacggaga    8400
ttcggtttta tataaataaa ctaaagatga catattagtg tgttgatgtc tcttcaggat    8460 aattttgtt tgaaataata tggtaatgtc ttgtctaaat ttgtgtacat aattcttact    8520
gatttttgga ttgttggatt tttataaaca aatctggggc ccaagcggcc gcaagtatga    8580
actaaaatgc atgtaggtgt aagagctcat ggagagcatg gaatattgta tccgaccatg    8640
taacagtata ataactgagc tccatctcac ttcttctatg aataaacaaa ggatgttatg    8700
atatattaac actctatcta tgcacccttat tgttctatga taaatttcct cttattatta    8760
taaatcatct gaatcgtgac ggcttatgga atgcttcaaa tagtacaaaa acaaatgtgt    8820
actataagac tttctaaaca attctaacct tagcattgtg aacgagacat aagtgttaag    8880
aagacataac aattataatg gaagaagttt gtctccattt atatattata tattacccac    8940
ttatgtatta tattaggatg ttaaggagac ataacaatta taagagaga agtttgtatc    9000 catttatata ttatatacta cccatttata tattatactt atccacttat ttaatgtctt    9060
tataaggttt gatccatgat atttctaata ttttagttga tatgtatatg aaaaggtact    9120
atttgaactc tcttactctg tataaaggtt ggatcatcct taaagtgggt ctatttaatt    9180
ttattgcttc ttacagataa aaaaaaaatt atgagttggt ttgataaaat attgaaggat    9240
ttaaaataat aataaataac atataatata tgtatataaa tttattataa tataacatttt   9300 atctataaaa aagtaaatat tgtcataaat ctatacaatc gtttagcctt gctggaacga    9360
atctcaatta tttaaacgag agtaaacata tttgactttt tggttattta acaaattatt    9420
atttaacact atatgaaatt ttttttttta tcagcaaaga ataaaattaa attaagaagg    9480
acaatggtgt cccaatcctt atacaaccaa cttccacaag aaagtcaagt cagagacaac    9540
aaaaaaacaa gcaaaggaaa ttttttaatt tgagttgtct tgtttgctgc ataatttatg    9600
cagtaaaaca ctacacataa ccctttttagc agtagagcaa tggttgaccg tgtgcttagc    9660
ttcttttatt ttatttttttt atcagcaaag aataaataaa ataaaatgag acacttcagg    9720
gatgtttcaa cgtacgtctt tccacaatac ataactatta attaatctta aataaataaa    9780
ggataaaata tttttttttc ttcataaagt taaaatatgt tatttttttgt ttagatgtat    9840 attcgaataa atctaaatat atgataatga tttttttatat tgattaaaca tataatcaat    9900
```

```
attaaatatg atattttttt ataaggttg tacacataat tttataagga taaaaaatat    9960
gataaaaata aattttaaat attttatat ttacgagaaa aaaaaatatt ttagccataa   10020
ataaatgacc agcatatttt acaaccttag taattcataa attcctatat gtatatttga  10080
aattaaaaac agataatcgt taagggaagg aatcctacgt catctcttgc catttgtttt  10140
tcatgcaaac agaaagggac gaaaaaccac ctcaccatga atcactcttc acaccatttt  10200
tactagcaaa caagtctcaa caactgaagc cagctctctt tccgtttctt tttacaacac  10260
tttctttgaa atagtagtat tttttttcac atgatttatt aacgtgccaa aagatgctta  10320
ttgaatagag tgcacatttg taatgtacta ctaattagaa catgaaaaag cattgttcta  10380
acacgataat cctgtgaagg cgttaactcc aaagatccaa tttcactata taaattgtga  10440
cgaaagcaaa atgaattcac atagctgaga gagaaaggaa aggttaacta agaagcaata  10500
cttcagcggc cgcttctagc tagctagggt ttgggtagtg agtgtaataa agttgcaaag  10560
tttttggtta ggttacgttt tgaccttatt attatagttc aaagggaaac attaattaaa  10620
ggggattatg aagtgggctc tcttgattct tggatgagga tcttactggg tgaattgagc  10680
tgcttagcta tggatcccac agttctaccc atcaataagt gcttttgtgg tagtcttgtg  10740
gcttccatat ctggggagct tcatttgcct ttatagtatt aaccttctcc aagaacaaag  10800
agagcccaca cccttctctt cttttctctc ataataattt aaatttgtta tagactctaa  10860
actttaaatg ttttttttga gttttttccg ttttctctt ttgccatgat cccgttcttg   10920
ctgtggagta accttgtccg aggtatgtgc atgattagat ccatacttaa tttgtgtgca  10980
tcacgaaggt gaggttgaaa tgaacttgtc ttttttgacc ttttaggaaa gttctttttgt 11040
tgcagtaatc aattttaatt agttttaatt gacactatta cttttattgt catctttgtt  11100
agttttattg ttgaattgag tgcatattc ctaggaaatt ctcttaccta acattttta    11160
tacagatcta tgctcttggc tcttgccctt actcttggcc ttgtgttggt tatttgtcta  11220
catatttatt gactggtcga tgagacatgt cacaattctt gggcttattt gttggtctaa  11280
taaaaggagt gcttattgaa agatcaagac ggagattcgg ttttatataa ataaactaaa  11340
gatgacatat tagtgtgttg atgtctcttc aggataattt ttgtttgaaa taatatggta  11400
atgtcttgtc taaatttgtg tacataattc ttactgattt tttggattgt tggatttta   11460
taaacaaatc tgcggccgca tgagccgtaa aggttcaata caacgagtgc ttgttttctt  11520
agggacaagc attgtactta tgtatgattc tgtgtaacca tgagtcttcc acgttgtact  11580
aatgtgaagg gcaaaaataa aacacagaac aagttcgttt ttctcaaata atgtgaaggt  11640
agaaaatgga accatgcctc ctctcttgca tgtgatttaa aatattagca gatggtacgt  11700
cgagtcgacc tgcaggtcga ctcgacgtac gtcctcgaag agaagggtta ataacacatt  11760
ttttaacatt tttaacacaa attttagtta tttaaaaatt tattaaaaaa tttaaaataa  11820
gaagaggaac tctttaaata aatctaactt acaaaattta tgattttaa taagttttca   11880
ccaataaaaa atgtcataaa aatatgttaa aaagtatatt atcaatattc tctttatgat  11940
aaataaaaag aaaaaaaaaa taaaagttaa gtgaaaatga gattgaagtg actttaggtg  12000
tgtataaata tatcaacccc gccaacaatt tatttaatcc aaatatattg aagtatatta  12060
ttccatagcc tttatttatt tatatattta ttatataaaa gctttatttg ttctaggttg  12120
ttcatgaaat atttttttgg ttttatctcc gttgtaagaa aatcatgtgc tttgtgtcgc  12180
cactcactat tgcagctttt tcatgcattg gtcagattga cggttgattg tattttgtt   12240
ttttatggtt ttgtgttatg acttaagtct tcatctcttt atctcttcat caggtttgat  12300
```

```
ggttacctaa tatggtccat gggtacatgc atggttaaat taggtggcca actttgttgt   12360
gaacgataga attttttta tattaagtaa actatttta tattatgaaa taataataaa    12420
aaaaatattt tatcattatt aacaaaatca tattagttaa tttgttaact ctataataaa   12480
agaaatactg taacattcac attacatggt aacatctttc caccctttca tttgtttttt   12540
gtttgatgac ttttttctt gtttaaattt atttcccttc ttttaaattt ggaatacatt   12600
atcatcatat ataaactaaa atactaaaaa caggattaca caaatgataa ataataacac   12660
aaatatttat aaatctagct gcaatatatt taaactagct atatcgatat tgtaaaataa   12720
aactagctgc attgatactg ataaaaaaat atcatgtgct ttctggactg atgatgcagt   12780
atacttttga cattgccttt attttatttt tcagaaaagc tttcttagtt ctgggttctt   12840
cattatttgt ttcccatctc cattgtgaat tgaatcattt gcttcgtgtc acaaatacaa   12900
tttagntagg tacatgcatt ggtcagattc acggtttatt atgtcatgac ttaagttcat   12960
ggtagtacat tacctgccac gcatgcatta tattggttag atttgatagg caaatttggt   13020
tgtcaacaat ataaatataa ataatgtttt tatattacga ataacagtg atcaaaacaa    13080 acagttttat cttattaac aagattttgt ttttgtttga tgacgttttt taatgtttac    13140
gctttccccc ttcttttgaa tttagaacac tttatcatca taaaatcaaa tactaaaaaa   13200
attacatatt tcataaataa taacacaaat attttaaaa atctgaaat aataatgaac     13260 aatattacat attatcacga aaattcatta ataaaaatat tatataaata aatgtaata    13320 gtagttatat gtaggaaaaa agtactgcac gcataatata tacaaaaaga ttaaaatgaa   13380
ctattataaa taataacact aaattaatgg tgaatcatat caaaataatg aaaaagtaaa   13440
taaaatttgt aattaacttc tatatgtatt acacacacaa ataataaata atagtaaaaa   13500
aaattatgat aaatatttac catctcataa gatatttaaa ataatgataa aaatatagat   13560 tatttttat gcaactagct agccaaaaag agaacacggg tatatataaa aagagtacct   13620
ttaaattcta ctgtacttcc tttattcctg acgttttat atcaagtgga catacgtgaa   13680
gattttaatt atcagtctaa atatttcatt agcacttaat acttttctgt tttattccta   13740
tcctataagt agtcccgatt ctcccaacat tgcttattca cacaactaac taagaaagtc   13800
ttccatagcc ccccaagcgg ccgctagtcg actaagtcat caactattcc aagctacgta   13860
tttgggagtt tgtggagtac agcaagatga tatacctaga cggtgatatc caagttttg    13920 acaacattga ccacttgttt gacttgcctg ataactactt ctatgcggtg atggactgtt   13980
tctgtgagcc aacttggggc cacactaaac aatatcagat cggttactgc cagcagtgcc   14040
cccataaggt tcagtggccc actcactttg ggcccaaacc tcctctctat ttcaatgctg   14100
gcatgtttgt gtatgagccc aatttggcta cttaccgtga cctccttcaa acagtccaag   14160
tcacccagcc cacttccttt gctgaacagg attttttgaa catgtacttc aaggacaaat   14220
ataggccaat tcctaatgtc tacaatcttg tgctggccat gctgtggcgt caccctgaga   14280
acgttgagct tgacaaagtt aaagtggttc actactgtgc tgctgggtct aagccttgga   14340
ggtacactgg gaagtgactc gaggtcatca attactccaa gctacgtatt tgggagttcg   14400
tggagtacaa gaagacgata tacctagacg gtgacatcca agtatttgga aacatagacc   14460
acttgtttga tctgcctgat aattatttct atgcggtgat ggattgtttc tgcgagaaga   14520
cttggagcca caccctcag ttccagattg ggtactgcca acagtgccct gataaggttc    14580
aatggccctc tcactttggt tccaaacctc ctctatattt caatgctggc atgtttgttt   14640
```

```
atgagcctaa tctcgacacc taccgtgatc ttctccaaac tgtccaactc accaagccca   14700
cttcttttgc tgagcaggac tttctcaaca tgtacttcaa ggacaagtac aagccaatac   14760
cgaacatgta caaccttgtg ctggccatgt tgtggcgtca ccctgaaaat gttgaacttg   14820
ataaagttca agtggttcat tactgtgctg ctgggtctaa gccttggagg ttcactggga   14880
agtaactgca ggtcatcaac tactccaagc tccgtatatg ggagtttgtg gagtacagca   14940
agatgatata cttggacgga gacattgagg tatatgagaa catagaccac ctatttgacc   15000
tacctgatgg taacttttac gctgtgatgg attgtttctg cgagaagaca tggagtcaca   15060
cccctcagta caaggtgggt tactgccagc aatgcccgga gaaggtgcgg tggcccaccg   15120
aattgggtca gccccccttct ctttacttca acgctggcat gttcgtgttc gaacccaaca   15180
tcgccaccta tcatgaccta ttgaaaacgg tgcaagtcac cactcccacc tcgttcgctg   15240
aacaagattt cttgaacatg tacttcaagg acatttacaa gccaatccct ttaaattaca   15300
atcttgtcct cgccatgctg tggcgccacc cggaaaacgt taaattagac caagtcaagg   15360
ttgttcacta ttgcgcagcg gggtccaagc catggagata tacggggaag tagcctaggc   15420
gtacgcaggt aagtttctgc ttctacctttt gatatatata taataattat cattaattag   15480
tagtaatata atatttcaaa tatttttttc aaaataaaag aatgtagtat atagcaattg   15540
cttttctgta gtttataagt gtgtatattt taatttataa cttttctaat atatgaccaa   15600
aacatggtga tgtgcaggtc ctaggctact tcccgtata tctccatggc ttggaccccg   15660
ctgcgcaata gtgaacaacc ttgacttggt ctaatttaac gttttccggg tggcgccaca   15720
gcatggcgag gacaagattg taatttaaag ggattggctt gtaaatgtcc ttgaagtaca   15780
tgttcaagaa atcttgttca gcgaacgagg tgggagtggt gacttgcacc gttttcaata   15840
ggtcatgata ggtggcgatg ttgggttcga acacgaacat gccagcgttg aagtaaagag   15900
aaggggggctg acccaattcg gtgggccacc gcaccttctc cgggcattgc tggcagtaac   15960
ccaccttgta ctgaggggtg tgactccatg tcttctcgca gaaacaatcc atcacagcgt   16020
aaaagttacc atcaggtagg tcaaataggt ggtctatgtt ctcatatacc tcaatgtctc   16080
cgtccaagta tatcatcttg ctgtactcca caaactccca tatacggagc ttggagtagt   16140
tgatgacctg cagttacttc ccagtgaacc tccaaggctt agacccagca gcacagtaat   16200
gaaccacttg aactttatca agttcaacat tttcagggtg acgccacaac atggccagca   16260
caaggttgta catgttcggt attggcttgt acttgtcctt gaagtacatg ttgagaaagt   16320
cctgctcagc aaaagaagtg ggcttggtga gttggacagt ttggagaaga tcacggtagg   16380
tgtcgagatt aggctcataa acaaacatgc cagcattgaa atatagagga ggtttggaac   16440
caaagtgaga gggccattga accttatcag ggcactgttg gcagtaccca atctggaact   16500
gaggggtgtg gctccaagtc ttctcgcaga aacaatccat caccgcatag aaataattat   16560
caggcagatc aaacaagtgg tctatgtttc caaatacttg gatgtcaccg tctaggtata   16620
tcgtcttctt gtactccacg aactcccaaa tacgtagctt ggagtaattg atgacctcga   16680
gtcacttccc agtgtaccte caaggcttag acccagcagc acagtagtga accactttaa   16740
ctttgtcaag ctcaacgttc tcaggtgac gccacagcat ggccagcaca agattgtaga   16800
cattaggaat tggcctatat ttgtccttga agtacatgtt caaaaaatcc tgttcagcaa   16860
aggaagtggg ctgggtgact tggactgttt gaaggaggtc acggtaagta gccaaattgg   16920
gctcatacac aaacatgcca gcattgaaat agagaggagg tttgggccca aagtgagtgg   16980
gccactgaac cttatggggg cactgctggc agtaaccgat ctgatattgt ttagtgtggc   17040
```

-continued

```
cccaagttgg ctcacagaaa cagtccatca ccgcatagaa gtagttatca ggcaagtcaa   17100
acaagtggtc aatgttgtca aaaacttgga tatcaccgtc taggtatatc atcttgctgt   17160
actccacaaa ctcccaaata cgtagcttgg aatagttgat gacttagtcg actagcggcc   17220
gcgacacaag tgtgagagta ctaaataaat gctttggttg tacgaaatca ttacactaaa   17280
taaaataatc aaagcttata tatgccttcc gctaaggccg aatgcaaaga aattggttct   17340
ttctcgttat cttttgccac ttttactagt acgtattaat tactacttaa tcatctttgt   17400
ttacggctca ttatatccgg tctaggccaa ggccgcgaag ttaaaagcaa tgttgtcact   17460
tgtacgtact aacacatgat gtgatagttt atgctagcta gctataacat aagctgtctc   17520
tgagtgtgtt gtatattaat aaagatcatc actggtgaat ggtgatcgtg tacgtaccct   17580
acttagtagg caatggaagc acttagagtg tgctttgtgc atggccttgc ctctgttttg   17640
agacttttgt aatgttttcg agtttaaatc tttgcctttg cgtacgtggg cggatcccct   17700
gcaggagatc caagcttgg                                                17719
```

```
<210> SEQ ID NO 2
<211> LENGTH: 17679
<212> TYPE: DNA
<213> ORGANISM: Artificial Sequence
<220> FEATURE:
<223> OTHER INFORMATION: synthesized DNA of PHP50573
<220> FEATURE:
<221> NAME/KEY: misc_feature
<222> LOCATION: (12882)..(12882)
<223> OTHER INFORMATION: n is a, c, g, or t

<400> SEQUENCE: 2
```

```
ggagatccaa gcttggcgcg ccggaattaa ttaggtaatt tcacgcgccg gatccttaat     60
taagtctaga gtcgactgtt taattctagt ggccggccca gctgatgatc ccggtgaagt    120
tcctattccg aagttcctat tctccagaaa gtataggaac ttcactagag cttgcggccg    180
ctcgagttct atagtgtcac ctaaatcgta tgtgtatgat acataaggtt atgtattaat    240
tgtagccgcg ttctaacgac aatatgtcca tatggtgcac tctcagtaca atctgctctg    300
atgccgcata gttaagccag ccccgacacc cgccaacacc cgctgacgcg ccctgacggg    360
cttgtctgct cccggcatcc gcttacagac aagctgtgac cgtctccggg agctgcatgt    420
gtcagaggtt ttcaccgtca tcaccgaaac gcgcgagacg aaagggcctc gtgatacgcc    480
tatttttata ggttaatgtc atgaccaaaa tcccttaacg tgagttttcg ttccactgag    540
cgtcagaccc cgtagaaaag atcaaaggat cttcttgaga tcctttttt ctgcgcgtaa    600 tctgctgctt gcaaacaaaa aaaccaccgc taccagcggt ggtttgtttg ccggatcaag    660
agctaccaac tctttttccg aaggtaactg gcttcagcag agcgcagata ccaaatactg    720
tccttctagt gtagccgtag ttaggccacc acttcaagaa ctctgtagca ccgcctacat    780
acctcgctct gctaatcctg ttaccagtgg ctgctgccag tggcgataag tcgtgtctta    840
ccgggttgga ctcaagacga tagttaccgg ataaggcgca gcggtcgggc tgaacggggg    900
gttcgtgcac acagcccagc ttggagcgaa cgacctacac cgaactgaga tacctacagc    960
gtgagcattg agaaagcgcc acgcttcccg aaggagaaa ggcggacagg tatccggtaa   1020
gcggcagggt cggaacagga gagcgcacga gggagcttcc agggggaaac gcctggtatc   1080
tttatagtcc tgtcgggttt cgccacctct gacttgagcg tcgatttttg tgatgctcgt   1140
caggggggcg gagcctatgg aaaaacgcca gcaacgcggc ctttttacgg ttcctggcct   1200
```

```
tttgctggcc ttttgctcac atgttctttc ctgcgttatc ccctgattct gtggataacc    1260
gtattaccgc ctttgagtga gctgataccg ctcgccgcag ccgaacgacc gagcgcagcg    1320
agtcagtgag cgaggaagcg gaagagcgcc caatacgcaa accgcctctc cccgcgcgtt    1380
ggccgattca ttaatgcagg ttgatcagat ctcgatcccg cgaaattaat acgactcact    1440
atagggagac cacaacggtt tccctctaga ataattttg tttaacttta agaaggagat     1500
atacccatgg aaaagcctga actcaccgcg acgtctgtcg agaagtttct gatcgaaaag    1560
ttcgacagcg tctccgacct gatgcagctc tcggagggcg aagaatctcg tgctttcagc    1620
ttcgatgtag gagggcgtgg atatgtcctg cgggtaaata gctgcgccga tggtttctac    1680
aaagatcgtt atgtttatcg gcactttgca tcggccgcgc tcccgattcc ggaagtgctt    1740
gacattgggg aattcagcga gagcctgacc tattgcatct cccgccgtgc acagggtgtc    1800
acgttgcaag acctgcctga aaccgaactg cccgctgttc tgcagccggt cgcggaggct    1860
atggatgcga tcgctgcggc cgatcttagc cagacgagcg gttcggccc attcggaccg      1920 caaggaatcg gtcaatacac tacatggcgt gatttcatat gcgcgattgc tgatccccat    1980
gtgtatcact ggcaaactgt gatggacgac accgtcagtg cgtccgtcgc gcaggctctc    2040
gatgagctga tgctttgggc cgaggactgc cccgaagtcc ggcacctcgt gcacgcggat    2100
ttcggctcca acaatgtcct gacggacaat ggccgcataa cagcggtcat tgactggagc    2160
gaggcgatgt cggggattc ccaatacgag gtcgccaaca tcttcttctg gaggccgtgg      2220
ttggcttgta tggagcagca gacgcgctac ttcgagcgga ggcatccgga gcttgcagga    2280
tcgccgcggc tccgggcgta tatgctccgc attggtcttg accaactcta tcagagcttg    2340
gttgacggca atttcgatga tgcagcttgg gcgcagggtc gatgcgacgc aatcgtccga    2400
tccggagccg ggactgtcgg gcgtacacaa atcccgca gaagcgcggc cgtctggacc       2460
gatggctgtg tagaagtact cgccgatagt ggaaaccgac gccccagcac tcgtccgagg    2520
gcaaaggaat agtgaggtac agcttggatc gatccggctg ctaacaaagc ccgaaaggaa    2580
gctgagttgg ctgctgccac cgctgagcaa taactagcat aaccccttgg ggcctctaaa    2640
cgggtcttga ggggtttttt gctgaaagga ggaactatat ccggatgatc gtcgaggcct    2700
cacgtgttaa caagcttgca tgccggttta acagtcgag gtcgacggta tcgataagct      2760
tgttaacaga agttcctatt ccgaagttcc tattctctag aaagtatagg aacttccacc    2820
acacaacaca atggcggcca ccgcttccag aaccacccga ttctcttctt cctcttcaca    2880
ccccaccttc cccaaacgca ttactagatc caccctccct ctctctcatc aaaccctcac    2940
caaacccaac cacgctctca aaatcaaatg ttccatctcc aaaccccca ggcggcgcc      3000 cttcaccaag gaagcgccga ccacggagcc cttcgtgtca cggttcgcct ccggcgaacc    3060
tcgcaagggc gcggacatcc ttgtggaggc gctggagagg cagggcgtga cgacggtgtt    3120
cgcgtacccc ggcggtgcgt cgatggagat ccaccaggcg ctcacgcgct ccgccgccat    3180
ccgcaacgtg ctccccgcgcc acgagcaggg cggcgtcttc gccgccgaag gctacgcgcg    3240
ttcctccggc ctccccggcg tctgcattgc cacctccggc cccggcgcca ccaacctcgt    3300
gagcggcctc gccgacgctt taatggacag cgtcccagtc gtcgccatca ccggccaggt    3360
cgcccgccgg atgatcggca ccgacgcctt ccaagaaacc ccgatcgtgg aggtgagcag    3420
atccatcacg aagcacaact acctcatcct cgacgtcgac gacatccccc gcgtcgtcgc    3480
cgaggctttc ttcgtcgcca cctccggccg ccccggtccg gtcctcatcg acattcccaa    3540
agacgttcag cagcaactcg ccgtgcctaa ttgggacgag cccgttaacc tccccggtta    3600
```

```
cctcgccagg ctgcccaggc cccccgccga ggcccaattg gaacacattg tcagactcat    3660
catgagggcc caaaagcccg ttctctacgt cggcggtggc agtttgaatt ccagtgctga    3720
attgaggcgc tttgttgaac tcactggtat tcccgttgct agcactttaa tgggtcttgg    3780
aacttttcct attggtgatg aatattccct tcagatgctg ggtatgcatg gtactgttta    3840
tgctaactat gctgttgaca atagtgattt gttgcttgcc tttggggtaa ggtttgatga    3900
ccgtgttact gggaagcttg aggcttttgc tagtagggct aagattgttc acattgatat    3960
tgattctgcc gagattggga agaacaagca ggcgcacgtg tcggtttgcg cggatttgaa    4020
gttggccttg aagggaatta atatgatttt ggaggagaaa ggagtggagg gtaagtttga    4080
tcttggaggt tggagagaag agattaatgt gcagaaacac aagtttccat tgggttacaa    4140
gacattccag gacgcgattt ctccgcagca tgctatcgag gttcttgatg agttgactaa    4200
tggagatgct attgttagta ctggggttgg gcagcatcaa atgtgggctg cgcagtttta    4260
caagtacaag agaccgaggc agtggttgac ctcaggggt  cttggagcca tgggttttgg    4320
attgcctgcg gctattggtg ctgctgttgc taaccctggg gctgttgtgg ttgacattga    4380
tggggatggt agtttcatca tgaatgttca ggagttggcc actataagag tggagaatct    4440
cccagttaag atattgttgt tgaacaatca gcatttgggt atggtggttc agtgggagga    4500
taggttctac aagtccaata gagctcacac ctatcttgga gatccgtcta gcagagcga    4560 gatattccca aacatgctca gtttgctga  tgcttgtggg ataccggcag cgcgagtgac    4620
gaagaaggaa gagcttagag cggcaattca gagaatgttg gacacccctg ccccctacct    4680
tcttgatgtc attgtgcccc atcaggagca tgtgttgccg atgattccca gtaatggatc    4740
cttcaaggat gtgataactg agggtgatgg tagaacgagg tactgactag ctagtcagtt    4800
aacctagact tgtccatctt ctggattggc caacttaatt aatgtatgaa ataaaaggat    4860
gcacacatag tgacatgcta atcactataa tgtgggcatc aaagtgtgt  gttatgtgta    4920 attactagtt atctgaataa aagagaaaga gatcatccat atttcttatc ctaaatgaat    4980
gtcacgtgtc tttataattc tttgatgaac cagatgcatt tcattaacca aatccatata    5040
catataaata ttaatcatat ataattaata tcaattgggt tagcaaaaca aatctagtct    5100
aggtgtgttt tgcccccaag cttatcgata ccgtcggcgc ggggtacgtt agctgattaa    5160
gtcagcatgc gcggccggcg tatgaactaa aatgcatgta ggtgtaagag ctcatggaga    5220
gcatggaata ttgtatccga ccatgtaaca gtataataac tgagctccat ctcacttctt    5280
ctatgaataa acaaaggatg ttatgatata ttaacactct atctatgcac cttattgttc    5340
tatgataaat ttcctcttat tattataaat catctgaatc gtgacggctt atggaatgct    5400
tcaaatagta caaaaacaaa tgtgtactat aagactttct aaacaattct aaccttagca    5460
ttgtgaacga gacataagtg ttaagaagac ataacaatta taatggaaga gtttgtctc    5520 catttatata ttatatatta cccacttatg tattatatta ggatgttaag gagacataac    5580
aattataaag agagaagttt gtatccattt atatattata tactacccat ttatatatta    5640
tacttatcca cttatttaat gtctttataa ggtttgatcc atgatatttc taatatttta    5700
gttgatatgt atatgaaaag gtactatttg aactctctta ctctgtataa aggttggatc    5760
atccttaaag tgggtctatt taattttatt gcttcttaca gataaaaaaa aaattatgag    5820
ttggtttgat aaaatattga aggatttaaa ataataataa ataacatata atatatgtat    5880
ataaatttat tataatataa catttatcta taaaaaagta aatattgtca taaatctata    5940
```

```
caatcgttta gccttgctgg aacgaatctc aattatttaa acgagagtaa acatatttga    6000 cttttttggtt atttaacaaa ttattattta acactatatg aaattttttt ttttatcagc   6060
aaagaataaa attaaattaa gaaggacaat ggtgtcccaa tccttataca accaacttcc    6120
acaagaaagt caagtcagag acaacaaaaa aacaagcaaa ggaaattttt taatttgagt    6180
tgtcttgttt gctgcataat ttatgcagta aaacactaca cataacccett ttagcagtag   6240 agcaatggtt gaccgtgtgc ttagcttctt ttattttatt tttttatcag caaagaataa    6300
ataaaataaa atgagacact tcagggatgt ttcaacaggt acccatcact taagtggcgc    6360
gccgtcgacg gatccgtacg atccatgccc ttcatttgcc gcttattaat taatttggta    6420
acagtccgta ctaatcagtt acttatcctt cccccatcat aattaatctt ggtagtctcg    6480
aatgccacaa cactgactag tctcttggat cataagaaaa agccaaggaa caaaagaaga    6540
caaaacacaa tgagagtatc ctttgcatag caatgtctaa gttcataaaa ttcaaacaaa    6600
aacgcaatca cacacagtgg acatcactta tccactagct gatcaggatc gccgcgtcaa    6660
gaaaaaaaaa ctggaccccca aaagccatgc acaacaacac gtactcacaa aggtgtcaat   6720
cgagcagccc aaaacattca ccaactcaac ccatcatgag ccctcacatt tgttgtttct    6780
aacccaacct caaactcgta ttctcttccg ccacctcatt tttgtttatt tcaacacccg    6840
tcaaactgca tgccacccc gtggccaaatg tccatgcatg ttaacaagac ctatgactat    6900
aaatagctgc aatctcggcc caggttttca tcatcaagaa ccagttcaat atcctagtac    6960
accgtattaa agaatttaag atatactgcg gccgcatgac tatcgactca caatactaca    7020
agtcgcgaga caaaaacgac acggcaccca aaatcgcggg aatccgatat gccccgctat    7080
cgacaccatt actcaaccga tgtgagacct tctctctggt ctggcacatt tcagcattc    7140 ccactttcct cacaattttc atgctatgct gcgcaattcc actgctctgg ccatttgtga    7200
ttgcgtatgt agtgtacgct gttaaagacg actccccgtc caacggagga gtggtcaagc    7260
gatactcgcc tatttcaaga aacttcttca tctggaagct cttttggccgc tacttcccca    7320 taactctgca caagacggtg gatctggagc ccacgcacac atactaccct ctggacgtcc    7380
aggagtatca cctgattgct gagagatact ggccgcagaa caagtacctc cgagcaatca    7440
tctccaccat cgagtacttt ctgcccgcct tcatgaaacg gtctctttct atcaacgagc    7500
aggagcagcc tgccgagcga gatcctctcc tgtctcccgt ttctcccagc tctccgggtt    7560
ctcaacctga caagtggatt aaccacgaca gcagatatag ccgtggagaa tcatctggct    7620
ccaacggcca cgcctcgggc tccgaactta acggcaacgg caacaatggc accactaacc    7680
gacgaccttt gtcgtccgcc tctgctggct ccactgcatc tgattccacg cttcttaacg    7740
ggtccctcaa ctcctacgcc aaccagatca ttggcgaaaa cgacccacag ctgtcgccca    7800
caaaactcaa gcccactggc agaaaataca tcttcggcta ccaccccac ggcattatcg     7860 gcatgggagc ctttggtgga attgccaccg agggagctgg atggtccaag ctctttccgg    7920
gcatccctgt ttctcttatg actctcacca acaacttccg agtgcctctc tacagagagt    7980
acctcatgag tctgggagtc gcttctgtct ccaagaagtc ctgcaaggcc ctcctcaagc    8040
gaaaccagtc tatctgcatt gtcgttggtg gagcacagga aagtcttctg gccagacccg    8100
gtgtcatgga cctggtgcta ctcaagcgaa agggttttgt tcgacttggt atggaggtcg    8160
gaaatgtcgc ccttgttccc atcatggcct ttggtgagaa cgacctctat gaccaggtta    8220
gcaacgacaa gtcgtccaag ctgtaccgat tccagcagtt tgtcaagaac ttccttggat    8280
tcacccttcc tttgatgcat gcccgaggcg tcttcaacta cgatgtcggt cttgtcccct    8340
```

```
acaggcgacc cgtcaacatt gtggttggtt cccccattga cttgccttat ctcccacacc    8400
ccaccgacga agaagtgtcc gaataccacg accgatacat cgccgagctg cagcgaatct    8460
acaacgagca caaggatgaa tatttcatcg attggaccga ggagggcaaa ggagcccag     8520 agttccgaat gattgagtaa gcggccgcaa gtatgaacta aaatgcatgt aggtgtaaga    8580
gctcatggag agcatggaat attgtatccg accatgtaac agtataataa ctgagctcca    8640
tctcacttct tctatgaata aacaaaggat gttatgatat attaacactc tatctatgca    8700
ccttattgtt ctatgataaa tttcctctta ttattataaa tcatctgaat cgtgacggct    8760
tatggaatgc ttcaaatagt acaaaaacaa atgtgtacta aagactttc taaacaattc     8820 taaccttagc attgtgaacg agacataagt gttaagaaga cataacaatt ataatggaag    8880
aagtttgtct ccatttatat attatatatt acccacttat gtattatatt aggatgttaa    8940
ggagacataa caattataaa gagagaagtt tgtatccatt tatatattat atactaccca    9000
tttatatatt atacttatcc acttatttaa tgtctttata aggtttgatc catgatattt    9060
ctaatatttt agttgatatg tatatgaaaa ggtactattt gaactctctt actctgtata    9120
aaggttggat catccttaaa gtgggtctat ttaattttat tgcttcttac agataaaaaa    9180
aaaattatga gttggtttga taaaatattg aaggatttaa aataataata aataacatat    9240
aatatatgta tataaattta ttataatata acatttatct ataaaaaagt aaatattgtc    9300
ataaatctat acaatcgttt agccttgctg gaacgaatct caattatttta aacgagagta   9360 aacatatttg acttttggt tatttaacaa attattattt aacactatat gaaattttt      9420 tttttatcag caaagaataa aattaaatta agaaggacaa tggtgtccca atccttatac    9480
aaccaacttc cacaagaaag tcaagtcaga gacaacaaaa aacaagcaa aggaaatttt      9540 ttaatttgag ttgtcttgtt tgctgcataa tttatgcagt aaaacactac acataaccct    9600
tttagcagta gagcaatggt tgaccgtgtg cttagcttct tttattttat ttttttatca    9660
gcaaagaata aataaaataa aatgagacac ttcagggatg tttcaacgta cgtcttttcca  9720 caatacataa ctattaatta atcttaaata aataaaggat aaaatatttt tttttcttca    9780
taaagttaaa atatgttatt ttttgtttag atgtatattc gaataaatct aaatatatga    9840
taatgatttt ttatattgat taaacatata atcaatatta aatatgatat tttttttatat    9900 aggttgtaca cataatttta taaggataaa aaatatgata aaaataaatt ttaaatatttt   9960 ttatatttac gagaaaaaaa aatatttag ccataaataa atgaccagca tatttacaa      10020 ccttagtaat tcataaattc ctatatgtat atttgaaatt aaaaacagat aatcgttaag    10080
ggaaggaatc ctacgtcatc tcttgccatt tgttttcat gcaaacagaa agggacgaaa     10140
aaccacctca ccatgaatca ctcttcacac catttttact agcaaacaag tctcaacaac    10200
tgaagccagc tctctttccg tttcttttta caacactttc tttgaaatag tagtattttt    10260
tttcacatga tttattaacg tgccaaaaga tgcttattga atagagtgca catttgtaat    10320
gtactactaa ttagaacatg aaaaagcatt gttctaacac gataatcctg tgaaggcgtt    10380
aactccaaag atccaatttc actatataaa ttgtgacgaa agcaaaatga attcacatag    10440
ctgagagaga aaggaaaggt taactaagaa gcaatacttc agcggccgct tctagctagc    10500 tagggttttgg gtagtgagtg taataaagtt gcaaagtttt tggttaggtt acgttttgac    10560
cttattatta tagttcaaag ggaaacatta attaaagggg attatgaagt gggctctctt    10620
gattcttgga tgaggatctt actgggtgaa ttgagctgct tagctatgga tcccacagtt    10680
```

```
ctacccatca ataagtgctt ttgtggtagt cttgtggctt ccatatctgg ggagcttcat    10740
ttgcctttat agtattaacc ttctccaaga acaaagagag cccacaccct tctcttcttt    10800
tctctcataa taatttaaat ttgttataga ctctaaactt taaatgtttt ttttgaagtt    10860
tttccgtttt tctcttttgc catgatcccg ttccttgctgt ggagtaacct tgtccgaggt    10920
atgtgcatga ttagatccat acttaatttg tgtgcatcac gaaggtgagg ttgaaatgaa    10980
ctttgctttt ttgacctttt aggaaagttc ttttgttgca gtaatcaatt ttaattagtt    11040
ttaattgaca ctattacttt tattgtcatc tttgttagtt ttattgttga attgagtgca    11100
tatttcctag gaaattctct tacctaacat ttttttataca gatctatgct cttggctctt    11160
gcccttactc ttggccttgt gttggttatt tgtctacata tttattgact ggtcgatgag    11220
acatgtcaca attcttgggc ttatttgttg gtctaataaa aggagtgctt attgaaagat    11280
caagacggag attcggtttt atataaataa actaaagatg acatattagt gtgttgatgt    11340
ctcttcagga taatttttgt ttgaaataat atggtaatgt cttgtctaaa tttgtgtaca    11400
taattcttac tgatttttg gattgttgga ttttataaa caaatctgcg gccgcatgag    11460
ccgtaaaggt tcaatacaac gagtgcttgt tttcttaggg acaagcattg tacttatgta    11520
tgattctgtg taaccatgag tcttccacgt tgtactaatg tgaagggcaa aaataaaaca    11580
cagaacaagt tcgttttttct caaataatgt gaaggtagaa aatggaacca tgcctcctct    11640
cttgcatgtg atttaaaata ttagcagatg gtacgtcgag tcgacctgca ggtcgactcg    11700
acgtacgtcc tcgaagagaa gggttaataa cacatttttt aacattttta acacaaattt    11760
tagttattta aaaatttatt aaaaaattta aaataagaag aggaactctt taaataaatc    11820
taacttacaa aatttatgat ttttaataag ttttcaccaa taaaaaatgt cataaaaata    11880
tgttaaaaag tatattatca atattctctt tatgataaat aaaaagaaaa aaaaaataaa    11940
agttaagtga aaatgagatt gaagtgactt taggtgtgta taaatatatc aaccccgcca    12000
acaatttatt taatccaaat atattgaagt atattattcc atagccttta tttatttata    12060
tatttattat ataaaagctt tatttgttct aggttgttca tgaaatattt ttttggtttt    12120
atctccgttg taagaaaatc atgtgctttg tgtcgccact cactattgca gcttttcat     12180 gcattggtca gattgacggt tgattgtatt tttgttttt atggttttgt gttatgactt     12240
aagtcttcat ctctttatct cttcatcagg tttgatggtt acctaatatg gtccatgggt    12300
acatgcatgg ttaaattagg tggccaactt tgttgtgaac gatagaattt tttttatatt    12360
aagtaaacta ttttttatatt atgaaataat aataaaaaaa atattttatc attattaaca    12420
aaatcatatt agttaatttg ttaactctat aataaaagaa atactgtaac attcacatta    12480
catggtaaca tctttccacc ctttcatttg ttttttgttt gatgacttttt tttcttgttt    12540 aaatttattt cccttctttt aaatttggaa tacattatca tcatatataa actaaaatac    12600
taaaaacagg attacacaaa tgataaataa taacacaaat atttataaat ctagctgcaa    12660
tatatttaaa ctagctatat cgatattgta aaataaaact agctgcattg atactgataa    12720
aaaaatatca tgtgcttttct ggactgatga tgcagtatac ttttgacatt gcctttattt    12780 tattttttcag aaaagctttc ttagttctgg gttcttcatt atttgttttcc catctccatt    12840 gtgaattgaa tcatttgctt cgtgtcacaa atacaattta gntaggtaca tgcattggtc    12900
agattcacgg tttattatgt catgacttaa gttcatggta gtacattacc tgccacgcat    12960
gcattatatt ggttagattt gataggcaaa tttggttgtc aacaatataa atataaataa    13020
tgtttttata ttacgaaata acagtgatca aaacaaacag ttttatcttt attaacaaga    13080
```

```
ttttgttttt gtttgatgac gttttttaat gtttacgctt tcccccttct tttgaattta    13140
gaacacttta tcatcataaa atcaaatact aaaaaaatta catatttcat aaataataac    13200
acaaatattt ttaaaaaatc tgaaataata atgaacaata ttacatatta tcacgaaaat    13260
tcattaataa aaatattata taaataaaat gtaatagtag ttatatgtag gaaaaaagta    13320
ctgcacgcat aatatataca aaagattaa aatgaactat tataaataat aacactaaat     13380
taatggtgaa tcatatcaaa ataatgaaaa agtaaataaa atttgtaatt aacttctata    13440
tgtattacac acacaaataa taaataatag taaaaaaaat tatgataaat atttaccatc    13500
tcataagata tttaaaataa tgataaaaat atagattatt ttttatgcaa ctagctagcc    13560
aaaaagagaa cacgggtata tataaaaaga gtacctttaa attctactgt acttcctta    13620 ttcctgacgt ttttatatca agtggacata cgtgaagatt ttaattatca gtctaaatat    13680
ttcattagca cttaatactt ttctgtttta ttcctatcct ataagtagtc ccgattctcc    13740
caacattgct tattcacaca actaactaag aaagtcttcc atagcccccc aagcggccgc    13800
tagtcgacta agtcatcaac tattccaagc tacgtatttg ggagtttgtg gagtacagca    13860
agatgatata cctagacggt gatatccaag tttttgacaa cattgaccac ttgtttgact    13920
tgcctgataa ctacttctat gcggtgatgg actgtttctg tgagccaact tggggccaca    13980
ctaaacaata tcagatcggt tactgccagc agtgccccca taaggttcag tggcccactc    14040
actttgggcc caaacctcct ctctatttca atgctggcat gtttgtgtat gagcccaatt    14100
tggctactta ccgtgacctc cttcaaacag tccaagtcac ccagcccact tcctttgctg    14160
aacaggattt tttgaacatg tacttcaagg acaaatatag gccaattcct aatgtctaca    14220
atcttgtgct ggccatgctg tggcgtcacc ctgagaacgt tgagcttgac aaagttaaag    14280
tggttcacta ctgtgctgct gggtctaagc cttggaggta cactgggaag tgactcgagg    14340
tcatcaatta ctccaagcta cgtatttggg agttcgtgga gtacaagaag acgatatacc    14400
tagacggtga catccaagta tttggaaaca tagaccactt gtttgatctg cctgataatt    14460
atttctatgc ggtgatggat tgtttctgcg agaagacttg gagccacacc cctcagttcc    14520
agattgggta ctgccaacag tgccctgata aggttcaatg gccctctcac tttggttcca    14580
aacctcctct atatttcaat gctggcatgt ttgtttatga gcctaatctc gacacctacc    14640
gtgatcttct ccaaactgtc caactcacca agcccacttc ttttgctgag caggacttc     14700 tcaacatgta cttcaaggac aagtacaagc caataccgaa catgtacaac cttgtgctgg    14760
ccatgttgtg gcgtcaccct gaaaatgttg aacttgataa agttcaagtg gttcattact    14820
gtgctgctgg gtctaagcct tggaggttca ctgggaagta actgcaggtc atcaactact    14880
ccaagctccg tatatgggag tttgtggagt acagcaagat gatatacttg gacgagaca     14940 ttgaggtata tgagaacata gaccacctat ttgacctacc tgatggtaac ttttacgctg    15000
tgatggattg tttctgcgag aagacatgga gtcacacccc tcagtacaag gtgggttact    15060
gccagcaatg cccggagaag gtgcggtggc ccaccgaatt gggtcagccc ccttctcttt    15120
acttcaacgc tggcatgttc gtgttcgaac ccaacatcgc cacctatcat gacctattga    15180
aaacggtgca agtcaccact cccacctcgt tcgctgaaca agatttcttg aacatgtact    15240
tcaaggacat ttacaagcca atccctttaa attacaatct tgtcctcgcc atgctgtggc    15300
gccacccgga aaacgttaaa ttagaccaag tcaaggttgt tcactattgc gcagcggggt    15360
ccaagccatg gagatatacg gggaagtagc ctaggcgtac gcaggtaagt ttctgcttct    15420
```

```
acctttgata tatatataat aattatcatt aattagtagt aatataatat ttcaaatatt   15480
tttttcaaaa taaaagaatg tagtatatag caattgcttt tctgtagttt ataagtgtgt   15540
atattttaat ttataacttt tctaatatat gaccaaaaca tggtgatgtg caggtcctag   15600
gctacttccc cgtatatctc catggcttgg accccgctgc gcaatagtga acaaccttga   15660
cttggtctaa tttaacgttt tccgggtggc gccacagcat ggcgaggaca agattgtaat   15720
ttaaagggat tggcttgtaa atgtccttga agtacatgtt caagaaatct tgttcagcga   15780
acgaggtggg agtggtgact tgcaccgttt tcaataggtc atgataggtg gcgatgttgg   15840
gttcgaacac gaacatgcca gcgttgaagt aaagagaagg gggctgaccc aattcggtgg   15900
gccaccgcac cttctccggg cattgctggc agtaacccac cttgtactga ggggtgtgac   15960
tccatgtctt ctcgcagaaa caatccatca cagcgtaaaa gttaccatca ggtaggtcaa   16020
ataggtggtc tatgttctca tataccctcaa tgtctccgtc caagtatatc atcttgctgt   16080
actccacaaa ctcccatata cggagcttgg agtagttgat gacctgcagt tacttcccag   16140
tgaacctcca aggcttagac ccagcagcac agtaatgaac cacttgaact ttatcaagtt   16200
caacattttc agggtgacgc cacaacatgg ccagcacaag gttgtacatg ttcggtattg   16260
gcttgtactt gtccttgaag tacatgttga gaaagtcctg ctcagcaaaa gaagtgggct   16320
tggtgagttg gacagtttgg agaagatcac ggtaggtgtc gagattaggc tcataaacaa   16380
acatgccagc attgaaatat agaggaggtt tggaaccaaa gtgagagggc cattgaacct   16440
tatcagggca ctgttggcag tacccaatct ggaactgagg ggtgtggctc caagtcttct   16500
cgcagaaaca atccatcacc gcatagaaat aattatcagg cagatcaaac aagtggtcta   16560
tgtttccaaa tacttggatg tcaccgtcta ggtatatcgt cttcttgtac tccacgaact   16620
cccaaatacg tagcttggag taattgatga cctcgagtca cttcccagtg tacctccaag   16680
gcttagaccc agcagcacag tagtgaacca ctttaacttt gtcaagctca acgttctcag   16740
ggtgacgcca cagcatggcc agcacaagat tgtagacatt aggaattggc ctatatttgt   16800
ccttgaagta catgttcaaa aaatcctgtt cagcaaagga agtgggctgg gtgacttgga   16860
ctgtttgaag gaggtcacgg taagtagcca aattgggctc atacacaaac atgccagcat   16920
tgaaatagag aggaggtttg ggcccaaagt gagtgggcca ctgaacctta tgggggcact   16980
gctggcagta accgatctga tattgtttag tgtggcccca agttggctca cagaaacagt   17040
ccatcaccgc atagaagtag ttatcaggca agtcaaacaa gtggtcaatg ttgtcaaaaa   17100
cttggatatc accgtctagg tatatcatct tgctgtactc cacaaactcc caaatacgta   17160
gcttggaata gttgatgact tagtcgacta gcggccgcga cacaagtgtg agagtactaa   17220
ataaatgctt tggttgtacg aaatcattac actaaataaa ataatcaaag cttatatatg   17280
ccttccgcta aggccgaatg caaagaaatt ggttctttct cgttatcttt tgccacttttt  17340 actagtacgt attaattact acttaatcat ctttgtttac ggctcattat atccggtcta   17400
ggccaaggcc gcgaagttaa aagcaatgtt gtcacttgta cgtactaaca catgatgtga   17460
tagtttatgc tagctagcta aacataagc tgtctctgag tgtgttgtat attaataaag    17520
atcatcactg gtgaatggtg atcgtgtacg taccctactt agtaggcaat ggaagcactt   17580
agagtgtgct ttgtgcatgg ccttgcctct gttttgagac ttttgtaatg ttttcgagtt   17640
taaatctttg cctttgcgta cgtgggcgga tcccctgca                          17679
```

<210> SEQ ID NO 3
<211> LENGTH: 22374

<212> TYPE: DNA
<213> ORGANISM: Artificial Sequence
<220> FEATURE:
<223> OTHER INFORMATION: synthesized DNA of PHP64612

<400> SEQUENCE: 3

```
cctcacgtgt taacagaagt tcctattccg aagttcctat tctctagaaa gtataggaac      60
ttccaccaca caacacaatg gcggccaccg cttccagaac cacccgattc tcttcttcct     120
cttcacaccc caccttcccc aaacgcatta ctagatccac cctccctctc tctcatcaaa     180
ccctcaccaa acccaaccac gctctcaaaa tcaaatgttc catctccaaa cccccacgg      240
cggcgccctt caccaaggaa gcgccgacca cggagccctt cgtgtcacgg ttcgcctccg     300
gcgaacctcg caagggcgcg gacatccttg tggaggcgct ggagaggcag ggcgtgacga     360
cggtgttcgc gtaccccggc ggtgcgtcga tggagatcca ccaggcgctc acgcgctccg     420
ccgccatccg caacgtgctc ccgcgccacg agcagggcgg cgtcttcgcc gccgaaggct     480
acgcgcgttc ctccggcctc cccggcgtct gcattgccac ctccggcccc ggcgccacca     540
acctcgtgag cggcctcgcc gacgctttaa tggacagcgt cccagtcgtc gccatcaccg     600
gccaggtcag ccgccggatg atcggcaccg acgccttcca agaaacccg atcgtggagg      660
tgagcagatc catcacgaag cacaactacc tcatcctcga cgtcgacgac atccccgcg      720
tcgtcgccga ggctttcttc gtcgccacct ccggccgccc cggtccggtc ctcatcgaca     780
ttcccaaaga cgttcagcag caactcgccg tgcctaattg ggacgagccc gttaacctcc     840
ccggttacct cgccaggctg cccaggcccc ccgccgaggc ccaattggaa cacattgtca     900
gactcatcat ggaggcccaa agcccgttc tctacgtcgg cggtggcagt ttgaattcca      960
gtgctgaatt gaggcgcttt gttgaactca ctggtattcc cgttgctagc actttaatgg    1020
gtcttggaac ttttcctatt ggtgatgaat attcccttca gatgctgggt atgcatggta    1080
ctgtttatgc taactatgct gttgacaata gtgatttgtt gcttgccttt ggggtaaggt    1140
ttgatgaccg tgttactggg aagcttgagg cttttgctag tagggctaag attgttcaca    1200
ttgatattga ttctgccgag attgggaaga caagcaggc gcacgtgtcg gtttgcgcgg     1260
atttgaagtt ggccttgaag ggaattaata tgattttgga ggagaaagga gtggagggta    1320
agtttgatct tggaggttgg agagaagaga ttaatgtgca gaaacacaag tttccattgg    1380
gttacaagac attccaggac gcgatttctc cgcagcatgc tatcgaggtt cttgatgagt    1440
tgactaatgg agatgctatt gttagtactg gggttgggca gcatcaaatg tgggctgcgc    1500
agttttacaa gtacaagaga ccgaggcagt ggttgacctc aggggggtctt ggagccatgg    1560
gttttggatt gcctgcggct attggtgctg ctgttgctaa ccctggggct gttgtggttg    1620
acattgatgg ggatggtagt ttcatcatga atgttcagga gttggccact ataagagtgg    1680
agaatctccc agttaagata ttgttgttga caatcagca tttgggtatg gtggttcagt    1740
gggaggatag gttctacaag tccaatagag ctcacaccta tcttggagat ccgtctagcg    1800
agagcgagat attcccaaac atgctcaagt ttgctgatgc ttgtgggata ccggcagcgc    1860
gagtgacgaa gaaggaagag cttagagcgg caattcagag aatgttggac acccctggcc    1920
cctaccttct tgatgtcatt gtgccccatc aggagcatgt gttgccgatg attcccagta    1980
atggatcctt caaggatgtg ataactgagg gtgatggtag aacgaggtac tgactagcta    2040
gtcagttaac ctagacttgt ccatcttctg gattggccaa cttaattaat gtatgaaata    2100
aaaggatgca cacatagtga catgctaatc actataatgt gggcatcaaa gttgtgtgtt    2160
```

```
atgtgtaatt actagttatc tgaataaaag agaaagagat catccatatt tcttatccta    2220
aatgaatgtc acgtgtcttt ataattcttt gatgaaccag atgcatttca ttaaccaaat    2280
ccatatacat ataaatatta atcatatata attaatatca attgggttag caaaacaaat    2340
ctagtctagg tgtgttttgc ccccaagctt atcgataccg tcggcgcggg gtacgttagc    2400
tgattaagtc agcatgcgcg gccggcgtat gaactaaaat gcatgtaggt gtaagagctc    2460
atggagagca tggaatattg tatccgacca tgtaacagta taataactga gctccatctc    2520
acttcttcta tgaataaaca aaggatgtta tgatatatta acactctatc tatgcacctt    2580
attgttctat gataaatttc ctcttattat tataaatcat ctgaatcgtg acggcttatg    2640
gaatgcttca aatagtacaa aaacaaatgt gtactataag actttctaaa caattctaac    2700
cttagcattg tgaacgagac ataagtgtta agaagacata acaattataa tggaagaagt    2760
ttgtctccat ttatatatta tatattaccc acttatgtat tatattagga tgttaaggag    2820
acataacaat tataaagaga gaagtttgta tccatttata tattatatac tacccattta    2880
tatattatac ttatccactt atttaatgtc tttataaggt ttgatccatg atatttctaa    2940
tattttagtt gatatgtata tgaaaaggta ctatttgaac tctcttactc tgtataaagg    3000
ttggatcatc cttaaagtgg gtctatttaa ttttattgct tcttacagat aaaaaaaaaa    3060
ttatgagttg gtttgataaa atattgaagg atttaaaata ataataaata acatataata    3120
tatgtatata aatttattat aatataacat ttatctataa aaaagtaaat attgtcataa    3180
atctatacaa tcgtttagcc ttgctggaac gaatctcaat tatttaaacg agagtaaaca    3240
tatttgactt tttggttatt taacaaatta ttatttaaca ctatatgaaa tttttttttt    3300
tatcagcaaa gaataaaatt aaattaagaa ggacaatggt gtcccaatcc ttatacaacc    3360
aacttccaca agaaagtcaa gtcagagaca acaaaaaaac aagcaaagga aattttttaa    3420
tttgagttgt cttgtttgct gcataattta tgcagtaaaa cactacacat aacccttttta    3480
gcagtagagc aatggttgac cgtgtgctta gcttcttttta ttttattttt ttatcagcaa    3540
agaataaata aaataaaatg agacacttca gggatgtttc aacaggtacc catcacttaa    3600
gtggcgcgcc gtcgacggat ccgtacccat ctgcaggtaa attgcagctg aaggacagtg    3660
aagggtgaat ttatccattt aaaccatttt ctttttaaca catttcttat ggtaatctct    3720
tctcactaca ctataaaaat ggcttctcaa tcccatttc tacatcatcc cattctattg    3780
agttttgttt atttgctttc actttttttt ttatctgcct cttcccttaa tttgcttgac    3840
ttcttcttca catttgctt tgttttctcc tccggcttcc ggtatttcaa attcaagatg    3900
agcaagttga aatttataaa tagaaataca gatattattt acaacgtcaa atctttggta    3960
ttttcaatat ttgaatgggg taaatttgtc atatagtcat catcactgac tacttatcta    4020
acctatttaa tttggagcat attctttata aggtccctct cacggccaat gtctaattat    4080
tgatatacag ctcttgtttt ctagtgctgc ttataatatt atctacacat atatatggta    4140
ctgcacacta ctactatata gtagtaagta aactagcaac agccggggcc aaactccaat    4200
aactaggcat tgggggtttag ttggtaatat aaatataaca tcaaaaagtc tttgcttgtg    4260
acgaacatca caatgcaccc accattgatg ccacgacaga cattgttaat ttttttttta    4320
attttttaaaa aagaagcaat tccaatagtt ctatattaca atctcacgtg atccaagcac    4380
aacgtttcat ttttttgtaca tgctcgatat ataaataata tttcatttta tagtaaaata    4440
taatgacatt ttcgaatata attttttgaaa tttcattttc caaatgaaat actaatatta    4500
atattaatga gattaccaca aatcatgtta tgaatgaaat aaagagtttt ggcattctaa    4560
```

```
ctttctttga atagaacaaa atgtatacaa cactctccat atatacacga tttattcagg    4620
gatcatatac attctctcat gattaacata gtctgctttc ttcacgtcta agcagataat    4680
ttttggtcca caagataaaa ttatcattag tcgttttaat taattccttg agcatcaagc    4740
actaaaataa ttaaacttct ccattaccaa aaaaaaaaga taggtgattc agtaacatgt    4800
agtactagta ctactgattt tttttttctt ttgattttaa tgaatggttc gtatcgagca    4860
tcgagaaatc catttattag gtgtgtaatg taatagtagt atttccttga ttttcagtaa    4920
taagatggat tcttacattt atatctgttt gacagaaaat gttgtcaatg catttcttgg    4980
gcacaaagtt ttttgaaaca tgaattaatt ttttcaaaat atttatgaca tcaaattgac    5040
cctaaaataa gtgataaagc tttaacgtgg aatgacatta attttccat gataaataaa     5100
acacttaaaa cattttaata ttaatattat aatcagttac aactatgttc aattaatgca    5160
ataacttta aataaatatt aaaatatttt ttttctgttc tccaataaag agatcttgtt     5220
gcacggaaaa agtcacattc ttatttagta aaaaattata attattgttt gaaaaatatc    5280
attttcactg cagaaaattt gatccagctc tacagatcat acttttattg tacaataata    5340
caataaaaat attcatctgc aggaaatatc attttcattg tacaataata taagataaaa    5400
tataccag aaaagaaaaa gaaactgatg tggcacaatg tattcactga aagaatgcat      5460
attgtatttc accttttcaag cagcactaag aatatacttc ttttattata cttgtgcatt   5520
tactcaacca ccctcggtgg agtaagaaag aagatagata aaagtttttt ttgacatttg    5580
gtgaatctct taattaaaaa aataaaataa tccatttcct ttatttaatt tcttttttcc    5640
catctgtgaa attccaattc tgcttcgcgc tcctgtctat aaattgactt agccaccacc    5700
tcagtttcca ttcattcact tcttctcttt atacccccccc tctctttttt gcgttcattc   5760
tgttttcgta agtactgttg ttttttctctt ctatttcttt ttttgtttgt gttgttttt    5820
tttcttcctt atcgttgttc tgcctctcct ctgtttcggt gctctgttca ccacttccac    5880
gtgagaatga tcttccttct ttgcatgttc attctctcgt gaccactgga tcagactcca    5940
tgttctgatc cagggtctct ctctaacgcc tgtactttca tccatgacca ccttaaaaac    6000
aacatggggg tggtgctgtt acactaactc tgttctggg gtgctgtctt tgttcaatttt   6060
tactcagaaa atatctttc ttggattcta ttcggtgtgt gggaacatga tcctgtcggt     6120
cggttgtttt taggttaatc cttaactggt tacaaggatc taacgcttga atgcatgtcc    6180
tgagttaaag aaacaaaaga agaacacacc tagtacagcc tggcctcgaa ccaagaactt    6240
ctttgttggt ttctcattat tactaaaata aaataaagta tacgttttct tttttctttg    6300
ggatgaacgg ttcagactta tgagaagttt aagctaatcc tgtagtggag tgttcaattt    6360
attttaaact ttaaagcaat agctcaagca ctaaacttct ttttcaagtt caaccacttt    6420
ggtagcttgc taattgctgc tattgttcta attaattaat gtaattattg tttaaaaaag    6480
aaaagttggg gacactggaa taaaaagtg tactatctgg caattattct tctgcagcaa     6540
tgtttgaggt tgaaatctta gtagaacaaa gtagaagatc tggtatttat attttttgta   6600
gacagatggt gggggtgggt ggtaggcctt gaaatccaat atagttttgt agaataattt    6660
tattattttt tttttttgct cacttgtttg tggtattgat tttgtgatga ctcaagatta    6720
atgatttacc ttcatttttt tcatggtgac atattatgta tattcttgat ctgtttctta    6780
cacttctttt tcgttgttgt agctgttgaa gtctgcggcc gcatgaagag gtctccagca    6840
tcttcttgtt catcatctac ttcctctgtt gggtttgaag ctcccattga aaaagaagg     6900
```

```
cctaagcatc caaggaggaa taatttgaag tcacaaaaat gcaagcagaa ccaaaccacc   6960
actggtggca gaagaagctc tatctataga ggagttacaa ggcataggtg gacagggagg   7020
tttgaagctc acctatggga taagagctct tggaacaaca ttcagagcaa gaagggtcga   7080
caagtttatt tggggggcata tgatactgaa gaatctgcag cccgtaccta tgaccttgca   7140
gcccttaaat actggggaaa agatgcaacc ctgaatttcc cgatagaaac ttataccaag   7200
gagctcgagg aaatggacaa ggtttcaaga gaagaatatt tggcttcttt gcggcgccaa   7260
agcagtggct tttctagagg cctgtctaag taccgtgggg ttgctaggca tcatcataat   7320
ggtcgctggg aagcacgaat tggaagagta tgcggaaaca agtacctcta cttgggggaca   7380 tataaaactc aagaggaggc agcagtggca tatgacatgg cagcaataga gtaccgtgga   7440
gtcaatgcag tgaccaattt tgacataagc aactacatgg acaaaataaa gaagaaaaat   7500
gaccaaaccc aacaacaaca aacagaagca caaacggaaa cagttcctaa ctcctctgac   7560
tctgaagaag tagaagtaga acaacagaca acaacaataa ccacaccacc cccatctgaa   7620
aatctgcaca tgccaccaca gcagcaccaa gttcaataca ccccccatgt ctctccaagg   7680
gaagaagaat catcatcact gatcacaatt atggaccatg tgcttgagca ggatctgcca   7740
tggagcttca tgtacactgg cttgtctcag tttcaagatc caaacttggc tttctgcaaa   7800
ggtgatgatg acttggtggg catgtttgat agtgcagggt ttgaggaaga cattgatttt   7860
ctgttcagca ctcaacctgg tgatgagact gagagtgatg tcaacaatat gagcgcagtt   7920
ttggatagtg ttgagtgtgg agacacaaat ggggctggtg gaagcatgat gcatgtggat   7980
aacaagcaga gatagtatc atttgcttct tcaccatcat ctacaactac agtttcttgt   8040
gactatgctc tagatctatg agcggccgca tttcgcacca aatcaatgaa agtaataatg   8100
aaaagtctga ataagaatac ttaggcttag atgcctttgt tacttgtgta aaataacttg   8160
agtcatgtac ctttggcgga aacagaataa ataaaggtg aaattccaat gctctatgta   8220
taagttagta atacttaatg tgttctacgg ttgtttcaat atcatcaaac tctaattgaa   8280
actttagaac cacaaatctc aatctttct taatgaaatg aaaaatctta attgtaccat   8340
gtttatgtta aacaccttac aattaattgg ttggagagga ggaccaaccg atgggacaac   8400
attgggagaa agagattcaa tggagatttg ataggagaa caacattctt tttcacttca   8460
atacaagatg agtgcaacac taaggatatg tatgagactt tcagaagcta cgacaacata   8520
gatgagtgag gtggtgattc ctagcaagaa agacattaga ggaagccaaa atcgaacaag   8580
gaagacatca agggcaagag acaggaccat ccatctcagg aaaaggagct ttgggatagt   8640
ccgagaagtt gtacaagaaa ttttttggag ggtgagtgat gcattgctgg tgactttaac   8700
tcaatcaaaa ttgagaaaga aagaaaaggg aggggctca catgtgaata gaagggaaac   8760
gggagaattt tacagttttg atctaatggg catcccagct agtggtaaca tattccacat   8820
gtttaacctt cacgtacgaa accaactgcg tttggggctc cagattaaac gacgccgttt   8880
cgttcctttc gcttcacggc ttaacgatgt cgtttctgtc tgtgcccaaa aataaaggc   8940 atttgttatt tgcaccagat atttactaag tgcaccctag tttgacaagt aggcgataat   9000
tacaaataga tgcggtgcaa ataataaatt ttgaaggaaa taattacaaa agaacagaac   9060
ttatatttac tttatttaa aaaactaaaa tgaaagaaca aaaaagtaa aaatacaaa    9120 aaatgtgctt taaccacttt cattatttgt tacagaaagt atgattctac tcaaattgat   9180
ctgttgtatc tggtgctgcc ttgtcacact ggcgatttca atccctaaa gatatggtgc   9240 aaactgcgaa gtgatcaata tctgctcggt taatttagat taattaataa tattcaacgt   9300
```

```
gatgtaccaa aaaaagacaa ttttttgctc cattgacaaa ttaaacctca tcaaggtaat    9360
ttccaaacct ataagcaaaa aaatttcaca ttaattggcc cgcaatccta ttagtcttat    9420
tatactagag taggaaaaaa aacaattaca caacttgtct tattattctc tatgctaatg    9480 aatattttc cctttgtta gaaatcagtg tttcctaatt tattgagtat taattccact     9540
caccgcatat atttaccgtt gaataagaaa attttacaca taattctttt taagataaat    9600
aattttttta tactagatct tatatgatta cgtgaagcca agtgggttat actaatgata    9660
tataatgttt gatagtaatc agtttataaa ccaaatgcat ggaaatgtta cgtggaagca    9720
cgtaaattaa caagcattga agcaaatgca gccaccgcac caaaaccacc ccacttcact    9780
tccacgtacc atattccatg caactacaac accctaaaac ttcaataaat gcccccacct    9840
tcacttcact tcacccatca atagcaagcg gccgcaccat ggcgatttcc gatgagcctg    9900
aaagtgtagc cactgctctc aaccactctt ccctgcgccg ccgtccctcc gccacctcca    9960
ccgccggcct cttcaattcg cctgagacaa ccaccgacag ttccggtgat gacttggcca   10020
aggattctgg ttccgacgac tccatcaaca acgacgacgc cgccgtcaat tcccaacagc   10080
aaaacgaaaa acaagacact gatttctccg tcctcaaatt cgcctaccgt ccttccgtcc   10140
ccgctcaccg caaagtgaag gaaagtccgc tcagctccga cactattttc cgtcagagtc   10200
acgcgggcct cttcaacctt tgtatagtag tccttgttgc tgtgaatagc cgactcatca   10260
ttgagaattt aatgaagtat ggttggttga tcaaatctgg cttttggttt agtgcaaagt   10320
cattgagaga ctggcccctt ttcatgtgtt gtctttctct tgtggtattt cctttcgctg   10380
cctttatggt ggagaagttg gcacaacgga agtgtatacc cgaaccagtt gttgttgtac   10440
ttcatataat cattacctca acttcgcttt tctatccagt tttagttatt ctcaagtgtg   10500
attctgcttt tgtatcaggt gtcacgttaa tgctgttttc ttgtgttgta tggttaaaat   10560
tggtgtcttt tgcacataca aactatgata tgagagcact taccaaatta gttgaaaagg   10620
gagaagcact gctcgatact ctgaacatgg agtatcctta caacgtaacc ttcaagagct   10680
tggcatattt cctgcttgcc cctacattat gttaccagcc aagctatcct cgcacacctt   10740
atattcgaaa gggttggttg tttcgccaac ttgtcaagct gatagtattt acaggagtta   10800
tgggatttat aatagaacaa tatattaatc ccatagtaca aaattcacag catcctctca   10860
agggaaacct tctttacgcc accgagagag ttctgaagct ttctgttcca aatttatatg   10920
tgtggctctg catgttctat tgcttttcc acctttggtt aaatatcgtg gcagagcttc   10980
ttcgatttgg tgatcgtgaa ttctacaagg attggtggaa tgccaaaact gtcgaagatt   11040
attggaggat gtggaatatg cctgttcaca aatggatgat ccgccaccta tattttccat   11100
gtttaaggca cggtctacca aaggctgctg ctctttttaat ttccttcctg gtttctgctt   11160
tattccatga gctgtgcatt gctgttcctt gccacatgtt caagttgtgg gctttcggtg   11220
gaattatgtt tcaggttcct ttggtcttga tcactaatta tctgcaaaat aaattcaaaa   11280
actcaatggt tggaaatatg atttttttggt tcatattcag tatcgttggt caacctatgt   11340
gtgtactgct atactaccat gacttgatga ataggaaagg caaacttgac tgagcggccg   11400
cgaagttaaa agcaatgttg tcacttgtcg tactaacaca tgatgtgata gtttatgcta   11460
gctagctata acataagctg tctctgagtg tgttgtatat taataaagat catcactggt   11520
gaatggtgat cgtgtacgta ccctacttag taggcaatgg aagcacttag agtgtgcttt   11580
gtgcatggcc ttgcctctgt tttgagactt ttgtaatgtt ttcgagttta aatctttgcc   11640
```

```
tttgcgtacg tctttccaca atacataact attaattaat cttaaataaa taaaggataa   11700
aatattttt  tttcttcata aagttaaaat atgttatttt ttgtttagat gtatattcga   11760
ataaatctaa atatatgata atgatttttt atattgatta aacatataat caatattaaa   11820
tatgatattt ttttatatag gttgtacaca taattttata aggataaaaa atatgataaa   11880
aataaatttt aaatatttt  atatttacga gaaaaaaaaa tattttagcc ataaataaat   11940
gaccagcata ttttacaacc ttagtaattc ataaattcct atatgtatat ttgaaattaa   12000
aaacagataa tcgttaaggg aaggaatcct acgtcatctc ttgccatttg tttttcatgc   12060
aaacagaaag ggacgaaaaa ccacctcacc atgaatcact cttcacacca tttttactag   12120
caaacaagtc tcaacaactg aagccagctc tctttccgtt tcttttttaca cactttctt   12180
tgaaatagta gtatttttt  tcacatgatt tattaacgtg ccaaaagatg cttattgaat   12240
agagtgcaca tttgtaatgt actactaatt agaacatgaa aaagcattgt tctaacacga   12300
taatcctgtg aaggcgttaa ctccaaagat ccaatttcac tatataaatt gtgacgaaag   12360
caaaatgaat tcacatagct gagagagaaa ggaaaggtta actaagaagc aatacttcag   12420
cggccgcatg ccgaatcccg aggctcacca cccctcccgg tcccgggccc ggccctccac   12480
gtcagccgcg gcccgccccc cggcccgggc ccgcgtctcc ctccgccagc ttctgcgcgt   12540
ggcatcagtc gcgagcggca tccagttcgg gtgggcctta cagctctctc tgctgacgcc   12600
ctacgttcag cagctgggga tcccccacca atgggccagc atcatctggc tctgcggccc   12660
agtctccggc ctcttcgtgc agcccctcgt cggccacatg agcgaccgct gcaccagccg   12720
ctacggccgc gcaggccct  tcatcctcgt cggcgccgtc gccatcgtcg ccgctgttct   12780
cgtcatcgct tacgccgccg acatcggctg gctcctcggc gacaccgcgg actaccgccc   12840
tgccgccatc accgtcttca tcgtcggctt ctggatcctc gacgtcgcta acaacgtcac   12900
gcaaggtccc tgccgtgcct tgctcggtga tctcactagc aaggatcctc gaaggacacg   12960
tgttgcaaat gcttattact cactgtttat ggccattggt aacattcttg gctatgcaac   13020
tggatcatat agtggttggt acaagatttt tacttttgcc cttttcccctg cttgcacaat   13080
tagttgtgca atctcaagt  ctgctttctt tcttgacatt gctttcattg cggtcacaac   13140
atatatcagc atcatggcag ctcatgaagt gcctctaaat tcaagtgagg cggcccatgc   13200
tgaagcaggg gcaggggagt caggtagtgc agaagaagct ttcatgtggg aattatttgg   13260
gacattcaaa tattttacaa cccctgtatg gataattctg tctgttactg ctctgacatg   13320
gattgggtgg ttcccatttta ctctctttga tactgattgg atgggtcgag agatttatgg   13380
tggtgatcca aatcaaggcc ttgtttatga tactggagtt agaatgggag cacttggttt   13440
gttgcttaat tcagttgttc ttgcattaac atcattgttc atggagaggc tatgcaggaa   13500
gaggggagct ggttttgtgt ggggaatctc aaatatcatg atgaccgttt gctttcttgc   13560
aatgctagta gtaacctatg tggcaaataa catgggctat ataggcaaag atttaccacc   13620
aactggcatt gtgatagctg cgttgattat ctttaccatt cttgggtttc cactggcaat   13680
cacttatagt gttccatatg ccttaatttc cacacatatt gagtcattgg gactcggcca   13740
agggttatca atgggtgtcc taaatctggc aatagtggtc ccacagataa tagtgtcact   13800
gggaagtgga ccatgggatc agctatttgg tggaggaaac tccccagcct ttgctgtggc   13860
agctgtttca gcccttatca gtggactcat agctgtgttg ctattcctc gatctggtgc   13920
tcaaaaggct cgaagccatg tatgagcggc cgcctgaacg ggaattaaac ctataaacat   13980
aaatataaat aatatatata aacctaagtg tctaagttcc ataaattaag ctgtagtctc   14040
```

```
tggcttaaaa catgttaggt ttgtttatac aagtagttgg atgtttggag tacttcggtc   14100
ttttgcgtac catcaatatt taagaactaa gttagttatg ttccgtaact tatgggctct   14160
taattaaact atatctgcac aaaattatat atatatcaaa tgtgatggta tgtggactat   14220
aaaaagatat ggttgagaac cacaaacttt gaaacttcga ataatatatt gccagtgaca   14280
gtcttgttga tttgttatag caagtcctat tttcttaatc attgctttgt tttaacgtac   14340
ctagatttca taacttttgt ctttgtctca agctgaacct aatgatgata gtaatattaa   14400
cttattgtat aggggtattt cataggataa aaaatgatgt gcaattacgt gtagaccaaa   14460
tattacttga tgacagatgg cctgcaggat ccatgccctt catttgccgc ttattaatta   14520
atttggtaac agtccgtact aatcagttac ttatccttcc cccatcataa ttaatcttgg   14580
tagtctcgaa tgccacaaca ctgactagtc tcttggatca taagaaaaag ccaaggaaca   14640
aaagaagaca aaacacaatg agagtatcct ttgcatagca atgtctaagt tcataaaatt   14700
caaacaaaaa cgcaatcaca cacagtggac atcacttatc cactagctga tcaggatcgc   14760
cgcgtcaaga aaaaaaaact ggaccccaaa agccatgcac aacaacacgt actcacaaag   14820
gtgtcaatcg agcagcccaa aacattcacc aactcaaccc atcatgagcc ctcacatttg   14880
ttgtttctaa cccaacctca aactcgtatt ctcttccgcc acctcatttt tgtttatttc   14940
aacacccgtc aaactgcatg ccaccccgtg gccaaatgtc catgcatgtt aacaagacct   15000
atgactataa atagctgcaa tctcggccca ggttttcatc atcaagaacc agttcaatat   15060
cctagtacac cgtattaaag aatttaagat atactgcggc cgctagtcga ctaagtcatc   15120
aactattcca agctacgtat ttgggagttt gtggagtaca gcaagatgat atacctagac   15180
ggtgatatcc aagtttttga caacattgac cacttgtttg acttgcctga taactacttc   15240
tatgcggtga tggactgttt ctgtgagcca acttggggcc acactaaaca atatcagatc   15300
ggttactgcc agcagtgccc ccataaggtt cagtggccca ctcactttgg gcccaaacct   15360
cctctctatt tcaatgctgg catgtttgtg tatgagccca atttggctac ttaccgtgac   15420
ctccttcaaa cagtccaagt cacccagccc acttcctttg ctgaacagga ttttttgaac   15480
atgtacttca aggacaaata taggccaatt cctaatgtct acaatcttgt gctggccatg   15540
ctgtggcgtc accctgagaa cgttgagctt gacaaagtta agtggttca ctactgtgct   15600 gctgggtcta agccttggag gtacactggg aagtgactcg aggtcatcaa ttactccaag   15660
ctacgtattt gggagttcgt ggagtacaag aagacgatat acctagacgg tgacatccaa   15720
gtatttggaa acatagacca cttgtttgat ctgcctgata attatttcta tgcggtgatg   15780
gattgtttct gcgagaagac ttggagccac acccctcagt tccagattgg gtactgccaa   15840
cagtgccctg ataaggttca atggccctct cactttggtt ccaaacctcc tctatatttc   15900
aatgctggca tgtttgttta tgagcctaat ctcgacacct accgtgatct tctccaaact   15960
gtccaactca ccaagcccac ttctttttgct gagcaggact ttctcaacat gtacttcaag   16020
gacaagtaca agccaatacc gaacatgtac aaccttgtgc tggccatgtt gtggcgtcac   16080
cctgaaaatg ttgaacttga taagttcaa gtggttcatt actgtgctgc tgggtctaag   16140
ccttggaggt tcactgggaa gtaactgcag gtcatcaact actccaagct ccgtatatgg   16200
gagtttgtgg agtacagcaa gatgatatac ttggacggag acattgaggt atatgagaac   16260
atagaccacc tatttgacct acctgatggt aacttttacg ctgtgatgga ttgtttctgc   16320
gagaagacat ggagtcacac ccctcagtac aaggtgggtt actgccagca atgcccggag   16380
```

```
aaggtgcggt ggcccaccga attgggtcag ccccttctc tttacttcaa cgctggcatg   16440
ttcgtgttcg aacccaacat cgccacctat catgacctat tgaaaacggt gcaagtcacc   16500
actcccacct cgttcgctga acaagatttc ttgaacatgt acttcaagga catttacaag   16560
ccaatccctt taaattacaa tcttgtcctc gccatgctgt ggcgccaccc ggaaaacgtt   16620
aaattagacc aagtcaaggt tgttcactat tgcgcagcgg ggtccaagcc atggagatat   16680
acggggaagt agcctaggcg tacgcaggta agtttctgct tctacctttg atatatatat   16740
aataattatc attaattagt agtaatataa tatttcaaat attttttca aaataaaaga   16800 atgtagtata tagcaattgc ttttctgtag tttataagtg tgtatatttt aatttataac   16860
ttttctaata tatgaccaaa acatggtgat gtgcaggtcc taggctactt ccccgtatat   16920
ctccatggct tggaccccgc tgcgcaatag tgaacaacct tgacttggtc taatttaacg   16980
ttttccgggt ggcgccacag catggcgagg acaagattgt aatttaaagg gattggcttg   17040
taaatgtcct tgaagtacat gttcaagaaa tcttgttcag cgaacgaggt gggagtggtg   17100
acttgcaccg ttttcaatag gtcatgatag gtggcgatgt tgggttcgaa cacgaacatg   17160
ccagcgttga agtaaagaga aggggctga cccaattcgg tgggccaccg caccttctcc   17220
gggcattgct ggcagtaacc caccttgtac tgaggggtgt gactccatgt cttctcgcag   17280
aaacaatcca tcacagcgta aaagttacca tcaggtaggt caaataggtg gtctatgttc   17340
tcatataccg caatgtctcc gtccaagtat atcatcttgc tgtactccac aaactcccat   17400
atacggagct tggagtagtt gatgacctgc agttacttcc cagtgaacct ccaaggctta   17460
gacccagcag cacagtaatg aaccacttga actttatcaa gttcaacatt ttcagggtga   17520
cgccacaaca tggccagcac aaggttgtac atgttcggta ttggcttgta cttgtccttg   17580
aagtacatgt tgagaaagtc ctgctcagca aaagaagtgg gcttggtgag ttggacagtt   17640
tggagaagat cacggtaggt gtcgagatta ggctcataaa caaacatgcc agcattgaaa   17700
tatagaggag gtttggaacc aaagtgagag ggccattgaa ccttatcagg gcactgttgg   17760
cagtacccaa tctggaactg aggggtgtgg ctccaagtct tctcgcagaa acaatccatc   17820
accgcataga aataattatc aggcagatca aacaagtggt ctatgtttcc aaatacttgg   17880
atgtcaccgt ctaggtatat cgtcttcttg tactccacga actcccaaat acgtagcttg   17940
gagtaattga tgacctcgag tcacttccca gtgtacctcc aaggcttaga cccagcagca   18000
cagtagtgaa ccactttaac tttgtcaagc tcaacgttct cagggtgacg ccacagcatg   18060
gccagcacaa gattgtagac attaggaatt ggcctatatt tgtccttgaa gtacatgttc   18120
aaaaaatcct gttcagcaaa ggaagtgggc tgggtgactt ggactgtttg aaggaggtca   18180
cggtaagtag ccaaattggg ctcatacaca aacatgccag cattgaaata gagaggaggt   18240
ttgggcccaa agtgagtggg ccactgaacc ttatggggc actgctggca gtaaccgatc   18300
tgatattgtt tagtgtggcc ccaagttggc tcacagaaac agtccatcac cgcatagaag   18360
tagttatcag gcaagtcaaa caagtggtca atgttgtcaa aaacttggat atcaccgtct   18420
aggtatatca tcttgctgta ctccacaaac tcccaaatac gtagcttgga atagttgatg   18480
acttagtcga ctagcggccg caagtatgaa ctaaaatgca tgtaggtgta agagctcatg   18540
gagagcatgg aatattgtat ccgaccatgt aacagtataa taactgagct ccatctcact   18600
tcttctatga ataaacaaag gatgttatga tatattaaca ctctatctat gcaccttatt   18660
gttctatgat aaatttcctc ttattattat aaatcatctg aatcgtgacg cttatggaa   18720 tgcttcaaat agtacaaaaa caaatgtgta ctataagact ttctaaacaa ttctaacctt   18780
```

```
agcattgtga acgagacata agtgttaaga agacataaca attataatgg aagaagtttg    18840
tctccattta tatattatat attacccact tatgtattat attaggatgt taaggagaca    18900
taacaattat aaagagagaa gtttgtatcc atttatatat tatatactac ccatttatat    18960
attatactta tccacttatt taatgtcttt ataaggtttg atccatgata tttctaatat    19020
tttagttgat atgtatatga aaaggtacta tttgaactct cttactctgt ataaaggttg    19080
gatcatcctt aaagtgggtc tatttaattt tattgcttct tacagataaa aaaaaaatta    19140
tgagttggtt tgataaaata ttgaaggatt taaaataata ataaataaca tataatatat    19200
gtatataaat ttattataat ataacattta tctataaaaa agtaaatatt gtcataaatc    19260
tatacaatcg tttagccttg ctggaacgaa tctcaattat ttaaacgaga gtaaacatat    19320 ttgactttt ggttatttaa caaattatta tttaacacta tatgaaattt ttttttttat    19380
cagcaaagaa taaaattaaa ttaagaagga caatggtgtc ccaatcctta tacaaccaac    19440
ttccacaaga aagtcaagtc agagacaaca aaaaaacaag caaaggaaat tttttaattt    19500
gagttgtctt gtttgctgca taatttatgc agtaaaacac tacacataac cctttagca    19560 gtagagcaat ggttgaccgt gtgcttagct tcttttattt tattttttta tcagcaaaga    19620
ataaataaaa taaatgaga cacttcaggg atgtttcaac ctgcagggca tgcaagcttg    19680
gcgcgccgga attaattagg taatttcacg cgccggatcc ttaattaagt ctagagtcga    19740
ctgtttaatt ctagtggccg gcctctgcct gcgttctgct gtggaagttc ctattccgaa    19800
gttcctattc tccagaaagt ataggaactt cacatgctgc ctcgtgcaag tcacgatctc    19860
gagttctata gtgtcaccta aatcgtatgt gtatgataca taaggttatg tattaattgt    19920
agccgcgttc taacgacaat atgtccatat ggtgcactct cagtacaatc tgctctgatg    19980
ccgcatagtt aagccagccc cgacacccgc caacacccgc tgacgcgccc tgacgggctt    20040
gtctgctccc ggcatccgct tacagacaag ctgtgaccgt ctccgggagc tgcatgtgtc    20100
agaggttttc accgtcatca ccgaaacgcg cgagacgaaa gggcctcgtg atacgcctat    20160
ttttataggt taatgtcatg accaaaatcc cttaacgtga gttttcgttc cactgagcgt    20220
cagaccccgt agaaaagatc aaaggatctt cttgagatcc ttttttttctg cgcgtaatct    20280 gctgcttgca acaaaaaaa ccaccgctac cagcggtggt ttgtttgccg atcaagagc    20340 taccaactct ttttccgaag gtaactggct tcagcagagc gcagatacca atactgtcc    20400 ttctagtgta gccgtagtta ggccaccact tcaagaactc tgtagcaccg cctacatacc    20460
tcgctctgct aatcctgtta ccagtggctg ctgccagtgg cgataagtcg tgtcttaccg    20520
ggttggactc aagacgatag ttaccggata aggcgcagcg gtcgggctga acggggggtt    20580
cgtgcacaca gcccagcttg gagcgaacga cctacaccga actgagatac ctacagcgtg    20640
agcattgaga aagcgccacg cttcccgaag ggagaaaggc ggacaggtat ccggtaagcg    20700
gcagggtcgg aacaggagag cgcacgaggg agcttccagg gggaaacgcc tggtatcttt    20760
atagtcctgt cgggtttcgc cacctctgac ttgagcgtcg atttttgtga tgctcgtcag    20820
gggggcggag cctatggaaa aacgccagca acgcggcctt tttacggttc ctggccttt    20880 gctggccttt tgctcacatg ttctttcctg cgttatcccc tgattctgtg ataaccgta    20940 ttaccgcctt tgagtgagct gataccgctc gccgcagccg aacgaccgag cgcagcgagt    21000
cagtgagcga ggaagcggaa gagcgcccaa tacgcaaacc gcctctcccc gcgcgttggc    21060
cgattcatta atgcaggttg atcagatctc gatcccgcga aattaatacg actcactata    21120
```

```
gggagaccac aacggtttcc ctctagaaat aattttgttt aactttaaga aggagatata    21180
cccatggaaa agcctgaact caccgcgacg tctgtcgaga agtttctgat cgaaaagttc    21240
gacagcgtct ccgacctgat gcagctctcg gagggcgaag aatctcgtgc tttcagcttc    21300
gatgtaggag ggcgtggata tgtcctgcgg gtaaatagct gcgccgatgg ttttctacaaa    21360 gatcgttatg tttatcggca ctttgcatcg gccgcgctcc cgattccgga agtgcttgac    21420
attggggaat tcagcgagag cctgacctat gcatctccc gccgtgcaca gggtgtcacg    21480
ttgcaagacc tgcctgaaac cgaactgccc gctgttctgc agccggtcgc ggaggctatg    21540
gatgcgatcg ctgcggccga tcttagccag acgagcgggt tcggcccatt cggaccgcaa    21600
ggaatcggtc aatacactac atggcgtgat ttcatatgcg cgattgctga tccccatgtg    21660
tatcactggc aaactgtgat ggacgacacc gtcagtgcgt ccgtcgcgca ggctctcgat    21720
gagctgatgc tttgggccga ggactgcccc gaagtccggc acctcgtgca cgcggatttc    21780
ggctccaaca atgtcctgac ggacaatggc cgcataacag cggtcattga ctggagcgag    21840
gcgatgttcg gggattccca atacgaggtc gccaacatct tcttctggag gccgtggttg    21900
gcttgtatgg agcagcagac gcgctacttc gagcggaggc atccggagct tgcaggatcg    21960
ccgcggctcc gggcgtatat gctccgcatt ggtcttgacc aactctatca gagcttggtt    22020
gacggcaatt tcgatgatgc agcttgggcg cagggtcgat gcgacgcaat cgtccgatcc    22080
ggagccggga ctgtcgggcg tacacaaatc gcccgcagaa gcgcggccgt ctggaccgat    22140
ggctgtgtag aagtactcgc cgatagtgga aaccgacgcc ccagcactcg tccgagggca    22200
aaggaatagt gaggtacagc ttggatcgat ccggctgcta acaaagcccg aaaggaagct    22260
gagttggctg ctgccaccgc tgagcaataa ctagcataac cccttggggc ctctaaacgg    22320
gtcttgaggg gtttttttgct gaaaggagga actatatccg gatgatcgtc gagg    22374
```

<210> SEQ ID NO 4
<211> LENGTH: 22047
<212> TYPE: DNA
<213> ORGANISM: Artificial Sequence
<220> FEATURE:
<223> OTHER INFORMATION: synthesized DNA of PHP64613
<220> FEATURE:
<221> NAME/KEY: misc_feature
<222> LOCATION: (16211)..(16211)
<223> OTHER INFORMATION: n is a, c, g, or t

<400> SEQUENCE: 4

```
cctcacgtgt taacagaagt tcctattccg aagttcctat tctctagaaa gtataggaac     60
ttccaccaca caacacaatg gcggccaccg cttccagaac cacccgattc tcttcttcct    120
cttcacaccc caccttcccc aaacgcatta ctagatccac cctccctctc tctcatcaaa    180
ccctcaccaa acccaaccac gctctcaaaa tcaaatgttc catctccaaa ccccccacgg    240
cggcgccctt caccaaggaa gcgccgacca cggagcccct cgtgtcacgg ttcgcctccg    300
gcgaacctcg caagggcgcg acatccttg tggaggcgct ggagaggcag ggcgtgacga    360
cggtgttcgc gtaccccggc ggtgcgtcga tggagatcca ccaggcgctc acgcgctccg    420
ccgccatccg caacgtgctc ccgcgccacg agcagggcgg cgtcttcgcc gccgaaggct    480
acgcgcgttc ctccggcctc cccggcgtct gcattgccac ctccggcccc ggcgccacca    540
acctcgtgag cggcctcgcc gacgcttaa tggacagcgt cccagtcgtc gccatcaccg    600
gccaggtcag ccgccggatg atcggcaccg acgccttcca agaaacccg atcgtggagg    660 tgagcagatc catcacgaag cacaactacc tcatcctcga cgtcgacgac atccccgcg    720
```

```
tcgtcgccga ggctttcttc gtcgccacct ccggccgccc cggtccggtc ctcatcgaca    780
ttcccaaaga cgttcagcag caactcgccg tgcctaattg ggacgagccc gttaacctcc    840
ccggttacct cgccaggctg cccaggcccc ccgccgaggc ccaattggaa cacattgtca    900
gactcatcat ggaggcccaa aagcccgttc tctacgtcgg cggtggcagt ttgaattcca    960
gtgctgaatt gaggcgcttt gttgaactca ctggtattcc cgttgctagc actttaatgg   1020
gtcttggaac ttttcctatt ggtgatgaat attcccttca gatgctgggt atgcatggta   1080
ctgtttatgc taactatgct gttgacaata gtgatttgtt gcttgccttt ggggtaaggt   1140
ttgatgaccg tgttactggg aagcttgagg cttttgctag tagggctaag attgttcaca   1200
ttgatattga ttctgccgag attgggaaga caagcaggc gcacgtgtcg gtttgcgcgg   1260
atttgaagtt ggccttgaag ggaattaata tgattttgga ggagaaagga gtggagggta   1320
agtttgatct tggaggttgg agagaagaga ttaatgtgca gaaacacaag tttccattgg   1380
gttacaagac attccaggac gcgatttctc cgcagcatgc tatcgaggtt cttgatgagt   1440
tgactaatgg agatgctatt gttagtactg gggttgggca gcatcaaatg tgggctgcgc   1500
agttttacaa gtacaagaga ccgaggcagt ggttgacctc aggggggtctt ggagccatgg   1560
gttttggatt gcctgcggct attggtgctg ctgttgctaa ccctggggct gttgtggttg   1620
acattgatgg ggatggtagt ttcatcatga atgttcagga gttggccact ataagagtgg   1680
agaatctccc agttaagata ttgttgttga caatcagca tttgggtatg gtggttcagt   1740
gggaggatag gttctacaag tccaatagag ctcacaccta tcttggagat ccgtctagcg   1800
agagcgagat attcccaaac atgctcaagt tgctgatgc ttgtgggata ccggcagcgc   1860
gagtgacgaa gaaggaagag cttagagcgg caattcagag aatgttggac accctggcc   1920
cctaccttct tgatgtcatt gtgccccatc aggagcatgt gttgccgatg attcccagta   1980
atggatcctt caaggatgtg ataactgagg gtgatggtag aacgaggtac tgactagcta   2040
gtcagttaac ctagacttgt ccatcttctg gattggccaa cttaattaat gtatgaaata   2100
aaaggatgca cacatagtga catgctaatc actataatgt gggcatcaaa gttgtgtgtt   2160
atgtgtaatt actagttatc tgaataaaag agaaagagat catccatatt tcttatccta   2220
aatgaatgtc acgtgtcttt ataattcttt gatgaaccag atgcatttca ttaaccaaat   2280
ccatatacat ataaatatta atcatatata attaatatca attgggttag caaaacaaat   2340
ctagtctagg tgtgttttgc ccccaagctt atcgataccg tcggcgcggg gtacgttagc   2400
tgattaagtc agcatgcgcg gccggcgtat gaactaaaat gcatgtaggt gtaagagctc   2460
atggagagca tggaatattg tatccgacca tgtaacagta taataactga gctccatctc   2520
acttcttcta tgaataaaca aaggatgtta tgatatatta acactctatc tatgcacctt   2580
attgttctat gataaatttc ctcttattat tataaatcat ctgaatcgtg acggcttatg   2640
gaatgcttca aatagtacaa aaacaaatgt gtactataag actttctaaa caattctaac   2700
cttagcattg tgaacgagac ataagtgtta agaagacata acaattataa tggaagaagt   2760
ttgtctccat ttatatatta tatattaccc acttatgtat tatattagga tgttaaggag   2820
acataacaat tataaagaga gaagtttgta tccatttata tattatatac tacccattta   2880
tatattatac ttatccactt atttaatgtc tttataaggt ttgatccatg atatttctaa   2940
tattttagtt gatatgtata tgaaaaggta ctatttgaac tctcttactc tgtataaagg   3000
ttggatcatc cttaaagtgg gtctatttaa ttttattgct tcttacagat aaaaaaaaaa   3060
```

```
ttatgagttg gtttgataaa atattgaagg atttaaaata ataataaata acatataata    3120
tatgtatata aatttattat aatataacat ttatctataa aaaagtaaat attgtcataa    3180
atctatacaa tcgtttagcc ttgctggaac gaatctcaat tatttaaacg agagtaaaca    3240
tatttgactt tttggttatt taacaaatta ttatttaaca ctatatgaaa tttttttttt    3300
tatcagcaaa gaataaaatt aaattaagaa ggacaatggt gtcccaatcc ttatacaacc    3360
aacttccaca agaaagtcaa gtcagagaca acaaaaaaac aagcaaagga aatttttaa     3420
tttgagttgt cttgtttgct gcataattta tgcagtaaaa cactacacat aacccttta    3480
gcagtagagc aatggttgac cgtgtgctta gcttctttta ttttattttt ttatcagcaa    3540
agaataaaata aaataaaatg agacacttca gggatgtttc aacaggtacc catcacttaa    3600
gtggcgcgcc gtcgacggat ccgtacccat ctgcaggtaa attgcagctg aaggacagtg    3660
aagggtgaat ttatccattt aaaccatttt ctttttaaca catttcttat ggtaatctct    3720
tctcactaca ctataaaaat ggcttctcaa tcccattttc tacatcatcc cattctattg    3780
agttttgttt atttgctttc acttttttt ttatctgcct cttcccttaa tttgcttgac     3840
ttcttcttca cattttgctt tgttttctcc tccggcttcc ggtatttcaa attcaagatg    3900
agcaagttga aatttataaa tagaaataca gatattattt acaacgtcaa atctttggta    3960
ttttcaatat ttgaatgggg taaatttgtc atatagtcat catcactgac tacttatcta    4020
acctatttaa tttggagcat attcttata aggtccctct cacggccaat gtctaattat     4080
tgatatacag ctcttgtttt ctagtgctgc ttataatatt atctacacat atatatggta    4140
ctgcacacta ctactatata gtagtaagta aactagcaac agccggggcc aaactccaat    4200
aactaggcat tgggggttag ttggtaatat aaatataaca tcaaaaagtc tttgcttgtg    4260
acgaacatca caatgcaccc accattgatg ccacgacaga cattgttaat tttttttta    4320
attttaaaa aagaagcaat tccaatagtt ctatattaca atctcacgtg atccaagcac     4380
aacgttttcat ttttttgtaca tgctcgatat ataaataata tttcatttta tagtaaaata    4440
taatgacatt ttcgaatata attttgaaa tttcatttc caaatgaaat actaatatta     4500
atattaatga gattaccaca aatcatgtta tgaatgaaat aaagagtttt ggcattctaa    4560
ctttctttga atagaacaaa atgtatacaa cactctccat atatacacga tttattcagg    4620
gatcatatac attctctcat gattaacata gtctgctttc ttcacgtcta agcagataat    4680
ttttggtcca caagataaaa ttatcattag tcgtttaat taattccttg agcatcaagc     4740
actaaaataa ttaaacttct ccattaccaa aaaaaaaga taggtgattc agtaacatgt    4800
agtactagta ctactgattt ttttttcctt ttgattttaa tgaatggttc gtatcgagca    4860
tcgagaaatc catttattag gtgtgtaatg taatagtagt atttccttga ttttcagtaa    4920
taagatggat tcttacattt atatctgttt gacagaaaat gttgtcaatg catttcttgg    4980
gcacaaagtt ttttgaaaca tgaattaatt tttcaaaat atttatgaca tcaaattgac     5040
cctaaaataa gtgataaagc tttaacgtgg aatgacatta atttttccat gataaataaa    5100
acacttaaaa catttttaata ttaatattat aatcagttac aactatgttc aattaatgca    5160
ataacttttta aataaatatt aaaatatttt ttttctgttc tccaataaag agatcttgtt    5220
gcacggaaaa agtcacattc ttatttagta aaaaattata attattgttt gaaaaatatc    5280
attttcactg cagaaaattt gatccagctc tacagatcat actttttattg tacaataata    5340
caataaaaat attcatctgc aggaaaatatc attttcattg tacaataata taagataaa     5400
tatataccag aaaagaaaaa gaaactgatg tggcacaatg tattcactga aagaatgcat    5460
```

```
attgtatttc accttttcaag cagcactaag aatatacttc ttttattata cttgtgcatt    5520
tactcaacca ccctcggtgg agtaagaaag aagatagata aaagtttttt ttgacatttg    5580
gtgaatctct taattaaaaa aataaaataa tccatttcct ttatttaatt tcttttttcc    5640
catctgtgaa attccaattc tgcttcgcgc tcctgtctat aaattgactt agccaccacc    5700
tcagtttcca ttcattcact tcttctcttt atacccccc tctcttttt gcgttcattc      5760 tgttttcgta agtactgttg ttttctctt ctatttcttt ttttgtttgt gttgtttttt     5820
tttcttcctt atcgttgttc tgcctctcct ctgtttcggt gctctgttca ccacttccac    5880
gtgagaatga tcttccttct ttgcatgttc attctctcgt gaccactgga tcagactcca    5940
tgttctgatc cagggtctct ctctaacgcc tgtactttca tccatgacca ccttaaaaac    6000
aacatggggg tggtgctgtt acactaactc tgtttctggg gtgctgtctt tgttcaattt    6060
tactcagaaa atatcttttc ttggattcta ttcggtgtgt gggaacatga tcctgtcggt    6120
cggttgtttt taggttaatc cttaactggt tacaaggatc taacgcttga atgcatgtcc    6180
tgagttaaag aaacaaaaga agaacacacc tagtacagcc tggcctcgaa ccaagaactt    6240
ctttgttggt ttctcattat tactaaaata aaataaagta tacgttttct tttttctttg    6300
ggatgaacgg ttcagactta tgagaagttt aagctaatcc tgtagtggag tgttcaattt    6360
attttaaact ttaaagcaat agctcaagca ctaaacttct ttttcaagtt caaccacttt    6420
ggtagcttgc taattgctgc tattgttcta attaattaat gtaattattg tttaaaaaag    6480
aaaagttggt gacactggaa taaaaaagtg tactatctgg caattattct tctgcagcaa    6540
tgtttgaggt tgaaatctta gtagaacaaa gtagaagatc tggtatttat attttttgta    6600
gacagatggg gggggtgggt ggtaggcctt gaaatccaat atagttttgt agaataattt    6660 tattatttt tttttttgct cacttgtttg tggtattgat tttgtgatga ctcaagatta    6720
atgatttacc ttcatttttt tcatggtgac atattatgta tattcttgat ctgtttctta    6780
cacttctttt tcgttgttgt agctgttgaa gtctgcggcc gcatgaagag gtctccagca    6840
tcttcttgtt catcatctac ttcctctgtt gggtttgaag ctcccattga aaaagaagg    6900 cctaagcatc caaggaggaa taatttgaag tcacaaaaat gcaagcagaa ccaaccacc    6960 actggtggca gaagaagctc tatctataga ggagttacaa ggcataggtg gacagggagg    7020
tttgaagctc acctatggga taagagctct tggaacaaca ttcagagcaa gaagggtcga    7080
caagtttatt tggggggcata tgatactgaa gaatctgcag cccgtaccta tgaccttgca    7140
gcccttaaat actgggaaa agatgcaacc ctgaatttcc cgatagaaac ttataccaag    7200
gagctcgagg aaatggacaa ggtttcaaga gaagaatatt tggcttcttt gcggcgccaa    7260
agcagtggct tttctagagg cctgtctaag taccgtgggg ttgctaggca tcatcataat    7320
ggtcgctggg aagcacgaat tggaagagta tgcggaaaca agtacctcta cttggggaca    7380
tataaaactc aagaggaggc agcagtggca tatgacatgg cagcaataga gtaccgtgga    7440
gtcaatgcag tgaccaattt tgacataagc aactacatgg acaaaataaa gaagaaaaat    7500
gaccaaaccc aacaacaaca aacagaagca caaacggaaa cagttcctaa ctcctctgac    7560
tctgaagaag tagaagtaga acaacagaca acaacaataa ccacaccacc cccatctgaa    7620
aatctgcaca tgccaccaca gcagcaccaa gttcaataca ccccccatgt ctctccaagg    7680
gaagaagaat catcatcact gatcacaatt atggaccatg tgcttgagca ggatctgcca    7740
tggagcttca tgtacactgg cttgtctcag tttcaagatc caaacttggc tttctgcaaa    7800
```

```
ggtgatgatg acttggtggg catgtttgat agtgcagggt ttgaggaaga cattgatttt   7860
ctgttcagca ctcaacctgg tgatgagact gagagtgatg tcaacaatat gagcgcagtt   7920
ttggatagtg ttgagtgtgg agacacaaat ggggctggtg gaagcatgat gcatgtggat   7980
aacaagcaga agatagtatc atttgcttct tcaccatcat ctacaactac agtttcttgt   8040
gactatgctc tagatctatg agcggccgca tttcgcacca aatcaatgaa agtaataatg   8100
aaaagtctga ataagaatac ttaggcttag atgcctttgt tacttgtgta aaataacttg   8160
agtcatgtac ctttggcgga aacagaataa ataaaaggtg aaattccaat gctctatgta   8220
taagttagta atacttaatg tgttctacgg ttgtttcaat atcatcaaac tctaattgaa   8280
actttagaac cacaaatctc aatctttttct taatgaaatg aaaaatctta attgtaccat   8340
gtttatgtta aacaccttac aattaattgg ttggagagga ggaccaaccg atgggacaac   8400
attgggagaa agagattcaa tggagatttg gataggagaa caacattctt tttcacttca   8460
atacaagatg agtgcaacac taaggatatg tatgagactt tcagaagcta cgacaacata   8520
gatgagtgag gtggtgattc ctagcaagaa agacattaga ggaagccaaa atcgaacaag   8580
gaagacatca agggcaagag acaggaccat ccatctcagg aaaaggagct ttgggatagt   8640
ccgagaagtt gtacaagaaa tttttttggag ggtgagtgat gcattgctgg tgactttaac   8700
tcaatcaaaa ttgagaaaga aagaaaaggg aggggctca catgtgaata aagggaaac    8760
gggagaattt tacagttttg atctaatggg catcccagct agtggtaaca tattcaccat   8820
gtttaacctt cacgtacgat ccatgcccctt catttgccgc ttattaatta atttggtaac   8880
agtccgtact aatcagttac ttatccttcc cccatcataa ttaatcttgg tagtctcgaa   8940
tgccacaaca ctgactagtc tcttggatca taagaaaaag ccaaggaaca aagaagaca    9000
aaacacaatg agagtatcct ttgcatagca atgtctaagt tcataaaatt caaacaaaaa   9060
cgcaatcaca cacagtggac atcacttatc cactagctga tcaggatcgc cgcgtcaaga   9120
aaaaaaaact ggaccccaaa agccatgcac aacaacacgt actcacaaag gtgtcaatcg   9180
agcagcccaa aacattcacc aactcaaccc atcatgagcc ctcacatttg ttgtttctaa   9240
cccaacctca aactcgtatt ctcttccgcc acctcatttt tgtttattc aacacccgtc    9300
aaactgcatg ccaccccgtg gccaaatgtc catgcatgtt aacaagacct atgactataa   9360
atagctgcaa tctcggccca ggttttcatc atcaagaacc agttcaatat cctagtacac   9420
cgtattaaag aatttaagat atactgcggc cgcatgacta tcgactcaca atactacaag   9480
tcgcgagaca aaaacgacac ggcacccaaa atcgcgggaa tccgatatgc cccgctatcg   9540
acaccattac tcaaccgatg tgagaccttc tctctggtct ggcacatttt cagcattccc   9600
actttcctca caattttcat gctatgctgc gcaattccac tgctctggcc atttgtgatt   9660
gcgtatgtag tgtacgctgt taaagacgac tccccgtcca acggaggagt ggtcaagcga   9720
tactcgccta tttcaagaaa cttcttcatc tggaagctct ttggccgcta cttccccata   9780
actctgcaca agacggtgga tctggagccc acgcacacat actaccctct ggacgtccag   9840
gagtatcacc tgattgctga gagatactgg ccgcagaaca agtacctccg agcaatcatc   9900
accaccatcg agtactttct gcccgccttc atgaaacggt ctctttctat caacgagcag   9960
gagcagcctg ccgagcgaga tcctctcctg tctcccgttt ctcccagctc tccgggttct  10020
caacctgaca agtggattaa ccacgacagc agatatagcc gtggagaatc atctggctcc  10080
aacggccacg cctcgggctc cgaacttaac ggcaacggca caacggcac cactaaccga   10140
cgacctttgt cgtccgcctc tgctggctcc actgcatctg attccacgct tcttaacggg  10200
```

```
tccctcaact cctacgccaa ccagatcatt ggcgaaaacg acccacagct gtcgcccaca   10260
aaactcaagc ccactggcag aaaatacatc ttcggctacc accccacgg cattatcggc    10320 atgggagcct ttggtggaat tgccaccgag ggagctggat ggtccaagct ctttccgggc   10380
atccctgttt ctcttatgac tctcaccaac aacttccgag tgcctctcta cagagagtac   10440
ctcatgagtc tgggagtcgc ttctgtctcc aagaagtcct gcaaggccct cctcaagcga   10500
aaccagtcta tctgcattgt cgttggtgga gcacaggaaa gtcttctggc cagaccggt    10560 gtcatggacc tggtgctact caagcgaaag ggttttgttc gacttggtat ggaggtcgga   10620
aatgtcgccc ttgttcccat catggccttt ggtgagaacg acctctatga ccaggttagc   10680
aacgacaagt cgtccaagct gtaccgattc cagcagtttg tcaagaactt ccttggattc   10740
acccttcctt tgatgcatgc ccgaggcgtc ttcaactacg atgtcggtct tgtcccctac   10800
aggcgacccg tcaacattgt ggttggttcc cccattgact tgccttatct cccacacccc   10860
accgacgaag aagtgtccga ataccacgac cgatacatcg ccgagctgca gcgaatctac   10920
aacgagcaca aggatgaata tttcatcgat tggaccgagg agggcaaagg agccccagag   10980
ttccgaatga ttgagtaagc ggccgcaagt atgaactaaa atgcatgtag gtgtaagagc   11040
tcatggagag catggaatat tgtatccgac catgtaacag tataataact gagctccatc   11100
tcacttcttc tatgaataaa caaaggatgt tatgatatat taacactcta tctatgcacc   11160
ttattgttct atgataaatt tcctcttatt attataaatc atctgaatcg tgacggctta   11220
tggaatgctt caaatagtac aaaaacaaat gtgtactata agactttcta aacaattcta   11280
accttagcat tgtgaacgag acataagtgt taagaagaca taacaattat aatggaagaa   11340
gtttgtctcc atttatatat tatatattac ccactatgt attatattag gatgttaagg     11400
agacataaca attataaaga gagaagtttg tatccattta tatattatat actacccatt   11460
tatatattat acttatccac ttatttaatg tctttataag gtttgatcca tgatatttct   11520 aatatttag ttgatatgta tatgaaaagg tactatttga actctcttac tctgtataaa     11580
ggttggatca tccttaaagt gggtctattt aatttattg cttcttacag ataaaaaaaa     11640
aattatgagt tggtttgata aaatattgaa ggatttaaaa taataataaa taacatataa   11700
tatatgtata taaatttatt ataatataac atttatctat aaaaaagtaa atattgtcat   11760
aaatctatac aatcgtttag ccttgctgga acgaatctca attatttaaa cgagagtaaa   11820
catatttgac tttttggtta tttaacaaat tattatttaa cactatatga aattttttt    11880 tttatcagca aagaataaaa ttaaattaag aaggacaatg gtgtcccaat ccttatacaa   11940
ccaacttcca caagaaagtc aagtcagaga caacaaaaaa acaagcaaag gaatttttt    12000 aatttgagtt gtcttgtttg ctgcataatt tatgcagtaa aacactacac ataaccttt    12060 tagcagtaga gcaatggttg accgtgtgct tagcttcttt tattttattt ttttatcagc   12120
aaagaataaa taaataaaa tgagacactt cagggatgtt tcaacgtact ttctagacgt    12180
acgtctttcc acaatacata actattaatt aatcttaaat aaataaagga taaaatattt   12240 tttttcttc ataagttaa aatatgttat ttttgttta gatgtatatt cgaataaatc      12300
taaatatatg ataatgattt tttatattga ttaaacatat aatcaatatt aaatatgata   12360
tttttttata taggttgtac acataatttt ataaggataa aaaatatgat aaaaatatat   12420
tttaaatatt tttatattta cgagaaaaaa aaatatttta gccataaata aatgaccagc   12480 atatttaca accttagtaa ttcataaatt cctatatgta tatttgaaat taaaaacaga   12540
```

```
taatcgttaa gggaaggaat cctacgtcat ctcttgccat ttgttttttca tgcaaacaga    12600
aagggacgaa aaaccacctc accatgaatc actcttcaca ccattttttac tagcaaacaa    12660
gtctcaacaa ctgaagccag ctctctttcc gtttcttttt acaacacttt ctttgaaata    12720
gtagtatttt ttttcacatg atttattaac gtgccaaaag atgcttattg aatagagtgc    12780
acatttgtaa tgtactacta attagaacat gaaaaagcat tgttctaaca cgataatcct    12840
gtgaaggcgt taactccaaa gatccaattt cactatataa attgtgacga agcaaaatg     12900
aattcacata gctgagagag aaaggaaagg ttaactaaga agcaatactt cagcggccgc    12960
atgccgaatc ccgaggctca ccaccccctcc cggtcccggg cccggccctc cacgtcagcc    13020
gcggcccgcc ccccggcccg ggcccgcgtc tccctccgcc agcttctgcg cgtggcatca    13080
gtcgcgagcg gcatccagtt cgggtgggcc ttacagctct ctctgctgac gccctacgtt    13140
cagcagctgg ggatccccca ccaatgggcc agcatcatct ggctctgcgg cccagtctcc    13200
ggcctcttcg tgcagcccct cgtcggccac atgagcgacc gctgcaccag ccgctacggc    13260
cgccgcaggc ccttcatcct cgtcggcgcc gtcgccatcg tcgccgctgt tctcgtcatc    13320
gcttacgccg ccgacatcgg ctggctcctc ggcgacaccg cggactaccg ccctgccgcc    13380
atcaccgtct tcatcgtcgg cttctggatc ctcgacgtcg ctaacaacgt cacgcaaggt    13440
ccctgccgtg ccttgctcgg tgatctcact agcaaggatc ctcgaaggac acgtgttgca    13500
aatgcttatt actcactgtt tatggccatt ggtaacattc ttggctatgc aactggatca    13560
tatagtggtt ggtacaagat ttttacttttt gccctttccc ctgcttgcac aattagttgt    13620
gcaaatctca agtctgcttt ctttcttgac attgctttca ttgcggtcac aacatatatc    13680
agcatcatgg cagctcatga agtgcctcta aattcaagtg aggcggccca tgctgaagca    13740
ggggcagggg agtcaggtag tgcagaagaa gctttcatgt gggaattatt tgggacattc    13800
aaatatttta caacccctgt atggataatt ctgtctgtta ctgctctgac atggattggg    13860
tggttcccat ttactctctt tgatactgat tggatgggtc gagagattta tggtggtgat    13920
ccaaatcaag gccttgttta tgatactgga gttagaatgg gagcacttgg tttgttgctt    13980
aattcagttg ttcttgcatt aacatcattg ttcatggaga ggctatgcag gaagagggga    14040
gctggttttg tgtggggaat ctcaaatatc atgatgaccg tttgctttct tgcaatgcta    14100
gtagtaacct atgtggcaaa taacatgggc tatataggca aagatttacc accaactggc    14160
attgtgatag ctgcgttgat tatctttacc attcttgggt ttccactggc aatcacttat    14220
agtgttccat atgccttaat ttccacacat attgagtcat tgggactcgg ccaagggtta    14280
tcaatgggtg tcctaaatct ggcaatagtg gtcccacaga taatagtgtc actgggaagt    14340
ggaccatggg atcagctatt tggtggagga aactccccag cctttgctgt ggcagctgtt    14400
tcagccctta tcagtggact catagctgtg ttggctattc ctcgatctgg tgctcaaaag    14460
gctcgaagcc atgtatgagc ggccgcctga acgggaatta aacctataaa cataaatata    14520
aataatatat ataaacctaa gtgtctaagt tccataaatt aagctgtagt ctctggctta    14580
aaacatgtta ggtttgttta tacaagtagt tggatgtttg gagtacttcg gtcttttgcg    14640
taccatcaat atttaagaac taagttagtt atgttccgta acttatgggc tcttaattaa    14700
actatatctg cacaaaatta tatatatatc aaatgtgatg gtatgtggac tataaaaaga    14760
tatggttgag aaccacaaac tttgaaactt cgaataatat attgccagtg acagtcttgt    14820
tgatttgtta tagcaagtcc tattttctta atcattgctt tgttttaacg tacctagatt    14880
tcataacttt tgtctttgtc tcaagctgaa cctaatgatg atagtaatat taacttattg    14940
```

```
tatagggta tttcatagga taaaaaatga tgtgcaatta cgtgtagacc aaatattact   15000
tgatgacaga tggcctgcag gtcgactcga cgtacgtcct cgaagagaag ggttaataac   15060
acattttta acattttaa cacaaatttt agttatttaa aaatttatta aaaaatttaa    15120
aataagaaga ggaactcttt aaataaatct aacttacaaa atttatgatt tttaataagt   15180
tttcaccaat aaaaaatgtc ataaaaatat gttaaaaagt atattatcaa tattctcttt   15240
atgataaata aaagaaaaa aaaaataaaa gttaagtgaa aatgagattg aagtgacttt    15300
aggtgtgtat aaatatatca accccgccaa caatttattt aatccaaata tattgaagta   15360
tattattcca tagcctttat ttatttatat atttattata taaaagcttt atttgttcta   15420
ggttgttcat gaaatatttt tttggtttta tctccgttgt aagaaaatca tgtgctttgt   15480
gtcgccactc actattgcag cttttcatg cattggtcag attgacggtt gattgtattt    15540
ttgttttta tggttttgtg ttatgactta agtcttcatc tctttatctc ttcatcaggt   15600
ttgatggtta cctaatatgg tccatgggta catgcatggt taaattaggt ggccaacttt   15660
gttgtgaacg atagaattt tttatatta agtaaactat ttttatatta tgaaataata   15720
ataaaaaaaa tattttatca ttattaacaa aatcatatta gttaatttgt taactctata   15780
ataaagaaa tactgtaaca ttcacattac atggtaacat cttccacccc tttcatttgt   15840
tttttgtttg atgactttt ttcttgttta aatttatttc ccttctttta aatttggaat    15900
acattatcat catatataaa ctaaaatact aaaaacagga ttacacaaat gataaataat   15960
aacacaaata tttataaatc tagctgcaat atatttaaac tagctatatc gatattgtaa   16020
aataaaacta gctgcattga tactgataaa aaaatatcat gtgctttctg gactgatgat   16080
gcagtatact tttgacattg cctttatttt attttttcaga aaagcttct tagttctggg   16140
ttcttcatta tttgtttccc atctccattg tgaattgaat catttgcttc gtgtcacaaa   16200
tacaatttag ntaggtacat gcattggtca gattcacggt ttattatgtc atgacttaag   16260
ttcatggtag tacattacct gccacgcatg cattatattg gttagatttg ataggcaaat   16320
ttggttgtca acaatataaa tataaataat gtttttatat tacgaaataa cagtgatcaa   16380
aacaaacagt tttatcttta ttaacaagat tttgttttg tttgatgacg ttttttaatg    16440
tttacgcttt cccccttctt ttgaatttag aacactttat catcataaaa tcaaatacta   16500
aaaaaattac atatttcata aataataaca caaatatttt taaaaaatct gaaataataa   16560
tgaacaatat tacatattat cacgaaaatt cattaataaa aatattatat aaataaaatg   16620
taatagtagt tatatgtagg aaaaaagtac tgcacgcata atatatacaa aaagattaaa   16680
atgaactatt ataataata acactaaatt aatggtgaat catatcaaaa taatgaaaaa   16740
gtaaataaaa tttgtaatta acttctatat gtattcacaca cacaaataat aaataatagt   16800
aaaaaaatt atgataaata tttaccatct cataagatat ttaaaataat gataaaaata   16860
tagattattt tttatgcaac tagctagcca aaaagagaac acgggtatat ataaaaagag   16920
taccttaaa ttctactgta cttcctttat tcctgacgtt tttatatcaa gtggacatac    16980
gtgaagattt taattatcag tctaaatatt tcattagcac ttaatacttt tctgttttat   17040
tcctatccta taagtagtcc cgattctccc aacattgctt attcacacaa ctaactaaga   17100
aagtcttcca tagcccccca agcggccgct ctagaccacc taacatcacc accgttgttg   17160
ccaatgtcac caccgagcaa ttacccaagg ctcgtggagg aagtgggcgt gccttcgtga   17220
cctttcttgc tggaaacggt gattatgtaa agggtgttgt gggtttggcc aaaggactga   17280
```

```
gaaaggccaa aagcatgtac cctttggtgg ttgctgtgtt accagatgtt cctgaagaac    17340
atcgtgcgat tctcaaatcc caaggttgca ttgtcaggga gattgaacct gtgtaccctc    17400
ctgagaacca gacccagttc gggatccata ttacgtcatc aactattcca agctacgtat    17460
ttgggagttt gtggagttca gcaagatgat atacctagac ggtgatatac aagtgtttga    17520
caatattgac cacttgtttg acttgcctga taactacttt tatgcggtga tggactgttt    17580
ttgtgagccc acttggggcc acactctgca gtcatgacct attgaaaacg gtgcaagtca    17640
ccactcccac ctcgttcgct gaacaagatt tcttgaacat gtacttcaag gacatttaca    17700
ggccaatccc tttaaattac aatcttgtcc tcgccatgct gtggcgccac ccggaaaacg    17760
ttaaattaga ccaagtcaag gttgttcact attgcgcagc ggggtccaag ccatggagat    17820
atacggggaa ggaagagaat atgcagaggg aggacataaa gatgctggtg aagaaatggt    17880
gggatatcta caatgatgct tcgcttgact acaagccatt gatgaatgca agtgaagctc    17940
cagcagcgga tggtgttgac attgaacaat tcgtgcaggc tctatcagag gttggtcatg    18000
ttcaatatgt caccgaattc tatgtcctcc ctctgcatat tctcttcctt ccccgtatat    18060
ctccatggct tggaccccgc tgcgcaatag tgaacaacct tgacttggtc taatttaacg    18120
ttttccgggt ggcgccacag catggcgagg acaagattgt aatttaaagg gattggcttg    18180
taaatgtcct tgaagtacat gttcaagaaa tcttgttcag cgaacgaggt gggagtggtg    18240
acttgcaccg ttttcaatag gtcatgaaag cttacacaaa catgccagca ttgaaataga    18300
gaggaggctt gggcccaaag tgagtgggcc actgaacctt atgagggcac tgctggcagt    18360
atccgatttg atactgcaga gtgtggcccc aagtgggctc acaaaaacag tccatcaccg    18420
cataaaagta gttatcaggc aagtcaaaca agtggtcaat attgtcaaac acttgtatat    18480
caccgtctag gtatatcatc ttgctgaact ccacaaactc ccaaatacgt agcttggaat    18540
agttgatgac gtaatatgtc gaccgaactg ggtctggttc tcaggagggt acacaggttc    18600
aatctccctg acaatgcaac cttgggattt gagaatctca cgatgttctt caggaacatc    18660
tggtaacaca gcaaccacca aagggtacat gcttttggcc tttctcagtc ctttggccaa    18720
acccacgaca ccctttacgt aatcaccgtt cccagcaaga aaggtcacga aggcacgccc    18780
acttcctcca cgagccttgg gtaattgctc ggtggtgaca ttggcaacaa cggtggtgat    18840
gttaggtggg cggccgcgac acaagtgtga gagtactaaa taaatgcttt ggttgtacga    18900
aatcattaca ctaaataaaa taatcaaagc ttatatatgc cttccgctaa ggccgaatgc    18960
aaagaaattg gttctttctc gttatctttt gccactttta ctagtacgta ttaattacta    19020
cttaatcatc tttgtttacg gctcattata tccggtctag gccaaggccg cgaagttaaa    19080
agcaatgttg tcacttgtac gtactaacac atgatgtgat agtttatgct agctagctat    19140
aacataagct gtctctgagt gtgttgtata ttaataaaga tcatcactgg tgaatggtga    19200
tcgtgtacgt accctactta gtaggcaatg gaagcactta gagtgtgctt tgtgcatggc    19260
cttgcctctg ttttgagact tttgtaatgt tttcgagttt aaatctttgc ctttgcgtac    19320
gtgggcggat cccctgcagg gcatgcaagc ttggcgcgcc ggaattaatt aggtaatttc    19380
acgcgccgga tccttaatta agtctagagt cgactgttta attctagtgg ccggcctctg    19440
cctgcgttct gctgtggaag ttcctattcc gaagttccta ttctcagaa agtataggaa    19500 cttcacatgc tgcctcgtgc aagtcacgat ctcgagttct atagtgtcac ctaaatcgta    19560
tgtgtatgat acataaggtt atgtattaat tgtagccgcg ttctaacgac aatatgtcca    19620
tatggtgcac tctcagtaca atctgctctg atgccgcata gttaagccag ccccgacacc    19680
```

```
cgccaacacc cgctgacgcg ccctgacggg cttgtctgct cccggcatcc gcttacagac   19740
aagctgtgac cgtctccggg agctgcatgt gtcagaggtt ttcaccgtca tcaccgaaac   19800
gcgcgagacg aaagggcctc gtgatacgcc tatttttata ggttaatgtc atgaccaaaa   19860
tcccttaacg tgagttttcg ttccactgag cgtcagaccc cgtagaaaag atcaaaggat   19920
cttcttgaga tcctttttt ctgcgcgtaa tctgctgctt gcaaacaaaa aaaccaccgc   19980
taccagcggt ggtttgtttg ccggatcaag agctaccaac tcttttccg aaggtaactg   20040 gcttcagcag agcgcagata ccaaatactg tccttctagt gtagccgtag ttaggccacc   20100
acttcaagaa ctctgtagca ccgcctacat acctcgctct gctaatcctg ttaccagtgg   20160
ctgctgccag tggcgataag tcgtgtctta ccgggttgga ctcaagacga tagttaccgg   20220
ataaggcgca gcggtcgggc tgaacggggg gttcgtgcac acagcccagc ttggagcgaa   20280
cgacctacac cgaactgaga tacctacagc gtgagcattg agaaagcgcc acgcttcccg   20340
aagggagaaa ggcggacagg tatccggtaa gcggcagggt cggaacagga gagcgcacga   20400
gggagcttcc agggggaaac gcctggtatc tttatagtcc tgtcgggttt cgccacctct   20460
gacttgagcg tcgatttttg tgatgctcgt caggggggcg gagcctatgg aaaaacgcca   20520
gcaacgcggc cttttacgg ttcctggcct tttgctggcc ttttgctcac atgttctttc   20580
ctgcgttatc ccctgattct gtggataacc gtattaccgc ctttgagtga gctgataccg   20640
ctcgccgcag ccgaacgacc gagcgcagcg agtcagtgag cgaggaagcg gaagagcgcc   20700
caatacgcaa accgcctctc cccgcgcgtt ggccgattca ttaatgcagg ttgatcagat   20760
ctcgatcccg cgaaattaat acgactcact atagggagac cacaacggtt tccctctaga   20820
aataattttg tttaacttta agaaggagat atacccatgg aaaagcctga actcaccgcg   20880
acgtctgtcg agaagtttct gatcgaaaag ttcgacagcg tctccgacct gatgcagctc   20940
tcggagggcg aagaatctcg tgctttcagc ttcgatgtag gagggcgtgg atatgtcctg   21000
cgggtaaata gctgcgccga tggtttctac aaagatcgtt atgtttatcg gcactttgca   21060
tcggccgcgc tcccgattcc ggaagtgctt gacattgggg aattcagcga gagcctgacc   21120
tattgcatct cccgccgtgc acagggtgtc acgttgcaag acctgcctga accgaactg    21180 cccgctgttc tgcagccggt cgcggaggct atggatgcga tcgctgcggc cgatcttagc   21240
cagacgagcg ggttcggccc attcggaccg caaggaatcg gtcaatacac tacatggcgt   21300
gatttcatat gcgcgattgc tgatccccat gtgtatcact ggcaaactgt gatggacgac   21360
accgtcagtg cgtccgtcgc gcaggctctc gatgagctga tgctttgggc cgaggactgc   21420
cccgaagtcc ggcacctcgt gcacgcggat ttcggctcca acaatgtcct gacggacaat   21480
ggccgcataa cagcggtcat tgactggagc gaggcgatgt tcgggattc ccaatacgag   21540 gtcgccaaca tcttcttctg gaggccgtgg ttggcttgta tggagcagca gacgcgctac   21600
ttcgagcgga ggcatccgga gcttgcagga tcgccgcggc tccgggcgta tatgctccgc   21660
attggtcttg accaactcta tcagagcttg gttgacggca atttcgatga tgcagcttgg   21720
gcgcagggtc gatgcgacgc aatcgtccga tccggagccg gactgtcgg gcgtacacaa   21780 atcgcccgca gaagcgcggc cgtctggacc gatggctgtg tagaagtact cgccgatagt   21840
ggaaaccgac gccccagcac tcgtccgagg gcaaaggaat agtgaggtac agcttggatc   21900
gatccggctc ctaacaaagc ccgaaaggaa gctgagttgg ctgctgccac cgctgagcaa   21960
taactagcat aaccccttgg ggcctctaaa cgggtcttga ggggttttt gctgaaagga   22020
```

```
ggaactatat ccggatgatc gtcgagg                                       22047
```

<210> SEQ ID NO 5
<211> LENGTH: 4376
<212> TYPE: DNA
<213> ORGANISM: Artificial Sequence
<220> FEATURE:
<223> OTHER INFORMATION: synthesized DNA of PHP25066A
<220> FEATURE:
<221> NAME/KEY: misc_feature
<222> LOCATION: (3187)..(3187)
<223> OTHER INFORMATION: n is a, c, g, or t

<400> SEQUENCE: 5

```
cgcgccaagc ttggatctcc tgcaggatct ggccggccgg atctcgtacg gatccgtcga      60
ctctagaggc cggccgatcc atgcccttca tttgccgctt attaattaat ttggtaacag     120
tccgtactaa tcagttactt atccttcccc catcataatt aatcttggta gtctcgaatg     180
ccacaacact gactagtctc ttggatcata agaaaaagcc aaggaacaaa agaagacaaa     240
acacaatgag agtatccttt gcatagcaat gtctaagttc ataaaattca aacaaaaacg     300
caatcacaca cagtggacat cacttatcca ctagctgatc aggatcgccg cgtcaagaaa     360
aaaaaactgg accccaaaag ccatgcacaa caacacgtac tcacaaaggt gtcaatcgag     420
cagcccaaaa cattcaccaa ctcaacccat catgagccct cacatttgtt gtttctaacc     480
caacctcaaa ctcgtattct cttccgccac ctcattttg tttatttcaa cacccgtcaa     540
actgcatgcc accccgtggc caaatgtcca tgcatgttaa caagacctat gactataaat     600
agctgcaatc tcggcccagg ttttcatcat caagaaccag ttcaatatcc tagtacaccg     660
tattaaagaa tttaagatat actgcggccg cgtcatcaac tattccaagc tacgtatttg     720
ggagtttgtg gagtacagca agatgatata cctagacggt gatatccaag tttttgacaa     780
cattgaccac ttgtttgact tgcctgataa ctacttctat gcggtgatgg actgtttctg     840
tgagccaact tggggccaca ctaaacaata tcagatcggt tactgccagc agtgccccca     900
taaggttcag tggcccactc actttgggcc caaacctcct ctctatttca atgctggcat     960
gtttgtgtat gagcccaatt tggctactta ccgtgacctc cttcaaacag tccaagtcac    1020
ccagcccact tcctttgctg aacaggattt tttgaacatg tacttcaagg acaaatatag    1080
gccaattcct aatgtctaca atcttgtgct ggccatgctg tggcgtcacc ctgagaacgt    1140
tgagcttgac aaagttaaag tggttcacta ctgtgctgct gggtctaagc cttggaggta    1200
cactgggaag tgactcgagg tcatcaatta ctccaagcta cgtatttggg agttcgtgga    1260
gtacaagaag acgatatacc tagacggtga catccaagta tttggaaaca tagaccactt    1320
gtttgatctg cctgataatt atttctatgc ggtgatggat tgtttctgcg agaagacttg    1380
gagccacacc cctcagttcc agattgggta ctgccaacag tgccctgata aggttcaatg    1440
gccctctcac tttggttcca aacctcctct atatttcaat gctggcatgt ttgtttatga    1500
gcctaatctc gacacctacc gtgatcttct ccaaactgtc caactcacca gcccacttc    1560 ttttgctgag caggactttc tcaacatgta cttcaaggac aagtacaagc caataccgaa    1620
catgtacaac cttgtgctgg ccatgttgtg gcgtcaccct gaaaatgttg aacttgataa    1680
agttcaagtg gttcattact gtgctgctgg gtctaagcct tggaggttca ctgggaagta    1740
actgcaggtc atcaactact ccaagctccg tatatgggag tttgtggagt acagcaagat    1800
gatatacttg gacggagaca ttgaggtata tgagaacata gaccacctat ttgacctacc    1860
tgatggtaac ttttacgctg tgatggattg tttctgcgag aagacatgga gtcacacccc    1920
```

```
tcagtacaag gtgggttact gccagcaatg cccggagaag gtgcggtggc ccaccgaatt    1980
gggtcagccc ccttctcttt acttcaacgc tggcatgttc gtgttcgaac ccaacatcgc    2040
cacctatcat gacctattga aaacggtgca agtcaccact cccacctcgt tcgctgaaca    2100
agatttcttg aacatgtact tcaaggacat ttacaagcca atccctttaa attacaatct    2160
tgtcctcgcc atgctgtggc gccacccgga aaacgttaaa ttagaccaag tcaaggttgt    2220
tcactattgc gcagcggggt ccaagccatg gagatatacg gggaagtagc ggccgcttgg    2280
ggggctatgg aagactttct tagttagttg tgtgaataag caatgttggg agaatcggga    2340
ctacttatag gataggaata aaacagaaaa gtattaagtg ctaatgaaat atttagactg    2400
ataattaaaa tcttcacgta tgtccacttg atataaaaac gtcaggaata aaggaagtac    2460
agtagaattt aaaggtactc ttttttatata tacccgtgtt ctcttttttgg ctagctagtt    2520 gcataaaaaa taatctatat ttttatcatt attttaaata tcttatgaga tggtaaatat    2580
ttatcataat ttttttttact attatttatt atttgtgtgt gtaatacata tagaagttaa    2640
ttacaaattt tatttacttt ttcattattt tgatatgatt caccattaat ttagtgttat    2700
tatttataat agttcatttt aatcttttttg tatatattat gcgtgcagta cttttttcct    2760
acatataact actattacat tttatttata taatattttt attaatgaat tttcgtgata    2820
atatgtaata ttgttcatta ttatttcaga ttttttaaaa atatttgtgt tattatttat    2880
gaaatatgta atttttttag tatttgattt tatgatgata aagtgttcta aattcaaaag    2940 aaggggaaa gcgtaaacat taaaaaacgt catcaaacaa aaacaaaatc ttgttaataa     3000
agataaaact gtttgttttg atcactgtta tttcgtaata taaaaacatt atttatattt    3060
atattgttga caaccaaatt tgcctatcaa atctaaccaa tataatgcat gcgtggcagg    3120
taatgtacta ccatgaactt aagtcatgac ataataaacc gtgaatctga ccaatgcatg    3180
tacctancta aattgtattt gtgacacgaa gcaaatgatt caattcacaa tggagatggg    3240
aaacaaataa tgaagaaccc agaactaaga aagcttttct gaaaaataaa ataaaggcaa    3300
tgtcaaaagt atactgcatc atcagtccag aaagcacatg atattttttt atcagtatca    3360
atgcagctag ttttattttta caatatcgat atagctagtt taaatatatt gcagctagat    3420
ttataaatat ttgtgttatt atttatcatt tgtgtaatcc tgtttttagt attttagttt    3480
atatatgatg ataatgtatt ccaaatttaa aagaagggaa ataaatttaa acaagaaaaa    3540
aagtcatcaa acaaaaaaca aatgaaaggg tggaaagatg ttaccatgta atgtgaatgt    3600
tacagtattt cttttattat agagttaaca aattaactaa tatgattttg ttaataatga    3660
taaaatattt ttttttattat tatttcataa tataaaaata gtttacttaa tataaaaaaa    3720
attctatcgt tcaacacaaa gttggccacc taatttaacc atgcatgtac ccatggacca    3780
tattaggtaa ccatcaaacc tgatgaagag ataaagagat gaagacttaa gtcataacac    3840
aaaaccataa aaaacaaaaa tacaatcaac cgtcaatctg accaatgcat gaaaaagctg    3900
caatagtgag tggcgacaca agcacatga ttttcttaca acggagataa aaccaaaaaa    3960
atatttcatg aacaacctag aacaaataaa gcttttatat aataaatata taaataaata    4020
aaggctatgg aataatatac ttcaatatat ttggattaaa taaattgttg gcggggttga    4080
tatatttata cacacctaaa gtcacttcaa tctcattttc acttaacttt tattttttttt    4140 ttcttttttat ttatcataaa gagaatattg ataatatact ttttaacata ttttttatgac    4200 atttttttatt ggtgaaaact tattaaaaat cataaatttt gtaagttaga tttattttaaa    4260
```

-continued

| | |
|---|---|
| gagttcctct tcttatttta aatttttta taaatttta aataactaaa atttgtgtta | 4320 |
| aaaatgttaa aaatgtgtt attaaccctt ctcttcgagg acctgcaggt cgacgg | 4376 |

<210> SEQ ID NO 6
<211> LENGTH: 15128
<212> TYPE: DNA
<213> ORGANISM: Artificial Sequence
<220> FEATURE:
<223> OTHER INFORMATION: synthesized DNA of PHP64207A

<400> SEQUENCE: 6

| | |
|---|---|
| cgcgccggta ccgggccccc cctcgagtgg cgttagctga ttaagtcagc atgcgcggcc | 60 |
| ggccgcaagc tctagtgaag ttcctatact ttctggagaa taggaacttc ggaataggaa | 120 |
| cttcaccggg atcatcagct gggccggccg gtacctcagc tgatgggtct agaactagaa | 180 |
| acgtgatgcc acttgttatt gaagtcgatt acagcatcta ttctgtttta ctatttataa | 240 |
| ctttgccatt tctgactttt gaaaactatc tctggatttc ggtatcgctt tgtgaagatc | 300 |
| gagcaaaaga gacgttttgt ggacgcaatg gtccaaatcc gttctacatg aacaaattgg | 360 |
| tcacaatttc cactaaaagt aaataaatgg caagttaaaa aaggaatatg cattttactg | 420 |
| attgcctagg tgagctccaa gagaagttga atctacacgt ctaccaaccg ctaaaaaaag | 480 |
| aaaaacattg aatatgtaac ctgattccat tagcttttga cttcttcaac agattctcta | 540 |
| cttagatttc taacagaaat attattacta gcacatcatt ttcagtctca ctacagcaaa | 600 |
| aaatccaacg gcacaataca gacaacagga gatatcagac tacagagata gatagatgct | 660 |
| actgcatgta gtaagttaaa taaaaggaaa ataaaatgtc ttgctaccaa aactactaca | 720 |
| gactatgatg ctcaccacag gccaaatcct gcaactagga cagcattatc ttatatatat | 780 |
| tgtacaaaac aagcatcaag gaacatttgg tctaggcaat cagtacctcg ttctaccatc | 840 |
| accctcagtt atcacatcct tgaaggatcc attactggga atcatcggca acacatgctc | 900 |
| ctgatggggc acaatgacat caagaaggta ggggccaggg gtgtccaaca ttctctgaat | 960 |
| tgccgctcta agctcttcct tcttcgtcac tcgcgctgcc ggtatcccac aagcatcagc | 1020 |
| aaacttgagc atgtttggga atatctcgct ctcgctagac ggatctccaa gataggtgtg | 1080 |
| agctctattg gacttgtaga acctatcctc ccactgaacc accatacccc aatgctgatt | 1140 |
| gttcaacaac aatatcttaa ctgggagatt ctccactctt atagtggcca actcctgaac | 1200 |
| attcatgatg aaactaccat ccccatcaat gtcaaccaca acagcccccag ggttagcaac | 1260 |
| agcagcacca atagccgcag gcaatccaaa acccatggct ccaagacccc ctgaggtcaa | 1320 |
| ccactgcctc ggtctcttgt acttgtaaaa ctgcgcagcc cacatttgat gctgcccaac | 1380 |
| cccagtacta acaatagcat ctccattagt caactcatca agaacctcga tagcatgctg | 1440 |
| cggagaaatc gcgtcctgga atgtcttgta acccaatgga aacttgtgtt tctgcacatt | 1500 |
| aatctcttct ctccaacctc caagatcaaa cttaccctcc actccttct cctccaaaat | 1560 |
| catattaatt cccttcaagg ccaacttcaa atccgcgcaa accgacacgt gcgcctgctt | 1620 |
| gttcttccca atctcggcag aatcaatatc aatgtgaaca atcttagccc tactagcaaa | 1680 |
| agcctcaagc ttcccagtaa cacggtcatc aaaccttacc ccaaaggcaa gcaacaaatc | 1740 |
| actattgtca acagcatagt tagcataaac agtaccatgc atacccagca tctgaaggga | 1800 |
| atattcatca ccaataggaa aagttccaag acccattaaa gtgctagcaa cgggaatacc | 1860 |
| agtgagttca acaaagcgcc tcaattcagc actggaattc aaactgccac cgccgacgta | 1920 |
| gagaacgggc ttttgggcct ccatgatgag tctgacaatg tgttccaatt gggcctcggc | 1980 |

```
gggggggcctg ggcagcctgg cgaggtaacc ggggaggtta acgggctcgt cccaattagg    2040
cacggcgagt tgctgctgaa cgtctttggg aatgtcgatg aggaccggac cggggcggcc    2100
ggaggtggcg acgaagaaag cctcggcgac gacgcggggg atgtcgtcga cgtcgaggat    2160
gaggtagttg tgcttcgtga tggatctgct cacctccacg atcgggtttt cttggaaggc    2220
gtcggtgccg atcatccggc ggctgacctg gccggtgatg gcgacgactg ggacgctgtc    2280
cattaaagcg tcggcgaggc cgctcacgag gttggtggcg ccggggccgg aggtggcaat    2340
gcagacgccg gggaggccgg aggaacgcgc gtagccttcg gcggcgaaga cgccgccctg    2400
ctcgtggcgc gggagcacgt tgcggatggc ggcggagcgc gtgagcgcct ggtggatctc    2460
catcgacgca ccgccggggt acgcgaacac cgtcgtcacg ccctgcctct ccagcgcctc    2520
cacaaggatg tccgcgccct tgcgaggttc gccggaggcg aaccgtgaca cgaagggctc    2580
cgtggtcggc gcttccttgg tgaagggcgc cgccgtgggg ggtttggaga tggaacattt    2640
gattttgaga gcgtggttgg gtttggtgag ggtttgatga gagagaggga gggtggatct    2700
agtaatgcgt ttggggaagg tggggtgtga agaggaagaa gagaatcggg tggttctgga    2760
agcggtggcc gccattgtgt tgtgtggtgg aagttcctat actttctaga gaataggaac    2820
ttcggaatag gaacttctgt tgttatactt caaaaactgc acaacaagcc tagagttagt    2880
acctaaacag taaatttaca acagagagca aagacacatg caaaaatttc agccataaaa    2940
aaagttataa tagaatttaa agcaaaagtt tcattttttta aacatatata caaacaaact    3000
ggatttgaag gaagggatta attccccctgc tcaaagtttg aattcctatt gtgacctata    3060
ctcgaataaa attgaagcct aaggaatgta tgagaaacaa gaaaacaaaa caaaactaca    3120
gacaaacaag tacaattaca aaattcgcta aaattctgta atcaccaaac cccatctcag    3180
tcagcacaag gcccaaggtt tattttgaaa taaaaaaaaa gtgattttat ttctcataag    3240
ctaaaagaaa gaaaggcaat tatgaaatga tttcgactag atctgaaagt caaacgcgta    3300
ttccgcagat attaaagaaa gagtagagtt tcacatggat cctagatgga cccagttgag    3360
gaaaaagcaa ggcaaagcaa accagaagtg caagatccga aattgaacca cggaatctag    3420
gatttggtag agggagaaga aaagtacctt gagaggtaga agagaagaga agagcagaga    3480
gatatatgaa cgagtgtgtc ttggtctcaa ctctgaagcg atacgagttt agaggggagc    3540
attgagttcc aatttatagg gaaaccgggt ggcaggggtg agttaatgac ggaaaagccc    3600
ctaagtaacg agattggatt gtgggttaga ttcaaccgtt tgcatccgcg gcttagattg    3660
gggaagtcag agtgaatctc aaccgttgac tgagttgaaa attgaatgta gcaaccaatt    3720
gagccaaccc cagcctttgc cctttgattt tgatttgttt gttgcatact ttttatttgt    3780
cttctggttc tgactctctt tctctcgttt caatgccagg ttgcctactc ccacaccact    3840
cacaagaaga ttctactgtt agtattaaat attttttaat gtattaaatg atgaatgctt    3900
ttgtaaacag aacaagacta tgtctaataa gtgtcttgca acattttta agaaattaaa    3960 aaaaatatat ttattatcaa aatcaaatgt atgaaaaatc atgaataata taattttata    4020 catttttta aaaatctttt taatttctta attaatatct taaaataat gattaatatt    4080 taacccaaaa taattagtat gattggtaag gaagatatcc atgttatgtt tggatgtgag    4140
tttgatctag agcaaagctt gggaagggcg aattccagca cactggcggc cgttactagt    4200
gtttgatcct ctagacgtac gaaaccaact gcgtttgggg ctccagatta acgacgccg    4260 tttcgttcct ttcgcttcac ggcttaacga tgtcgtttct gtctgtgccc aaaaaataaa    4320
```

```
ggcatttgtt atttgcacca gatatttact aagtgcaccc taatttgaca agtaggcgat   4380
aattacaaat agatgcggtg caaataataa attttgaagg aaataattac aaaagaacag   4440
aacttatatt tactttattt taaaaaacta aaatgaaaga acaaaaaaag taaaaaatac   4500
aaaaaatgtg ctttaaccac tttcattatt tgttacagaa agtatgattc tactcaaatt   4560
gatctgttgt atctggtgct gccttgtcac actggcgatt tcaatcccct aaagatatgg   4620
tgcaaactgc gaagtgatca atatctgctc ggttaattta gattaattaa taatattcaa   4680
cgtgatgtac caaaaaaaga caatttttg ctccattgtc aaattaaacc tcatcaaggt   4740
aatttccaaa cctataagca aaaaaatttc acattaattg gcccgcaatc ctattagtct   4800
tattatacta gagtaggaaa aaaaacaatt acacaacttg tcttattatt ctctatgcta   4860
atgaatattt ttcccttttg ttagaaatca gtgtttccta atttattgag tattaattcc   4920
actcaccgca tatatttacc gttgaataag aaaattttac acataattct ttttaagata   4980 aataatttt ttatactaga tcttatgat ttacgtgaag ccaagtgggt tatactaatg   5040
atatataatg tttgatagta atcagtttat aaaccaaatg catggaaatg ttacgtggaa   5100
gcacgtaaat taacaagcat tgaagcaaat gcagccaccg caccaaaacc accccacttc   5160
acttccacgt accatattcc atgcaactac aacaccctaa aacttcaata aatgccccca   5220
ccttcacttc acttcaccca tcaatagcaa gcggccgcac catggcgatt tccgatgagc   5280
ctgaaagtgt agccactgct ctcaaccact cttccctgcg ccgccgtccc tccgccacct   5340
ccaccgccgg cctcttcaat tcgcctgaga caaccaccga cagttccggt gatgacttgg   5400
ccaaggattc tggttccgac gactccatca acaacgacga cgccgccgtc aattcccaac   5460
agcaaaacga aaacaagac actgatttct ccgtcctcaa attcgcctac cgtccttccg   5520
tccccgctca ccgcaaagtg aaggaaagtc cgctcagctc cgacactatt ttccgtcaga   5580
gtcacgcggg cctcttcaac cttttgtatag tagtccttgt tgctgtgaat agccgactca   5640
tcattgagaa tttaatgaag tatggttggt tgatcaaatc tggcttttgg tttagtgcaa   5700
agtcattgag agactggccc cttttcatgt gttgtctttc tcttgtggta tttcctttcg   5760
ctgcctttat ggtggagaag ttggcacaac ggaagtgtat acccgaacca gttgttgttg   5820
tacttcatat aatcattacc tcaacttcgc ttttctatcc agttttagtt attctcaagt   5880
gtgattctgc ttttgtatca ggtgtcacgt taatgctgtt ttcttgtgtt gtatggttaa   5940
aattggtgtc ttttgcacat acaaactatg atatgagagc acttaccaaa ttagttgaaa   6000
agggagaagc actgctcgat actctgaaca tggagtatcc ttacaacgta accttcaaga   6060
gcttggcata tttcctgctt gccctacat tatgttacca gccaagctat cctcgcacac   6120
cttatattcg aaagggttgg ttgtttcgcc aacttgtcaa gctgatagta tttacaggag   6180
ttatgggatt tataatagaa caatatatta atcccatagt acaaaattca cagcatcctc   6240
tcaagggaaa ccttctttac gccaccgaga gagttctgaa gctttctgtt ccaaatttat   6300
atgtgtggct ctgcatgttc tattgctttt tccaccttg gttaaatatc gtggcagagc   6360
ttcttcgatt tggtgatcgt gaattctaca aggattggtg gaatgccaaa actgtcgaag   6420
attattggag gatgtggaat atgcctgttc acaaatggat gatccgccac ctatattttc   6480
catgtttaag gcacggtcta ccaaaggctg ctgctctttt aatttccttc ctggtttctg   6540
ctttattcca tgagctgtgc attgctgttc cttgccacat gttcaagttg tgggctttcg   6600
gtggaattat gtttcaggtt cctttggtct tgatcactaa ttatctgcaa aataaattca   6660
aaaactcaat ggttggaaat atgatttttt ggttcatatt cagtatcgtt ggtcaaccta   6720
```

```
tgtgtgtact gctatactac catgacttga tgaataggaa aggcaaactt gactgagcgg    6780
ccgcgaagtt aaaagcaatg ttgtcacttg tacgtactaa cacatgatgt gatagtttat    6840
gctagctagc tataacataa gctgtctctg agtgtgttgt atattaataa agatcatcac    6900
tggtgaatgg tgatcgtgta cgtaccctac ttagtaggca atggaagcac ttagagtgtg    6960
ctttgtgcat ggccttgcct ctgttttgag acttttgtaa tgttttcgag tttaaatctt    7020
tgcctttgcg tacgtctttc cacaatacat aactattaat taatcttaaa taaataaagg    7080
ataaaatatt ttttttttctt cataaagtta aaatatgtta ttttttgttt agatgtatat   7140
tcgaataaat ctaaatatat gataatgatt tttatattg attaaacata taatcaatat     7200
taaatatgat atttttttat ataggttgta cacataattt tataaggata aaaaatatga    7260
taaaaataaa ttttaaatat ttttatattt acgagaaaaa aaaatatttt agccataaat    7320
aaatgaccag catattttac aaccttagta attcataaat tcctatatgt atatttgaaa    7380
ttaaaaacag ataatcgtta agggaaggaa tcctacgtca tctcttgcca tttgttttc     7440
atgcaaacag aaagggacga aaaaccacct caccatgaat cactcttcac accatttta    7500
ctagcaaaca agtctcaaca actgaagcca gctctctttc cgtttctttt tacaacactt   7560
tctttgaaat agtagtattt tttttcacat gatttattaa cgtgccaaaa gatgcttatt    7620
gaatagagtg cacatttgta atgtactact aattagaaca tgaaaaagca ttgttctaac    7680
acgataatcc tgtgaaggcg ttaactccaa agatccaatt tcactatata aattgtgacg    7740
aaagcaaaat gaattcacat agctgagaga gaaaggaaag gttaactaag aagcaatact    7800
tcagcggccg catgccgaat cccgaggctc accacccctc ccggtcccgg gcccggccct    7860
ccacgtcagc cgcggccgc ccccggcc gggcccgcgt ctccctccgc cagcttctgc      7920
gcgtggcatc agtcgcgagc ggcatccagt tcgggtgggc cttacagctc tctctgctga    7980
cgccctacgt tcagcagctg gggatccccc accaatgggc cagcatcatc tggctctgcg    8040
gcccagtctc cggcctcttc gtgcagcccc tcgtcggcca catgagcgac cgctgcacca    8100
gccgctacgg ccgccgcagg cccttcatcc tcgtcggcgc cgtcgccatc gtcgccgctg    8160
ttctcgtcat cgcttacgcc gccgacatcg gctggctcct cggcgacacc gcggactacc    8220
gccctgccgc catcaccgtc ttcatcgtcg gcttctggat cctcgacgtc gctaacaacg    8280
tcacgcaagg tccctgccgt gccttgctcg gtgatctcac tagcaaggat cctcgaagga    8340
cacgtgttgc aaatgcttat tactcactgt ttatggccat tggtaacatt cttggctatg    8400
caactggatc atatagtggt tggtacaaga ttttacttt tgcccttcc cctgcttgca     8460
caattagttg tgcaaatctc aagtctgctt tctttcttga cattgctttc attgcggtca    8520
caacatatat cagcatcatg gcagctcatg aagtgcctct aaattcaagt gaggcggcc    8580
atgctgaagc aggggcaggg gagtcaggta gtgcagaaga agctttcatg tgggaattat    8640
ttgggacatt caaatatttt acaaccctg tatggataat tctgtctgtt actgctctga    8700
catgattgg gtggttccca tttactctct ttgatactga ttggatgggt cgagagattt    8760
atggtggtga tccaaatcaa ggccttgttt atgatactgg agttagaatg ggagcacttg    8820
gtttgttgct taattcagtt gttcttgcat taacatcatt gttcatggag aggctatgca    8880
ggaagagggg agctggtttt gtgtgggaa tctcaaatat catgatgacc gtttgctttc     8940
ttgcaatgct agtagtaacc tatgtggcaa ataacatggg ctatataggc aaagatttac    9000
caccaactgg cattgtgata gctgcgttga ttatctttac cattcttggg tttccactgg    9060
```

```
caatcactta tagtgttcca tatgccttaa tttccacaca tattgagtca ttgggactcg   9120
gccaagggtt atcaatgggt gtcctaaatc tggcaatagt ggtcccacag ataatagtgt   9180
cactgggaag tggaccatgg gatcagctat ttggtggagg aaactcccca gcctttgctg   9240
tggcagctgt ttcagccctt atcagtggac tcatagctgt gttggctatt cctcgatctg   9300
gtgctcaaaa ggctcgaagc catgtatgag cggccgcctg aacgggaatt aaacctataa   9360
acataaatat aaataatata tataaaccta agtgtctaag ttccataaat taagctgtag   9420
tctctggctt aaaacatgtt aggtttgttt atacaagtag ttggatgttt ggagtacttc   9480
ggtcttttgc gtaccatcaa tatttaagaa ctaagttagt tatgttccgt aacttatggg   9540
ctcttaatta aactatatct gcacaaaatt atatatatat caaatgtgat ggtatgtgga   9600
ctataaaaag atatggttga gaaccacaaa ctttgaaact tcgaataata tattgccagt   9660
gacagtcttg ttgatttgtt atagcaagtc ctattttctt aatcattgct ttgttttaac   9720
gtacctagat ttcataactt ttgtctttgt ctcaagctga acctaatgat gatagtaata   9780
ttaacttatt gtataggggt atttcatagg ataaaaaatg atgtgcaatt acgtgtagac   9840
caaatattac ttgatgacag atggcctgca ggatccatgc ccttcatttg ccgcttatta   9900
attaatttgg taacagtccg tactaatcag ttacttatcc ttcccccatc ataattaatc   9960
ttggtagtct cgaatgccac aacactgact agtctcttgg atcataagaa aaagccaagg  10020
aacaaaagaa gacaaaacac aatgagagta tcctttgcat agcaatgtct aagttcataa  10080
aattcaaaca aaaacgcaat cacacacagt ggacatcact tatccactag ctgatcagga  10140
tcgccgcgtc aagaaaaaaa aactggaccc caaaagccat gcacaacaac acgtactcac  10200
aaaggtgtca atcgagcagc ccaaaacatt caccaactca acccatcatg agccctcaca  10260
tttgttgttt ctaacccaac ctcaaactcg tattctcttc cgccacctca tttttgttta  10320
tttcaacacc cgtcaaactg catgccaccc cgtggccaaa tgtccatgca tgttaacaag  10380
acctatgact ataaatagct gcaatctcgg cccaggtttt catcatcaag aaccagttca  10440
atatcctagt acaccgtatt aaagaattta agatatactg cggccgctag tcgactaagt  10500
catcaactat tccaagctac gtatttggga gtttgtggag tacagcaaga tgatatacct  10560
agacggtgat atccaagttt ttgacaacat tgaccacttg tttgacttgc ctgataacta  10620
cttctatgcg gtgatggact gttttctgtga gccaacttgg ggccacacta aacaatatca  10680
gatcggttac tgccagcagt gcccccataa ggttcagtgg cccactcact tgggcccaa   10740 acctcctctc tatttcaatg ctggcatgtt tgtgtatgag cccaatttgg ctacttaccg  10800
tgacctcctt caaacagtcc aagtcaccca gcccacttcc tttgctgaac aggatttttt  10860
gaacatgtac ttcaaggaca aatataggcc aattcctaat gtctacaatc ttgtgctggc  10920
catgctgtgg cgtcaccctg agaacgttga gcttgacaaa gttaaagtgg ttcactactg  10980
tgctgctggg tctaagcctt ggaggtacac tgggaagtga ctcgaggtca tcaattactc  11040
caagctacgt atttgggagt tcgtggagta caagaagacg atataccagt acggtgacat  11100
ccaagtattt ggaaacatag accacttgtt tgatctgcct gataattatt tctatgcggt  11160
gatggattgt ttctgcgaga agacttggag ccacacccct cagttccaga ttgggtactg  11220
ccaacagtgc cctgataagg ttcaatggcc ctctcacttt ggttccaaac ctcctctata  11280
tttcaatgct ggcatgtttg tttatgagcc taatctcgac acctaccgtg atcttctcca  11340
aactgtccaa ctcaccaagc ccacttcttt tgctgagcag gactttctca acatgtactt  11400
caaggacaag tacaagccaa taccgaacat gtacaacctt gtgctggcca tgttgtggcg  11460
```

```
tcaccctgaa aatgttgaac ttgataaagt tcaagtggtt cattactgtg ctgctgggtc   11520
taagccttgg aggttcactg ggaagtaact gcaggtcatc aactactcca agctccgtat   11580
atgggagttt gtggagtaca gcaagatgat atacttggac ggagacattg aggtatatga   11640
gaacatagac cacctatttg acctacctga tggtaacttt tacgctgtga tggattgttt   11700
ctgcgagaag acatggagtc acacccctca gtacaaggtg ggttactgcc agcaatgccc   11760
ggagaaggtg cggtggccca ccgaattggg tcagcccccct tctctttact tcaacgctgg   11820
catgttcgtg ttcgaaccca acatcgccac ctatcatgac ctattgaaaa cggtgcaagt   11880
caccactccc acctcgttcg ctgaacaaga tttcttgaac atgtacttca aggacattta   11940
caagccaatc cctttaaatt acaatcttgt cctcgccatg ctgtggcgcc acccggaaaa   12000
cgttaaatta gaccaagtca aggttgttca ctattgcgca gcggggtcca agccatggag   12060
atatacgggg aagtagccta ggcgtacgca ggtaagtttc tgcttctacc tttgatatat   12120
atataataat tatcattaat tagtagtaat ataatatttc aaatattttt ttcaaaataa   12180
aagaatgtag tatatagcaa ttgcttttct gtagtttata agtgtgtata ttttaattta   12240
taacttttct aatatatgac caaaacatgg tgatgtgcag gtcctaggct acttccccgt   12300
atatctccat ggcttggacc ccgctgcgca atagtgaaca accttgactt ggtctaattt   12360
aacgttttcc gggtggcgcc acagcatggc gaggacaaga ttgtaattta aagggattgg   12420
cttgtaaatg tccttgaagt acatgttcaa gaaatcttgt tcagcgaacg aggtgggagt   12480
ggtgacttgc accgttttca ataggtcatg ataggtggcg atgttgggtt cgaacacgaa   12540
catgccagcg ttgaagtaaa gagaaggggg ctgacccaat tcggtgggcc accgcacctt   12600
ctccgggcat tgctggcagt aacccacctt gtactgaggg gtgtgactcc atgtcttctc   12660
gcagaaacaa tccatcacag cgtaaaagtt accatcaggt aggtcaaata ggtggtctat   12720
gttctcatat acctcaatgt ctccgtccaa gtatatcatc ttgctgtact ccacaaactc   12780
ccatatacgg agcttggagt agttgatgac ctgcagttac ttcccagtga acctccaagg   12840
cttagaccca gcagcacagt aatgaaccac ttgaacttta tcaagttcaa cattttcagg   12900
gtgacgccac aacatggcca gcacaaggtt gtacatgttc ggtattggct tgtacttgtc   12960
cttgaagtac atgttgagaa agtcctgctc agcaaaagaa gtgggcttgg tgagttggac   13020
agtttggaga agatcacggt aggtgtcgag attaggctca taaacaaaca tgccagcatt   13080
gaaatataga ggaggtttgg aaccaaagtg agagggccat tgaaccttat cagggcactg   13140
ttggcagtac ccaatctgga actgaggggt gtggctccaa gtcttctcgc agaaacaatc   13200
catcaccgca tagaaataat tatcaggcag atcaaacaag tggtctatgt ttccaaatac   13260
ttggatgtca ccgtctaggt atatcgtctt cttgtactcc acgaactccc aaatacgtag   13320
cttggagtaa ttgatgacct cgagtcactt cccagtgtac ctccaaggct tagacccagc   13380
agcacagtag tgaaccactt taactttgtc aagctcaacg ttctcagggt gacgccacag   13440
catggccagc acaagattgt agacattagg aattggccta tatttgtcct tgaagtacat   13500
gttcaaaaaa tcctgttcag caaaggaagt gggctgggtg acttggactg tttgaaggag   13560
gtcacggtaa gtagccaaat tgggctcata cacaaacatg ccagcattga aatagagagg   13620
aggtttgggc ccaaagtgag tgggccactg aaccttatgg gggcactgct ggcagtaacc   13680
gatctgtatt tgtttagtgt ggccccaagt tggctcacag aaacagtcca tcaccgcata   13740
gaagtagtta tcaggcaagt caaacaagtg gtcaatgttg tcaaaaactt ggatatcacc   13800
```

| | |
|---|---:|
| gtctaggtat atcatcttgc tgtactccac aaactcccaa atacgtagct tggaatagtt | 13860 |
| gatgacttag tcgactagcg gccgcaagta tgaactaaaa tgcatgtagg tgtaagagct | 13920 |
| catggagagc atggaatatt gtatccgacc atgtaacagt ataataactg agctccatct | 13980 |
| cacttcttct atgaataaac aaaggatgtt atgatatatt aacactctat ctatgcacct | 14040 |
| tattgttcta tgataaattt cctcttatta ttataaatca tctgaatcgt gacggcttat | 14100 |
| ggaatgcttc aaatagtaca aaaacaaatg tgtactataa gactttctaa acaattctaa | 14160 |
| ccttagcatt gtgaacgaga cataagtgtt aagaagacat aacaattata atggaagaag | 14220 |
| tttgtctcca tttatatatt atatattacc cacttatgta ttatattagg atgttaagga | 14280 |
| gacataacaa ttataaagag agaagtttgt atccatttat atattatata ctacccattt | 14340 |
| atatattata cttatccact tatttaatgt ctttataagg tttgatccat gatatttcta | 14400 |
| atatttagt tgatatgtat atgaaaaggt actatttgaa ctctcttact ctgtataaag | 14460 |
| gttggatcat ccttaaagtg ggtctattta attttattgc ttcttacaga taaaaaaaaa | 14520 |
| attatgagtt ggtttgataa aatattgaag gatttaaaat aataataaat aacatataat | 14580 |
| atatgtatat aaatttatta taatataaca tttatctata aaaaagtaaa tattgtcata | 14640 |
| aatctataca atcgtttagc cttgctggaa cgaatctcaa ttatttaaac gagagtaaac | 14700 |
| atatttgact ttttggttat ttaacaaatt attatttaac actatatgaa attttttttt | 14760 |
| ttatcagcaa agaataaaat taaattaaga aggacaatgg tgtcccaatc cttatacaac | 14820 |
| caacttccac aagaaagtca agtcagagac aacaaaaaaa caagcaaagg aaatttttta | 14880 |
| atttgagttg tcttgtttgc tgcataattt atgcagtaaa acactacaca taaccctttt | 14940 |
| agcagtagag caatggttga ccgtgtgctt agcttctttt atttttatttt tttatcagca | 15000 |
| aagaataaat aaaataaaat gagacacttc agggatgttt caacctgcag gtcgactcta | 15060 |
| gtaagctaaa caccggtgtt aattaggtaa tttcaccgcg tctagtgagc tcggtacccg | 15120 |
| ggtaccgg | 15128 |

<210> SEQ ID NO 7
<211> LENGTH: 3965
<212> TYPE: DNA
<213> ORGANISM: Artificial Sequence
<220> FEATURE:
<223> OTHER INFORMATION: synthesized DNA of PHP17522A

<400> SEQUENCE: 7

| | |
|---|---:|
| ggtcgactct agtaagcttt gctctagatc aaactcacat ccaaacataa catggatatc | 60 |
| ttccttacca atcatactaa ttattttggg ttaaatatta atcattattt ttaagatatt | 120 |
| aattaagaaa ttaaaagatt ttttaaaaaa atgtataaaa ttatattatt catgattttt | 180 |
| catacatttg atttttgataa taaatatatt ttttttaatt tcttaaaaaa tgttgcaaga | 240 |
| cacttattag acatagtctt gttctgttta caaaagcatt catcatttaa tacattaaaa | 300 |
| aatatttaat actaacagta gaatcttctt gtgagtggtg tgggagtagg caacctggca | 360 |
| ttgaaacgag agaaagagag tcagaaccag aagacaaata aaagtatgc aacaaacaaa | 420 |
| tcaaaatcaa agggcaaagg ctggggttgg ctcaattggt tgctacattc aattttcaac | 480 |
| tcagtcaacg gttgagattc actctgactt ccccaatcta agccgcggat gcaaacggtt | 540 |
| gaatctaacc cacaatccaa tctcgttact tagggctttt ccgtcatta actcacccct | 600 |
| gccacccggt ttccctataa attggaactc aatgctcccc tctaaactcg tatcgcttca | 660 |
| gagttgagac caagacacac tcgttcatat atctctctgc tcttctcttc tcttctacct | 720 |

```
ctcaaggtac ttttcttctc cctctaccaa atcctagatt ccgtggttca atttcggatc     780
ttgcacttct ggtttgcttt gccttgcttt ttcctcaact gggtccatct aggatccatg     840
tgaaactcta ctctttcttt aatatctgcg gaatacgcgt ttgactttca gatctagtcg     900
aaatcatttc ataattgcct ttctttcttt tagcttatga gaataaaat cactttttt      960 ttatttcaaa ataaaccttg ggccttgtgc tgactgagat ggggtttggt gattacagaa    1020
ttttagcgaa ttttgtaatt gtacttgttt gtctgtagtt ttgttttgtt ttcttgtttc    1080
tcatacattc cttaggcttc aattttattc gagtataggt cacaatagga attcaaactt    1140
tgagcagggg aattaatccc ttccttcaaa tccagtttgt ttgtatatat gtttaaaaaa    1200
tgaaactttt gctttaaatt ctattataac tttttttatg gctgaaattt ttgcatgtgt    1260
ctttgctctc tgttgtaaat ttactgttta ggtactaact ctaggcttgt tgtgcagttt    1320
ttgaagtata accatgccac acaacacaat ggcggccacc gcttccagaa ccacccgatt    1380
ctcttcttcc tcttcacacc ccaccttccc caaacgcatt actagatcca cctccctct    1440 ctctcatcaa accctcacca aacccaacca cgctctcaaa atcaaatgtt ccatctccaa    1500 acccccacg gcggcgccct tcaccaagga agcgccgacc acggagccct tcgtgtcacg    1560
gttcgcctcc ggcgaacctc gcaagggcgc ggacatcctt gtggaggcgc tggagaggca    1620
gggcgtgacg acggtgttcg cgtaccccgg cggtgcgtcg atggagatcc accaggcgct    1680
cacgcgctcc gccgccatcc gcaacgtgct cccgcgccac gagcagggcg gcgtcttcgc    1740
cgccgaaggc tacgcgcgtt cctccggcct ccccggcgtc tgcattgcca cctccggccc    1800
cggcgccacc aacctcgtga gcggcctcgc cgacgcttta atggacagcg tcccagtcgt    1860
cgccatcacc ggccaggtcg cccgccggat gatcggcacc gacgccttcc aagaaacccc    1920
gatcgtggag gtgagcagat ccatcacgaa gcacaactac ctcatcctcg acgtcgacga    1980
catcccccgc gtcgtcgccg aggctttctt cgtcgccacc tccggccgcc ccggtccggt    2040
cctcatcgac attcccaaag acgttcagca gcaactcgcc gtgcctaatt gggacgagcc    2100
cgttaacctc cccggttacc tcgccaggct gcccaggccc cccgccgagg cccaattgga    2160
acacattgtc agactcatca tggaggccca aaagcccgtt ctctacgtcg gcggtggcag    2220
tttgaattcc agtgctgaat tgaggcgctt tgttgaactc actggtattc ccgttgctag    2280
cactttaatg ggtcttggaa cttttcctat tggtgatgaa tattcccttc agatgctggg    2340
tatgcatggt actgtttatg ctaactatgc tgttgacaat agtgatttgt tgcttgcctt    2400
tggggtaagg tttgatgacc gtgttactgg gaagcttgag gcttttgcta gtaggctaa    2460 gattgttcac attgatattg attctgccga gattgggaag aacaagcagg cgcacgtgtc    2520
ggtttgcgcg gatttgaagt tggccttgaa gggaattaat atgattttgg aggagaaagg    2580
agtggagggt aagtttgatc ttggaggttg gagagaagag attaatgtgc agaaacacaa    2640
gtttccattg ggttacaaga cattccagga cgcgatttct ccgcagcatg ctatcgaggt    2700
tcttgatgag ttgactaatg gagatgctat tgttagtact ggggttgggc agcatcaaat    2760
gtgggctgcg cagtttttaca agtacaagag accgaggcag tggttgacct caggggtct    2820 tggagccatg ggttttggat tgcctgcggc tattggtgct gctgttgcta accctggggc    2880
tgttgtggtt gacattgatg gggatggtag tttcatcatg aatgttcagg agttggccac    2940
tataagagtg gagaatctcc cagttaagat attgttgttg aacaatcagc atttgggtat    3000
ggtggttcag ttggaggata ggttctacaa gtccaataga gctcacacct atcttggaga    3060
```

```
tccgtctagc gagagcgaga tattcccaaa catgctcaag tttgctgatg cttgtgggat    3120
accggcagcg cgagtgacga agaaggaaga gcttagagcg gcaattcaga gaatgttgga    3180 caccccctggc ccctaccttc ttgatgtcat tgtgccccat caggagcatg tgttgccgat    3240
gattcccagt aatggatcct tcaaggatgt gataactgag ggtgatggta gaacgaggta    3300
ctgattgcct agaccaaatg ttccttgatg cttgttttgt acaatatata taagataatg    3360
ctgtcctagt tgcaggattt ggcctgtggt gagcatcata gtctgtagta gttttggtag    3420
caagacattt tattttcctt ttatttaact tactacatgc agtagcatct atctatctct    3480
gtagtctgat atctcctgtt gtctgtattg tgccgttgga ttttttgctg tagtgagact    3540
gaaaatgatg tgctagtaat aatatttctg ttagaaatct aagtagagaa tctgttgaag    3600
aagtcaaaag ctaatggaat caggttacat attcaatgtt tttctttttt tagcggttgg    3660
tagacgtgta gattcaactt ctcttggagc tcacctaggc aatcagtaaa atgcatattc    3720 ctttttaac ttgccattta tttacttta gtggaaattg tgaccaattt gttcatgtag      3780
aacggatttg gaccattgcg tccacaaaac gtctcttttg ctcgatcttc acaaagcgat    3840
accgaaatcc agagatagtt ttcaaaagtc agaaatggca agttataaa tagtaaaaca     3900 gaatagatgc tgtaatcgac ttcaataaca agtggcatca cgtttctagt tctagacccg    3960
ggtac                                                                3965
```

<210> SEQ ID NO 8
<211> LENGTH: 6270
<212> TYPE: DNA
<213> ORGANISM: Artificial Sequence
<220> FEATURE:
<223> OTHER INFORMATION: synthesized DNA of PHP17734A
<220> FEATURE:
<221> NAME/KEY: misc_feature
<222> LOCATION: (4389)..(4389)
<223> OTHER INFORMATION: n is a, c, g, or t

<400> SEQUENCE: 8

```
cgcgccaagc ttggatccgc ccgatccctc aattcttcta agataaaaaa tttaacagca     60 atactttta aacaaattca ttcaaaattg ttttgcaaat tgcatttgat aaataattta     120
atcaagtact tacgccacac caacttacaa caatgtcata cataaatcat agtgtgacat    180
tattgcgatt tttgtactga aaaataatat ttttaaaata tatgtacgaa ggcaaagagc    240
taaactttgt tgttctatct ctatttcaaa ttcttccttt ccatctctct ttttttcttt    300
caattcaccc ttcacattct ctttcaattg aggaatggtt caacactacg tgcgataggc    360
taaatgtcac ttccacttta atataaataa aggatcatat tcttgtatca attgataaag    420 aaagttttt ttttcttcat gttttttatct gcctctaact actagtaagt gctattaatt    480
agagcttaag ttgcatagaa ttaaagagaa acatttgaga gttgagagat gattagcaat    540
aattttaatc aataacttta atcaataact tttagtatat ttcgcatttg atttaacttt    600
ttattatcct ttttcaaatt attctttcaa aatgatatca ttttaaatat taatacaaat    660
cttaacatca tttggaaggg ataacggaga gacaatttgg aagggataag agaagtcaat    720
ttcatcccca attagattaa tcgaccgttt atgtaagccc ctattgcacg agtggttgat    780
tgccacgtgt ccctaacact gtgttgaagc tcgttgcaaa cagacacgcg gcaattacgt    840
gtaagacgat tagtccaata atcctcagaa acttgccacg cgtactgcac tgacacgtgt    900 gcaaagata gcgccgcacc taatctcatt tatttggtag catgcggtgt gctgttgaaa     960
gaagaaagaa cctaagtgag aaacaaagaa aggaaataat tgatctttga aaatgcaggg    1020
```

```
aggaaagaaa gctggaggcg gccgggctag agcggccgga gctggtcatc tcgctcatcg    1080
tcgagtcggc ggccggagct ggtcatctcg ctcatcgtcg agtcggcggc cgctgagctg    1140
atttaaatca ccactgtcaa aaccaccatc accgacgctc aagccaaggt cgccaccgat    1200
catggtcgtg cctacgtcac cttcctcgcc ggaaacggtg actatgtgaa aggtgtcgtt    1260
ggcttggcaa aaggtctgag aaaagtgaag agcatgtacc ctctggtggt tgcagtgcta    1320
cccgatgttc cccaagatca ccgcaacatt ctcacctccc aaggttgcat tgttagagag    1380
attgagcccg tgtacccccc agagaatcaa acccagtttg ccatggcata ttacgtcatc    1440
aactattcca agctacgtat ttgggagttt gtggagtaca gcaagatgat atacctagac    1500
ggtgatatcc aagttttga caacattgac cacttgggat cgatcctgag ctgatttaaa    1560
ccaccgttgt tgccaatgtc accaccgagc aattacccaa ggctcgtgga ggaagtgggc    1620
gtgccttcgt gacctttctt gctgggaacg gtgattacgt aaagggtgtc gtgggtttgg    1680
ccaaaggact gagaaaggcc aaaagcatgt acccttggt ggttgctgtg ttaccagatg    1740
ttcctgaaga acatcgtgag attctcaaat cccaaggttg cattgtcagg gagattgaac    1800
ctgtgtaccc tcctgagaac cagacccagt tcgtcatggc ctattatgtc atcaattact    1860
ccaagctacg tatttgggag ttcgtggagt acaagaagac gatataccta gacggtgaca    1920
tccaagtatt tggaaacata gaccacttgt ttgatctgtg agctgattta agcggccgcc    1980
gactcgacga tgagcgagat gaccagctcc ggccgccgac tcgacgatga gcgagatgac    2040
cagctccggc cgcaagtatg aactaaaatg cacgtaggtg taagagctca tggagagcat    2100
ggaatattgt atccgaccat gtaacagtat aataactgag ctccatctca cttcttctat    2160
gaataaacaa aggatgttat gatatattaa cactctatct atgcaccta ttgttctatg    2220 ataaatttcc tcttattatt ataaatcatc tgaatcgtga cggcttatgg aatgcttcaa    2280
atagtacaaa aacaaatgtg tactataaga cttttctaaac aattctaact ttagcattgt    2340
gaacgagaca taagtgttaa aagacataa caattataat ggaagaagtt tgtctccatt    2400
tatatattat atattaccca cttatgtatt atattaggat gttaaggaga cataacaatt    2460
ataaagagag aagtttgtat ccatttatat attatatact acccatttat atattatact    2520
tatccactta tttaatgtct ttataaggtt tgatccatga tatttctaat attttagttg    2580
atatgtatat gaagggtac tatttgaact ctcttactct gtataaaggt tggatcatcc    2640
ttaaagtggg tctatttaat tttattgctt cttacagata aaaaaaaat tatgagttgg    2700 tttgataaaa tattgaagga tttaaaataa taataaataa catataatat atgtatataa    2760
atttattata atataacatt tatctataaa aaagtaaata ttgtcataaa tctatacaat    2820
cgtttagcct tgctggacga atctcaatta tttaaacgag agtaaacata tttgactttt    2880
tggttattta acaaattatt atttaacact atatgaaatt tttttttta tcagcaaaga    2940 ataaaattaa attaaggagg acaatggtgt cccaatcctt atacaaccaa cttccacaag    3000
aaagtcaagt cagagacaac aaaaaaacaa gcaaggaaa tttttaatt tgagttgtct    3060 tgtttgctgc ataatttatg cagtaaaaca ctacacataa ccccttttagc agtaaagcaa    3120 tggttgaccg tgtgcttagc ttctttatt ttatttttt atcagcaaag aataaataaa    3180
ataaaatgag acacttcagg gatgtttcaa cggatcctcg aagagaaggg ttaataacac    3240
attttttaac attttaaca caaattttag ttatttaaaa atttattaaa aaatttaaaa    3300
taagaagagg aactctttaa ataaatctaa cttacaaaat ttatgatttt taataagttt    3360
```

```
tcaccaataa aaaatgtcat aaaaatatgt taaaaagtat attatcaata ttctctttat    3420
gataaataaa agaaaaaaaa aaataaaagt taagtgaaaa tgagattgaa gtgactttag    3480
gtgtgtataa atatatcaac cccgccaaca atttatttaa tccaaatata ttgaagtata    3540
ttattccata gcctttattt atttatatat ttattatata aaagcttttat ttgttctagg   3600 ttgttcatga aatattttttt tggttttatc tccgttgtaa gaaaatcatg tgctttgtgt   3660
cgccactcac tattgcagct ttttcatgca ttggtcagat tgacggttga ttgtatttt     3720 gttttttatg gttttgtgtt atgacttaag tcttcatctc tttatctctt catcaggttt    3780
gatggttacc taatatggtc catgggtaca tgcatggtta aattaggtgg ccaactttgt    3840
tgtgaacgat agaattttt ttatattaag taaactattt ttatattatg aaataataat    3900
aaaaaaaata tttatcatt attaacaaaa tcatattagt taatttgtta actctataat    3960
aaaagaaata ctgtaacatt cacattacat ggtaacatct ttccacccctt tcatttgttt   4020 tttgtttgat gacttttttt cttgtttaaa tttatttccc ttctttttaaa tttggaatac   4080 attatcatca tatataaact aaaatactaa aaacaggatt acacaaatga taaataataa   4140
cacaaatatt tataaatcta gctgcaatat atttaaacta gctatatcga tattgtaaaa   4200
taaaactagc tgcattgata ctgataaaaa aatatcatgt gctttctgga ctgatgatgc   4260
agtatacttt tgacattgcc tttatttttat tttcagaaaa agcttcctta gttctgggtt    4320
cttcattatt tgtttcccat ctccattgtg aattgaatca tttgcttcgt gtcacaaata    4380
caatttagnt aggtacatgc attggtcaga ttcacggttt attatgtcat gacttaagtt    4440
catggtagta cattacctgc cacgcatgca ttatattggt tagatttgat aggcaaattt    4500
ggttgtcaac aatataaata taaataatgt ttttatatta cgaaataaca gtgatcaaaa    4560
caaacagttt tatctttatt aacaagattt tgttttttgtt tgatgacgtt ttttaatgtt    4620
tacgctttcc cccttctttt gaatttagaa cactttatca tcataaaatc aaatactaaa    4680
aaaattacat atttcataaa taataacaca aatattttta aaaatctga aataataatg    4740 aacaatatta catattatca cgaaaattca ttaataaaaa tattatataa ataaaatgta    4800
atagtagtta tatgtaggaa aaaagtactg cacgcataat atatacaaaa agattaaaat    4860
gaactattat aaataataac actaaattaa tggtgaatca tatcaaaata atgaaaaagt    4920
aaataaaatt tgtaattaac ttctatatgt attacacaca caaataataa ataatagtaa    4980
aaaaaattat gataaatatt taccatctca taagatattt aaaataatga taaaaatata    5040
gattattttt tatgcaacta gctagccaaa aagagaacac gggtatatat aaaaagagta    5100
cctttaaatt ctactgtact tcctttattc ctgacgtttt tatatcaagt ggacatacgt    5160
gaagatttta attatcagtc taaatatttc attagcactt aatactttttc tgttttattc    5220 ctatcctata agtagtcccg attctcccaa cattgcttat tcacacaact aactaagaaa    5280
gtcttccata gccccccaag cggccggagc tggtcatctc gctcatcgtc gagtcggcgg    5340
ccggagctgg tcatctcgct catcgtcgag tcggcggccg ctgagtgatt gctcacgagt    5400
gtggtcacca tgccttcagc aagtaccaat gggttgatga tgttgtgggt ttgacccttc    5460
actcaacact tttagtccct tatttctcat ggaaaataag ccatcgccgc catcactcca    5520
acacaggttc ccttgaccgt gatgaagtgt ttgtcccaaa accaaaatcc aaagttgcat    5580
ggttttccaa gtacttaaac aaccctctag gaagggctgt ttctcttctc gtcacactca    5640
caatagggtg gcctatgtat ttagccttca atgtctctgg tagaccctat gatagttttg    5700
caagccacta ccacccttat gctcccatat attctaaccg tgagaggctt ctgatctatg    5760
```

```
tctctgatgt tgctttgttt tctgtgactt actctctcta ccgtgttgca accctgaaag      5820
ggttggtttg gctgctatgt gtttatgggg tgcctttgct cattgtgaac ggttttcttg      5880
tgactatcac atatttgcag cacacacact ttgccttgcc tcattacgat tcatcagaat      5940
gggactggct gaagggagct ttggcaacta tggacagaga ttaagcggcc gccgactcga      6000
cgatgagcga gatgaccagc tccggccgcc gactcgacga tgagcgagat gaccagctcc      6060
ggccgcgaca caagtgtgag agtactaaat aaatgctttg gttgtacgaa atcattacac      6120
taaataaaat aatcaaagct tatatatgcc ttccgctaag gccgaatgca agaaattgg       6180 ttctttctcg ttatcttttg ccacttttac tagtacgtat taattactac ttaatcatct      6240
ttgtttacgg ctcattatat ccgtcgacgg                                       6270
```

<210> SEQ ID NO 9
<211> LENGTH: 6638
<212> TYPE: DNA
<213> ORGANISM: Artificial Sequence
<220> FEATURE:
<223> OTHER INFORMATION: synthesized DNA of PHP29252A
<220> FEATURE:
<221> NAME/KEY: misc_feature
<222> LOCATION: (1190)..(1190)
<223> OTHER INFORMATION: n is a, c, g, or t

<400> SEQUENCE: 9

```
cgcgccaagc ttggatcctc gaagagaagg gttaataaca cattttttaa cattttttaac      60 acaaatttta gttatttaaa aatttattaa aaaatttaaa ataagaagag gaactctttta    120 aataaatcta acttacaaaa tttatgattt ttaataagtt ttcaccaata aaaaatgtca     180
taaaaatatg ttaaaaagta tattatcaat attctctttta tgataaataa aaagaaaaaa    240
aaaataaaag ttaagtgaaa atgagattga agtgacttta ggtgtgtata aatatatcaa     300
ccccgccaac aatttattta atccaaatat attgaagtat attattccat agcctttatt     360
tatttatata tttattatat aaaagcttta tttgttctag gttgttcatg aaatattttt     420
ttggttttat ctccgttgta agaaaatcat gtgctttgtg tcgccactca ctattgcagc     480 ttttttcatgc attggtcaga ttgacggttg attgtatttt tgtttttttat ggttttgtgt    540 tatgacttaa gtcttcatct ctttatctct tcatcaggtt tgatggttac ctaatatggt     600
ccatgggtac atgcatggtt aaattaggtg gccaactttg ttgtgaacga tagaattttt     660
tttatattaa gtaaactatt tttatattat gaaataataa taaaaaaaat attttatcat     720
tattaacaaa atcatattag ttaatttgtt aactctataa taaaagaaat actgtaacat     780
tcacattaca tggtaacatc tttccaccct ttcatttgtt ttttgtttga tgactttttt      840
tcttgtttaa atttatttcc cttcttttaa atttggaata cattatcatc atatataaac     900
taaaatacta aaaacaggat tacacaaatg ataaataata acacaaatat ttataaatct     960
agctgcaata tatttaaact agctatatcg atattgtaaa ataaaactag ctgcattgat    1020
actgataaaa aaatatcatg tgcttctgg actgatgatg cagtatactt ttgacattgc     1080 ctttattttta tttttcagaa aagctttctt agttctgggt tcttcattat ttgtttccca    1140
tctccattgt gaattgaatc atttgcttcg tgtcacaaat acaatttagn taggtacatg    1200
cattggtcag attcacggtt tattatgtca tgacttaagt tcatggtagt acattacctg    1260
ccacgcatgc attatattgg ttagatttga taggcaaatt tggttgtcaa caatataaat    1320
ataaataatg tttttatatt acgaaataac agtgatcaaa acaaacagtt ttatctttat    1380
```

-continued

```
taacaagatt ttgttttgt ttgatgacgt tttttaatgt ttacgctttc cccccttcttt      1440 tgaatttaga acactttatc atcataaaat caaatactaa aaaaattaca tatttcataa      1500
ataataacac aaatatttt aaaaaatctg aaataataat gaacaatatt acatattatc      1560
acgaaaattc attaataaaa atattatata aataaaatgt aatagtagtt atatgtagga      1620
aaaaagtact gcacgcataa tatatacaaa aagattaaaa tgaactatta taaataataa      1680
cactaaatta atggtgaatc atatcaaaat aatgaaaaag taaataaaat ttgtaattaa      1740
cttctatatg tattacacac acaaataata aataatagta aaaaaaatta tgataaatat      1800
ttaccatctc ataagatatt taaaataatg ataaaaatat agattatttt ttatgcaact      1860
agctagccaa aaagagaaca cgggtatata taaaagagt acctttaaat tctactgtac       1920
ttcctttatt cctgacgttt ttatatcaag tggacatacg tgaagatttt aattatcagt      1980
ctaaatattt cattagcact taatactttt ctgttttatt cctatcctat aagtagtccc      2040
gattctccca acattgctta ttcacacaac taactaagaa agtcttccat agcccccaa       2100 gcggccgcta gtcgactaag tcatcaacta ttccaagcta cgtatttggg agtttgtgga     2160
gtacagcaag atgatatacc tagacggtga tatccaagtt tttgacaaca ttgaccactt     2220
gtttgacttg cctgataact acttctatgc ggtgatggac tgtttctgtg agccaacttg     2280
gggccacact aaacaatatc agatcggtta ctgccagcag tgcccccata aggttcagtg     2340
gcccactcac tttgggccca acctcctct ctatttcaat gctggcatgt tgtgtatga       2400 gcccaatttg gctacttacc gtgacctcct tcaaacagtc caagtcaccc agcccacttc     2460
ctttgctgaa caggattttt tgaacatgta cttcaaggac aaatataggc caattcctaa     2520
tgtctacaat cttgtgctgg ccatgctgtg gcgtcaccct gagaacgttg agcttgacaa     2580
agttaaagtg gttcactact gtgctgctgg gtctaagcct tggaggtaca ctgggaagtg     2640
actcgaggtc atcaattact ccaagctacg tatttgggag ttcgtggagt acaagaagac     2700
gatataccta gacggtgaca tccaagtatt tggaaacata gaccacttgt ttgatctgcc     2760
tgataattat ttctatgcgg tgatggattg tttctgcgag aagacttgga gccacacccc     2820
tcagttccag attgggtact gccaacagtg ccctgataag gttcaatggc cctctcactt     2880
tggttccaaa cctcctctat atttcaatgc tggcatgttt gtttatgagc ctaatctcga     2940
cacctaccgt gatcttctcc aaactgtcca actcaccaag cccacttctt ttgctgagca     3000
ggactttctc aacatgtact tcaaggacaa gtacaagcca ataccgaaca tgtacaacct     3060
tgtgctggcc atgttgtggc gtcaccctga aaatgttgaa cttgataaag ttcaagtggt     3120
tcattactgt gctgctgggt ctaagccttg gaggttcact gggaagtaac tgcaggtcat     3180
caactactcc aagctccgta tatgggagtt tgtggagtac agcaagatga tatacttgga     3240
cggagacatt gaggtatatg agaacataga ccacctattt gacctacctg atggtaactt     3300
ttacgctgtg atggattgtt tctgcgagaa acatggagt cacacccctc agtacaaggt     3360
gggttactgc cagcaatgcc cggagaaggt gcggtggccc accgaattgg gtcagccccc     3420
ttctctttac ttcaacgctg gcatgttcgt gttcgaaccc aacatcgcca cctatcatga     3480
cctattgaaa acggtgcaag tcaccactcc cacctcgttc gctgaacaag atttcttgaa     3540
catgtacttc aaggacattt acaagccaat ccctttaaat tacaatcttg tcctcgccat     3600
gctgtggcgc cacccggaaa acgttaaatt agaccaagtc aaggttgttc actattgcgc     3660 agcgggtcc aagccatgga gatatacggg gaagtagcct aggtgagctg atttaagatt      3720
tatcaaaagt tggggttaca aattttggaa gcttcagtgt ggaagtaata gacccagttt     3780
```

```
ctgactatct ggagctattg gagacagtat ttgattttca gctaatcaga ggtcttcttt    3840
cacgtccaga ttttaggttt atatttgatg ccatgcatgc agttactggt gcttatgcta    3900
aacccatctt cgttgataaa ctcggtgcta gtctggattc aatttcaaat ggaatccctt    3960
tggaagattt tggacatggc catcctgatc ctaatctaac atatgcgaag gatcttgtcg    4020
acattctgta tgctgaaaat ggacctgatt ttggagctgc cagtgatggg gatggtgata    4080
gaaatatgat tttaggaaga agtttctttg taactccttc agactctgta gcagttattg    4140
cagccaatgc aagagaagcg attccatact tcaagaacgg tgttaagggt cttgctcgat    4200
caatgccaac aagcggtgct ctggaccgtg ctgctaaaaa attgaacctc cctttctgag    4260
ctgatttaac gtacgcaggt aagtttctgc ttctaccttt gatatatata taataattat    4320
cattaattag tagtaatata atatttcaaa tatttttttc aaaataaaag aatgtagtat    4380
atagcaattg cttttctgta gtttataagt gtgtatattt taatttataa cttttctaat    4440
atatgaccaa acatggtga tgtgcaggtc ctgcaggtta aatcagctca gaaagggagg    4500
ttcaattttt tagcagcacg gtccagagca ccgcttgttg gcattgatcg agcaagaccc    4560
ttaacaccgt tcttgaagta tggaatcgct tctcttgcat tggctgcaat aactgctaca    4620
gagtctgaag gagttacaaa gaaacttctt cctaaaatca tatttctatc accatcccca    4680
tcactggcag ctccaaaatc aggtccattt tcagcataca gaatgtcgac aagatccttc    4740
gcatatgtta gattaggatc aggatggcca tgtccaaaat cttccaaagg gattccattt    4800
gaaattgaat ccagactagc accgagttta tcaacgaaga tgggtttagc ataagcacca    4860
gtaactgcat gcatggcatc aaatataaac ctaaaatctg gacgtgaaag aagacctctg    4920
attagctgaa aatcaaatac tgtctccaat agctccagat agtcagaaac tgggtctatt    4980
acttccacac tgaagcttcc aaaatttgta accccaactt ttgataaatc ttaaatcagc    5040
tcacctaggc tacttccccg tatatctcca tggcttggac cccgctgcgc aatagtgaac    5100
aaccttgact tggtctaatt taacgttttc cgggtggcgc cacagcatgg cgaggacaag    5160
attgtaattt aaagggattg gcttgtaaat gtccttgaag tacatgttca agaaatcttg    5220
ttcagcgaac gaggtgggag tggtgacttg caccgttttc aataggtcat gataggtggc    5280
gatgttgggt tcgaacacga acatgccagc gttgaagtaa agagaagggg gctgacccaa    5340
ttcggtgggc caccgcacct tctccgggca ttgctggcag taacccacct tgtactgagg    5400
ggtgtgactc catgtcttct cgcagaaaca atccatcaca gcgtaaaagt taccatcagg    5460
taggtcaaat aggtggtcta tgttctcata tacctcaatg tctccgtcca agtatatcat    5520
cttgctgtac tccacaaact cccatatacg gagcttggag tagttgatga cctgcagtta    5580
cttcccagtg aacctccaag gcttagaccc agcagcacag taatgaacca cttgaacttt    5640
atcaagttca acattttcag ggtgacgcca caacatggcc agcacaaggt tgtacatgtt    5700
cggtattggc ttgtacttgt ccttgaagta catgttgaga aagtcctgct cagcaaaaga    5760
agtgggcttg gtgagttgga cagtttggag aagatcacgg taggtgtcga gattaggctc    5820
ataaacaaac atgccagcat tgaaatatag aggaggtttg gaaccaaagt gagagggcca    5880
ttgaacctta tcagggcact gttggcagta cccaatctgg aactgagggg tgtggctcca    5940
agtcttctcg cagaaacaat ccatcaccgc atagaaataa ttatcaggca gatcaaacaa    6000
gtggtctatg tttccaaata cttggatgtc accgtctagg tatatcgtct tcttgtactc    6060
cacgaactcc caaatacgta gcttggagta attgatgacc tcgagtcact tcccagtgta    6120
```

-continued

```
cctccaaggc ttagacccag cagcacagta gtgaaccact ttaactttgt caagctcaac    6180
gttctcaggg tgacgccaca gcatggccag cacaagattg tagacattag gaattggcct    6240
atatttgtcc ttgaagtaca tgttcaaaaa atcctgttca gcaaaggaag tgggctgggt    6300
gacttggact gttttgaagga ggtcacggta agtagccaaa ttgggctcat acacaaacat    6360
gccagcattg aaatagagag gaggtttggg cccaaagtga gtgggccact gaaccttatg    6420
ggggcactgc tggcagtaac cgatctgata ttgtttagtg tggccccaag ttggctcaca    6480
gaaacagtcc atcaccgcat agaagtagtt atcaggcaag tcaaacaagt ggtcaatgtt    6540
gtcaaaaact tggatatcac cgtctaggta tatcatcttg ctgtactcca caaactccca    6600
aatacgtagc ttggaatagt tgatgactta gtcgacgg                           6638
```

<210> SEQ ID NO 10
<211> LENGTH: 3984
<212> TYPE: DNA
<213> ORGANISM: Artificial Sequence
<220> FEATURE:
<223> OTHER INFORMATION: synthesized DNA of PHP19031A

<400> SEQUENCE: 10

```
cgcgccaagc ttggatccta gaactagaaa cgtgatgcca cttgttattg aagtcgatta      60
cagcatctat tctgttttac tatttataac tttgccattt ctgactttg aaaactatct     120 ctggatttcg gtatcgcttt gtgaagatcg agcaaaagag acgttttgtg gacgcaatgg     180
tccaaatccg ttctacatga acaaattggt cacaatttcc actaaaagta ataaatggc     240 aagttaaaaa aggaatatgc attttactga ttgcctaggt gagctccaag agaagttgaa     300
tctacacgtc taccaaccgc taaaaaaaga aaaacattga tatgtaacct gattccatta     360
gcttttgact tcttcaacag attctctact tagatttcta acagaaatat tattactagc     420
acatcatttt cagtctcact acagcaaaaa atccaacggc acaatacaga caacaggaga     480
tatcagacta cagagataga tagatgctac tgcatgtagt aagttaaata aaaggaaaat     540
aaaatgtctt gctaccaaaa ctactacaga ctatgatgct caccacaggc caaatcctgc     600
aactaggaca gcattatctt atatatattg tacaaaacaa gcatcaagga acatttggtc     660
taggcaatca gtacctcgtt ctaccatcac cctcagttat cacatccttg aaggatccat     720
tactgggaat catcggcaac acatgctcct gatggggcac aatgacatca agaaggtagg     780
ggccaggggt gtccaacatt ctctgaattg ccgctctaag ctcttccttc ttcgtcactc     840
gcgctgccgg tatcccacaa gcatcagcaa acttgagcat gtttgggaat atctcgctct     900
cgctagacgg atctccaaga taggtgtgag ctctattgga cttgtagaac ctatcctcca     960
actgaaccac catacccaaa tgctgattgt caacaacaa tatcttaact gggagattct    1020
ccactcttat agtggccaac tcctgaacat tcatgatgaa actaccatcc ccatcaatgt    1080
caaccacaac agccccaggg ttagcaacag cagcaccaat agccgcaggc aatccaaaac    1140
ccatggctcc aagaccccct gaggtcaacc actgcctcgg tctcttgtac ttgtaaaact    1200
gcgcagccca catttgatgc tgcccaaccc cagtactaac aatagcatct ccattagtca    1260
actcatcaag aacctcgata gcatgctgcg gagaaatcgc gtcctggaat gtcttgtaac    1320
ccaatggaaa cttgtgtttc tgcacattaa tctcttctct ccaacctcca agatcaaact    1380
taccctccac tcctttctcc tccaaaaatca tattaattcc cttcaaggcc aacttcaaat    1440
ccgcgcaaac cgacacgtgc gcctgcttgt tcttcccaat ctcggcagaa tcaatatcaa    1500
tgtgaacaat cttagcccta ctagcaaaag cctcaagctt cccagtaaca cggtcatcaa    1560
```

```
accttacccc aaaggcaagc aacaaatcac tattgtcaac agcatagtta gcataaacag    1620
taccatgcat acccagcatc tgaagggaat attcatcacc aataggaaaa gttccaagac    1680
ccattaaagt gctagcaacg ggaataccag tgagttcaac aaagcgcctc aattcagcac    1740
tggaattcaa actgccaccg ccgacgtaga gaacgggctt ttgggcctcc atgatgagtc    1800
tgacaatgtg ttccaattgg gcctcggcgg ggggcctggg cagcctggcg aggtaaccgg    1860
ggaggttaac gggctcgtcc caattaggca cggcgagttg ctgctgaacg tctttgggaa    1920
tgtcgatgag gaccggaccg gggcggccgg aggtggcgac gaagaaagcc tcggcgacga    1980
cgcgggggat gtcgtcgacg tcgaggatga ggtagttgtg cttcgtgatg gatctgctca    2040
cctccacgat cgggtttct tggaaggcgt cggtgccgat catccggcgg gcgacctggc    2100
cggtgatggc gacgactggg acgctgtcca ttaaagcgtc ggcgaggccg ctcacgaggt    2160
tggtggcgcc ggggccggag gtggcaatgc agacgccggg gaggccggag gaacgcgcgt    2220
agccttcggc ggcgaagacg ccgccctgct cgtggcgcgg gagcacgttg cggatggcgg    2280
cggagcgcgt gagcgcctgg tggatctcca tcgacgcacc gccggggtac gcgaacaccg    2340
tcgtcacgcc ctgcctctcc agcgcctcca aaggatgtc cgcgcccttg cgaggttcgc    2400
cggaggcgaa ccgtgacacg aagggctccg tggtcggcgc ttccttggtg aagggcgccg    2460
ccgtgggggg tttggagatg gaacatttga ttttgagagc gtggttgggt ttggtgaggg    2520
tttgatgaga gagagggagg gtggatctag taatgcgttt ggggaaggtg gggtgtgaag    2580
aggaagaaga gaatcgggtg gttctggaag cggtggccgc cattgtgttg tgtggcatgg    2640
ttatacttca aaaactgcac aacaagccta gagttagtac ctaaacagta aatttacaac    2700
agagagcaaa gacacatgca aaaatttcag ccataaaaaa agttataata gaatttaaag    2760
caaaagtttc atttttttaaa catatataca aacaaactgg atttgaagga agggattaat    2820 tccccctgctc aaagtttgaa ttcctattgt gacctatact cgaataaaat tgaagcctaa    2880
ggaatgtatg agaaacaaga aaacaaaaca aaactacaga caaacaagta caattacaaa    2940
attcgctaaa attctgtaat caccaaaccc catctcagtc agcacaaggc ccaaggttta    3000
ttttgaaata aaaaaaaagt gatttttattt ctcataagct aaaagaaaga aaggcaatta    3060
tgaaatgatt tcgactagat ctgaaagtcc aacgcgtatt ccgcagatat taaagaaaga    3120
gtagagtttc acatggatcc tagatggacc cagttgagga aaaagcaagg caaagcaaac    3180
cagaagtgca agatccgaaa ttgaaccacg gaatctagga tttggtagag ggagaagaaa    3240
agtaccttga gaggtagaag agaagagaag agcagagaga tatatgaacg agtgtgtctt    3300
ggtctcaact ctgaagcgat acgagtttag aggggagcat tgagttccaa tttataggga    3360
aaccgggtgg caggggtgag ttaatgacgg aaaagcccct aagtaacgag attggattgt    3420
gggttagatt caaccgtttg catccgcggc ttagattggg gaagtcagag tgaatctcaa    3480
ccgttgactg agttgaaaat tgaatgtagc aaccaattga gccaacccca gcctttgccc    3540
tttgattttg atttgtttgt tgcatacttt ttatttgtct tctggttctg actctctttc    3600
tctcgtttca atgccaggtt gcctactccc acaccactca caagaagatt ctactgttag    3660
tattaaatat ttttaatgt attaaatgat gaatgctttt gtaaacagaa caagactatg    3720
tctaataagt gtcttgcaac attttttaag aaattaaaaa aaatatattt attatcaaaa    3780
tcaaatgtat gaaaaatcat gaataatata attttataca ttttttttaaa aaatcttttta   3840 atttcttaat taatatctta aaaataatga ttaatattta acccaaaata attagtatga    3900
```

-continued

| | |
|---|---|
| ttggtaagga agatatccat gttatgtttg gatgtgagtt tgatctagag caaagcttac | 3960 |
| tagagtcgac cgatccgtcg acgg | 3984 |

<210> SEQ ID NO 11
<211> LENGTH: 3162
<212> TYPE: DNA
<213> ORGANISM: Artificial Sequence
<220> FEATURE:
<223> OTHER INFORMATION: synthesized DNA of PHP29882A

<400> SEQUENCE: 11

| | |
|---|---|
| cgcgccaagc ttttgatcca tgcccttcat ttgccgctta ttaattaatt tggtaacagt | 60 |
| ccgtactaat cagttactta ccttccccc atcataatta atcttggtag tctcgaatgc | 120 |
| cacaacactg actagtctct tggatcataa gaaaaagcca aggaacaaaa gaagacaaaa | 180 |
| cacaatgaga gtatcctttg catagcaatg tctaagttca taaaattcaa acaaaaacgc | 240 |
| aatcacacac agtggacatc acttatccac tagctgatca ggatcgccgc gtcaagaaaa | 300 |
| aaaaactgga ccccaaaagc catgcacaac aacacgtact cacaaggtg tcaatcgagc | 360 |
| agcccaaaac attcaccaac tcacccatc atgagccctc acatttgttg tttctaaccc | 420 |
| aacctcaaac tcgtattctc ttccgccacc tcatttttgt ttatttcaac acccgtcaaa | 480 |
| ctgcatgcca ccccgtggcc aaatgtccat gcatgttaac aagacctatg actataaata | 540 |
| gctgcaatct cggcccaggt tttcatcatc aagaaccagt tcaatatcct agtacaccgt | 600 |
| attaaagaat ttaagatata ctgcggccct aggtgagctg atttaagatt tatcaaaagt | 660 |
| tggggttaca aattttggaa gcttcagtgt ggaagtaata gacccagttt ctgactatct | 720 |
| ggagctattg gagacagtat ttgattttca gctaatcaga ggtcttcttt cacgtccaga | 780 |
| ttttaggttt atatttgatg ccatgcatgc agttactggt gcttatgcta aacccatctt | 840 |
| cgttgataaa ctcggtgcta gtctggattc aatttcaaat ggaatccctt ggaagatttt | 900 |
| tggacatggc catcctgatc ctaatctaac atatgcgaag gatcttgtcg acattctgta | 960 |
| tgctgaaaat ggacctgatt ttggagctgc cagtgatggg gatggtgata gaaatatgat | 1020 |
| tttaggaaga gtttctttg taactccttc agactctgta gcagttattg cagccaatgc | 1080 |
| aagagaagcg attccatact tcaagaacgg tgttaagggt cttgctcgat caatgccaac | 1140 |
| aagcggtgct ctggaccgtg ctgctaaaaa attgaacctc cctttctgag ctgatttaac | 1200 |
| gtacgcaggt aagtttctgc ttctaccttt gatatatata taataattat cattaattag | 1260 |
| tagtaatata atatttcaaa tattttttc aaaataaaag aatgtagtat atagcaattg | 1320 |
| cttttctgta gtttataagt gtgtatattt taatttataa cttttctaat atatgaccaa | 1380 |
| aacatggtga tgtgcaggtc ctgcaggtta aatcagctca gaaagggagg ttcaattttt | 1440 |
| tagcagcacg gtccagagca ccgcttgttg gcattgatcg agcaagaccc ttaacaccgt | 1500 |
| tcttgaagta tggaatcgct tctcttgcat tggctgcaat aactgctaca gagtctgaag | 1560 |
| gagttacaaa gaaacttctt cctaaaatca tatttctatc accatcccca tcactggcag | 1620 |
| ctccaaaatc aggtccattt tcagcataca gaatgtcgac aagatccttc gcatatgtta | 1680 |
| gattaggatc aggatggcca tgtccaaaat cttccaaagg gattccattt gaaattgaat | 1740 |
| ccagactagc accgagttta tcaacgaaga tgggtttagc ataagcacca gtaactgcat | 1800 |
| gcatggcatc aaatataaac ctaaaatctg gacgtgaaag aagacctctg attagctgaa | 1860 |
| aatcaaatac tgtctccaat agctccagat agtcagaaac tgggtctatt acttccacac | 1920 |
| tgaagcttcc aaaatttgta accccaactt ttgataaatc ttaaatcagc tcacctaggg | 1980 |

```
ccgcaagtat gaactaaaat gcatgtaggt gtaagagctc atggagagca tggaatattg    2040
tatccgacca tgtaacagta taataactga gctccatctc acttcttcta tgaataaaca    2100
aaggatgtta tgatatatta acactctatc tatgcacctt attgttctat gataaatttc    2160
ctcttattat tataaatcat ctgaatcgtg acggcttatg gaatgcttca atagtacaa     2220 aaacaaatgt gtactataag actttctaaa caattctaac cttagcattg tgaacgagac    2280
ataagtgtta agaagacata acaattataa tggaagaagt tgtctccat ttatatatta    2340 tatattaccc acttatgtat tatattagga tgttaaggag acataacaat tataaagaga    2400
gaagtttgta tccatttata tattatatac tacccattta tatattatac ttatccactt    2460
atttaatgtc tttataaggt ttgatccatg atatttctaa tattttagtt gatatgtata    2520
tgaaagggta ctatttgaac tctcttactc tgtataaagg ttggatcatc cttaaagtgg    2580
gtctatttaa ttttattgct tcttacagat aaaaaaaaaa ttatgagttg gtttgataaa    2640
atattgaagg atttaaaata ataataaata acatataata tatgtatata aatttattat    2700
aatataacat ttatctataa aaagtaaat attgtcataa atctatacaa tcgtttagcc     2760
ttgctggacg aatctcaatt atttaaacga gagtaaacat atttgacttt ttggttattt    2820
aacaaattat tatttaacac tatatgaaat tttttttttt atcagcaaag aataaaatta    2880
aattaagaag gacaatggtg tcccaatcct tatacaacca acttccacaa gaaagtcaag    2940
tcagagacaa caaaaaaaca agcaaaggaa atttttttaat ttgagttgtc ttgtttgctg   3000
cataatttat gcagtaaaac actacacata accccttttag cagtagagca atggttgacc   3060
gtgtgcttag cttctttat tttattttt tatcagcaaa gaataaataa aataaaatga     3120
gacacttcag ggatgtttca acaagcttgg atccgtcgac gg                       3162
```

<210> SEQ ID NO 12
<211> LENGTH: 9744
<212> TYPE: DNA
<213> ORGANISM: Artificial Sequence
<220> FEATURE:
<223> OTHER INFORMATION: synthesized DNA of PHP29959A
<220> FEATURE:
<221> NAME/KEY: misc_feature
<222> LOCATION: (4621)..(4621)
<223> OTHER INFORMATION: n is a, c, g, or t

<400> SEQUENCE: 12

```
cgcgccggta ccgggccccc cctcgaggtc gacggtatcg ataagcttga tatcgaattc     60
ctgcagcccg gggatccac tagttctaga gcggccgcg ccgtcgacgg atataatgag     120
ccgtaaacaa agatgattaa gtagtaatta atacgtacta gtaaaagtgg caaaagataa     180
cgagaaagaa ccaatttctt tgcattcggc cttagcggaa ggcatatata agctttgatt    240 atttattta gtgtaatgat ttcgtacaac caaagcattt atttagtact ctcacacttg     300
tgtcgcggcc gctagtcgac taagtcatca actattccaa gctacgtatt gggagtttg     360 tggagtacag caagatgata tacctagacg gtgatatcca agttttgac aacattgacc    420 acttgtttga cttgcctgat aactacttct atgcggtgat ggactgtttc tgtgagccaa    480
cttggggcca cactaaacaa tatcagatcg gttactgcca gcagtgcccc cataaggttc    540
agtggcccac tcactttggg cccaaacctc ctctctattt caatgctggc atgtttgtgt    600
atgagcccaa tttggctact taccgtgacc tccttcaaac agtccaagtc acccagccca    660
cttcctttgc tgaacaggat tttttgaaca tgtacttcaa ggacaaatat aggccaattc    720
```

```
ctaatgtcta caatcttgtg ctggccatgc tgtggcgtca ccctgagaac gttgagcttg    780
acaaagttaa agtggttcac tactgtgctg ctgggtctaa gccttggagg tacactggga    840
agtgactcga ggtcatcaat tactccaagc tacgtatttg ggagttcgtg gagtacaaga    900
agacgatata cctagacggt gacatccaag tatttggaaa catagaccac ttgtttgatc    960
tgcctgataa ttatttctat gcggtgatgg attgttctg cgagaagact tggagccaca   1020
cccctcagtt ccagattggg tactgccaac agtgccctga taaggttcaa tggccctctc   1080
actttggttc caaacctcct ctatatttca atgctggcat gtttgtttat gagcctaatc   1140
tcgacaccta ccgtgatctt ctccaaactg tccaactcac caagcccact tcttttgctg   1200
agcaggactt tctcaacatg tacttcaagg acaagtacaa gccaataccg aacatgtaca   1260
accttgtgct ggccatgttg tggcgtcacc ctgaaaatgt tgaacttgat aaagttcaag   1320
tggttcatta ctgtgctgct gggtctaagc cttggaggtt cactgggaag taactgcagg   1380
tcatcaacta ctccaagctc cgtatatggg agtttgtgga gtacagcaag atgatatact   1440
tggacggaga cattgaggta tatgagaaca tagaccacct atttgaccta cctgatggta   1500
acttttacgc tgtgatggat gtttctgcg agaagacatg gagtcacacc cctcagtaca   1560
aggtgggtta ctgccagcaa tgcccggaga aggtgcggtg gcccaccgaa ttgggtcagc   1620 cccttctct ttacttcaac gctggcatgt tcgtgttcga acccaacatc gccacctatc   1680
atgaccattt gaaaacggtg caagtcacca ctcccacctc gttcgctgaa caagatttct   1740
tgaacatgta cttcaaggac atttacaagc caatcccttt aaattacaat cttgtcctcg   1800
ccatgctgtg gcgccacccg gaaaacgtta aattagacca agtcaaggtt gttcactatt   1860
gcgcagcggg gtccaagcca tggagatata cggggaagta gcctaggacc tgcacatcac   1920
catgttttgg tcatatatta gaaaagttat aaattaaaat atacacactt ataaactaca   1980
gaaaagcaat tgctatatac tacattcttt tattttgaaa aaatatttg aaatattata   2040 ttactactaa ttaatgataa ttattatata tatatcaaag gtagaagcag aaacttacct   2100
gcgtacgcct aggctacttc cccgtatatc tccatggctt ggaccccgct gcgcaatagt   2160
gaacaacctt gacttggtct aatttaacgt tttccgggtg cgccacagc atggcgagga   2220 caagattgta atttaaaggg attggcttgt aaatgtcctt gaagtacatg ttcaagaaat   2280
cttgttcagc gaacgaggtg ggagtggtga cttgcaccgt tttcaatagg tcatgatagg   2340
tggcgatgtt gggttcgaac acgaacatgc cagcgttgaa gtaaagagaa gggggctgac   2400
ccaattcggt gggccaccgc accttctccg ggcattgctg gcagtaaccc accttgtact   2460
gaggggtgtg actccatgtc ttctcgcaga aacaatccat cacagcgtaa aagttaccat   2520
caggtaggtc aaataggtgg tctatgttct catataccct aatgtctccg tccaagtata   2580
tcatcttgct gtactccaca aactcccata tacggagctt ggagtagttg atgacctgca   2640
gttacttccc agtgaacctc caaggcttag acccagcagc acagtaatga accacttgaa   2700
ctttatcaag ttcaacattt tcagggtgac gccacaacat ggccagcaca aggttgtaca   2760
tgttcggtat tggcttgtac ttgtccttga agtacatgtt gagaaagtcc tgctcagcaa   2820
aagaagtggg cttggtgagt tggacagttt ggagaagatc acggtaggtg tcgagattag   2880
gctcataaac aaacatgcca gcattgaaat atagaggagg tttggaacca agtgagagg   2940 gccattgaac cttatcaggg cactgttggc agtacccaat ctggaactga ggggtgtggc   3000
tccaagtctt ctcgcagaaa caatccatca ccgcatagaa ataattatca ggcagatcaa   3060
acaagtggtc tatgtttcca aatacttgga tgtcaccgtc taggtatatc gtcttcttgt   3120
```

```
actccacgaa ctcccaaata cgtagcttgg agtaattgat gacctcgagt cacttcccag    3180
tgtacctcca aggcttagac ccagcagcac agtagtgaac cactttaact tgtcaagct    3240 caacgttctc agggtgacgc cacagcatgg ccagcacaag attgtagaca ttaggaattg    3300
gcctatattt gtccttgaag tacatgttca aaaaatcctg ttcagcaaag gaagtgggct    3360
gggtgacttg gactgtttga aggaggtcac ggtaagtagc caaattgggc tcatacacaa    3420
acatgccagc attgaaatag agaggaggtt tgggcccaaa gtgagtgggc cactgaacct    3480
tatgggggca ctgctggcag taaccgatct gatattgttt agtgtggccc caagttggct    3540
cacagaaaca gtccatcacc gcatagaagt agttatcagg caagtcaaac aagtggtcaa    3600
tgttgtcaaa aacttggata tcaccgtcta ggtatatcat cttgctgtac tccacaaact    3660
cccaaatacg tagcttggaa tagttgatga cttagtcgac tagcggccgc ttgggggct    3720 atggaagact ttcttagtta gttgtgtgaa taagcaatgt tgggagaatc gggactactt    3780
ataggatagg aataaaacag aaaagtatta agtgctaatg aaatatttag actgataatt    3840
aaaatcttca cgtatgtcca cttgatataa aaacgtcagg aataaaggaa gtacagtaga    3900
atttaaaggt actctttta tatatacccg tgttctcttt ttggctagct agttgcataa    3960
aaaataatct atatttttat cattatttta aatatcttat gagatggtaa atatttatca    4020
taattttttt tactattatt tattatttgt gtgtgtaata catatagaag ttaattacaa    4080
attttattta cttttcatt attttgatat gattcaccat taatttagtg ttattattta    4140
taatagttca tttaatctt tttgtatata ttatgcgtgc agtactttt tcctacatat    4200 aactactatt acattttatt tatataatat ttttattaat gaattttcgt gataatatgt    4260
aatattgttc attattattt cagatttttt aaaaatattt gtgttattat ttatgaaata    4320
tgtaattttt ttagtatttg attttatgat gataaagtgt tctaaattca aagaagggg    4380 gaaagcgtaa acattaaaaa acgtcatcaa acaaaaacaa aatcttgtta ataaagataa    4440
aactgtttgt tttgatcact gttatttcgt aatataaaaa cattatttat atttatattg    4500
ttgacaacca aatttgccta tcaaatctaa ccaatataat gcatgcgtgg caggtaatgt    4560
actaccatga acttaagtca tgacataata aaccgtgaat ctgaccaatg catgtaccta    4620
nctaaattgt atttgtgaca cgaagcaaat gattcaattc acaatggaga tgggaaacaa    4680
ataatgaaga acccagaact aagaaagctt ttctgaaaaa taaaataaag gcaatgtcaa    4740
aagtatactg catcatcagt ccagaaagca catgatattt tttatcagt atcaatgcag    4800 ctagttttat tttacaatat cgatatagct agtttaaata tattgcagct agatttataa    4860
atatttgtgt tattatttat catttgtgta atcctgtttt tagtatttta gtttatatat    4920
gatgataatg tattccaaat ttaaagaag ggaaataaat ttaaacaaga aaaaagtca    4980 tcaaacaaaa acaaatgaa agggtggaaa gatgttacca tgtaatgtga atgttacagt    5040
atttctttta ttatagagtt aacaaattaa ctaatatgat tttgttaata atgataaaat    5100
atttttttta ttattatttc ataatataaa aatagtttac ttaatataaa aaaaattcta    5160
tcgttcacaa caaagttggc cacctaattt aaccatgcat gtacccatgg accatattag    5220
gtaaccatca aacctgatga agagataaag agatgaagac ttaagtcata acacaaaacc    5280
ataaaaaaca aaaatacaat caaccgtcaa tctgaccaat gcatgaaaaa gctgcaatag    5340
tgagtggcga cacaaagcac atgattttct tacaacggag ataaaccaa aaaaatattt    5400 catgaacaac ctagaacaaa taaagctttt atataataaa tatataaata aataaaggct    5460
```

```
atggaataat atacttcaat atatttggat taaataaatt gttggcgggg ttgatatatt    5520
tatacacacc taaagtcact tcaatctcat tttcacttaa cttttatttt ttttttcttt    5580
ttatttatca taaagagaat attgataata tactttttaa catattttta tgacattttt    5640
tattggtgaa aacttattaa aaatcataaa ttttgtaagt tagatttatt taaagagttc    5700
ctcttcttat tttaaatttt ttaataaatt tttaaataac taaaatttgt gttaaaaatg    5760
ttaaaaaagt gtgttattaa cccttctctt cgaggatcca agcttggcgc gggccgccac    5820
cgcggtgggg tcgactctag taagctttgc tctagatcaa actcacatcc aaacataaca    5880
tggatatctt ccttaccaat catactaatt attttgggtt aaatattaat cattattttt    5940
aagatattaa ttaagaaatt aaaagatttt ttaaaaaaat gtataaaatt atattattca    6000
tgatttttca tacatttgat tttgataata aatatatttt ttttaatttc ttaaaaaatg    6060
ttgcaagaca cttattagac atagtcttgt tctgtttaca aaagcattca tcatttaata    6120
cattaaaaaa tatttaatac taacagtaga atcttcttgt gagtggtgtg ggagtaggca    6180
acctggcatt gaaacgagag aaagagagtc agaaccagaa gacaaataaa aagtatgcaa    6240
caaacaaatc aaaatcaaag ggcaaaggct ggggttggct caattggttg ctacattcaa    6300
ttttcaactc agtcaacggt tgagattcac tctgacttcc ccaatctaag ccgcggatgc    6360
aaacggttga atctaaccca caatccaatc tcgttactta ggggcttttc cgtcattaac    6420
tcaccctgc caccggttt ccctataaat tggaactcaa tgctcccctc taaactcgta    6480
tcgcttcaga gttgagacca agacacactc gttcatatat ctctctgctc ttctcttctc    6540
ttctacctct caaggtactt tcttctccc tctaccaaat cctagattcc gtggttcaat    6600
ttcggatctt gcacttctgg tttgcttttgc cttgcttttt cctcaactgg gtccatctag    6660
gatccatgtg aaactctact ctttctttaa tatctgcgga atacgcgttg gactttcaga    6720
tctagtcgaa atcatttcat aattgccttt ctttctttta gcttatgaga aataaaatca    6780
ctttttttt atttcaaaat aaaccttggg ccttgtgctg actgagatgg ggtttggtga    6840
ttacagaatt ttagcgaatt ttgtaattgt acttgtttgt ctgtagtttt gttttgtttt    6900
cttgtttctc atacattcct taggcttcaa ttttattcga gtataggtca caataggaat    6960
tcaaactttg agcaggggaa ttaatccctt ccttcaaatc cagtttgttt gtatatatgt    7020
ttaaaaaatg aaacttttgc tttaaattct attataactt ttttatggc tgaaattttt    7080
gcatgtgtct ttgctctctg ttgtaaattt actgtttagg tactaactct aggcttgttg    7140
tgcagttttt gaagtataac catgccacac aacacaatgg cggccaccgc ttccagaacc    7200
acccgattct cttcttcctc ttcacacccc accttcccca aacgcattac tagatccacc    7260
ctccctctct ctcatcaaac cctcaccaaa cccaaccacg ctctcaaaat caaatgttcc    7320
atctccaaac cccccacggc ggcgcccttc accaaggaag cgccgaccac ggagcccttc    7380
gtgtcacggt tcgcctccgg cgaacctcgc aagggcgcgg acatccttgt ggaggcgctg    7440
gagaggcagg gcgtgacgac ggtgttcgcg taccccggcg gtgcgtcgat ggagatccac    7500
caggcgctca cgcgctccgc cgccatccgc aacgtgctcc cgcgccacga gcagggcggc    7560
gtcttcgccg ccgaaggcta cgcgcgttcc tccggcctcc ccggcgtctg cattgccacc    7620
tccggccccg gcgccaccaa cctcgtgagc ggcctcgccg acgctttaat ggacagcgtc    7680
ccagtcgtcg ccatcaccgg ccaggtcgcc cgccggatga tcggcaccga cgccttccaa    7740
gaaaccccga tcgtggaggt gagcagatcc atcacgaagc acaactacct catcctcgac    7800
gtcgacgaca tccccgcgt cgtcgccgag gctttcttcg tcgccacctc cggccgcccc    7860
```

```
ggtccggtcc tcatcgacat tcccaaagac gttcagcagc aactcgccgt gcctaattgg    7920
gacgagcccg ttaacctccc cggttacctc gccaggctgc ccaggccccc cgccgaggcc    7980
caattggaac acattgtcag actcatcatg gaggcccaaa agcccgttct ctacgtcggc    8040
ggtggcagtt tgaattccag tgctgaattg aggcgctttg ttgaactcac tggtattccc    8100
gttgctagca ctttaatggg tcttggaact tttcctattg gtgatgaata ttcccttcag    8160
atgctgggta tgcatggtac tgtttatgct aactatgctg ttgacaatag tgatttgttg    8220
cttgcctttg gggtaaggtt tgatgaccgt gttactggga agcttgaggc ttttgctagt    8280
agggctaaga ttgttcacat tgatattgat tctgccgaga ttgggaagaa caagcaggcg    8340
cacgtgtcgg tttgcgcgga tttgaagttg gccttgaagg gaattaatat gattttggag    8400
gagaaaggag tggagggtaa gtttgatctt ggaggttgga gagaagagat taatgtgcag    8460
aaacacaagt ttccattggg ttacaagaca ttccaggacg cgatttctcc gcagcatgct    8520
atcgaggttc ttgatgagtt gactaatgga gatgctattg ttagtactgg ggttgggcag    8580
catcaaatgt gggctgcgca gttttacaag tacaagagac cgaggcagtg gttgacctca    8640
gggggtcttg gagccatggg ttttggattg cctgcggcta ttggtgctgc tgttgctaac    8700
cctggggctg ttgtggttga cattgatggg gatggtagtt tcatcatgaa tgttcaggag    8760
ttggccacta taagagtgga gaatctccca gttaagatat tgttgttgaa caatcagcat    8820
ttgggtatgg tggttcagtt ggaggatagg ttctacaagt ccaatagagc tcacacctat    8880
cttggagatc cgtctagcga gagcgagata ttcccaaaca tgctcaagtt tgctgatgct    8940
tgtgggatac cggcagcgcg agtgacgaag aaggaagagc ttagagcggc aattcagaga    9000
atgttggaca cccctggccc ctaccttctt gatgtcattg tgccccatca ggagcatgtg    9060
ttgccgatga ttcccagtaa tggatccttc aaggatgtga taactgaggg tgatggtaga    9120
acgaggtact gattgcctag accaaatgtt ccttgatgct tgttttgtac aatatatata    9180
agataatgct gtcctagttg caggatttgg cctgtggtga gcatcatagt ctgtagtagt    9240
tttggtagca agacatttta ttttcctttt atttaactta ctacatgcag tagcatctat    9300
ctatctctgt agtctgatat ctcctgttgt ctgtattgtg ccgttggatt ttttgctgta    9360
gtgagactga aaatgatgtg ctagtaataa tatttctgtt agaaatctaa gtagagaatc    9420
tgttgaagaa gtcaaaagct aatggaatca ggttacatat caatgttttt cttttttttag   9480 cggttggtag acgtgtagat tcaacttctc ttggagctca cctaggcaat cagtaaaatg    9540
catattcctt ttttaacttg ccatttattt acttttagtg gaaattgtga ccaatttgtt    9600
catgtagaac ggatttggac cattgcgtcc acaaaacgtc tcttttgctc gatcttcaca    9660
aagcgatacc gaaatccaga gatagttttc aaaagtcaga aatggcaaag ttataaatag    9720
taaaacagaa tagatgctgt aatc                                           9744
```

NON-DESTRUCTIVE ASSAY FOR SOYBEAN SEEDS USING NEAR INFRARED ANALYSIS

BACKGROUND

Soybeans are the world's foremost provider of vegetable protein and oil. Soybean oil is used in food and industrial products. Soybean flakes remaining after the removal of oil can be processed into various edible soy protein products, or used to produce soybean meal for animal feeds.

Soybean seed reserves can be repartitioned through plant research and breeding techniques. Analytical techniques facilitate research by permitting assessment of the composition of the soybean seed, soybean flakes and soybean meal.

SUMMARY

Non-destructive methods for accurately measuring the amount of a sucrosyl-oligosaccharide, such as stachyose, or a combination of stachyose and raffinose, in a soybean seed are provided which include steps of directing near infrared light from a light source onto a soybean seed to form modified light from the soybean seed, receiving the modified light in an imaging device, and measuring the amount of a sucrosyl-oligosaccharide in the soybean seed based on the received modified light. The amount of the sucrosyl-oligosaccharide can be measured to an accuracy that is within 0.2 wt. %, 0.3 wt. %, 0.4 wt. %, 0.5 wt. %, 0.6 wt. %, 0.7 wt. %, 0.8 wt. %, 0.9 wt. %, 1 wt. %, 1.1 wt. %, 1.2 wt. %, 1.3 wt. %, 1.4 wt. %, or 1.5 wt. % of the amount measured using a standard reference analytical method. Following measurements, the seed can be optionally transported to a first or second location depending on whether the amount of sucrosyl-oligosaccharide measured is above or below a threshold value. The threshold value for stachyose can be selected to be, for example, 1 wt. %, 0.9 wt. %, 0.8 wt. %, 0.7 wt. %, 0.6 wt. %, 0.5 wt. %, 0.4 wt. %, 0.3 wt. %, 0.2 wt. % or 0.1 wt. %.

The methods can be used with a single seed or a plurality of seeds in a batch and the method steps can be repeated multiple times. The sucrosyl-oligosaccharide can be accurately measured in at least 80%, 85%, 90%, 95%, 96%, 97%, 98% or 99% of the measurements taken. The methods are non-destructive and preserve the viability of the seed or otherwise permit other compositional analyses or processing to be undertaken. For stachyose measurements, the imaging device can be calibrated using a plurality of soybean seeds having variable stachyose contents falling in a range that includes values of less than 0.1 wt. %, 0.2 wt. %, or 0.3 wt. % stachyose and more than 4.5 wt. %, 5 wt. % or 5.5 wt. % stachyose. In some embodiments, the seed is genetically modified to overexpress a diglyceride acyltransferase.

Provided are methods for measuring stachyose in a population of soybean seeds by directing near infrared light from a light source onto a first and second subsample of a population of soybean seeds to form a first and second modified light, which is received in an imaging device and used to measure the amount of a sucrosyl-oligosaccharide in the first and second subsamples. The first and second subsamples are separated when the amount of stachyose measured differs by at least 1 percentage point between the subsamples and are combined when the amount of stachyose differs by less than 0.2 percentage points between the first and second subsamples. The population can, for example include genetically modified and unmodified soybean seeds, such as a modified diacylglycerol transferase and the oil content of the modified beans may be at least 1 percentage point higher than of the unmodified soybean seeds.

Provided are methods for processing soybean seeds which have been genetically modified to contain high oil, high protein, or a combination thereof compared with unmodified soybean seeds which include the steps of directing near infrared light from a light source onto a sample comprising or being a soybean seed to form modified light from the soybean seed which is received in an imaging device and used to measure the amount of a sucrosyl-oligosaccharide, such as stachyose or a combination of stachyose and raffinose, in the sample. The method steps can be repeated for at least 10 samples and soybean seeds above a threshold value, which indicates high oil, high protein, or a combination thereof, can be separated from soybean seeds below the threshold value. The method is sufficiently robust such that at least 90% of the soybean seeds below the threshold value are modified soybean seeds or at least 90% of the seeds above the threshold value are unmodified soybean seeds. The amount of sucrosyl-oligosaccharide can be measured to an accuracy that is within 0.2 wt. %, 0.3 wt. %, 0.4 wt. %, 0.5 wt. %, 0.6 wt. %, 0.7 wt. %, 0.8 wt. %, 0.9 wt. %, 1 wt. %, 1.1 wt. %, 1.2 wt. %, 1.3 wt. %, 1.4 wt. %, or 1.5 wt. % of the amount measured using a standard reference analytical method. In some embodiments, at least one of the modified seeds that is separated is grown and crossed with the same or a different soybean plant to produce progeny seed. The progeny seed can be grown and crossed with another plant having a genetic modification, such as a recombinant construct incorporated into its genome, to produce further progeny seed, the genetic modification optionally providing one or more traits such as herbicide tolerance, disease resistance, insect resistance, increased grain yield, increased nutritional content, increased growth rate, enhanced stress tolerance, altered maturity. The method can include an initial step of separating the sample comprising the soybean seed from the plurality of seeds such as in an automated method. The method can include the step of measuring the amount of oil in the seed based on the received modified light.

Provided are methods for processing soybean seeds which include seeds genetically modified to contain increased oil and increased protein and unmodified soybean seeds. The methods include the steps of directing near infrared light from a light source onto a sample comprising a soybean seed to form modified light from the soybean seed which is received in an imaging device and used to measure the amount of a sucrosyl-oligosaccharide, such as stachyose or a combination of stachyose and raffinose, in the soybean seed. The method steps are repeated for at least 100 samples or seeds. The amount of sucrosyl-oligosaccharide measured below a threshold value indicates high oil and high protein in the soybean seed and the measurements taken are such that at least 90% of the soybean seeds below the threshold value are the modified soybean seeds or at least 90% of the seeds above the threshold value are the unmodified soybean seeds. The seeds above the threshold value can differ by a least 1 wt. % stachyose from the seeds below the threshold value. The seeds can be further processed for removal of oil and production of soy flakes or meal.

Provided are methods for measuring the amount of a sucrosyl-oligosaccharide, such as stachyose, or a combination of stachyose and raffinose, in soybean meal or soybean flakes. The methods include the steps of directing near infrared light from a light source onto a soybean meal sample to form modified light from the soybean meal sample which is received in an imaging device and used to measure the amount of a sucrosyl-oligosaccharide in the soybean meal sample. The amount of the sucrosyl-oligosaccharide can be measured to an accuracy that is within 0.1 wt. %, 0.2 wt. %, 0.3 wt. %, 0.4 wt. %, 0.5 wt. %, 0.6 wt. %, 0.7 wt. %, 0.8 wt. %, 0.9 wt. %, 1 wt. %, 1.1 wt. %, 1.2 wt. %, 1.3 wt. %, 1.4 wt. %, or 1.5 wt. % of the amount measured using a standard reference analytical method.

DETAILED DESCRIPTION

Systems and methods for the sampling of soybean seeds and measurement of soybean seed components are provided, which permit individual seed analysis, soybean meal, flake or powder analysis, or analysis of bulk seeds in an accurate, non-destructive and efficient manner. The term "soybean" refers to the species *Glycine max, Glycine soja*, or any species or line that is sexually cross compatible with *Glycine max*. Unless indicated to the contrary, seed as used herein means soybean seed. Following analysis, the soybean seeds can be grown and allowed to self or be crossed with genetically different soybean plants to produce progeny seed that can be used in a plant breeding program. The systems and methods further permit efficient processing of the soybeans according to their composition, such as to produce oil and protein flakes or meal. The analysis includes accurate measurement of one or more sucrosyl-oligosaccharides. A sucrosyl-oligosaccharide is generally understood to be a short-chain, non-digestible oligosaccharide such as stachyose, raffinose and verbascose. Because verbascose and other minor sucrosyl-oligosaccharides are present in very low amounts, as used in this application, a sucrosyl-oligosaccharide means one or more of stachyose and raffinose.

Destructive analytical methods for the measurement of seed components such as oil, fatty acids, protein and sucrosyl-oligosaccharides are those which directly measure the component including steps such as powdering the material, extraction of the sucrosyl-oligosaccharide, and detection of the amount or concentration of sucrosyl-oligosaccharide using chromatographic methods. Certain of these methods are accredited by professional associations (e.g., American Oil Chemists Society (AOCS); the American Association of Analytical Chemists (AOAC); American Association of Cereal Chemists (AACC) or international standards accreditation agencies, e.g., The Codex Alimentarius, International Organization for Standards (ISO) and the International Union of Pure and Applied Chemistry (IUPAC)). While accurate, such methods are time consuming and typically require a large sample size; for example, 60 g or more of whole soybeans, a portion of which may be used to determine the moisture contents of the samples, to enable compositional reporting on a defined moisture basis. For example, an accredited method for oil content is AOCS Official Method Ba 3-38 which gravimetrically measures the oil content of powdered seed material after extraction with petroleum ether. An example of an accredited method for protein content is AOAC 990.03 or AOCS Ba 4e-93 which determine the protein content of ground soybean powders by combustion analysis.

Destructive analytical methods for analysis of raffinose and stachyose can be based on methods that have been validated for quantitation of simple sugars in cereal products (e.g., AACC Method 80-04 Determination of Simple Sugars (fructose, glucose, sucrose, maltose and lactose) in Cereal Products-HPLC Method; AOAC Official Method 982.14 Glucose, Fructose, Sucrose, and Maltose in Presweetened to Cereals; Black, L. T., and Glover, J. D., 1980. A Simple and rapid HPLC analysis of sugars in soybeans and the factors affecting their standardization. Journal of the American Oil Chemists Society 1980; 143. However, a harmonized cross-validated method is not available.

Methods, systems and devices provided herein measure the amount of one or more sucrosyl-oligosaccharides in a soybean seed using non-destructive methods to an accuracy that is representative of the amount measured using standard reference analytical methods. The term "accuracy" refers to the degree to which the result of a measurement, calculation, or specification conforms to the correct value, a standard, or reference value. Useful examples of such values which may be achieved are accuracies within at least 25%, 20%, 19%, 18%, 17%, 16%, 15%, 14%, 13%, 12%, 11%, 10%, 9%, 8%, 7%, 6%, 5%, 4%, 3%, 2%, or 1% of the amount measured using a standard reference analytical method as described herein, such as by weight. The accurate measurements may be achieved for at least 75%, 80%, 85%, 90%, 95%, 96%, 97%, 98%, 99%, 99.5%, or 99.9% of a population of seeds, a plurality of seeds, a plurality of individual or a plurality of seed samples measured. The size of the population or plurality of seeds can be at least 1, 2, 3, 4, 5, 10, 15, 20, 25, 30, 35, 40, 45, 50, 60, 70, 80, 90, 100, 150, 200, 250, 300, 400, 500, 750, 1000, 2000, 3000, 5000, 10000, 100000, or 1,000,000 individual seeds or seed batches. The term "reference chemistry" refers to the benchmark values obtained for the measurements of the compositions analyzed herein, using standard reference analytical methods. As used herein, the "standard reference analytical method" used for measuring stachyose, raffinose or a combination thereof is a chromatographic (wet-chemistry) technique performed as follows. One of skill in the art will understand that certain substitutions in the components and steps used in the following methods may be made without affecting the results of the analysis:

Grinding:

Analysis is performed on soybeans, ground into fine powders with a particle size ranging between 0.5 to 0.9 mm. For single soybean seed, grinding is performed in Spex Certiprep ½×2" polycarbonate vials with cap (cat #3116PC). A ⅜" stainless steel ball bearing is used to pulverize the seed using a Spex Certiprep 2000 Geno/Grinder at 1500 strokes/min for three, 30 second bursts, with a 1-minute rest between each cycle. Samples are retained in the grinding vial at room temperature, in the dark, to minimize moisture loss prior to further analysis.

For bulk samples, approximately seventy-five gram batches of beans are ground in a Foss Knifetec 1095 grinder (commercially available from FOSS North America, Eden Prairie, Minn.). The grinding chamber is cooled prior to and during the process by a circulating chiller set to 14° C. Samples are ground for 6×10 second bursts using a standard rotor blade. At the conclusion of each 10 second grinder burst the chamber is opened and the powder in the chamber is loosened and any material adhering to the chamber wall is returned to the center of the chamber, using a small rubber spatula. After grinding the powders are quantitatively recovered from the chamber and transferred to plastic specimen cups fitted with airtight lids (Fisher Brand, part number 14828321) to ensure minimal moisture loss prior to analysis. The sample chamber and blade are cleaned thoroughly with a soft brush and pneumatic air prior to introduction of the next sample. Sample cups were stored at room temperature in the dark prior to further analysis. Ground samples were not sieved or otherwise treated prior to further analysis, this ensured that the sub-aliquot analyzed is fully representative of the original bulk sample and allows small subsamples to be used to provide data that is representative of the whole.

Powder Moisture Content Determination:

The moisture contents of the ground soybean powders are determined according to AOCS Official Method Ba 2a-38, which can be modified for small samples as described below. In order to standardize analytical results for moisture content, 100-200 mg samples are weighed (recorded to an accuracy of 0.1 mg) into 13×100 mm sample tubes (VWR part number 53283-800). The samples are placed in a forced draft oven, set to 130° C. for two hours and are then allowed to equilibrate to room temperature, in a desiccator, prior to reweighing. Moisture contents are calculated according to the following formula:

$$\text{Moisture} = \frac{(\text{wt. tube} + \text{tissue as is} - \text{wt. tube}) - (\text{wt. tube} + \text{tissue dry} - \text{wt. tube})}{(\text{wt. tube} + \text{tissue as is} - \text{wt. tube})} \times 100$$

Moisture contents are used to adjust analytical results to a common moisture content using the following formula:

$$\text{Analyte at desired moisture content, \%} = \frac{F(100 - \% \text{ moisture content desired})}{(100 - \% \text{ moisture content of ground sample})}$$

Where F is the measured wt. % of the analyte in the ground sample.

Extraction of Soluble Carbohydrates:

Prior to carbohydrate analysis samples are de-fatted as follows: Weigh powdered sample (approximately 20-30 mg; to an accuracy of 0.1 mg) into 13×100 mm tube (with Teflon® lined cap; VWR (53283-800)) and record weight. Add 2 mL Heptane, vortex and place into an ultrasonic bath (VWR Scientific Model 750D) at 60° C. for 15 min at full sonification-power (~360W). Centrifuge for 5 min at 1700×g at room temperature. Decant the supernatant to a clean 13×100 mm glass tube; this sample is used to determine fatty acid profiles of the extracted oil. Add 1 mL acetone to the de-fatted pellet, vortex mix to disperse the material into the acetone and dry in a SpeedVac (Thermo Fisher Scientific 275 Aiken Road, Ashville, N.C. 28804). To the dry pellet add 2 mL of 80% ethanol. Vortex to break up pellet as much as possible. Extract on sonicator for 15 min at 60° C. Centrifuge for 5 min at 1700×g. Transfer supernatant to a clean 13×100 mm tube. Repeat the ethanol extraction two more times, combining all of the supernatants. Add 100 µL of phenyl-β-D glucopyranoside internal standard (phenyl-β-D glucopyranoside stock 0.5000+/−0.0010 g in 100 ml water) to the combined supernatant. Dry the extract in the SpeedVac and analyze for soluble carbohydrates as described below. Add 1 ml acetone to the extracted pellets and dry in the SpeedVac.

Starch Digestion and Extraction:

The starch digestion is performed directly on the acetone dried pellets from soluble carbohydrate extraction. Add 100 units of α-Amylase (α-amylase; Heat Stable from *Bacillus licheniformis* Sigma-Aldrich A-4551) in 0.9 mL 50 mM MOPS (3-(N-Morpholino) propane sulfonic acid) buffer pH 7.0, containing 5 mM $CaCl_2$ and mix. Place tubes into a heating block at 90° C. for 75 minutes. Mix several times during hydrolysis. Allow the tubes to cool to room temperature and add 5 units of Amyloglucosidase (commercially available from Roche 11 202 367 001) in 0.6 mL of 285 mM acetate buffer, pH 4.5 and incubate in a reciprocating water bath at 55° C. for 15-18 hours. Remove rack of tubes and bring to room temperature. Add 4.5 mL of absolute ethanol to each tube, to attain a final ethanol concentration 80% and vortex mix. Extract on sonicator for 15 min at 60° C. Centrifuge 5 min at 1700×g and decant supernatant to a 13×100 mm tube and immediately place tube in SpeedVac to reduce the volume. Extract pellet a further 2 times with 2 mL 80% ethanol, combining supernatant with above each time. Add 100 µL of phenyl-β-D glucopyranoside (see above) to the combined supernatant before it is fully dry. Once the extract in the SpeedVac is dry analyze for soluble carbohydrates as described below.

Total Soluble Carbohydrate Derivatization and Analysis:

The dried samples from the soluble and starch extractions described above along with sets of sugar standard mixtures (containing; pinitol, sorbitol, fructose, glucose, myo-inositol, sucrose, raffinose and stachyose; at 0, 0.05, 0.1, 0.5, 1.00, 2.00, and 3.00 mg/tube; each containing the same amount (0.5 mg) of phenyl-β-D glucopyranoside internal standard) were solubilized in 1 ml anhydrous pyridine (Sigma-Aldrich P57506) containing 30 mg/ml of hydroxylamine HCl (Sigma-Aldrich 159417). Samples were placed on an orbital shaker (350 rpm) overnight and were then heated for 1 hr (75° C.) with vigorous vortex mixing applied every 15 min. After cooling to room temperature 1 ml hexamethyldisilazane (Sigma-Aldrich H-4875) and 100 µL trifluoroacetic acid (Sigma-Aldrich T-6508) are added. The samples are vortex mixed and the precipitates are allowed to settle prior to transferring the supernatants to GC sample vials.

Samples are analyzed on an Agilent 6890 gas chromatography system fitted with a DB-17MS capillary column (30 m×0.32 mm×0.25 um film). Inlet and detector temperatures are both 2750. After injection (2 µL, 20:1 split) the initial column temperature (150° C.) was increased to 1800 at a rate 3° C./min and then at 25° C./min to a final temperature of 3200. The final temperature is maintained for 10 min. Hydrogen gas is used as the carrier at a linear velocity of 51 cm/sec. Detection is by flame ionization. A 1 m length of plain 0.320 mm capillary tube (Agilent; 160-2325-5) is inserted between the inlet and the analytical column to act as a guard column. The two column sections are connected using a push-fit connector. Prior to all analytical runs three injections of a standard mixture containing 3 mg of each sugar is made to passivate the chromatography system. This process was found to enable full recovery of stachyose from the analytical samples, especially as the column aged. Ultra-Inert Inlet Liners (Agilent; 5190-3164) are used and are routinely changed based on indications of loss in stachyose recovery from the lowest concentration standard.

Data analysis is performed using Agilent ChemStation software. Each sugar is quantified relative to its own calibration curve, after dividing each individual peak by the area of the internal standard in each sample and standard. Final carbohydrate concentrations are expressed corrected for moisture content (see above). Residual sucrose, raffinose and stachyose recovered in the starch digestions are included in the total values reported for each sugar.

Soybean samples with a wide range in the amount sucrosyl-oligosaccharide, such as raffinose, stachyose, or a combination thereof can be accurately measured using these standard reference chemistry methods, facilitating the development spectroscopic techniques for accurate non-destructive measurements.

As used herein, the standard reference analytical method used for measuring the moisture content of whole beans is AOCS Official Method Ac 2-41, which measures the weight loss of a sample after a defined period in a forced draft oven heated to 130° C.

As used herein, the standard reference analytical method used for measuring the moisture content of soybean powders is AOCS Official Method Ba 2a-38, which measures the weight loss of a sample after a defined period in a forced draft oven heated to 130° C.

As used herein, the standard reference analytical method used for measuring oil is AOCS Official Method Ba 3-38 which gravimetrically measures the oil content of powdered seed material after extraction with petroleum ether.

As used herein, the standard reference analytical method used for measuring protein content is AOCS Ba 4e-93 which determines the protein content of ground soybean powders by combustion analysis.

As used herein, the standard reference analytical method used for measuring PROIL is the addition of the oil and protein contents determined by the standard reference analytical methods defined above.

As used herein, the standard reference analytical method used for determining fatty acid profiles is AOCS Official Method Ce 1e-91 on methyl esters derived from oil samples extracted from soybean powders.

The amount of sucrosyl-oligosaccharide such as stachyose, raffinose or a combination thereof in intact, whole, single or pooled soybean seeds can be measured using optical interrogation devices employing near infrared spectroscopy to an amount that is within at least 15%, 14%, 13%, 12%, 11%, 10%, 9%, 8%, 7%, 6%, 5%, 4%, 3%, 2%, or 1% of the amount measured using the standard reference analytical method described herein. Accuracy can be contrasted with precision, which refers to the closeness of two or more measurements to each other. Accurate and precise measurements of sucrosyl-oligosaccharides are achievable according to methods described herein. Precision with respect to the composition of soybean seed sample under analysis refers how closely replicate measurements of the same sample result in similar concentration or amounts being measured each time. Accuracy, with respect to the composition of soybean seed sample under analysis refers to the measured concentration or measured amount of the component of interest being similar to or the same as that obtained when running the standard reference analytical method on the same sample.

The accuracy obtained using the methods described herein is reproducible across multiple seeds or seed samples and facilitates high-throughput assessment on the composition of soybean seeds. For example, if a population of at least 10, 20, 50, 100, 250, 500, 1,000, 5,000, 10,000, 1,000,000, or 1,000,000 soybean seeds are measured using individual single-seed analysis, the amount of raffinose or stachyose may be accurately determined to within parameters described herein for at least 75%, 80%, 85%, 90%, 91%, 92%, 93%, 94%, 95%, 96%, 97%, 98%, 99%, 99.5% or 99.9% of the population of seeds.

Near Infrared Spectroscopy (NIRS) is a non-destructive tool for analyzing seed composition, with measurements based on the absorption of light energy (about 780 to 2500 nm) by H2O, C—C, C—H, O—H, N—H, S—H and C═O bonds in the organic constituents of the materials being analyzed. The present disclosure provides methods which are based on NIRS and on the absorption of light energy, in the near-infrared spectrum range (780 to 2500 nm), in the organic constituents of the materials being analyzed. Near infrared reflectance (NIR) and near infrared transmittance (NIT) light spectra can be collected and used. For example, methods described herein can be carried out as single-seed NIR (SS-NIR), bulk NIT or FT-NIR. The absorption of the light energy is proportional to the concentration of the constituent of interest and the modified light comprising one or more of transmitted and reflected light spectra from the seed can be converted to accurately measure the amounts or concentrations of the constituent of interest, such as a sucrosyl-oligosaccharide. "Modified light" as used in the context of this disclosure means light that is transmitted (transmitted light) and/or reflected (reflected light) from a seed or other object such as soybean meal or defatted soybean flakes after receiving light from a light source. Transflected light is a combination of reflected and transmitted light and is included in modified light.

In some embodiments, such as when single seed NIR (SS-NIR) is used, a suitable spectral range for a sucrosyl-oligosaccharide such as stachyose includes one or more values at or about 850 nm, 866 nm, 880 nm, 890 nm, 902 nm, 910 nm, 920 nm, 930 nm, 944 nm, 952 nm, 964 nm, 978 nm, 990 nm, 1004 nm, 1016 nm, 1032 nm, and 1042 nm, such as one or more values falling within 850-852 nm, 862-868 nm, 876-884 nm, 888-892 nm, 900-904 nm, 908-912 nm, 918-922 nm, 930-934 nm, 940-944 nm, 950-954 nm, 962-968 nm, 976-982 nm, 988-996 nm, 1000-1008 nm, 1012-1020 nm, 1026-1036 nm and 1040-1046 nm. In some embodiments, such as when FT-NIR is used, a suitable spectral region for a sucrosyl-oligosaccharide such as stachyose includes values at or about 1157-1283 nm and 1437-2254 nm. In some embodiments, such as when NIT is used for whole soybeans, a suitable spectral range for a sucrosyl-oligosaccharide such as stachyose includes values at or about 918, 930, 940, 950, 964, 980, and 996 nm.

In some embodiments, spectrometers are used to collect spectra from samples of soybeans, such as single seeds (e.g., SS-NIR), batches of seed from a single plant (e.g., FT-NIR), bulk samples from a field plot (e.g., NIT) or protein compositions such as protein meal and defatted soybean flakes (NIR). Protein meal can be produced by extracting oil from dried cleaned soybeans to produce dried defatted soy flakes, and processing the defatted soy flakes to produce soybean meal. Measurements taken are compared to the standard reference analytical method for samples sizes (single seeds or bulk samples). In some embodiments a diverse array of soybean samples grown in different seasons and different environments that display a wide range in the concentrations of the components are used to generate calibrations that provide for reliable and accurate measurements of the components.

In the methods provided, the conversion from modified light spectra from the soybean to the concentration of the constituent of interest is determined by a referencing to spectra from seeds where the constituent of interest has been measured using the standard reference analytical method for the component of interest as disclosed herein. Interpreting the near infrared spectral region (780-2500 nm) of seeds is complex for a number of reasons. Absorption in this region contains weaker overtones or harmonics of the fundamental frequencies and in combination bands, where absorption occurs in two or more overlapping fundamental bond energies. The energy absorption and resulting spectra are therefore composite vibrational signals of all of the resonating bonds within the organic components and water in the seed being analyzed. The spectral signal from any specific component is deciphered from the background and is influenced by the matrix that it is embedded in. For example, the molecular specific signal within an intact seed can be influenced by the environment such as geographic location, growing season, storage conditions and conditions during measurement, the genetic background, and the presence of similar molecules.

In some embodiments, accurate measurements of sucrosyl-oligosaccharides in a seed are achieved by utilizing a broad array of samples in which compounds with similar chemical compositions, such as sucrose, stachyose and raffinose, differ in a reciprocal manner. The sucrosyl-oligosaccharide specific signal is detected in the seed by having the sucrosyl-oligosaccharide present in a reciprocal concentration series of related molecules and visa-versa. A collection of mature soybean seeds that have significant differences in the concentrations of the sucrosyl-oligosaccharides facilitates this approach. The amount or concentration of sucrosyl-oligosaccharides can also be measured in seeds having the same or similar genetics that have been grown in multiple environments and over multiple seasons.

The measurements may be taken at any moisture content of the soybean. The moisture content of the soybean affects the weight percentages of components of the soybean, with drier beans generally having a higher weight percent of the component, such as oil, protein or sucrosyl-oligosaccharide. When comparing NIR-based measurements with standard reference analytical methods, measurements may be taken in each case at the same moisture content of soybean, or if measurements are taken at different moisture contents, the values obtained can be corrected to the same moisture content. Measurements can, for example, be taken at or standardized to a moisture content by weight of at least or at least about 0.01%, 0.1%, 0.5%, 1%, 2%, 3%, 4%, 5%, 6%, 7%, 8%, 9%, 10%, 11%, 12%, 13%, 14%, 15% or 20% and less than or less than about 35%, 30%, 25%, 20%, 19%, 18%, 17%, 16%, 15%, 14%, 13%, 12%, 11%, 10%, 9% or 8%. Unless indicated to the contrary, measurements described herein are at or about 13% by weight moisture content.

Provided are accurate non-destructive analytical NIRS-based methods for accurately measuring soluble carbohydrates such as sucrose and the sucrosyl-oligosaccharides raffinose and stachyose, which are appropriate for both single soybeans as well as bulk batches of soybeans and soybean meal. Following measurement, the seed remains viable and can be crossed with the same or different plant such as in a plant breeding program to produce progeny seed or processed for extraction of components such as oil and protein meal.

In the methods and systems provided, the amount or concentration of one or more sucrosyl-oligosaccharides in the seed can be accurately and non-destructively measured by interrogating a seed using an optical interrogation device, such as a spectrophotometer, which directs near-infrared light onto the seed, and using the reflected, transmitted or transflected (a combination of transmitted and reflected light) light spectra from the seed and detected by the optical interrogation device in combination with measurements used to generate calibration models obtained from previously assayed seed. In some embodiments, the seed is sorted or selected based on the amount or concentration of sucrosyl-oligosaccharide present in the seed. The seed can be a whole seed, an intact seed, a viable seed, an individual seed or a population of individual, whole, viable or intact seeds. In some embodiments, sorting decisions can be made following measurement and analysis of a single seed or following measurement and analysis of a population of seeds or a defined number of seeds assayed together in a seed sample.

When a number of seeds are assayed together, an average for the measured values across the population of seeds may be obtained either by pooling the data collected from individual seeds from that population or by using methods in which a pooled sample of the soybean seeds are measured simultaneously. Following analysis, the seed remains viable and may be planted and grown to produce a soybean plant. The seeds remain whole, intact or viable before and following the analysis process. Protein meal from soybeans can be similarly analyzed.

By plotting values from the standard reference analytical method against the measurements taken by non-destructive analysis for a particular constituent, the $R^2$ value can be used to indicate the proportion of the data that is accounted for by an ideal line plotted through it. A value of 1 indicates highest accuracy. The root mean square error of calibration (RMSEC) indicates the resolving power of the measured values and can give an indication of the statistical confidence as to whether two values differ significantly from each other. Typically, values differing by 2×the RMSEC differ from each other at the 95% confidence level. The root mean square error of cross validation (RMSECV) is another statistical parameter that is used to assess the quality of the calibrations Once a model (calibration) is created, the data for a group of samples are removed and the influence of their omission is assessed. In robust models the RMSECV is similar to RMSEC. The cross validation also allows aberrant values which may incorrectly influence a model to be identified for further analysis. The RMSECV also gives an estimate of the potential of the models to predict the composition of samples outside the range represented in the calibration set.

Using the methods disclosed herein seeds, such as unmodified seeds and modified seeds in one or more populations of seeds, differing in stachyose content by at least 0.5%, 1.0%, 1.25%, 1.5%, 1.75%, 2.0%, 2.5% or 3.0% and less than 6.0%, 5.0%, 4.0%, 3.5%, 3.0%, 2.5%, 2.0% or 1.5% (values are percentage points by weight) can be correctly identified for at least or at least about 80%, 85%, 90%, 91%, 92%, 93%, 94%, 95%, 96%, 97% or 98% of the population of seeds containing differing stachyose content.

The term "percentage point" (pp) difference, change, increase or decrease refers to the arithmetic difference of two percentages, e.g. [transgenic or genetically modified value (%)−control value (%)]=percentage points. For example, a modified seed may contain 20% by weight of a component and the corresponding unmodified control seed may contain 15% by weight of that component. The difference in the component between the control and transgenic seed would be expressed as 5 percentage points.

"Percent increase" or "percent decrease" refers to a change or difference expressed as a fraction of the control value, e.g. {[modified/transgenic/test value (%)−control value (%)]/control value (%)}×100%=percent change, or {[value obtained in a first location (%)−value obtained in second location (%)]/value in the second location (%)}×100=percent change. The term "total fatty acid content" refers to the sum of the five major fatty acid components found in soybeans, namely C16:0, C18:0, C18:1, C18:2, and C18:3. The term "total polyunsaturated fatty acid content" refers to the total C18:2 plus C18:3 content. The term "total saturated fatty acid content" refers to the total C16:0 plus C18:0 content.

Using the methods disclosed herein seeds, such as unmodified seeds and modified seeds, differing in raffinose content by at least 0.1%, 0.2%, 0.3%, 0.4%, 0.5%, 0.6%, 0.7%, 0.8%, 0.9%, 1% or 1.5% and less than 3%, 2.5%, 2%, 1.5%, 1%, 0.5%, 0.3% or 0.2% (values are percentage points by weight) in one or more populations of seeds can be correctly identified for at least or at least about 80%, 85%, 90%, 91%, 92%, 93%, 94%, 95%, 96%, 97% and 98% of the population of seeds.

The population can include at least or at least about 2, 5, 10, 15, 20, 25, 30, 35, 40, 35, 50, 55, 60, 65, 70, 75, 80, 85, 90, 95, 100, 125, 150, 175, 200, 250, 300, 350, 400, 450, 500, 600, 750, 1000, 5,000, 10,000 or 50,000 seeds and less than or less than about 5,000,000, 1,000,000, 500,000, 400,000, 250,000, 100,000, 50,000, 10,000, 5,000, 2,500, 1,000, 750, 600, 500, 400, 300, 200, 150, 100, 75, 50 or 25 seeds.

In some embodiments, single individual intact soybeans are analyzed one seed at a time, such as with single-seed NIR techniques (SS-NIR) utilizing reflected light, transmitted light or a combination thereof. Such methods are useful, for example, to identify an individual seed carrying the desired trait, such as a transgene, edited gene or mutant allele, which results in a desired composition. Following analysis according the methods described herein, the seed can be used in research and plant breeding programs. For example, the seed can be grown to produce a plant which is crossed with itself or another different plant to produce progeny seed.

In some embodiments, small bulk quantities of seed, such as the amount of seed harvested from a single soybean plant (about 50-300 seeds) which may be homozygous, are analyzed together. FT-NIR, which utilizes reflectance NIR, can be used as in methods described herein for soybean samples harvested from individual plants. Such methods are useful, for example, in assessing or ranking trait performance at the single plant level, and can be used to make selections of plants for their use in further research or breeding. Such assessments may be used in evaluations of transgenic events in controlled environment and field studies.

In some embodiments, bulk seed analysis (bulk NIT methods) are provided which typically require a mass of at least or at least about 100 g, 200 g, 250 g, 300 g, 350 g, or 400 g and less than or less than about 2000 g, 1000 g, 900 g, 800 g, 700 g or 500 g of sample. Such methods are useful, for example, in the analysis of seed grown in field test plots and yield trials or from a bulk harvest and the identification of modified seed from unmodified seed. Such methods can be used, for example, at grain receiving sites such as grain elevators to determine the composition and quality of seeds delivered and the value of the grain shipment. Such methods may include a step of sampling the seed using a sampling system such as AOCS Official Method Ac 1-45.

Commercial soybean cultivars are homozygous for most traits and may be modified to have additional traits introduced by backcrossing (e.g., introgression of the trait of interest can be achieved by crossing to a second line containing the trait and repeated backcrossing to the original line while selecting for the trait of interest), genetic modification, mutation or transformation. Such additional traits can include one or more transgenes or gene modifications which alter the composition of the soybean seed or provide other agronomic characteristics such as herbicide or insect resistance. Selection of lines can include, for example, selections based on one or more of the performance of the line which produced the seed being measured, determining the presence or absence of a transgene, mutation or genetic modification in the seed, and assessing whether a transgene, genetic modification or mutant gene or coding sequence has been inherited by a seed, for example, by introgression through crossing and breeding steps.

Soybean seeds used in the methods and systems described herein can be generated using one or more techniques disclosed herein that facilitate integration or expression of a target sequence in the plant or seed. Examples include one or more of a particle gun, *Agrobacterium*, single-site integration, CRISPR-Cas (clustered, regularly interspaced, short, palindromic repeats-Cas) technology, TALENs (transcription activator-like effector nucleases), zinc-finger proteins (ZNF) or combination thereof.

Modified seed means seed that contains a genetic modification that results in an alteration of the composition of the seed. Examples of altered composition includes one or more of an increase or decrease in oil, protein, one or more fatty acids, one or more amino acids, one or more sucrosyl-oligosaccharides, sucrose, one or more carbohydrates, cell wall polysaccharides, cell wall monosaccharide components, fiber, starch, fermentable starch, cellulose, biopolymers, pharmaceuticals, secondary compounds, metabolites and combinations thereof.

Examples of genetic modifications in modified seed include transformation, such as with a recombinant construct containing a target sequence of interest operably connected to heterologous promoter, natural or induced mutations, and genome editing which may encompass altering one or more soybean genomic DNA sequences or a pre-existing transgenic sequence including regulatory elements, coding and non-coding sequences. The modification can be a single nucleotide deletion, substitution, a full or partial gene deletion, or insertion or alteration of an enhancer sequence, such as a promoter or promoter element, to increase expression. Deletions may include deletion of one or more exon coding sequences of the gene or deletion of one or more regulatory elements of the gene.

As an example, the modified seed, cell or plant described herein can be generated using "custom" or engineered endonucleases such as meganucleases produced to modify plant genomes (see e.g., WO 2009/114321; Gao et al. (2010) Plant Journal 1:176-187). Another site-directed engineering is through the use of zinc finger domain recognition coupled with the restriction properties of restriction enzyme. See e.g., Urnov, et al., (2010) Nat Rev Genet. 11 (9):636-46; Shukla, et al., (2009) Nature 459 (7245):437-41. A transcription activator-like (TAL) effector-DNA modifying enzyme (TALE or TALEN) is also used to engineer changes in plant genome. See e.g., US20110145940, Cermak et al., (2011) Nucleic Acids Res. 39(12) and Boch et al., (2009), Science 326(5959): 1509-12. Site-specific modification of plant genomes can also be performed using the bacterial type II CRISPR (clustered regularly interspaced short palindromic repeats)/Cas (CRISPR-associated) system. See e.g., Belhaj et al., (2013), Plant Methods 9: 39; The Cas9/guide RNA-based system allows targeted cleavage of genomic DNA guided by a customizable small noncoding RNA in plants (see e.g., WO 2015026883A1, incorporated herein by reference). These methods are also useful in targeting nucleic acids to pre-engineered target recognition sequences in the genome. A "mutation", which is possessed by a mutant, refers to a detectable and heritable genetic change (either spontaneous or induced) not caused by segregation or genetic recombination.

Unmodified seed is seed which is similar to the modified seed but which lacks the genetic modification which alters the composition of the seed.

In some embodiments, the methods include measuring a different seed constituent, in combination with measuring a sucrosyl-oligosaccharide to provide additional compositional information, such as a compositional profile, about the seed. Such measurements can be carried out simultaneously with the measurements of sucrosyl-oligosaccharide and may be used to evaluate lines or seeds therefrom, such as modified lines or seeds. A "line" when referring to soybean, is a group of plants of similar parentage that display little or no genetic variation between individuals for a least one trait. Soybean lines are generally homozygous for almost all traits. Lines may be created by one or more generations of self-pollination and selection, or vegetative propagation from a single parent including by tissue or cell culture techniques.

Non-limiting examples of seed constituents which may be measured in the methods provided herein, including processing or sorting seeds, include proteins, oils, carbohydrates, fatty acids (such as one or more of oleic acid, palmitic acid, stearic acid, linoleic acid, linolenic acid, arachidic acid, erucic acid, behenic acid, lignoceric acid and myristic acid) and fatty acid profiles, amino acids, biopolymers, pharmaceuticals, starch, fermentable starch, secondary compounds, sucrosyl-oligosaccharides, metabolites and combinations thereof. For example, alterations, such as increases or decreases, in these constituents can be measured in combination with measuring the amount or concentration of one or more sucrosyl-oligosaccharides in a target or modified soybean seed and compared with a comparable control or unmodified soybean seed which does contain the modification contributing to the altered phenotype.

Soybean seeds that can be used in the methods and systems provided may be transgenic for one or more traits, for example through suppression or over-expression, and/or may have one or more mutations or genetic modifications, that result in a seed having a composition sufficiently different from comparable commodity, non-mutant, non-modified or non-transgenic soybean seeds to enable identification, separation and/or sorting of the transgenic, mutant or genetically modified seed from the comparable or control seed. For example, a low amount or concentration of sucrosyl-oligosaccharide in a soybean seed may indicate that the soybean seed is a modified seed containing one or more traits, such as one or more transgenic events or genetic modifications, that result in a high oil, high protein and/or altered fatty acid profile phenotype in the soybean seed compared with a comparable soybean seed not containing the trait or modification. Soybean seeds that have an amount or concentration of sucrosyl-oligosaccharide below a desired threshold (i.e., below a desired maximal amount) of sucrosyl-oligosaccharide and above a desired threshold (i.e. above a desired minimal amount) of oil content, protein content, or both oil and protein content can be selected and used in plant breeding or industrial processing. The methods described herein can also be used with modified soybean seeds that have an amount or concentration of sucrosyl-oligosaccharide below a desired threshold (i.e., below a desired maximal amount) of sucrosyl-oligosaccharide and above or below a desired threshold for one or more fatty acids. The threshold is to selected to enable sorting or separation of modified seeds from the comparable seeds not containing the transgenic trait or genetic modification. Protein meal can also be analyzed rapidly and non-destructively using the methods described herein, and protein meal produced from soybeans containing one or more genetic modifications such as the modifications described herein can be identified from meal produced from non-modified soybeans.

In some embodiments, the genetic modifications include one or more mutations or modifications that result in reduced amounts of stachyose, raffinose or a combination thereof in the soybean seed, such as the low1, low2, low3, low4 mutations described in U.S. Pat. Nos. 5,710,365, 6,147,193 and 6,653,451, mutations in stachyose synthase such as in the PI 603176A and PI 594012 soybean lines (Qui et al., Theor Appl Genet 2015, 128:2167), the mutations in raffinose synthase such as the RS2 or RS3 genes described in U.S. Pat. No. 8,728,726 and US Patent Publication No. 20130318660, the SG-ULRFO mutation described in US Patent Publication No. 20110003045, and the low phytate, low stachyose mutations described in U.S. Pat. No. 8,003,856.

In some embodiments, the genetic modifications include one or more mutations or modifications that result in increased oleic acid, such as in one or more FAD2 alleles, see, e.g. U.S. Pat. Nos. 9,198,365, 9,185,826, 7,531,718, 7,205,457, 7,067,722, 6,426,448, 6,229,033, 5,981,781 and US Patent Publication Nos. 20160186195, 20130219565.

The oleic acid may be increased to about 50%, 55%, 60%, 65%, 70%, 75%, 80%, 85% or 90% (such as at least about or at least 50%, 55%, 60%, 65%, 70%, 75%, 80% or 85% and less than or less than about 95%, 90%, 85%, 80%, 75%, 70%, or 65%; measured as a proportion of the total fatty acids) by suppressing or inhibiting expression of one or more FAD2 genes, such as by mutation, genome editing or transgenes, alone or in combination with other modifications described herein.

In some embodiments, the genetic modifications include one or more mutations or modifications that result in reduced linolenic acid, such as one or more FAD3 or fan (e.g. fan1, fan2, fan3) alleles found, for example, in mutant lines, A5, C1640, RG10, A16, A17, A23, A29 and in soybean lines having such alleles modified by genome editing or transformation. See, e.g. U.S. Pat. Nos. 8,901,375, 7,943,818, 7,205,457, 7,067,722, 6,133,509, 5,850,030, 5,710,369, 5,714,670, 5,763,745, 5,714,668, 5,534,425 and 5,714,670 and US Patent Publication Nos. 20160186195, 20130219565.

The linolenic acid may be decreased to about 6%, 5.5%, 5%, 4.5%, 4%, 3.5%, 3.0%, 2.9%, 2.8%, 2.7%, 2.6%, 2.5%, 2.4%, 2.3%, 2.3%, 2.1%, 2.0%, 1.9%, 1.8%, 1.7%, 1.6%, 1.5%, 1.4%, 1.3%, 1.2%, 1.1% or 1.0% (such as at least about or at least 0.5%, 0.6%. 0.7%, 0.8%, 0.9%, 1.0%, 1.1%, 1.2%, 1.3%, 1.4%, 1.5%, 1.6%, 1.7%, 1.8%, 1.9%, 2.0%, 2.1%, 2.2%, 2.3%, 2.4%, 2.5%, 2.6%, 2.7%, 2.5%, 2.9% or 3.0% and less than or less than about 6%, 5.5%, 5.0%, 4.5%, 4.0%, 3.5%, 3.4%, 3.3%, 3.2%, 3.1%, 3.0%, 2.9%, 2.8%, 2.7%, 2.6%, 2.5%, 2.4%, 2.3%, 2.2%, 2.1%, 2.0%, 1.9%, 1.8%, 1.7%, 1.6%, 1.5%, 1.4%, 1.3%, 1.2%, 1.1% or 1.0% measured as a proportion of the total fatty acids) by suppressing or inhibiting expression of one or more FAD3 genes, such as those disclosed herein and such as by mutation, genome editing or use of transgenes, alone or in combination with other modifications described herein.

In some embodiments, for example, components that can be used to modify the composition of the seed include increased expression of a DGAT (diglyceride acyltransferase; e.g. U.S. Pat. Nos. 8,153,859; 8,399,736; 9,187,736), such as DGAT1 (e.g. a soy DGAT1 or a modified soy DGAT1 expressing a polypeptide with one or more amino acid substitutions, e.g. U.S. Pat. Nos. 7,524,945, 8,497,362, 8,101,819, 8,455,714; 9,447,386) or DGAT2 (e.g. a *Yarrowia lipolytica* DGAT2, e.g. U.S. Pat. Nos. 9,574,207, 8,927,809; 8,993,840), suppression of one or more galactinol synthases (GAS; such as GAS1, GAS2 and GAS3, e.g. U.S. Pat. Nos. 9,574,207; 7,294,756; 6,967,262; 5,648,210; 5,773,699; 5,710,365; 6,147,193; 6,653,451), increased expression of a sucrose transporter, such as SUT2 or SUT4 (e.g. U.S. Pat. No. 8,993,840), expression of transcription factors such as ovule development protein (ODP; also known as Wrinkled1, see, e.g. U.S. Pat. Nos. 8,404,926 and 9,284,571), LEC1 or FUSCA3 (e.g. US Patent Publication No. 20160186195), phosphoglucomutase (PGM; U.S. Pat. Nos. 8,143,476, 8,829,273), fatty acid desaturase FAD3 (e.g. U.S. Pat. Nos. 7,081,564; 8,609,935; 5,981,781; US Patent Publication No. 20130219565) amiRNA fragments of fad2-1 b, fatBF, or fad3c (e.g. US Patent Publication No. 20130219565), carbonic anhydrase (e.g. US Patent Publication No. 20170029836), pectin acetyl esterase (PAE; e.g. U.S. Pat. No. 9,574,204), aldolase such as HpalL aldolases (e.g. U.S. Pat. No. 9,347,066), cytosolic pyrophosphatase (PPiase; e.g. US Patent Publication No. 20120174261), oxidoreductase and oxidoreductase motifs (ORMs; e.g. US Patent Publication No. 20110219474), or combinations thereof. Promoters that can be used include, for example, one or more of annexin promoter, beta-conglycinin α'-subunit promoter, glycinin 1 promoter, Kunitz trypsin Inhibitor 3 Promoter, albumin 2S promoter, s-adenosylmethionine synthetase promoter, sucrose synthase promoter such as a SUS2 promoter, late embryogensis abundant gene promoter. Other components which can be used include a yeast FLP-Recombinase to facilitate recombination at short flippase recognition target (FRT) sites. Further examples of components are provided in Table 1, which constructs can be used to generate modified or transgenic seeds having a wide range of amounts or concentrations of one or more sucrosyl-oligosaccharides. Any combination if these components described in this paragraph and in Table 1 may be expressed together. One or more of these components may also be combined with one or more of the modifications or mutations described herein, such as mutations or modifications affecting the fatty acid profile such as oleic acid, linolenic acid, linoleic acid, stearic acid or palmitic acid. Sequences disclosed herein include sequences that have at least or at least about 50%, 55%, 60%, 65%, 70%, 75%, 80%, 85%, 90%, 95%, 96%, 97%, 98%, 99% or 100% identity to the disclosed sequences, provided that the sequence functions for its intended purpose.

TABLE 1

List of promoters and gene/amiRNA/RNAi cassettes and their abbreviations

| Feature Name | Description | Reference |
| --- | --- | --- |
| ANN | Soy annexin promoter | U.S. Pat. No. 8,084,074 (e.g. the sequence identified as number 3) |
| BC | Soy beta-conglycinin α'-subunit promoter | Beachy et al., EMBO J. 4, 3047-3053 (1985) |
| FAD2 RNAi | RNAi construct containing fragments of soy fatty acid desaturase 2 genes and designed to silence them | U.S. Pat. No. 7,456,014 (e.g. the sequence identified as number 24) |
| FAD2/FATBamiRNA | Combined amiRNA comprising 396b-fad2-1b and 159-fatBF | US Patent Application Publication No. 20150089689 |
| FAD3amiRNA | amiRNA comprising 159-fad3c | US Patent Application Publication No. 20150089689 |
| GAS RNAi | RNAi construct containing fragments of soy galactinol synthases designed to silence them | U.S. Pat. No.7,476,778 (e.g. nucleotides encoding the sequences identified as numbers: 2, 4, 6) U.S. Pat. No. 7,456,014 (e.g. the sequence identified as number 29) |
| GM::HRA/GM-ALS | Soy Acetolactate Synthase gene and gene encoding a mutant soy ALS enzyme insensitive to sulfonylurea herbicides | U.S. Pat. No. 7,456,014 (e.g. the sequence identified as number 35) U.S. Pat. No. 7,217,858 (e.g. the sequences identified as numbers 22 and 23) |
| GM-DGAT1-C9C10C11 | Modified Soy diacylglycerol acyltransferase 1 | U.S. Pat. No. 8,101,819 |
| GM-ODP1 | Soy Ovule Development Protein 1 | US Patent Application Publication No. 2015-0143583. |
| GM-SUT4 | Soy Sucrose Transporter 4 | U.S. Pat. No. 8,993,840 |
| GY1 | Soybean Glycinin 1 Promoter | U.S. Pat. No. 8,084,074 |
| KTI | Soy Kunitz Trypsin Inhibitor 3 Promoter | Jofuku et al., Plant Cell 1: 1079-1093 (1989) |
| LEA | Soy Late Embryogenesis Abundant gene promoter | U.S. Pat. No. 7,456,014 |
| PGM RNAi | RNAi construct containing fragments of soy PGM designed to silence them | U.S. Pat. No. 7,323,560 |
| SALB | Soy albumin 2S promoter | U.S. Pat. No. 6,177,613 |
| SAMS | Soy S-adenosylmethionine synthetase promoter | U.S. Pat. No. 7,217,858 |
| SUS | GM::SUS2 Promoter | US Patent Application Publication No. 2015-0143583 |
| YLDGAT2 | *Yarrowia lipolitica* diacylglycerol acyltransferase 2 | U.S. Pat. No. 8,143,473 U.S. Pat. No. 8,143,476 |

TABLE 1-continued

List of promoters and gene/amiRNA/RNAi cassettes and their abbreviations

| Feature Name | Description | Reference |
|---|---|---|
| FLP-Recombinase | Yeast FLP-Recombinase | US Patent Application Publication No. 20160186195 |

Soybeans generated by modifying expression of these sequences and having different amounts of stachyose, raffinose, or both stachyose and raffinose can be used iteratively in the methods described herein to generate calibrations which provide accurate measurements of stachyose or both stachyose and raffinose. In some embodiments verbascose can be measured. As used herein, sucrosyl-oligosaccharide means the sum of stachyose and raffinose.

In some embodiments, the soybean is modified to have suppressed galactinol synthase (GAS) activity with one or more sequences that suppress expression of galactinol synthase (e.g. one or more of GAS1, GAS2 and GAS3) or raffinose synthase (e.g. RS2, RS3) activity (or a combination of GAS and raffinose synthase suppression), alone or in combination with increased DGAT activity (for example, by transforming with a yeast or soy DGAT described in Table 1 or genetically modifying the native DGAT or its regulatory sequences to enhance expression) and optionally other sequences, such as those described in Table 1, to increase oil and/or protein. Such enhanced expression or suppression can be achieved by one or more of genetic modification, such as by gene editing, the use of transgenes, or by mutation. Such seeds may have an amount of stachyose of about 0.1%, 0.2%, 0.3%, 0.4%, or 0.5%, such as at least about 0.05%, or 0.1%, 0.2%, 0.3%, 0.4% or 0.5% and less than about 2%, 1.5%, 1%, 0.9%, 0.8%, 0.7%, 0.6% or 0.5% stachyose (percentage points by weight). Such seeds may have an amount of sucrosyl-oligosaccharide of about 0.3%, 0.4%, 0.5% or 0.6%, such as at least about 0.05%, 0.1%, 0.2%, 0.3%, 0.4% or 0.5% and less than about 2%, 1.5%, 1%, 0.9%, 0.8%, 0.7%, 0.6% or 0.5% sucrosyl-oligosaccharides (percentage points by weight). By contrast, the comparable unmodified, control, null or wild-type seed may have a stachyose content of about 4%, such as at least about 1%, 2%, 2.5%, 3% or 3.5% and less than about 6%, 5.5%, 5% or 4.5% (percentage points by weight). The comparable unmodified, control, null or wild-type seed may have a sucrosyl-oligosaccharide content of about 5%, such as at least about 2%, 2.5%, 3%, 3.5%, 4%, or 4.5% and less than about 6.5%, 6%, 5.5%, or 5% (percentage points by weight).

Such modified seeds may also have an increased oil, protein or combination thereof in addition to reduced sucrosyl-oligosaccharide or stachyose. For example, such modified seeds may have an amount of oil in percentage points by weight of about 23%, 24%, 25%, 26%, 27%, 28%, 29%, 30%, such as at least about 21%, 22%, 23%, 24%, 25%, 26%, 27%, 28%, 29%, 30% and less than about 40%, 35%, 34%, 33%, 32%, 31%, 30%, 29% or 28% oil by weight. In contrast, a comparable unmodified, control, null or wild-type seed may have an amount of oil in percentage points by weight of about 16%, 17%, 18%, 19%, 20%, 21% or 22%, such as at least about 15%, 16%, 17%, 18%, 19%, 20% or 21% and less than about 23%, 22%, 21%, 20%, 19%, or 18% oil by weight. Useful examples of percent point increases in oil or total fatty acid content in a seed, such as a modified soybean seed described herein compared with a comparable or control soybean include, but are not limited to, percentage point increases by weight of at least 1%, 2%, 3%, 4% or 5% and less than 10%, 9%, 8%, 7%, 6%, 5% or 4%. Useful examples of the percent increases in oil or total fatty acid content in a modified soybean seed described herein compared with a comparable unmodified, control, null or wild-type soybean include, but are not limited to, percent increases of at least 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, or 40% and less than 99%, 95%, 90%, 80%, 70%, 60%, 50%, 40%, 35%, 30% and 25%.

Such modified seeds may have an amount of protein in percentage points by weight of about 38%, 39%, 40%, 41%, 42%, 43%, 44%, 45%, 46%, 47%, 48%, 49%, 50%, 51%, 52%, 53% or 54% such as at least about 35%, 36%, 37%, 38%, 39%, 40%, 41%, 42%, 43%, 44%, 45%, 46%, 47%, 48%, 49%, or 50% and less than about 55%, 54%, 53%, 52%, 51%, 50%, 49%, 48%, 47%, 46%, 45%, 44%, 43%, 42%, 41%, 40% or 39% protein. In contrast a comparable unmodified, control, null or wild-type seed may have an amount of protein in percentage points by weight of about 30%, 31%, 32%, 33%, 34%, 35%, 36%, 37%, or 38% such as at least about 25%, 26%, 27%, 28%, 29%, 30%, 31%, 32%, 33%, 34%, or 35% and less than about 38%, 37%, 36%, 35%, 34%, 33%, 32% 31%, 30%, 29% or 28% protein. Useful examples of percent point increases in protein (by weight) in a seed, such as a modified soybean seed compared with a comparable or control soybean include, but are not limited to, percentage point increases by weight of at least 0.2%, 0.3%, 0.4%, 0.5%, 0.6%, 0.7%, 0.8%, 0.9%, 1%, 1.1%, 1.2%, 1.3%, 1.4%, 1.5%, 1.6%, 1.7%, 1.8%, 1.9%, 2.0%, 2.1%, 2.2%, 2.3%, 2.4%, 2.5%, 2.6%, 2.7%, 2.8%, 2.9%, 3.0%, 3.1%, 3.2%, 3.3%, 3.4%, 3.5%, 3.6%, 3.7%, 3.8%, 3.9%, 4.0%, 4.1%, 4.2%, 4.3%, 4.4%, 4.5%, 4.6%, 4.7%, 4.8%, 4.9%, 5.0%, 6%, 7%, 8%, 9%, and 10% and less than 20%, 19%, 18%, 17%, 16%, 15%, 14%, 13%, 12%, 11%, 10%, 9%, 8%, 7%, 6%, 5% or 4%. Useful examples of the percent increases in protein content in a seed such as a modified seed compared with an unmodified, control, null or wild-type soybean seed described herein include, but are not limited to, percent increases of at least 5%, 10%, 15%, 20%, 25%, 30%, 35%, 40%, 45%, 50%, 55%, or 60% by weight and less than about 70%, 65%, 60%, 55%, 50%, 45%, 40%, 35%, 30%, 25%, 20%, 15% or 10%.

The methods can be used to accurately distinguish between individual soybean seeds, or populations or lines of soybeans that differ in percentage points by about 1% stachyose or sucrosyl-oligosaccharide, such as less than 3%, 2.5%, 2%, 1.9%, 1.8%, 1.7%, 1.6%, 1.5%, 1.4%, 1.3%, 1.2%, 1.1%, 1%, 0.9%, 0.8%, 0.7%, 0.6% or 0.5% stachyose or sucrosyl-oligosaccharide by weight and at least 0.1%, 0.2%, 0.3%, 0.4%, 0.5%, 0.6%, 0.7%, 0.85 or 0.9% stachyose or sucrosyl-oligosaccharide by weight. Values are given by weight percent.

The difference in sucrosyl-oligosaccharide, such as stachyose, between seed types being measured, such as a modified and unmodified seed as described herein, can be detected, for example, when the difference is at least 0.5 percentage points, 1.0 percentage points, 1.5 percentage points, 2.0 percentage points, 2.5 percentage points, 3.0 percentage points, or 4.0 percentage points and less than 5.0 percentage points, 4.5 percentage points, 4.0 percentage points, 3.5 percentage points, 3.0 percentage points, 2.5 percentage points, 2.0 percentage points, 1.5 percentage points, or 1.0 percentage points. Values are given by weight percent.

Useful examples of the amount of sucrosyl-oligosaccharide content in a seed such as a modified or unmodified soybean seed include, but are not limited to in percentage points by weight at least or at least about 0.1%, 0.2%, 0.25%, 0.5%, 1%, 1.5%, 2%, 2.5%, 3.0%, 3.5%, 4.0%, 4.5%, 5.0%, 5.5%, 6.0% or 6.5% and less than or less than about 7%, 6.5%, 6.0%, 5.0%, 4.5%, 4.0%, 3.5%, 3.0%, 2.9%, 2.8%, 2.7%, 2.6%, 2.5%, 2.4%, 2.3%, 2.2%, 2.1%, 2.0%, 1.9%, 1.8%, 1.7%, 1.6%, 1.5%, 1.4%, 1.3%, 1.2%, 1.1%, 1.0%, 0.9%, 0.8%, 0.7%, 0.6%, 0.5%, 0.4%, 0.3% or 0.2%.

The methods can be used to accurately distinguish between individual soybeans, or populations or lines of soybeans that differ by in percentage points by weight at or about 0.5%, 0.7%, 0.8%, 0.9%, 1.0%, 1.5%, 2.0%, 2.5%, 3%, 3.5%, 4%, 4.5% 5%, 5.5%, 6%, 7%, 8%, 9% or 10% oil, such as in percentage points at least 0.1%, 0.2%, 0.3%, 0.4%, 0.5%, 0.6%, 0.7%, 0.8%, 0.9%, 1.0%, 1.1%, 1.2%, 1.3%, 1.4%, 1.5%, 2%. 3%, 4%, or 5% oil and less than 15%, 10%, 5%, 4%, 3%, 2.5%, 2%, 1.9%, 1.8%, 1.7%, 1.6%, 1.5%, 1.4%, 1.3%, 1.2%, 1.1%, 1.0%, 0.9%, 0.8%, 0.7%, 0.6% or 0.5% oil.

The methods can be used to accurately distinguish between individual soybeans, or populations or lines of soybeans that differ in percentage points by weight at or about 1%, 1.5%, 2%, 2.5%, 3%, 3.5% 4%, 4.5%, 5%, 5.5%, 6%, 7%, 8%, 9%, 10%, 11%, 12%, 13%, 14%, 15%, 20% or 25% protein, such as at least 0.5%, 1%, 1.5%, 2%, 2.5%, 3%, 3.5%, 4%, 5%, 6%, 7%, 8%, 9%, and 10% protein and less than 30%, 25%, 20%, 15%, 10%, 9%, 8%, 7%, 6%, 5%, 4%, 3%, 2%, or 1% protein.

If a yeast DGAT, such as *Yarrowia lipolytica* diacylglycerol acyltransferase 2 or a soy DGAT, such as soy DGAT1, is expressed in a soybean seed, optionally with one or more sequences that results in GAS or raffinose synthase suppression, the seed may have an oleic acid content of about 30%, 31% or 32% such as at least about 22%, 23%, 24%, 25%, 26%, 27%, or 28% and less than about 40%, 35%, 34%, or 33%. Unless indicated to the contrary, all percent values for a particular fatty acid are expressed herein as a percentage of the total fatty acid content. The oleic acid can be measured in combination with measuring the amount of sucrosyl-oligosaccharide or stachyose or other components described herein. By contrast, the comparable unmodified, control, null or wild-type seed may have an oleic acid content of about 22% or 23%, such as at least about 19%, 20% or 21% and less than about 25%, 24.5% or 24%. For such modified beans, the threshold for oleic acid to distinguish between the modified and unmodified seed may be about 25% or 30% or 35%, such as at least about 21%, 22%, 23%, 23.5%, 24%, 24.5%, 25%, 25.5%, 26%, 26.5%, 27%, 28%, 29%, 30%, 31%, 32%, 33%, 34%, 35% or 36% and less than about 37%, 36%, 35%, 34%, 33%, 32%, 31%, 30%, 29%, 28%, 27% 27% or 26% oleic acid.

If a soy DGAT, such as the modified soy diacylglycerol acyltransferase 1 described in Table 1, or a yeast DGAT, such as *Yarrowia lipolytica* diacylglycerol acyitransferase 2 is expressed or over-expressed in a soybean seed, optionally with one or more sequences that results in GAS and/or raffinose synthase suppression, the seed may have a stearic acid content of about 5% (such as at least or at least about 4%, 4.5% or 5% and less than or less than about 10%, 9%, 8%, 7% or 6%) which can be measured in combination with measuring the amount of stachyose or sucrosyl-oligosaccharide or other components described herein. By contrast, the comparable unmodified seed may have a stearic acid content of about 3.5% (such as at least or at least about 3%, 3.1%, 3.2%, 3.3%, 3.4% or 3.5% and less than or less than about 3.7%, 3.8%, 3.9%, 4.0%, 4.1%, 4.2%, 4.3%, 4.4%, 4.5%, 4.6%, 4.7%, 4.8% or 4.9%, 5.0%, 5.5%).

If a DGAT, such as the modified soy diacylglycerol acyitransferase 1 described in Table 1, is expressed or over expressed in a soybean seed, optionally with one or more sequences that results in GAS suppression, the seed may have a palmitic acid content of about 12% or 13% (such as at least or at least about 11%, 11.1%, 11.2%, 11.3%, 11.4%, 11.5%, 11.6%, 11.7%, 11.8%, 11.9%, or 12% and less than or less than about 15%, 14.5%, 14%, 14.5%, 14%, 13.5%, 13.4%, 13.3%, 13.2%, 13.1%, 13%, 12.9%, 12.8%, 12.7%, 12.6% or 12.5%) which can be measured in combination with measuring the amount of sucrosyl-oligosaccharide or stachyose or other components described herein. By contrast, the comparable unmodified seed may have a palmitic acid content of about 10% or 11% (such as at least or at least about 9%, 9.1%, 9.2%, 9.3%, 9.4%, 9.5%, 9.6%, 9.7%, 9.8%, 9.9% or 10% and less than or less than about 12%, 11.9%, 11.8%, 11.7%, 11.6%, 11.5%, 11.4%, 11.3%, 11.2%, 11.1%, 11%, 10.9%, 10.8%, 10.7%, 10.6%, or 10.5%).

If a DGAT, such as the modified soy diacylglycerol acyitransferase 1 described in Table 1, or such as *Yarrowia lipolytica* diacylglycerol acyltransferase 2 is expressed or over-expressed in a soybean seed, optionally with one or more sequences that results in GAS suppression, the seed may have a linoleic acid content of about 45% (such as at least or at least about 25%, 30%, 35%, 40% or 45% and less than or less than about 55%, 54%, 53%, 52%, 51%, 50%, 49%, 48%, 47%, 46% or 45%) which can be measured in combination with measuring the amount of sucrosyl-oligosaccharide, such as stachyose or sucrosyl-oligosaccharide or other components described herein. By contrast, the comparable unmodified seed may have a linoleic acid content of about 55% (such as at least or at least about 50%, 51%, 52%, 53%, 54% or 55% and less than or less than about 65%, 64%, 63%, 62%, 61%, 60%, 59%, 58%, 57%, 56% or 55%).

A modified soybean seed such as a soybean seed with enhanced diacylglycerol acyltransferase (DGAT) activity, such as containing a modified soy DGAT1, for example described in Table 1, or a yeast DGAT, such as *Yarrowia lipolytica* diacylglycerol acyltransferase 2, optionally with one or more modified sequences that results in suppression of one or more GAS sequences, raffinose synthase sequences or both, may have a linolenic acid content of about 5% or 6% (such as at least or at least about 0.1%, 0.5%, 1%, 1.5%, 2%, 2.5%, 3%, 3.5%, 4% 4.5% or 5% and less than or less than about 10%, 9%, 8%, 7.5%, 7%, 6.9%, 6.8%, 6.7%, 6.6%, 6.5%, 6.4%, 6.3%, 6.2%, 6.1% or 6%) which can be measured in combination with measuring the amount of sucrosyl-oligosaccharide or stachyose or other components described herein. A modified soybean seed such as a soybean seed with one or more modified FAD3 genes, such as by mutation, genome editing or transgenes, alone or in combination with one or more of DGAT, GAS, raffinose synthase, and FAD sequences, may have a linolenic content of no more than about 0.5%, 1%, 1.5%, 2%, 2.5% or 3% (such as at least about or at least 0.1%, 0.2%, 0.3%, 0.4%, 0.5%, 0.6%, 0.7%, 0.8%, 0.9%, 1%, 1.5%, 2%, 2.5% or 3% and less than 6%, 5.5%, 5%, 4.5%, 4%, 3.5%, 3%, 2.5%, 2%, 1.5%, 1.4%, 1.3%, 1.2%, 1.1%, 1%, 0.9%, 0.8%, 0.7%, 0.6%, 0.5%, 0.4%, 0.3%, 0.2%, 0.1%, 0.05%). By contrast, the comparable unmodified seed may have a linolenic acid content of about 7% or 8% (such as at least or at least about 5%, 5.5%, 6%, 6.5%, or 7% and less than or less than about 12%, 11%, 10%, 9.5%, 9%, 8.5% or 8%. Linolenic acid may be further reduced in a modified soybean by modifying one or more of the FAD2 alleles such as described herein.

Fingerprints regarding the seed composition can be developed based on the modified light from the soybean seed, wherein a sorting decision is made based upon the measured amounts of sucrosyl-oligosaccharides, in any combination with one or more of the fatty acids (such as oleic acid content or saturated fatty acid content), oil content, or protein content in the soybean seed. The combined measurement can be used to increase accuracy as to whether a seed is modified or not. In some embodiments the soybean seed may contain low sucrosyl-oligosaccharide and, for example, high oil, high protein, one or more altered (increased or decreased) fatty acids, or a combination thereof. In some embodiments, the methods described herein for sorting a seed from a plurality of seeds further includes measuring the amount of oil, one or more fatty acids and/or protein in the seed based on the modified light from the soybean seed, wherein a decrease in the amount of sucrosyl-oligosaccharide correlates with an increase in the oil, protein, altered fatty acid content or combination thereof in the soybean seed.

Threshold values for one or more components can be useful for determining whether a soybean is modified or unmodified. The threshold value for a component measured in a soybean is a value selected to facilitate distinguishing, sorting or separating a soybean, such as a modified soybean, having an amount or concentration of the component that is different (for example, a significantly higher or lower amount or concentration of that component) from another soybean, such as an unmodified soybean.
The threshold value may vary depending on the moisture content of the soybean, and can be set or adjusted to 13% moisture. Values for sucrosyl-oligosaccharides, stachyose, raffinose, oil, protein, total soluble carbohydrate, sucrose and PROIL are provided as percentage points based on weight percent (wt. %). For the fatty acids, such as one or more of oleic acid, palmitic acid, stearic acid, linoleic acid, linolenic acid, values described are expressed as a percentage of that fatty acid relative to the total fatty acid pool.

For sucrosyl-oligosaccharide, (a combination of stachyose and raffinose) the threshold value include values at, about, at least, or at least about 0.1%, 0.2%, 0.25%, 0.5%, 1%, 1.25%, 1.5%, 2%, 2.5%, 3.0%, 3.5%, 4.0% sucrosyl-oligosaccharide and at, about, less than, or less than about 5.0%, 4.5%, 4.0%, 3.9%, 3.8%, 3.7%, 3.6%, 3.5%, 3.4%, 3.3%, 3.2%, 3.1%, 3.0%, 2.9%, 2.8%, 2.7%, 2.6%, 2.5%, 2.4%, 2.3%, 2.2%, 2.1%, 2.0%, 1.9%, 1.8%, 1.7%, 1.6%, 1.5%, 1.4%, 1.3%, 1.2%, 1.1%, 1.0%, 0.9%, 0.8%, 0.7%, 0.6%, 0.5%, 0.4%, 0.3% or 0.2% sucrosyl-oligosaccharide.

The threshold for stachyose to distinguish between the modified and unmodified seed may be about 1%, 1.5%, 2%, or 2.5%, such as at least about 0.1%, 0.5%, 0.6%, 0.7%, 0.8%, 0.9%, 1.0%, 1.5%, 2%, 2.5%, 3%, 3.5%, 4%, 4.5% or 5% stachyose and less than about 6.0%, 5.5%, 5%, 4.5%, 4%, 3.5%, 3%, 2.5%, 2%, 1.9%, 1.8%, 1.7%, 1.6%, 1.5%, 1.4%, 1.3%, 1.2%, 1.1%, 1%, 0.9%, 0.8%, 0.7%, 0.6%, 0.5%, 0.4%, 0.3% or 0.2% stachyose.

The threshold for raffinose to distinguish between the modified and unmodified to seed may be about 0.7% raffinose such as at least about 0.1%, 0.2%, 0.3%, 0.4%, 0.5%, 0.6%, 0.7%, 0.8%, 0.9%, or 1% raffinose and less than about 1.5%, 1.4%, 1.3%, 1.2%, 1%, 0.9%, 0.8% or 0.7% raffinose.

The threshold value for oil to assist in distinguishing between modified and unmodified seed may be at or about 17%, 18%, 19%, 20%, 21%, 22%, 23%, 24% or 25%, with the modified soybean, such as described herein, containing at least or at least about 19%, 19.5%, 20%, 20.5%, 21%, 21.5%, 22%, 22.5%, 23%, 23.5%, 24%, 24.5%, 25%, 26%, 27%, 28% or 29% oil and less than or less than about 32%, 31%, 30%, 29%, 28%, 27%, 26%, 25%, 24.5%, 24%, 23.5%, 23%, 22.5%, 22%, 21.5%, 21%, 20.5% or 20% oil and the comparable unmodified or null soybean containing at least or at least about 15%, 15.5%, 16%, 16.5%, 17%, 17.5% or 18% oil and less than or less than about 23%, 22.5%, 22%, 21.5%, 21%, 20.5%, 20%, 19.5%, 19%, 18.5%, 18%, 17.5% or 17% oil. The threshold value for oil includes values of at least or at least about 16%, 16.5%, 17%, 17.5%, 18%, 18.5%, 19%, 19.5%, 20%, 20.5%, 21%, 21.5%, 22%, 22.5%, 23%, 23.5% or 24% oil and less than or less than about 26%, 25.5%, 25%, 24.5%, 24%, 23.5%, 23%, 22.5%, 22%, 21.5%, 21%, 20.5%, 20%, 19.5%, 19%, 18.5% or 18% oil.

The threshold value for total protein to distinguish between the modified and unmodified seed may be at or about 32%, 33%, 34%, 35%, 36%, 37%, or 38%, with the modified soybean, such as described herein, containing at least or at least about 37%, 38%, 39%, 40%, 41%, 42%, 43%, 44%, 45%, 46%, 47%, 48%, 49% or 50% protein and less than or less than about 55%, 54%, 53%, 52%, 51%, 49%, 48%, 47%, 46%, 45%, 44%, 43%, 42%, 41% or 40% protein and the comparable unmodified or null soybean containing at least or at least about 30%, 31%, 32%, 33%, 34%, 35%, 36% or 37% protein and less than or less than about 39%, 38%, 37%, 36%, 35%, 34%, 33% or 32% protein. The threshold value for protein includes values of at least 32%, 33%, 34%, 35%, 36%, 37%, 38%, 39%, 40%, 41%, 42/o, 43%, 44%, 45%, 46%, 47% or 48% protein and less than or less than about 53%, 52%, 51%, 50%, 49%, 48%, 47%, 46%, 45%, 44%, 43%, 42%, 41%, 40%, 39%, 38%, 37%, 36%, 35%, 34% or 33% protein.

For palmitic acid, a suitable threshold value may be at or about 10.5% or 11%, with the modified soybean such as described herein containing at least or at least about 10.5%, 11%, 12%, or 13% and less than or less than about 20%, 15% 14% or 13% palmitic acid and the comparable unmodified or null soybean containing at least or at least about 5%, 7%, 8%, 9% or 10% and less than or less than about 11%, 10.5%, 10%, 9%, 8% or 7% palmitic acid. The threshold value for palmitic acid includes values at, about, at least or at least about 8%, 9%, 10%, 10.5%, 11% or 12% and at, about, less than or less than about 15%, 14%, 13%, 12%, 11% or 10.5%.

For stearic acid, a suitable threshold value may be at or about 4.5%, with the modified soybean such as described herein containing at least or at least about 4.5%, 5%, 5.5%, or 6% stearic acid and less than or less than about 10%, 9%, 8% or 7% stearic acid and the comparable unmodified or null soybean containing at least or at least about 2%, 2.5%, 3%, 3.5%, or 4% stearic acid and less than or less than about 4.5%, 4%, 3.5%, 3% or 2.5% stearic acid. The threshold value for stearic acid includes values at, about, at least or at least about 3%, 3.5%, 4%, 4.5%, or 5% and at, about, less than or less than about 6%, 5.5%, 5%, 4.5%, 4% or 3.5%.

For oleic acid, a suitable threshold value may be at or about 28%, with the modified soybean such as described herein containing at least or at least about 28%, 30%, 35%, 40%, 45%, 50%, 55%, 60%, 65%, 70%, 75%, 80% or 85% oleic acid and less than or less than about 95%, 90%, 85%, 80%, 75%, 70%, 65%, 60%, 55%, 50%, 45%, 40%, 35% or 30% oleic acid and the comparable unmodified or null soybean containing at least or at least about 10%, 15%, 20%, 25%, or 27% oleic acid and less than or less than about 28%, 25%, 20%, or 15% oleic acid. The threshold value for oleic acid includes values at, about, at least or at least about 18%, 19%, 20%, 21%, 22%, 23%, 24% or 25% and at, about, less than or less than about 75%, 50%, 45%, 40%, 35%, 30% or 28%.

For linoleic acid, a suitable threshold value may be at or about 50%, with the modified soybean such as described herein containing at least or at least about 30%, 35%, 40%, 45%, or 50% linoleic acid and less than or less than about 60%, 55%, 50%, 45%, 40%, or 35% linoleic acid and the comparable unmodified or null soybean containing at least or at least about 50%, 55%, or 60% linoleic acid and less than or less than about 65%, 60%, 55% or 50% linoleic acid. The threshold value for linoleic acid includes values at, about, at least or at least about 45%, 50%, or 55% and at, about, less than or less than about 60%, 55%, or 50%.

For linolenic acid, a suitable threshold value may be at or about 6.5%, with the modified soybean such as described herein containing at least or at least about 0.5%, 1%, 1.5%, 2%, 2.5%, 3%, 3.5%, 4%, 4.5%, 5%, 5.5% or 6% linolenic acid and less than or less than about 6.5%, 6%, 5.5%, 5%, 4.5%, 4%, 3.5%, 3%, 2.5%, 2%, 1.5% or 1% linolenic acid and the comparable unmodified or null soybean containing at least or at least about 6.5%, 7%, 7.5%, 8%, 8.5% or 9% linolenic acid and less than or less than about 10%, 9.5%, 9%, 8.5%, 8%, 7.5%, or 7% linolenic acid. The threshold value for linolenic acid includes values at, about, at least or at least about 1%, 1.5%, 2%, 2.5%, 3%, 3.5%, 4%, 4.5%, 5%, 5.5% or 6% and at, about, less than or less than about 10%, 9.5%, 9%, 8.5%, 8%, 7.5%, 7% or 6.5%.

For total saturated fatty acids (stearic acid plus palmitic acid), a suitable threshold value may be at or about 15.5%, with the modified soybean such as described herein containing at least or at least about 15.5%, 16%, 16.5%, 17%, 17.5%, 18%, 18.5%, 19% or 19.5% total saturated fatty acids and less than or less than about 30%, 25%, 20%, 19%, 18%, 17%, or 16% total saturated fatty acids and the comparable unmodified or null soybean containing at least or at least about 9%, 10%, 10.5%, 11%, 11.5%, 12%, 12.5%, 13%, 13.5%, 14%, 14.5% or 15% total saturated fatty acids and less than or less than about 15.5%, 15%, 14.5%, 14%, 13.5%, 13%, 12.5%, 12%, 11.5%, 11%, 10.5% or 10% total saturated fatty acids. The threshold value for total saturated fatty acids includes values at, about, at least or at least about 10.5%, 11%, 11.5%, 12%, 12.5%, 13%, 13.5%, 14%, 14.5%, or 15% and at, about, less than or less than about 10%, 9.5%, 9%, 8.5%, 8%, 7.5%, 7% or 6.5%.

In some embodiments, soybeans may be modified to have lower total saturated fatty acids (stearic acid plus palmitic acid) than unmodified soybeans, such as at least or at least about 4%, 5%, 6% or 7% total saturated fatty acids and less than about 15%, 12%, 10%, 9%, 8% or 7% with a threshold value of at, about, at least or at least about 5%, 6%, 6.5%, 7%, 7.5%, 8%, 8.5%, 9%, 9.5%, 10%, 10.5%, 11%, 11.5%, 12% or 12.5% and at, about, less than or less than about 18%, 17%, 16%, 15%, 14%, 13%, 12%, 11%, 10%, 9%, or 8%.

For total soluble carbohydrate, a suitable threshold value may be at or about 9%, with the modified soybean such as described herein containing at least or at least about 3%, 3.5%, 4%, 4.5%, 5%, 5.5%, 6%, 6.5%, 7%, 7.5%, 8% or 8.5% total soluble carbohydrate and less than or less than about 6.5%, 6%, 5.5%, 5%, 4.5%, 4%, 3.5%, 3%, 2.5%, 2%, 1.5% or 1% total soluble carbohydrate and the comparable unmodified or null soybean containing at least or at least about 9%, 9.5%, 10%, 10.5%, 11%, 11.5%, 12% or 12.5% total soluble carbohydrate and less than or less than about 15%, 14%, 13%, 12.5%, 12%, 11.5%, 11%, 10.5%, 10% or 9.5% total soluble carbohydrate. The threshold value for total soluble carbohydrate includes values at, about, at least or at least about 4%, 4.5%, 5%, 5.5%, 6%, 6.5%, 7%, 7.5%, 8%, 8.5%, or 9% and at, about, less than or less than about 9.5%, 10%, 10.5%, 11%, 11.5%, 12%, or 12.5%.

For sucrose, a suitable threshold value may be at or about 3.8%, with the modified soybean such as described herein containing at least or at least about 0.5%, 1%, 1.5%, 2%, 2.5%, 3%, or 3.5% sucrose and less than or less than about 3.8%, 3.5%, 3%, 2.5%, 2%, 1.5%, 1%, or 0.5% sucrose and the comparable unmodified or null soybean containing at least or at least about 3.8%, 4%, 4.5%, 5%, 5.5% or 6% sucrose and less than or less than about 7%, 6.5%, 6%, 5.5%, 5%, 4.5%, or 4% sucrose. The threshold value for sucrose includes values at, about, at least or at least about 1%, 1.5%, 2%, 2.5%, 3%, or 3.5% and at, about, less than or less than about 6%, 5.5%, 5%, 4.5%, 4%, 3.5%, 3% or 2.5%.

For the sum of oil and protein content, also referred to as the PROIL content, a suitable threshold value may be at or about 54%, with the modified soybean such as described herein containing at least or at least about 54%, 55%, 56%, 57%, 58%, 59%, 60%, 61%, 62% or 63% PROIL and less than or less than about 70%, 65%, 60%, 59%, 58%, 57%, 56%, or 55% PROIL and the comparable unmodified or null soybean containing at least or at least about 45%, 46%, 47%, 48%, 49%, 50%, 51%, 52% or 53% PROIL and less than or less than about 55%, 54%, 53%, 52%, 51%, 50%, or 49% PROIL. The threshold value for PROIL includes values at, about, at least or at least about 50%, 51%, 52%, 53%, 54%, or 55% and at, about, less than or less than about 64%, 63%, 62%, 61%, 60%, 59%, 58%, 57%, 56%, or 55%.

Useful examples of percent point increases in PROIL in a seed, such as a modified soybean seed compared with a comparable or control soybean include, but are not limited to, percentage point increases of at least or at least about 50%, 55%, 60%, 65%, 70%, 75%, 80%, 85%, 90%, or 95% and less than or less than about 98%, 97%, 96%, 95%, 90%, 85%, 80%, 75%, 70%, 65%, 60%, 65% 60%, 55%, 50%, 45% or 40%.

The methods may be used for seeds from plants with two, three, four, five or ten or more transgenes or genetic modifications, wherein accumulating or stacking of transgenic regions or genetic modifications into plants or lines is achieved by addition of transgenes by transformation, by genome editing, by crossing parent plants or lines containing different transgenic regions or modifications, or any combination thereof. Analyses can be conducted to select individual seeds on the basis of the presence of one or more characteristics associated with at least one transgene or modification. Such characteristics include, but are not limited to, a seed composition, a transgene per se, a genetic marker linked to a transgene or modification, mRNA expressed from a transgene or modification, and a protein product of a transgene or modified region or gene.

Methods and systems provided herein may include the step of confirming a phenotype, for example, by extracting or isolating nucleic acids, such as DNA, from a seed or population of seeds and using appropriate genetic techniques to analyze or detect the genotype. Such genetic techniques include, for example, contacting isolated or extracted nucleic acids with one or more genetic markers, the detection of single nucleotide polymorphisms, simple sequence repeats, restriction fragment length polymorphisms, haplotypes, tag SNPs, alleles of genetic markers, genes, DNA-derived sequences, RNA-derived sequences, promoters, 5' untranslated regions of genes, 3' untranslated regions of genes, microRNA, siRNA, quantitative trait loci (QTL), satellite markers, transgenes, mRNA, ds mRNA, transcriptional profiles, and methylation patters. Examples of genetic analyses to identify or select seeds for trait integration include, without limitation, identification of high recurrent parent allele frequencies, tracking of transgenes of interest or screening for the absence of unwanted transgenes, selection of hybrid testing seed, selection of seed expressing a gene of interest, selection of seed expressing a heritable phenotype, identification of seed with selected genetic loci, and zygosity testing.

Assaying of soybean seeds according to the provided methods and systems can also be done rapidly, with an accurate measure of the composition, such as the amount of sucrosyl-oligosaccharides, of the single soybean or a batch of soybeans achieved in less than 5, 4, 3, 2, or 1 minutes or less than one second following commencement of the method. For example, using FT-NIR, up to 100 g (about 400 to 500) soybean seeds as a single batch can be measured in less than 3, 2 or 1 minutes, for example, in about 1 to 2 minutes or 1 to 3 minutes. For example, using NIT, up to 500 g (about 2,500) soybean seeds can have seed composition, including sucrosyl-oligosaccharides, be measured in less than 3, 2 or 1 minutes, for example, in about 0.5 to 1 minutes, 0.5 to 2 minutes, 0.5 to 3 minutes, or 0.5 to 5 minutes. For example, using SS-NIR, a single seed can be measured in about 1 or 2 minutes, such as 0.5 to 3 minutes, 0.5 to 4 minutes or 0.5 to 5 minutes. Using SS-NIR, a single seed can also be measured in less than a second, such as at least 5, 10, 20, 30, 40, 50, 60, 70, 80, 90 or 100 soybean seeds per second and less than about 1000, 500, 400, 300, 200, or 100 seeds per second.

The methods and systems provided herein can enhance efficiency and facilitate high throughput of sorting and selecting seed and plants grown from the seed with a desired trait.

In some embodiments, the methods described herein are used in transgenic, genome modification or research breeding programs where sample size may be limited, such as a single seed from a segregating plant, and when intact viable seed are required for propagation and advancement. In some embodiments, the methods are used for seed analysis where destructive analytical methods are not desirable because intact seeds are required for processing or when there is insufficient time to undertake destructive analysis.

The progeny seed can be selected, bulked and used to make further breeding crosses or in further research. The progeny seed can be made subject to the methods of non-destructive analysis provided herein.

Also provided herein is a method for producing a soybean plant with one or more desired traits, e.g. transgenes or modifications. Donor soybean plants for a parental line containing the desired trait are selected. Selected plant material may represent, among others, an inbred line, a hybrid line, a heterogeneous population of soybean plants, or an individual plant. According to techniques well known in the art of plant breeding, the donor parental line is crossed with a second parental line. In some embodiments, the second parental line is a high yielding line. This cross produces a segregating plant population composed of genetically heterogeneous plants. Seeds of plants of the segregating plant population are screened for the desired trait using the analytical methods as disclosed herein. Further breeding may include, among other techniques, additional crosses with other lines, hybrids, backcrossing, or self-crossing. The result is a line of soybean plants that has the desirable trait and optionally also has other desirable traits from one or more other soybean lines.

The methods and systems provided herein provide an increased capacity to evaluate a larger number of breeding populations per field unit, and increased capacity to analyze breeding populations for desired traits prior to planting. For example, the methods and systems allow a breeder to analyze at least 100, 250, 500, or 1,000 seeds and sort or select the 5, 10, 25 or 50 desired seeds from that population for planting without having to plant assess, tag and sample the original population of 100, 250, 500, or 1,000 seeds. Very large sample sizes can be processed quickly by either single seed or bulk analysis, such as at least about 1 kg, 5 kg, 10 kg, 100 kg, 500 kg, 1000 kg, 1500 kg, 2000 kg, 3000 kg, 4000 kg or 5000 kg of soybean seeds per hour and less than 25,000 kg, 20,000 kg, 15,000 kg, 10,000 kg, 7,500 kg, 5,000 kg, 2,000 kg, 1000 kg, 500 kg, 100 kg, 10 kg or 5 kg soybean seeds per hour.

The methods and systems provided herein further permit quality assurance (QA) and quality control (QC) by assuring that soybean seeds are free of regulated or unwanted transgenes, undesirable genetic traits, or undesirable inherited phenotypes by identifying such phenotypes and discarding such seed.

Soybean seeds which can be used may additionally contain desirable agronomic traits that enhance production and consistency of production of soybean grain, such as herbicide tolerance, disease resistance, insect resistance, increased grain yield, increased nutritional content, increased growth rates, enhanced stress tolerance, altered maturity, and combinations thereof. Quality traits such as higher oil, higher protein, modifications in essential amino acids and protein compositional changes, changes in oil composition, nutritional traits such as vitamins, and traits with industrial uses including biodiesel, bio-lubricants, and polymers can also be identified and selected.

The methods and systems can be used in a plant breeding program which selects plants or seeds having a desired genetic or phenotypic trait, wherein a desired genetic trait includes one or more of a genotype, a haplotype, an allele, a sequence, a transcript profile, and a methylation pattern. The methods and systems may be further used in combination with plant breeding methods where a single seed selected or sorted is crossed or backcrossed and a single generation or multiple generations of progeny plants are generated. Seed of the progeny plants may be processed according to the methods described herein. The crossing and backcrossing steps of the first and subsequent generation of progeny plants and seeds may be carried out in any combination. The choice of breeding method depends on the mode of plant reproduction, the heritability of the trait(s) being improved, and the type of cultivar used commercially (e.g., hybrid cultivar, pureline cultivar, etc.). Selected, non-limiting approaches for breeding the plants are set forth below. It is further understood that any soybean lines, varieties or cultivars can be utilized in a breeding program. Factors including, for example, without limitation, emergence vigor, vegetative vigor, stress tolerance, disease resistance, branching, flowering, seed set, seed size, seed density, standability, and threshability may be selected for use in the breeding program.

In some embodiments, the single seed identity of the seed is preserved. Several methods of preserving single seed identity can be used while transferring or transporting seed from the location of the seed, such as at or following harvest, to the location where analysis is conducted, to the field or greenhouse location where the selected plants are to be grown. Methods include, but are not limited to, transferring selected individuals to seed tape, a cassette tray, or indexing tray, transplanting with peat pots, and hand-planting from individual seed packets.

The apparatus, device, system or method for measuring and sorting seeds can comprise or use a transport system which supports at least one seed at a time and exposes the at least one seed to an optical interrogation device or an imaging system, such as NIT, NIR or FT-NIR, which captures at least one near-infrared image of the at least one seed. The imaging system can be configured to accurately measure the amount of one or more sucrosyl-oligosaccharides in the first seed compared with the standard reference analytical method provided herein. The apparatus, device, system or method can include an electronic controller which makes a sorting decision with at least two sorting outcomes regarding the seed based on the modified light, image or near infrared spectra obtained from the seed and a sorting system to alter the path of the seed based on the sorting decision, wherein the electronic controller associates a first sorting outcome with the first seed and the electronic controller associates a second sorting outcome with the second seed. Seed containing low amounts of sucrosyl-oligosaccharides below (or at) a threshold value can be separated from seed containing higher amounts of sucrosyl-oligosaccharides above (or at) the threshold value. For example, greater confidence in the sorting decisions may achieved by combining the sucrosyl-oligosaccharide threshold value with a threshold value for one or more fatty acid percentages, altered, such as increased oil or protein content, changes in the soluble sugar levels, or a combination thereof. Each of these parameters can be measured from the same near infrared spectra captured from a single seed, bulk seeds or protein meal.

In some embodiments, a method for determining the amount of a sucrosyl-oligosaccharide in a single soybean seed or a sample of intact soybean seeds, comprises directing light from a light source onto a soybean seed or seeds to form modified light from the soybean seed or seeds; receiving the modified light in an imaging device, such as capturing the near infrared absorption spectra, and measuring to the amount of a sucrosyl-oligosaccharide in the seed or seeds based on the received modified light, the amount of sucrosyl-oligosaccharide being measured to an accuracy according to the standard reference analytical method provided herein.

The imaging device can be a commercially available infrared spectrometer, including for example, an infrared spectrometer, a Fourier transform infrared spectrometer, or a spectrophotometer with a diffuser and lens and filter array such as described in U.S. Pat. Nos. 9,500,523, 9,383,258, 9,377,396 and 9,291,504, or a seed sorting device such as described in U.S. Pat. No. 8,907,241 or a device useful for single seed analysis such as described in U.S. Pat. No. 8,965,060.

In some embodiments, a method for processing seeds or for determining the amount of a sucrosyl-oligosaccharide in a soybean seed comprises directing light from a light source onto an individual soybean seed to form modified light from the soybean seed; receiving the modified light in an imaging device; measuring the amount of a sucrosyl-oligosaccharide in the seed based on the received modified light, the amount of sucrosyl-oligosaccharide being measured to an accuracy that is within the parameters provided herein. The seed can be transported to a first location when the amount of sucrosyl-oligosaccharide measured is below a threshold value and transporting the seed to a different second location when the amount of sucrosyl-oligosaccharide measured is at or above the threshold value. The seed can be separated into modified and unmodified seed wherein the amount of sucrosyl-oligosaccharide, such as stachyose or a combination of stachyose and raffinose, differ between the modified and unmodified seed as described herein.

In some embodiments, the method or system includes an automated method or system, wherein a seed is separated from a plurality of seeds prior to directing light from a light source onto an individual soybean seed to form modified light from the soybean seed. The light source can be comprised in an optical interrogation device or system and comprises near infrared light such as a broad spectrum light source or a near infrared light source. The automated system may include a transport system for transporting separated seeds to the optical interrogation device and for transporting the seeds to one, two, three or more different locations based on the composition of the seed measured by the optical interrogation device. Individual seeds can be automatically transported to a first station for receiving light where light is directed from a light source on the individual soybean seed at a first station to form modified light, the modified light from the soybean seed is received in an imaging device, and the amount of one or more sucrosyl-oligosaccharides in the seed measured based on the modified light, to an accuracy as provided herein. The method may further comprise following the measurement of the amount of a sucrosyl-oligosaccharide, transporting the seed to a first location when the amount of sucrosyl-oligosaccharide measured is below a threshold value and transporting the seed to a different second location when the amount of sucrosyl-oligosaccharide measured is at or above the threshold value. All of the prior steps can be repeated for a second and subsequent individual seeds.

In some embodiments, a plurality of seeds to be measured either as single seeds or as a sample of intact seeds includes both modified and unmodified seeds as described herein, wherein the modified seeds are transported to the first location and the unmodified seeds are transported to the second location based on the compositional differences detected by the optical interrogation device. The steps of sorting a seed from a plurality of seeds and carrying out this method as disclosed herein can be repeated for at least a second, third or fourth seed. In some embodiments, seeds are selected or separated depending on the composition measured using the methods described herein.

The methods are suitable for measuring and processing small and large sample sizes. In some embodiments, a sample or population of at least 5, 10, 15, 20, 25, 30, 40, or 50 seeds and less than 250, 225, 200, 175, 150, 125, 100, 90, 80, 70, or 60 whole, intact and/or viable seeds are assayed together as a batch of seeds in the methods and systems provided. In some embodiments, a sample of at least 1 g, 5 g, 10 g, 100 g, 150 g, 200 g, 250 g, or 300 g seeds and less than 5000 g, 2000 g, 1000 g, 900 g, 800 g, 700 g, 600 g, or 500 g whole, intact and/or viable seeds are assayed together as a batch of seeds in the methods and systems provided. In some embodiments, at least 5, 10, 15, 20, 25, 30, 40, 50, 75, 100, 150, 200, 250, 500 or 1000 and less than 1,000,000, 500,000, 100,000, 75,000, 50,000, 25,000, 10,000, 5,000, 2,500, 1,000, 500, 250, 100, 75, 50 or 25 individual seeds, seed, meal or soybean flake batches, or seed populations are measured.

Methods and systems provided can be used to analyze individual seeds or seed batch samples within a population of seeds to measure one or more compositional differences in one or more components of the seed or seeds.

Following the measurement of the composition of the seeds, for example, the amount of sucrosyl-oligosaccharide, oil, protein, sugars, starch, carbohydrate, fiber or combination thereof, the soybean seeds can be processed. Processing steps can include one or more of dehulling of the soybeans, extraction of oil, for example by use of solvents, processing soy flakes to soy meal for animal feed, grinding soy flakes to produce soy flour, sizing soy flakes to produce soy grits or texturizing soy flakes to produce textured vegetable protein. Soy protein concentrates and isolated soy protein can be further refined and produced from soy flakes. The methods and systems provided may include the step of processing the soybeans into meal without the need for dehulling, based on the low non-digestible carbohydrate content, including one or more of stachyose and raffinose. The composition of the soy beans can be accurately measured in the field or at the grain elevator to facilitate processing decisions on a large scale. Protein meal can be accurately measured at the grain processing plants to determine meal quality and value.

Some embodiments include methods and systems for selecting a plant or plant seed, comprising directing light from a light source onto an individual soybean seed to form modified light from the soybean seed; receiving the modified light in an imaging device; measuring the amount of a sucrosyl-oligosaccharide in the seed based on the received modified light, the amount of sucrosyl-oligosaccharide being measured to an accuracy that is within an amount measured using the standard reference analytical methods as provided herein; transporting the seed to a first location when the amount of sucrosyl-oligosaccharide measured is below a threshold value and transporting the seed to a different second location when the amount of sucrosyl-oligosaccharide measured is at or above the threshold value. The seed from the first location and/or the second location can be grown to produce a plant which can be crossed with a different plant or selfed/allowed to self. The progeny seed produced from seed at the first location may contain a lower or reduced amount or concentration of sucrosyl-oligosaccharide, when compared to progeny seed produced from seed at the second location. The seed transported to either the first or second location and produced through crossing or selfing can be transgenic or non-transgenic and may comprise at least one recombinant construct in the genome, or may not comprise a recombinant construct in the genome. The seeds selected by the methods as disclosed herein may be further selected and used in breeding.

Some embodiments include methods for sorting seeds, the methods comprising directing light from a light source onto an individual soybean seed to form modified light from the soybean seed receiving the modified light in an imaging device measuring the amount of a sucrosyl-oligosaccharide in the seed based on the received to modified light, the amount of sucrosyl-oligosaccharide being measured to an accuracy that is within 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, or 2 percentage points of the amount measured using the standard reference analytical method; and transporting the seed to a first location when the amount of sucrosyl-oligosaccharide measured is below a threshold value and transporting the seed to a different second location when the amount of sucrosyl-oligosaccharide measured is at or above the threshold value. The method of sorting as disclosed herein may further comprise growing a plant from the sorted seed and crossing the plant with itself or a different plant and using the seed and plant in a breeding program as provided herein.

Any seed, including monocot and dicot seeds, may be adapted to be utilized in a method, systems or device provided herein. The seed may be, for example, alfalfa seed, apple seed, banana seed, barley seed, bean seed, broccoli seed, castor bean seed, citrus seed, clover seed, coconut seed, coffee seed, maize seed, cotton seed, cucumber seed, Douglas fir seed, Eucalyptus seed, Loblolly pine seed, linseed seed, melon seed, oat seed, olive seed, palm seed, pea seed, peanut seed, pepper seed, poplar seed, Radiata pine seed, rapeseed seed, rice seed, rye seed, sorghum seed, Southern pine seed, soybean seed, strawberry seed, sugar beet seed, sugarcane seed, sunflower seed, sweetgum seed, tea seed, tobacco seed, tomato seed, turf seed, wheat seed, and Arabidopsis seed.

Depending on the seed composition, the seed may be discarded prior to planting or planted such as when being used in a plant breeding program, or can be directed to an appropriate processing plant or process if the seed is harvested from a crop and intended for processing. Processing that may occur, depending on the seed composition, may include or exclude one or more of the steps of dehulling, extracting oil, processing meal and producing protein from the soybean. In general, soybean oil is produced from cleaned, tempered, dehulled, and flaked soybeans using solvent (hexane) extraction or a combination of physical pressure and/or solvent extraction.

The following examples are presented in order to more fully illustrate some embodiments of the invention. They should, in no way be construed, however, as limiting the broad scope of the invention. Those of ordinary skill in the art will readily adopt the underlying principles of this discovery to design various compounds without departing from the spirit of the current invention.

EXAMPLES

In the following Examples, parts and percentages are by weight and degrees are Celsius, unless otherwise stated. The meaning of abbreviations is as follows: "sec" means second(s), "min" means minute(s), "h" means hour(s), "d" means day(s), "μL" means microliter(s), "mL" means milliliter(s), "L" means liter(s), "μM" means micromolar, "mM" means millimolar, "M" means molar, "mmol" means millimole(s), "μmole" mean micromole(s), "g" means gram(s), "μg" means microgram(s), "ng" means nanogram(s), "U" means unit(s), "bp" means base pair(s) and "kB" means kilobase(s).

Example 1

Creation of Events Having Compositional Diversity
Soybean lines having a broad range of compositional diversity were created as described below.

RNAi was used to silence seed-specific gene expression of soy fatty acid desaturase 2 (fad2) to produce soybeans with a seed oil composition having increased oleic acid according to U.S. Pat. No. 7,456,014.

RNAi was used to silence seed-specific gene expression of soy phosphoglucomutase (PGM) to produce soybeans with a seed oil composition having increased oil and protein according to U.S. Pat. No. 7,323,560.

RNAi comprising polynucleotide fragments were prepared for galactinol synthase 1 (GAS1), according to U.S. Pat. No. 5,648,210, galactinol synthase 2 (GAS2) according to U.S. Pat. No. 6,967,262 and galactinol synthase 3 (GAS3) according to U.S. Pat. No. 7,294,756. The use of seed-specific silencing of gene expression of soy galactinol synthases (GAS) to produce soybeans with a decreased raffinose and stachyose carbohydrate content and increased sucrose content was carried out according to PCT/US14/48825.

Artificial microRNAs (amiRNAs) were used to silence seed-specific gene expression of soy fatty acid desaturase 3 (fad3) to produce soybeans with a seed oil composition having decreased alpha-linolenic acid according to PCT/US13/22654 and PCT/US14/48825.

Artificial microRNAs (amiRNAs) were used to silence seed-specific gene expression of soy fatty acid desaturase 2 (fad2) to produce soybeans with a seed oil composition having increased oleic acid according to PCT/US08/87082, PCT/US13/22654 and PCT/US14/48825.

Artificial microRNAs (amiRNAs) were used to silence seed-specific gene expression of soy fatty acid thioesterase 2 (fatB) to produce soybeans with a seed oil composition having decreased palmitic and stearic acids according to, for example, PCT/US13/22654 and PCT/US14/48825. Combining amiRNAs together to silence multiple genes such as fad2 and fatB was carried out according to, for example, PCT/US13/22654 and PCT/US14/48825.

A modified soy diacylglycerol acyltransferase 1 gene (GM-DGAT1-C9C10C11) under control of a seed-specific promoter was used to produce soybeans having higher oil and protein in the seed according to, for example, U.S. Pat. No. 8,101,819 and PCT/US14/48825.

A *Yarrowia lipolytica* diacylglycerol acyltransferase 2 gene (YL-DGAT2) under control of a seed-specific promoter was used to produce soybeans having higher oil and protein in the seed according to U.S. Pat. Nos. 8,143,473, 8,143,476 and in PCT/US14/48825.

YL-DGAT2, under control of a seed-specific promoter, was combined with a fad3 amiRNA under control of a seed-specific promoter, and with a GAS RNAi cassette under control of a seed-specific promoter according to PCT/US14/48825.

A soy sucrose transporter 4 (GM-SUT4) alone or in combination with YL-DGAT2 under control of a seed-specific promoter was used to produce soybeans having higher seed oil has according to U.S. Pat. No. 8,993,840.

A soy ovule development protein 1 (GM-ODP1) alone or in combination with YL-DGAT2 or GM-DGAT1-C9C10C11 under control of the soy sucrose synthase promoter was used to produce soybeans having higher oil and protein in the seed according to PCT/US12/70828.

Mutations in the sucrosyl-oligosaccharide pathway, such as low2 (mutant with reduced raffinose synthase expression leading to low stachyose and raffinose and elevated sucrose and galactinol and low4 (mutant with reduced myo-inositol-1P-synthase leading to low stachyose and raffinose) according to U.S. Pat. No. 6,653,451.

Wildtype commodity soybeans were also included in the test set along with transgenic null materials (i.e., lines that had undergone the typical transformation process but that were found, on subsequent analysis, to not be expressing the trait of interest). Varieties used included one or more of the following commercial or public varieties: 91M10, 92Y51, 92Y61, 93B67, 93B68, 93B86, 93M02, 93M11, 93M12, 93Y21, 93Y30, 93Y41, 93Y42, 93Y83, 93Y84, 94Y23, 95B34, 98Y11, ASGA232HS, EX82J07, JACK, P29T68PR, P32T80PR, SP6634911, YR25C09, YR37Y09.

A list of experiment names and the corresponding DNA constructs used to create soybean events having a range of compositions as described herein is shown in Table 2.

TABLE 2

Experiment names and corresponding DNA plasmids/DNA fragments used to create soybean events producing a diverse range of compositions.

| Experiment Name | Transformation Type | DNA Plasmid/Fragment | SEQ ID NO: | Second DNA Plasmid/Fragment | SEQ ID NO: |
|---|---|---|---|---|---|
| Soil2 | SSI | PHP48070 | 1 | n/a | n/a |
| Soil19 | SSI | PHP50573 | 2 | n/a | n/a |
| Soil91 | SSI | PHP64612 | 3 | n/a | n/a |
| Soil92 | SSI | PHP64613 | 4 | n/a | n/a |
| Meal18 | Random Particle Bombardment | PHP25066A | 5 | n/a | n/a |
| Oil119 | Random Particle Bombardment | PHP64207A | 6 | n/a | n/a |
| HOGAS | Random Particle Co-Bombardment | PHP17522A | 7 | PHP17734A | 8 |
| Meal34 | Random Particle Co-Bombardment | PHP29252A | 9 | PHP19031A | 10 |
| Meal36 | Random Particle Co-Bombardment | PHP29882A | 11 | PHP29959A | 12 |

The Soil 2 PHP48070 plasmid contains the following noted sequences: GAS hairpin from position: 13833-17206 of SEQ ID NO: 1, FAD2-specific amiRNA precursor from position: 6980-8557 of SEQ ID NO: 1, and the FAD3- specific amiRNA precursor from position: 10514-11472 of SEQ ID NO: 1.

The Soil 19 PHP50573 plasmid contains the following noted sequences: GAS hairpin from position: 13809-17182 of SEQ ID NO: 2, FAD3-specific amiRNA precursor from position: 10490-11448 of SEQ ID NO: 2, and the YL-DGAT2 from position: 6996-8540 of SEQ ID NO: 2.

The Soil 91 PHP64612 plasmid contains the following noted sequences: GAS hairpin from position: 15112-18485 of SEQ ID NO: 3, Gm_SUT4 from position: 12428-13945 of SEQ ID NO: 3, Gm_DGAT1 from position: 9879-11390 of SEQ ID NO: 3, and Gm_ODP1: from position: 6823-8058 of SEQ ID NO: 3.

The Soil 92 PHP64613 plasmid contains the following noted sequences: GAS hairpin from position: 17136-18849 of SEQ ID NO: 4, Gm_SUT4 from position: 12961-14478 of SEQ ID NO: 4, Gm_DGAT1 from position: 9454-10998 of SEQ ID NO: 4, and Gm_ODP1: from position: 6823-8058 of SEQ ID NO: 4.

The Meal 18 PHP25066A plasmid contains the following noted sequences: GAS suppression fragments from position: 76-2194 of SEQ ID NO: 5.

The Oil 119 PHP64207A plasmid contains the following noted sequences: GAS hairpin from position: 10496-13869 of SEQ ID NO: 6, Gm_SUT4 from position: 7812-9329 of SEQ ID NO: 6, and Gm_DGAT1 from position: 5262-6773 of SEQ ID NO: 6.

The HOGAS PHP17734A plasmid contains the following noted sequences: GAS suppression fragments from position: 1132-1977 of SEQ ID NO: 8 and a FAD2 suppression fragment from position: 5376-5986 of SEQ ID NO: 8. The HOGAS plasmid PHP17522A (SEQ ID NO: 7) contains a selectable marker (herbicide resistance).

The Meal 34 PHP29252A plasmid contains the following noted sequence: GAS/PGM hairpin structure from position: 2117-6630 of SEQ ID NO: 9. The Meal 34 plasmid PHP19031A (SEQ ID NO: 10) contains a selectable marker (herbicide resistance).

The Meal 36 PHP29882A plasmid contains the following noted sequence: PGM hairpin from position: 634-1973 of SEQ ID NO: 11. The Meal 36 PHP29959A plasmid contains the following noted sequence: GAS hairpin from position: 321-3694 of SEQ ID NO: 12.

Ascl fragments were prepared transformed into soy using particle gun bombardment, events were selected, plants grown and seed were harvested as described in U.S. Pat. No. 8,084,074 for random particle bombardment [Meal18 (PHP25066A) or Oil119 (PHP64207A)] and random particle co-bombardment [HOGAS (PHP17522A+PHP17734A), Meal34 (PHP29252A+PHP19031 A) or Meal36 (PHP29882A+PHP29959A)] experiments.

Transgenic SSI target event "A", previously described in U.S. Pat. No. 8,293,533, was transformed with the donor constructs [Soil2 (PHP48070), Soil19 (PHP50573), Soil91 (PHP64612) or Soil92 (PHP64613)] and the FLP recombinase construct PHP44664 as previously described in PCT/US14/48825 and events were selected, plants grown and seed were harvested as described previously and in U.S. Pat. No. 8,084,074.

Example 2

Reference Chemistry for Development of Single Seed Compositional Models.
2.1. Sample Preparation for Single Seed Reference Chemistry.

A single soybean was placed in a Spex Certiprep ½×2" polycarbonate vial with cap (cat #3116PC). A ⅜" stainless steel ball bearing was added. Grinding was performed in a Spex Certiprep 2000 Geno/Grinder at 1500 strokes/min for three 30 second intervals with a 1-minute rest between each cycle.
2.2. Lipid and Non-Structural Carbohydrate Extraction; GC Fatty Acid Profile Determinations Quantitative oil determinations were performed (on both the whole and ground bean samples) by NMR (see below). The lipid extracts of the single soybean powders were used solely to determine the fatty acid profiles. Three replicate extractions were performed on each sample as follows:
2.2.1. Weigh sample (approximately 20-50 mg; to an accuracy of 0.1 mg) into 13×100 mm tube (with Teflon® lined cap; VWR (53283-800) and record weight. In later studies sample size was standardized at ~20.0 mg.
2.2.2. Add 2 mL Heptane, vortex and place into an ultrasonic bath (VWR Scientific Model 750D) at 600 for 15 min at full sonification-power (~360W).
2.2.3. Centrifuge for 5 min at 1700×g at room temperature.
2.2.4. Decant the supernatant to a clean 13×100 mm glass tube.
2.3. Fatty Acid Profile Determination: GC Method:
2.3.1. Transfer 200 uL aliquot of the heptane extract into a clean screw top GC vial National Scientific (C4000-186W)
2.3.2. To the 200 uL add 300 uL heptane and 50 uL trimethylsulfonium hydroxide in methanol (JenaChem)
2.3.3. Shake the vials on an orbital shaker at room temperature for 15 minutes.
2.3.4. The fatty acid methyl esters were analyzed by directly injecting 1 uL samples (at a 5:1 split ratio) onto an Agilent 6890 gas chromatography system fitted with a Supelco Omegawax 320 (30 m×0.320 mm×0.25 um film) capillary column. Hydrogen was used as the carrier gas (39 cm/sec average linear velocity). Inlet and FID detector temperatures were held at 260° C. and the oven column temperature was ramped from 180 to 2400C at a rate of 12° C. per minute.
2.4. Non-Structural Carbohydrate Extraction:
2.4.1. Add 1 mL acetone to the heptane extracted pellet from the fatty acid profile method above, vortex mix to disperse the material into the acetone and dry in a SpeedVac.
2.4.2. To the dry pellet add 2 mL of 80% ethanol. Vortex to break up pellet as much as possible. Extract on sonicator (see 2.2.2) for 15 min at 600.
2.4.3. Centrifuge for 5 min at 1700×g. Transfer supernatant to a clean 13×100 mm tube.
2.4.4. Repeat Steps 2.4.2 and 2.4.3 two more times, combining the supernatant with the above (3) each time.
2.4.5. Add 100 µL of phenyl-β-D glucopyranoside internal standard (β-phenyglucopyranoside stock 0.5000+/−0.0010 g in 100 ml water) to the combined supernatant. Dry the extract in a SpeedVac and analyze for non-structural carbohydrates as described below.
2.4.6. Add 1 ml acetone and dry the remaining pellet in the SpeedVac.
2.5. Starch Digestion and Extraction:
2.5.1. Perform starch digestion directly on the acetone dried pellets from non-structural carbohydrate extraction.
2.5.2. Add 100 units of α-Amylase (α-amylase; Heat Stable from *Bacillus licheniformis* e.g. Sigma-Aldrich A-4551) in 0.9 mL 50 mM MOPS (3-(N-Morpholino) propane sulfonic acid) buffer pH 7.0, containing 5 mM $CaCl_2$ and mix.
2.5.3. Place tubes into a heating block at 90° C. for 75 minutes. Mix several times during hydrolysis.
2.5.4. Allow tubes to cool to room temperature and add 5 units of Amyloglucosidase (commercially available from Roche 11 202 367 001) in 0.6 mL of 285 mM acetate buffer, pH 4.5 and incubate in a reciprocating water bath at 55° C. for 15-18 hours.

2.5.5. Remove rack of tubes and bring to room temperature.
2.5.6. Add 4.5 mL of absolute ethanol to each tube to attain a final ethanol concentration 80% and vortex. Extract on sonicator for 15 min at 60° C.
2.5.7. Centrifuge 5 min at 1700×g and decant supernatant to a 13×100 mm tube and immediately place tube in SpeedVac to reduce the volume.2.5.8. Extract pellet a further 2 times with 2 mL 80% ethanol, combining supernatant with above each time.2.5.9. Add 100 µL of phenyl-J-D glucopyranoside (see 2.4.5) to the combined supernatant before it is fully dry. Once the extract in the SpeedVac is dry analyze for non-structural sugars as described below.2.5.10. Add 1 ml acetone and dry the remaining pellet in the SpeedVac and store (at −20° C.) for structural sugar analysis.

2.6. Total Soluble Carbohydrate Derivatization and Analysis.

2.6.1. The dried samples from the soluble and starch extractions described above along with sets of sugar standard (pinitol, sorbitol, fructose, glucose, β-phenyl glucopyranoside, sucrose, raffinose and stachyose; at 0, 0.05, 0.10, 0.50, 1.00, 2.00, 3.00, 4.00 and 5.00 mg/tube) mixtures were solubilized in anhydrous pyridine (Sigma-Aldrich P57506) containing 30 mg/ml of hydroxylamine HCl (Sigma-Aldrich 159417).
2.6.2. Samples were placed on an orbital shaker (300 rpm) overnight and were then heated for 1 hr (75° C.) with vigorous vortex mixing applied every 15 min.
2.6.3. After cooling to room temperature 1 ml hexamethyldisilazane (Sigma-Aldrich H-4875) and 100 µL trifluoroacetic acid (Sigma-Aldrich T-6508) were added. The samples were vortex mixed and the precipitates were allowed to settle prior to transferring the supernatants to GC sample vials.
2.6.4. Samples were analyzed on an Agilent 6890 gas chromatography system fitted with a DB-17MS capillary column (30 m×0.32 mm×0.25 um film). Inlet and detector temperatures were both 275° C. After injection (2 µL, 20:1 split) the initial column temperature (150° C.) was increased to 180° C. at a rate 3° C./min and then at 25° C./min to a final temperature of 320° C. The final temperature was maintained for 10 min. The carrier gas was H2 at a linear velocity of 51 cm/sec. Detection was by flame ionization. A 1 m length of plain 0.320 mm capillary tube (Agilent; 160-2325-5) was inserted between the inlet and the analytical column to act as a guard column. The two column sections were connected using a push-fit connector. Prior to all analytical runs three injections of a standard mixture containing 5 mg of each sugar was made to passivate the chromatography system. This process was found to enable full recovery of stachyose from the analytical samples, especially as the column aged. Ultra-Inert Inlet Liners (Agilent; 5190-3164) were also used and were routinely changed based on indications of loss in chromatographic performance.
2.6.5. Data analysis was performed using Agilent ChemStation software. Each sugar was quantified relative to its own calibration curve, after dividing each individual peak by the area of the internal standard in each sample and standard. Final carbohydrate concentrations were expressed on a weight percent basis, corrected for moisture content as set forth herein. Residual sucrose, raffinose and stachyose recovered in the starch digestions were included in the total values reported for each sugar.

2.7. Supplemental Methods.

Moisture Content Determinations were Performed According to American Oil Chemists Society (AOCS Official Method Ba 2a-38, Modified for Small Samples) as Follows:

2.7.1. Weigh powdered sample material (approximately 100 mg; to an accuracy of 0.1 mg) into a pre-weighed (and recorded) 13×100 mm glass tube VWR (53283-800) and weigh again.
2.7.2. Place samples into a forced air oven preheated to 130° C.
2.7.3. Allow material to dry for 2 h.
2.7.4. Remove tubes into a desiccator cabinet and allow to come to room temperature before weighing again.
2.7.5. Cap tube and save residual dried material for subsequent combustion analysis for protein (see below).
2.7.6. Store in a desiccator for further analysis.

2.8. Calculation of Moisture Content.

$$\text{Moisture} = \frac{(\text{wt. tube} + \text{tissue as is} - \text{wt. tube}) - (\text{wt. tube} + \text{tissue dry} - \text{wt. tube})}{(\text{wt. tube} + \text{tissue as is} - \text{wt. tube})} \times 100$$

2.9. Whole Seed Moisture Calibrations.

Whole seed moisture calibrations for the SS-NIR were developed according to the methods described below. Pods were harvested from Jack, 93B86 and 93Y21 soybeans between the R7 and R8 stage of development (i.e., yellow to brown pod stage) when the soybeans had moisture contents of below 20%. Beans were removed from the pods and their weight was measured and recorded to 0.0001 g accuracy prior to spectral capture using the SS-NIR instrument. The beans were then subjected to controlled drying (@105° C. in a forced draft oven for short periods of time) to attain a broad range of moisture contents before repeat weighing and spectral capture. A final dry weight for each bean was obtained after drying in a forced draft oven at 105° C. for 18 h. Moisture content was calculated as follows:

$$\text{moisture content} = \frac{((\text{wt. tube} + \text{bean as is}^* - \text{wt. tube}) - (\text{wt. tube} + \text{oven dried bean} - \text{wt. tube}))}{(\text{wt. of bean as is} - \text{wt. tube})^*} \times 100$$

*at time of spectral capture.

Alternatively, mature soybeans were placed in 5×6" aluminum foil trays in 1 gallon ZipLock® plastic bags. The relative humidity of the atmosphere within the bags was controlled by adding a second foil pan in which either a layer of self-indicating DrieRite desiccant (W.A. Hammond Inc; Xenia Ohio) or a saturated aqueous solution of sodium chloride (200 g NaCl in ⅓rd pan depth of water). A third bag containing seed but without any atmospheric moisture control was also set up. The beans were exposed to the controlled moisture atmospheres for one month prior to weighing followed by immediate spectral capture on the SS-NIR. In order to maintain the individual identity of each bean after scanning they were placed into 16×125 mm Pyrex® glass tubes. The beans were then dried according to AOCS Official Method Ac 2-41 (modified for small samples) as follows:

2.9.1. Place bean into a pre-weighed (and recorded) 16×125 mm glass tube and weigh again; record weights to an accuracy of 0.1 mg.

2.9.2. Place samples into a forced air oven preheated to 130° C.
2.9.3. Allow material to dry for 3 h.
2.9.4. Remove tubes into a desiccator cabinet and allow to come to room temperature before weighing again.

$$\text{moisture content} = \frac{((\text{wt. tube} + \text{bean as is}^* - \text{wt. tube}) - (\text{wt. tube} + \text{oven dried bean} - \text{wt. tube}))}{(\text{wt. of bean as is}^* - \text{wt. tube})} \times 100$$

*at time of spectral capture

Predictive spectral models for seed moisture content were developed by combining the spectral information with the measured moisture contents for each bean.

2.10. Protein Analysis.

Protein contents were estimated by combustion analysis of the oven dried powders described above. Analysis was performed on a Flash™ 1112 EA combustion analyzer (commercially available from Thermo Scientific) running in the Nitrogen, Carbon, Sulfur (NCS) mode. Samples of oven dried (according to AOCS Official Method Ba 2a-38 as described above) powdered samples, 4-8 mg (NCS Mode), weighed to an accuracy of 0.001 mg on a Mettler-Toledo MX5 microbalance were used for analysis. Protein contents were calculated by multiplying % N, determined by the analyzer, by 6.25. All samples were run in duplicate. If the difference between the protein contents of the replicate samples was >5% of the mean value, additional replicates were analyzed. Final protein contents were measured on a dry weight basis and adjusted to the desired moisture content.

Alternatively, the Thermo Scientific™ Flash™ 1112 EA combustion analyzer was run in N-protein mode, according to the Manufacturer's instructions, using aspartic acid as the standard. Samples of oven dried (according to AOCS Official Method Ba 2a-38 described above). The powdered samples, 30-40 mg, weighed to an accuracy of 0.001 mg on a Mettler-Toledo MX5 microbalance were used for analysis. Protein contents were calculated by multiplying % N, determined by the analyzer, by 6.25. All samples were run in duplicate. If the difference between the protein contents of the replicate samples was >5% of the mean value, additional replicates (if material was available) were analyzed. Final protein contents were measured on a dry weight basis and adjusted to the desired moisture content.

2.11. NMR Based Analysis of Seed Oil Content.

Whole seed and powdered sample oil contents were determined using a Maran Ultra NMR analyzer (Resonance Instruments Ltd, Whitney, Oxfordshire, UK). Samples (either individual intact soy seed or batches ~200 mg of ground soy powder) were placed into pre-weighed 2 ml polypropylene tubes (Corning Inc, Corning N.Y., USA; part #430917) previously labeled with unique bar code identifiers. Samples were placed into 96 place carriers and processed through the following series of steps by an Adept Cobra 600 SCARA robotic system.

2.11.1. Pick up tube using robotic arm fitted with a vacuum pickup device.
2.11.2. Read bar code.
2.11.3. Expose tube to antistatic device to ensure powdered samples do not adhere to the tube walls.
2.11.4. Weigh sample, to 0.1 mg accuracy.
2.11.5. NMR reading; measured as the intensity of the proton spin echo 1 msec after a 22.9 MHz signal was applied to the sample. Data was collected for 32 NMR scans per sample.
2.11.6. Return tube to rack.
2.11.7. Repeat process with next tube.

Bar codes, seed weights and NMR readings were recorded by a computer connected to the system.

Seed oil content was calculated as follows:

$$\% \text{ oil (\% wt. basis)} = \frac{[(NMR \text{ signal}/\text{seed wt. (g)}) - 70.58]}{351.45}$$

Calibration parameters were determined by precisely weighing samples of soy oil (ranging from 0.0050 to 0.0700 g at approximately 0.0050 g intervals; weighed to an accuracy of 0.0001 g) into the polypropylene tubes (see above) and subjecting them to NMR analysis. A calibration curve of oil content (% seed wt. basis; assuming a standard seed weight of 0.1500 g) to NMR value was established.

Analytical Methods for Bulk Samples.

2.12. Moisture Determinations and Creation of Bulk Bean Moisture Calibrations.

Field or greenhouse-grown soybeans varieties 93B86 (U.S. Pat. No. 6,610,910) and 93Y21 (commercially available from Pioneer Hybrid International) were harvested and the moisture calibrations for the FT-NIR were developed according to the methods described below. Pods were harvested from soybean plants between the R7 and R8 stage of development (i.e., yellow to brown pod stage) when the soybeans had moisture contents below 50 wt. %. Beans were removed from the pods and were separated into groups of approximately 25 g based on their state of maturity. The weight of the bean sample was measured and recorded to 0.0001 g accuracy, prior to FT-NIR spectral capture in a 54 mm spinning cup. The beans were then placed into 5"×6" foil trays and positioned in a laminar flow hood to dry at room temperature for varying times. After the seed had undergone measurable drying, the beans were weighed again and rescanned. This process was repeated until no further weight loss was observed. The samples were then taken to complete dryness using AOCS Official Method Ac 2-41, and were allowed to come to room temperature in a desiccator prior to weighing and rescanning on the FT-NIR. Moisture content was calculated as follows:

Moisture Content =

$$\frac{(\text{wt. of beans as is}^* - \text{wt. of oven dried beans})}{\text{wt. of bean as is}^*} \times 100$$

*at time of spectral capture.

Alternatively, mature soybeans were placed in 5"×6" aluminum foil trays in 1 gallon ZipLock® brand plastic sealable bags. The relative humidity of the atmosphere within the bags was controlled by adding a second foil pan which contained either a layer of self-indicating DrieRite desiccant (W.A. Hammond Inc; Xenia Ohio), or a saturated aqueous solution of sodium chloride. A third bag containing the seed tray but without any atmospheric moisture control was also set up. The beans were exposed to the controlled moisture atmospheres for one month prior to weighing followed by immediate spectral capture on the FT-NIR. The beans were then dried according to AOCS Official Method Ac 2-41, as described above, and scanned again. Predictive spectral models for seed moisture content were developed by combining the spectral information with the measured moisture contents for each bean sample.

2.13. Sample Grinding and Preparation for Bulk Reference Chemistry.

Seventy-five gram batches of beans were ground to a powder in a Foss Knifetec 1095 grinder (commercially available from FOSS North America, Eden Prairie, Minn.). The grinding chamber was cooled prior to and during the process by a circulating chiller set to 14° C. Samples were ground for 2×10 second bursts using a standard rotor blade. The ground sample was transferred to a 6" diameter stainless steel sieve (1 mm mesh) and sifted (resulting in less than 2% loss of material) before being placed into an airtight sample cup. The sample chamber and blade were cleaned thoroughly with a soft brush and pneumatic air prior to introduction of the next sample. Sample cups were stored at room temperature in the dark prior to further analysis.

In later experiments the grinding method was modified to remove the need for sifting. Under these conditions the beans were ground for 6×10 second bursts under the conditions described above. The chamber was opened between each burst and material adhering to the chamber wall was scraped off with a plastic spatula and returned to the center of the chamber. This grinding protocol was found to create a powdered sample that would pass through a US No 20 mesh sieve with no loss and be more suitable for crude fat extraction.

2.14. Crude Protein Analysis.

Crude Protein contents were measured by combustion analysis of the oven dried powders described above in accordance to AOCS Official Method Ba 4e-93. Analyses were either performed by a contract research organization according to Industry Standard methods for soybean or otherwise as described herein. The protocols are essentially the same as those used for single seed (Example 2.10) but have been modified to accommodate a larger sample size. Analysis was performed on a Thermo Scientific™ Flash™ 1112 EA combustion analyzer running in the N-Protein mode, following the manufacturer's recommendations. Samples of the dried powders, 30-40 mg, weighed to an accuracy of 0.001 mg on a Mettler-Toledo MX5 microbalance, were used for analysis. Protein contents were calculated by multiplying % N, determined by the analyzer, by 6.25. Final protein contents were expressed on a 13% moisture corrected basis. All samples were run in duplicate and further replication was performed if the difference between the replicate samples was >5% of the mean value.

2.15. Crude Fat/Oil Analysis

Crude Fat/Oil determinations were performed according to AOCS Official Method Ba 3-38. Analyses were either performed a commercial service laboratory (Eurofins Scientific Inc., Des Moines, Iowa 50321) or done using a Foss SoxTec 8000 Extraction Unit (commercially available from Foss Analytical AB Höganäs, Sweden), according to the manufacturers recommendations (Application Note_AN 3487), with slight modification. Powder samples taken at the time of analysis were subjected to moisture determinations using AOCS Official Method Ba 2a-38, as described above. Final crude oil contents were expressed on a 13% moisture corrected basis. All samples were run in duplicate.

Example 3

Single Seed Spectral Analysis of Soybeans and Development of Accurate Measurements Seed with a high degree of compositional diversity selected from the materials described in Example 1 were analyzed on a proprietary Single Seed Near Infrared (SS-NIR) spectrometer (U.S. Pat. No. 7,274,456 B2, issued Sep. 25, 2007; U.S. Pat. No. 7,508,517B2, issued Mar. 24, 2009). Briefly, in the SS-NIR system an individual bean was introduced into the analytical cell where it was illuminated from all points in three dimensions. The seed was tumbled with an air stream, within an approximated integrating sphere constructed from a 16-mm-diameter quartz cup coated with 6080 white reflectance coating (Labsphere, North Hutton, N.H.). Illumination was provided through 12 optical fibers, connected to four 20 Watt 8211-002 light bulbs (Welch Allyn, Skaneateles Falls, N.Y.), the ends of which were incorporated into the cell cover. The reflected spectral region from 904 to 1686 nm was collected through the apex of the cover of the sampling cell by an NIR512 spectrometer (Control Development, South Bend, Ind.). Each seed was scanned for 6 seconds to collect spectra that were optimized for maximal signal to noise ratio. Spectral quality was monitored during each sample scan by regularly checking the Root Mean Square (RMS) noise of the 100% lines. The 100% lines were computed by the ratio between every two spectra of the triplicate measurement for each sample. Under ideal, noise-free conditions, the 100% lines would be straight horizontal lines at zero absorbance units (AU) since all replicate spectra come from the same sample providing the same spectral features. To minimize instrumental drift, system noise, seed condition and other environmental changes, noise and off-sets were observed in the actual 100% lines. After scanning, the seed was ejected from the sample cup and transferred to an indexed sample tray. The individual identity of each seed was therefore preserved, facilitating instrument calibration.

Separate calibration models were generated for every constituent of interest using Partial Least Square (PLS) analysis coupled with an optimized number of latent variables, spectral range and spectral preprocessing, before being applied to online/offline compositional analysis of the individual seed components, such as the sucrosyl-oligosaccharides. The optimized number of latent variables, spectral range and spectral preprocessing were determined by analyzing the training and monitoring subset from the calibration data where the calibration performance reached an optimum level, in terms of Root Mean Square Error of Calibration (RMSEC) and Root Mean Square Error of Cross Validation (RMSECV). Taking stachyose as an example, the optimized number of latent variables was determined by the co-constituents with the least distinct spectral features. The calibration model used two components: the fewest latent variables and the most stachyose-related information. The balance of compromising these two components is dependent on the distinctness of the pure component spectrum for stachyose within the spectral matrix. For those co-constituents with distinct spectra, such as oil, a few PLS latent variables were used to capture enough information. More PLS latent variables were needed to separate stachyose from the co-constituents such as sucrose and raffinose which are chemically related and therefore give a high degree of spectral overlap. The optimized spectral range for stachyose was in the vicinity of 1000, 1200, 1380 and 1460 nm. These wavelengths enabled stachyose to be measured distinctly from the other constituents of the soybean seed. After the spectra were preprocessed for multiplicative scatter corrections, Savitsky-Golay derivatives and polynomial smoothing were applied in the spectral region between 904-1540 nm. The number of latent variables was determined as the fewest number of latent variables that resulted in an optimal calibration/cross validation accuracy as determined by the RMSEC (Root Mean Square Error of Calibration) and RMSECV (Root Mean Square Error of Cross Validation), respectively. The optimum calibration model was selected to based on the R2 (statistical measure of how close the predicted and reference chemistry data are fitted by the regression line), RMSEC (Root Mean Square Error of Calibration) and RMSECV (Root Mean Square Error of Cross Validation) statistics.

TABLE 3

Statistics for various seed component SS-NIR calibrations. The number of reference chemistry measurements used to develop the calibrations for each constituent are shown in column n. The dynamic range in composition underpinning each constituent calibration is shown in the range column. Under these conditions, stachyose could be detected as low as 0.05 wt. %.

| Constituent | n | Range (wt. %-wt. %) | $R^2$ | RMSEC | RMSECV |
|---|---|---|---|---|---|
| weight | 3096 | 0.09-0.30 | 0.99 | 4.2 mg | 4.4 mg |
| moisture | 618 | 5.4-15.7 | 0.94 | 0.51% | 0.54% |
| protein | 563 | 32.9-49.6 | 0.92 | 0.89% | 1.04% |
| oil | 1608 | 15.2-26.4 | 0.98 | 0.32% | 0.33% |
| oleic | 2725 | 12.8-90.1 | 0.99 | 2.80% | 2.83% |
| linoleic | 2725 | 1.1-61.8 | 0.98 | 2.67% | 2.72% |
| linolenic | 2725 | 1.1-12.7 | 0.92 | 0.81% | 0.86% |
| stearic | 2725 | 2.1-7.3 | 0.78 | 0.45% | 0.47% |
| palmitic | 2725 | 2.2-13.4 | 0.91 | 0.60% | 0.65% |
| stachyose | 730 | 0.05-5.5 | 0.91 | 0.52% | 0.56% |
| sucrose | 952 | 2.51-9.88 | 0.81 | 0.58% | 0.67% |
| total carbohydrate | 670 | 5.6-14.1 | 0.87 | 0.55% | 0.65% |

Stachyose measurements by SS-NIR and reference chemistry methods are shown in Table 4

TABLE 4

Stachyose contents of 20 individual T1 seed from Soil 2-7879-1-2-1 event. Each seed was analyzed by SS-NIR and was then ground and the stachyose content was measured using reference chemistry. Null segregants were identified (bold values underlined) based on the reference chemistry stachyose values. The mean and standard deviation (SD) values for the null and transgenic positive seed are also presented.

| Seed ID | Event ID | Stachyose by Reference Chemistry | Single Seed Stachyose by NIR |
|---|---|---|---|
| 1s | Soil 2 AFS 7879-1-2-1 T1 seed | 4.09 | 4.53 |
| 2s | Soil 2 AFS 7879-1-2-1 T1 seed | 0.22 | 0.83 |
| 3s | Soil 2 AFS 7879-1-2-1 T1 seed | 0.31 | 0.44 |
| 4s | Soil 2 AFS 7879-1-2-1 T1 seed | 0.22 | 0.56 |
| 5s | Soil 2 AFS 7879-1-2-1 T1 seed | 0.19 | 0.24 |
| 6s | Soil 2 AFS 7879-1-2-1 T1 seed | 0.29 | 0.82 |
| 7s | Soil 2 AFS 7879-1-2-1 T1 seed | 0.18 | 0.46 |
| 8s | Soil 2 AFS 7879-1-2-1 T1 seed | 0.42 | 0.33 |
| 9s | Soil 2 AFS 7879-1-2-1 T1 seed | 3.91 | 4.55 |
| 10s | Soil 2 AFS 7879-1-2-1 T1 seed | 0.09 | 0.37 |
| 11s | Soil 2 AFS 7879-1-2-1 T1 seed | 3.61 | 3.83 |
| 12s | Soil 2 AFS 7879-1-2-1 T1 seed | 0.08 | −0.01 |
| 13s | Soil 2 AFS 7879-1-2-1 T1 seed | 0.24 | 0.49 |
| 14s | Soil 2 AFS 7879-1-2-1 T1 seed | 0.14 | 0.31 |
| 15s | Soil 2 AFS 7879-1-2-1 T1 seed | 0.18 | 0.20 |
| 16s | Soil 2 AFS 7879-1-2-1 T1 seed | 0.22 | 0.97 |
| 17s | Soil 2 AFS 7879-1-2-1 T1 seed | 3.82 | 3.80 |
| 18s | Soil 2 AFS 7879-1-2-1 T1 seed | 0.28 | 0.65 |
| 19s | Soil 2 AFS 7879-1-2-1 T1 seed | 3.67 | 4.09 |
| 20s | Soil 2 AFS 7879-1-2-1 T1 seed | 0.41 | 0.70 |
| Mean Soil 2 AFS 7879-1-2-1 | | | |
| Null | | 3.82 | 4.16 |
| SD | | 0.19 | 0.37 |
| Mean Soil 2 AFS 7879-1-2-1 | | | |
| Pos | | 0.23 | 0.49 |
| SD | | 0.10 | 0.27 |

The construct used to create the Soil 92-2499.1.1.1 event contained transgenic components a *Yarrowia lipolytica*, Diacyl glycerol transferase-2 (DGAT-2) under the control of the strong seed specific β-Conglycinin promoter, the soy transcription factor ODP1, a sucrose transporter SUT4 and a GAS suppression component under the seed-specific kTi promoter. Seed from Soil 92 events have elevated oil, protein, oleic and stearic acids in conjunction with decreased linoleic and linolenic acids, sucrose and total soluble sugars. Lower stachyose contents would be expected and were measured using SS-NIR. The compositions of 36 T1 seed from the Soil 92-2499.1.1.1 event measured by NIR are given in Table 5A and 5B.

TABLE 5A

Single seed compositions for 36 T1 seed from Soil 92-2499.1.1.1 event. The composition of the seeds provided a distinct finger print that was used to discriminate between transgenic positive and null-segregant seed. Seed identified as null segregants are indicated in bold type and underlined.

| Seed ID | Event ID | Stachyose | Oil | Protein | Sucrose | Total soluble CBH |
|---|---|---|---|---|---|---|
| 14SN30-829 | Soil 92 SOY 2499.1.1.1 | 3.2 | 28.1 | 36.2 | 4.4 | 8.5 |
| 14SN30-830 | Soil 92 SOY 2499.1.1.1 | 3 | 25 | 43.6 | 4.2 | 7.8 |
| 14SN30-831 | Soil 92 SOY 2499.1.1.1 | 3.1 | 25.2 | 42.7 | 3.3 | 7.4 |
| 14SN30-832 | Soil 92 SOY 2499.1.1.1 | 4.4 | 19 | 40.1 | 6.1 | 11.5 |
| 14SN30-833 | Soil 92 SOY 2499.1.1.1 | 4.2 | 15.6 | 42.8 | 6.8 | 12.1 |
| 14SN30- | Soil 92 SOY | 3.3 | 28.2 | 46 | 3 | 7.4 |

TABLE 5A-continued

Single seed compositions for 36 T1 seed from Soil 92-2499.1.1.1 event. The composition of the seeds provided a distinct finger print that was used to discriminate between transgenic positive and null-segregant seed. Seed identified as null segregants are indicated in bold type and underlined.

| Seed ID | Event ID | Stachyose | Oil | Protein | Sucrose | Total soluble CBH |
|---|---|---|---|---|---|---|
| 834 | 2499.1.1.1 | | | | | |
| 14SN30-835 | Soil 92 SOY 2499.1.1.1 | 4.3 | 18.9 | 40.1 | 6.2 | 11.9 |
| 14SN30-836 | Soil 92 SOY 2499.1.1.1 | 3.1 | 27.1 | 42.3 | 2.9 | 6.6 |
| 14SN30-837 | Soil 92 SOY 2499.1.1.1 | 3.9 | 19.4 | 37.1 | 6.8 | 12.3 |
| 14SN30-838 | Soil 92 SOY 2499.1.1.1 | 2.4 | 25.5 | 43.4 | 4.3 | 7.3 |
| 14SN30-839 | Soil 92 SOY 2499.1.1.1 | 4.1 | 18 | 41.7 | 7 | 11.9 |
| 14SN30-840 | Soil 92 SOY 2499.1.1.1 | 3.2 | 27.1 | 40.9 | 3.4 | 7.2 |
| 14SN30-841 | Soil 92 SOY 2499.1.1.1 | 3.2 | 26.2 | 42.8 | 3.4 | 7.2 |
| 14SN30-842 | Soil 92 SOY 2499.1.1.1 | 4.2 | 19.9 | 38.9 | 6.4 | 12 |
| 14SN30-843 | Soil 92 SOY 2499.1.1.1 | 2.7 | 25.7 | 45.5 | 2.9 | 6.1 |
| 14SN30-844 | Soil 92 SOY 2499.1.1.1 | 3.4 | 26.6 | 40.7 | 2.7 | 6.6 |
| 14SN30-845 | Soil 92 SOY 2499.1.1.1 | 3.4 | 25 | 40.3 | 3 | 7.1 |
| 14SN30-846 | Soil 92 SOY 2499.1.1.1 | 3.8 | 27.5 | 41.8 | 3.5 | 8.1 |
| 14SN30-847 | Soil 92 SOY 2499.1.1.1 | 4 | 17.3 | 41.9 | 6.4 | 11.7 |
| 14SN30-848 | Soil 92 SOY 2499.1.1.1 | 4.1 | 20.2 | 37.8 | 6.7 | 12.1 |
| 14SN30-849 | Soil 92 SOY 2499.1.1.1 | 2.7 | 25.6 | 43.9 | 4.2 | 7 |
| 14SN30-850 | Soil 92 SOY 2499.1.1.1 | 2.5 | 28.8 | 41.4 | 3.6 | 6.6 |
| 14SN30-851 | Soil 92 SOY 2499.1.1.1 | 2.9 | 27.7 | 42.6 | 3.8 | 7.2 |
| 14SN30-852 | Soil 92 SOY 2499.1.1.1 | 2.7 | 25 | 44.3 | 4 | 7.2 |
| 14SN30-853 | Soil 92 SOY 2499.1.1.1 | 3.3 | 25.2 | 44.7 | 3.3 | 6.7 |
| 14SN30-854 | Soil 92 SOY 2499.1.1.1 | 4.3 | 19.6 | 37.4 | 7.1 | 13 |
| 14SN30-855 | Soil 92 SOY 2499.1.1.1 | 3.5 | 23.4 | 43 | 4.4 | 8.1 |
| 14SN30-856 | Soil 92 SOY 2499.1.1.1 | 4.7 | 19.8 | 38.5 | 7.3 | 12.7 |
| 14SN30-857 | Soil 92 SOY 2499.1.1.1 | 3 | 25.3 | 43.4 | 3.7 | 7.2 |
| 14SN30-858 | Soil 92 SOY 2499.1.1.1 | 3.4 | 25.8 | 40.6 | 4 | 7.6 |
| 14SN30-859 | Soil 92 SOY 2499.1.1.1 | 2.9 | 28.6 | 40.8 | 3.9 | 7.2 |
| 14SN30-860 | Soil 92 SOY 2499.1.1.1 | 3.3 | 26.6 | 39.5 | 4.1 | 8.1 |
| 14SN30-861 | Soil 92 SOY 2499.1.1.1 | 2.7 | 28.4 | 40 | 4.1 | 7.3 |
| 14SN30-862 | Soil 92 SOY 2499.1.1.1 | 2.9 | 25.1 | 43.7 | 3.9 | 7.4 |
| 14SN30-863 | Soil 92 SOY 2499.1.1.1 | 3.5 | 24 | 42 | 4 | 7.8 |
| 14SN30-864 | Soil 92 SOY 2499.1.1.1 | 3.8 | 19.9 | 41.8 | 4.5 | 8.9 |
| | Mean Soil 92 2499.1.1.1 T1 Null | 4.18 | 18.87 | 39.83 | 6.48 | 11.83 |
| | SD | 0.25 | 1.40 | 2.02 | 0.76 | 1.06 |
| | Mean 92 2499.1.1.1 T1 Pos | 3.08 | 26.27 | 42.24 | 3.68 | 7.31 |
| | SD | 0.34 | 1.49 | 2.13 | 0.51 | 0.56 |
| | Delta | −1.10 | 7.40 | 2.42 | −2.80 | −4.52 |

TABLE 5B

Single seed compositions (fatty acid methyl esters as a percent of the sum of all of the fatty acid methyl esters) for 36 T1 seed from Soil 92-2499.1.1.1 events (as in Table 5A). The composition of the seeds provided a distinct finger print that was used to discriminate between transgenic positive and null-segregant seed. Seed identified as null segregants are indicated in bold type and underlined.

| Seed ID | Event ID | Oleic | Linolenic | Palmitic | Stearic | Linoleic | Weight | Moisture |
|---|---|---|---|---|---|---|---|---|
| 14SN30-829 | Soil 92 SOY 2499.1.1.1 | 29.1 | 5.5 | 12.7 | 6.3 | 46.3 | 0.2 | 8.3 |
| 14SN30-830 | Soil 92 SOY 2499.1.1.1 | 28.6 | 5.3 | 12.8 | 6.1 | 48.2 | 0.3 | 8.1 |
| 14SN30-831 | Soil 92 SOY 2499.1.1.1 | 30.2 | 5.2 | 12.2 | 6.2 | 45.9 | 0.2 | 8.1 |
| 14SN30-832 | Soil 92 SOY 2499.1.1.1 | 20.4 | 9.9 | 11.3 | 4 | 54.9 | 0.3 | 8.9 |
| 14SN30-833 | Soil 92 SOY 2499.1.1.1 | 17.4 | 12 | 12 | 4.4 | 54.4 | 0.2 | 8.9 |
| 14SN30-834 | Soil 92 SOY 2499.1.1.1 | 38.2 | 7.4 | 12.9 | 9.3 | 34.7 | 0.2 | 7.2 |
| 14SN30-835 | Soil 92 SOY 2499.1.1.1 | 17.4 | 10.9 | 11.7 | 4.2 | 57.2 | 0.2 | 8.8 |
| 14SN30-836 | Soil 92 SOY 2499.1.1.1 | 35.1 | 4.8 | 12.2 | 7.4 | 40.8 | 0.2 | 8.1 |
| 14SN30-837 | Soil 92 SOY 2499.1.1.1 | 16.8 | 11 | 10.9 | 4.2 | 58.6 | 0.2 | 8.7 |
| 14SN30-838 | Soil 92 SOY 2499.1.1.1 | 29.6 | 4.2 | 12.2 | 6 | 48.6 | 0.3 | 8.1 |
| 14SN30-839 | Soil 92 SOY 2499.1.1.1 | 15.7 | 11 | 12 | 4.2 | 57.4 | 0.2 | 9.4 |
| 14SN30-840 | Soil 92 SOY 2499.1.1.1 | 32.9 | 4.4 | 12.4 | 6.8 | 42.7 | 0.2 | 7.9 |
| 14SN30-841 | Soil 92 SOY 2499.1.1.1 | 34 | 3.9 | 12.1 | 7 | 43.6 | 0.2 | 8.2 |
| 14SN30-842 | Soil 92 SOY 2499.1.1.1 | 18.2 | 9.8 | 11.6 | 4.3 | 56.8 | 0.2 | 9 |
| 14SN30-843 | Soil 92 SOY 2499.1.1.1 | 34 | 3.7 | 11.7 | 6.7 | 44.3 | 0.3 | 7.7 |
| 14SN30-844 | Soil 92 SOY 2499.1.1.1 | 33.3 | 5 | 13 | 7.5 | 40.8 | 0.2 | 8.2 |
| 14SN30-845 | Soil 92 SOY 2499.1.1.1 | 29.8 | 7.2 | 11.6 | 6.2 | 45.4 | 0.2 | 8.8 |
| 14SN30-846 | Soil 92 SOY 2499.1.1.1 | 32.1 | 7.6 | 12.1 | 7.5 | 42.3 | 0.2 | 7.5 |
| 14SN30-847 | Soil 92 SOY 2499.1.1.1 | 17.9 | 11.5 | 11 | 4.1 | 56.1 | 0.3 | 8.7 |
| 14SN30-848 | Soil 92 SOY 2499.1.1.1 | 16.7 | 10.4 | 11.8 | 4.3 | 57.8 | 0.2 | 8.9 |
| 14SN30-849 | Soil 92 SOY 2499.1.1.1 | 30.5 | 4.4 | 11.8 | 5.5 | 46.6 | 0.3 | 8.4 |
| 14SN30-850 | Soil 92 SOY 2499.1.1.1 | 36 | 3 | 11.4 | 6.3 | 40.9 | 0.2 | 7.6 |
| 14SN30-851 | Soil 92 SOY 2499.1.1.1 | 32.3 | 5.9 | 11.1 | 6.5 | 43.5 | 0.2 | 7.2 |
| 14SN30-852 | Soil 92 SOY 2499.1.1.1 | 32.1 | 4.6 | 11.2 | 6 | 44.6 | 0.2 | 8.3 |
| 14SN30-853 | Soil 92 SOY 2499.1.1.1 | 37.7 | 5.3 | 11.7 | 6.3 | 37.6 | 0.2 | 8.1 |
| 14SN30-854 | Soil 92 SOY 2499.1.1.1 | 18.5 | 10.4 | 10.4 | 4 | 56 | 0.2 | 8.9 |
| 14SN30-855 | Soil 92 SOY 2499.1.1.1 | 31.7 | 5 | 11.2 | 5.9 | 43.6 | 0.2 | 8.8 |
| 14SN30-856 | Soil 92 SOY 2499.1.1.1 | 20.2 | 9.2 | 11 | 4.2 | 53.6 | 0.2 | 9.2 |
| 14SN30-857 | Soil 92 SOY 2499.1.1.1 | 32.1 | 4.7 | 11.7 | 5.9 | 44 | 0.2 | 8.5 |
| 14SN30-858 | Soil 92 SOY 2499.1.1.1 | 32.2 | 6.1 | 11.3 | 5.6 | 42.7 | 0.2 | 8.1 |
| 14SN30-859 | Soil 92 SOY 2499.1.1.1 | 35.5 | 3.9 | 11.8 | 6.9 | 40.5 | 0.2 | 8 |
| 14SN30-860 | Soil 92 SOY 2499.1.1.1 | 31.7 | 5.2 | 11.5 | 5.7 | 44 | 0.2 | 8.6 |
| 14SN30-861 | Soil 92 SOY 2499.1.1.1 | 34.8 | 3.7 | 12.2 | 6.7 | 39.8 | 0.2 | 8.1 |
| 14SN30-862 | Soil 92 SOY 2499.1.1.1 | 32 | 4.9 | 11.6 | 6.1 | 44.2 | 0.2 | 8.5 |
| 14SN30-863 | Soil 92 SOY 2499.1.1.1 | 32.6 | 5.4 | 11.8 | 6 | 42.6 | 0.2 | 9.1 |

TABLE 5B-continued

Single seed compositions (fatty acid methyl esters as a percent of the sum of all of the fatty acid methyl esters) for 36 T1 seed from Soil 92-2499.1.1.1 events (as in Table 5A). The composition of the seeds provided a distinct finger print that was used to discriminate between transgenic positive and null-segregant seed. Seed identified as null segregants are indicated in bold type and underlined.

| Seed ID | Event ID | Oleic | Linolenic | Palmitic | Stearic | Linoleic | Weight | Moisture |
|---|---|---|---|---|---|---|---|---|
| 14SN30-864 | Soil 92 SOY 2499.1.1.1 Mean | 20.9 | 10.1 | 9.9 | 3.5 | 54.5 | 0.2 | 9 |
| | Null | 18.19 | 10.56 | 11.24 | 4.13 | 56.12 | 0.22 | 8.95 |
| | SD | 1.67 | 0.81 | 0.67 | 0.24 | 1.60 | 0.04 | 0.21 |
| | Mean Pos | 32.72 | 5.05 | 11.93 | 6.50 | 43.13 | 0.22 | 8.14 |
| | SD | 2.51 | 1.14 | 0.54 | 0.81 | 3.12 | 0.04 | 0.46 |
| | Delta | 14.53 | −5.51 | 0.69 | 2.37 | −12.99 | 0.00 | −0.81 |

From the results presented in Tables 5A and 5B, all components except for stachyose were measured at the expected values. Stachyose contents were lowered by an average of 1.1% (percentage points), instead of the expected at least 3% (percentage points) indicating that the construct did not produce the expected composition. Additional components were used to assist in distinguishing transgenic positive from null-segregant seeds where transgenic changes are subtle. For example, seeds 14SN30-846 and 14SN30-864 each had a stachyose content of 3.8%, which was the threshold used for discriminating between transgenic positive and null-segregant seed. By inspecting the other components (27.5% oil, 41.8% protein, 32.1% oleic, 3.5% sucrose, 8.1% soluble carbohydrates, 7.5% linolenic acid) it was apparent that 14SN30-846 was a transgenic positive seed and that 14SN30-864 (19.9% oil, 41.8% protein, 20.9% oleic, 4.5% sucrose, 8.9% soluble carbohydrates, 10.1% linolenic acid) was a null segregant.

The methods are also suitable for screening material generated in crossing experiments designed to introgress the low sucrosyl-oligosaccharide/high oil transgenes into elite soybean backgrounds. In this example pollen from heterozygous BC1F1 plants from the Oil 119 event (segregating for the transgenes for the low sucrosyl-oligosaccharide/high oil traits) was used to fertilize the emasculated receptive flowers of three elite soybean varieties. The cross fertilized plants were grown to maturity and the resulting BC2F1 seed harvested from the cross-pollinated flowers were analyzed by SS-NIR. This SS-NIR analysis allowed the non-destructive identification of seed carrying the desired transgenic phenotype (i.e., those displaying a low stachyose and high oil phenotype). These positively identified seed were grown and pollen from these plants was again used to pollinate the emasculated receptive flowers of the same three elite soybean varieties. The results in Table 6 show the composition of mature seed harvested after three rounds of backcrossing onto the recurrent female elite parent. In most cases a threshold value for stachyose content of 2.0% was used to differentiate between the wild type seeds (>2.0% stachyose; indicated with bold type and underlined) and those (<<2.0%) that resulted from successful transgene introgressions (Transgenic pos). Further confirmation of successful transgene introgressions was provided by the other constituents influenced by the transgenic traits i.e., elevated oil, protein and oleic acid, reduced levels of sucrose, total soluble carbohydrates and linolenic acid. Transgenic hybrid seed could be identified using SS-NIR by combining the low stachyose phenotype (of ≤0.32%) with a combination of high oil, high protein, high oleic acid, low sucrose, low total soluble carbohydrates and low linolenic acid phenotypes (dependent on the background) that result from the expression of the high oil components of the transgenic cassette. Soybeans seeds of varied genetic backgrounds outside of those used to generate the calibration curves could be successfully identified as containing introgressed transgenes.

TABLE 6A

SS-NIR compositions (oil/protein/carbohydrate (CBH)) for segregating seed resulting from backcrosses of an Oil 119 event. The construct used to create the Oil119 event contained the following transgenic components, a modified Glycine max diacyl glycerol transferase-1 (DGAT-1) under the control of the seed specific S-albumen promoter, a sucrose transporter SUT4 and a GAS 1, 2, 3 suppression component under the control of the strong seed specific β-conglycinin promoter. This construct conferred a low stachyose/high oil phenotype in three elite female soybean lines.

| Female/Male | Plant ID | SSNIR zyg call | Stachyose | Oil | Protein | Sucrose | Total soluble CBH |
|---|---|---|---|---|---|---|---|
| 92Y51/ BC75638705 | 4 | Wild type | 2.50 | 19.32 | 45.47 | 7.42 | 11.55 |
| 92Y51/ BC75638705 | 3 | Wild type | 2.61 | 19.08 | 45.93 | 7.32 | 11.65 |
| 92Y51/ BC75638705 | 2 | TG POS | 0.17 | 24.32 | 46.98 | 6.31 | 8.33 |
| 92Y51/ BC75638705 | 5 | TG POS | 0.25 | 24.61 | 46.60 | 7.54 | 7.97 |
| 92Y51/ BC75638705 | 1 | TG POS | 0.28 | 24.01 | 46.63 | 7.40 | 8.46 |

TABLE 6A-continued

SS-NIR compositions (oil/protein/carbohydrate (CBH)) for segregating seed resulting from backcrosses of an Oil 119 event. The construct used to create the Oil119 event contained the following transgenic components, a modified Glycine max diacyl glycerol transferase-1 (DGAT-1) under the control of the seed specific S-albumen promoter, a sucrose transporter SUT4 and a GAS 1, 2, 3 suppression component under the control of the strong seed specific β-conglycinin promoter. This construct conferred a low stachyose/high oil phenotype in three elite female soybean lines.

| Female/Male | Plant ID | SSNIR zyg call | | Stachyose | Oil | Protein | Sucrose | Total soluble CBH |
|---|---|---|---|---|---|---|---|---|
| | | Wild type | Mean | 2.55 | 19.20 | 45.70 | 7.37 | 11.60 |
| | | | SD | 0.08 | 0.17 | 0.32 | 0.07 | 0.07 |
| | | TG POS | Mean | 0.23 | 24.31 | 46.74 | 7.08 | 8.25 |
| | | | SD | 0.06 | 0.30 | 0.21 | 0.67 | 0.26 |
| 95Y40/ BC75638779 | 2 | Wild type | | 2.80 | 20.93 | 45.80 | 6.00 | 10.83 |
| 95Y40/ BC75638779 | 8 | Wild type | | 2.97 | 20.95 | 45.59 | 6.23 | 11.15 |
| 95Y40/ BC75638779 | 3 | Wild type | | 3.26 | 20.53 | 41.63 | 7.77 | 12.43 |
| 95Y40/ BC75638779 | 26 | Wild type | | 3.33 | 20.61 | 41.29 | 7.11 | 12.73 |
| 95Y40/ BC75638779 | 9 | Wild type | | 3.35 | 21.03 | 42.59 | 6.73 | 12.67 |
| 95Y40/ BC75638779 | 1 | Wild type | | 3.35 | 19.70 | 44.88 | 7.39 | 12.05 |
| 95Y40/ BC75638779 | 4 | Wild type | | 3.36 | 19.76 | 44.11 | 6.48 | 12.19 |
| 95Y40/ BC75638779 | 19 | Wild type | | 3.45 | 20.82 | 40.56 | 7.08 | 12.88 |
| 95Y40/ BC75638779 | 16 | Wild type | | 3.62 | 20.73 | 41.74 | 6.97 | 12.22 |
| 95Y40/ BC75638779 | 12 | Wild type | | 3.64 | 20.42 | 41.73 | 7.47 | 13.13 |
| 95Y40/ BC75638779 | 18 | Wild type | | 3.68 | 20.45 | 43.42 | 6.48 | 12.15 |
| 95Y40/ BC75638779 | 11 | Wild type | | 3.89 | 22.17 | 39.33 | 7.14 | 13.14 |
| 95Y40/ BC75638779 | 27 | TG POS | | −0.23 | 23.67 | 46.40 | 7.84 | 8.83 |
| 95Y40/ BC75638779 | 5 | TG POS | | 0.00 | 24.35 | 43.52 | 8.29 | 9.40 |
| 95Y40/ BC75638779 | 6 | TG POS | | 0.20 | 24.43 | 46.23 | 6.58 | 7.84 |
| 95Y40/ BC75638779 | 14 | TG POS | | 0.27 | 26.64 | 42.45 | 6.87 | 8.92 |
| 95Y40/ BC75638779 | 7 | TG POS | | 0.32 | 25.39 | 43.93 | 6.64 | 8.78 |
| 95Y40/ BC75638779 | 17 | TG POS | | 0.32 | 24.97 | 45.10 | 7.00 | 8.76 |
| 95Y40/ BC756387790 | 22 | TG POS | | 0.36 | 26.48 | 43.02 | 7.06 | 9.01 |
| 95Y40/ BC75638779 | 13 | TG POS | | 0.47 | 27.24 | 39.30 | 7.48 | 9.87 |
| 95Y40/ BC75638779 | 15 | TG POS | | 0.51 | 25.11 | 44.13 | 7.30 | 8.46 |
| 95Y40/ BC75638779 | 23 | TG POS | | 0.57 | 24.12 | 47.16 | 6.50 | 8.36 |
| 95Y40/ BC75638779 | 10 | TG POS | | 0.59 | 26.18 | 41.61 | 7.17 | 9.74 |
| 95Y40/ BC75638779 | 20 | TG POS | | 0.68 | 24.58 | 45.89 | 6.26 | 8.60 |
| 95Y40/ BC75638779 | 21 | TG POS | | 0.73 | 25.71 | 44.06 | 6.13 | 8.47 |
| 95Y40/ BC75638779 | 24 | TG POS | | 0.84 | 25.25 | 44.37 | 6.73 | 9.01 |
| 95Y40/ BC75638779 | 25 | TG POS | | 0.73 | 26.18 | 39.21 | 7.48 | 10.19 |
| | | Wild type | Mean | 3.39 | 20.67 | 42.72 | 6.90 | 12.30 |
| | | | SD | 0.30 | 0.64 | 2.05 | 0.53 | 0.72 |
| | | TG POS | Mean | 0.42 | 25.35 | 43.76 | 7.02 | 8.95 |
| | | | SD | 0.29 | 1.03 | 2.38 | 0.59 | 0.63 |
| 98Y11/ BC75638838 | 16 | Wild type | | 0.37 | 21.42 | 40.03 | 8.65 | 11.11 |
| 98Y11/ BC75638838 | 5 | Wild type | | 0.55 | 16.05 | 45.20 | 7.69 | 11.80 |
| 98Y11/ BC75638838 | 13 | Wild type | | 1.45 | 19.68 | 40.29 | 8.60 | 12.75 |

TABLE 6A-continued

SS-NIR compositions (oil/protein/carbohydrate (CBH)) for segregating seed resulting from backcrosses of an Oil 119 event. The construct used to create the Oil119 event contained the following transgenic components, a modified Glycine max diacyl glycerol transferase-1 (DGAT-1) under the control of the seed specific S-albumen promoter, a sucrose transporter SUT4 and a GAS 1, 2, 3 suppression component under the control of the strong seed specific β-conglycinin promoter. This construct conferred a low stachyose/high oil phenotype in three elite female soybean lines.

| Female/Male | Plant ID | SSNIR zyg call | Stachyose | Oil | Protein | Sucrose | Total soluble CBH |
|---|---|---|---|---|---|---|---|
| 98Y11/ BC75638838 | 12 | Wild type | 1.71 | 19.42 | 43.92 | 8.18 | 12.13 |
| 98Y11/ BC75638838 | 6 | Wild type | 1.83 | 19.81 | 39.92 | 8.73 | 13.17 |
| 98Y11/ BC75638838 | 11 | Wild type | 2.15 | 17.52 | 38.76 | 8.27 | 13.18 |
| 98Y11/ BC75638838 | 10 | Wild type | 2.63 | 18.03 | 47.73 | 6.66 | 11.19 |
| 98Y11/ BC75638838 | 7 | Wild type | 3.13 | 17.11 | 44.58 | 7.43 | 12.64 |
| 98Y11/ BC75638838 | 4 | TG POS | −0.66 | 22.72 | 46.17 | 7.93 | 8.96 |
| 98Y11/ BC75638838 | 14 | TG POS | −0.59 | 23.01 | 46.62 | 7.74 | 8.64 |
| 98Y11/ BC75638838 | 15 | TG POS | −0.36 | 21.30 | 49.38 | 7.01 | 8.05 |
| 98Y11/ BC75638838 | 2 | TG POS | −0.34 | 21.81 | 48.48 | 7.65 | 8.40 |
| 98Y11/ BC75638838 | 1 | TG POS | −0.13 | 20.70 | 47.63 | 7.55 | 8.83 |
| 98Y11/ BC75638838 | 8 | TG POS | 0.32 | 20.93 | 48.73 | 7.61 | 9.35 |
| 98Y11/ BC75638838 | 3 | TG POS | −0.23 | 18.19 | 44.31 | 7.84 | 9.31 |
| | Wild type | Mean | 1.72 | 18.63 | 42.55 | 8.03 | 12.25 |
| | | SD | 0.95 | 1.75 | 3.22 | 0.72 | 0.82 |
| | TG POS | Mean | −0.28 | 21.24 | 47.33 | 7.62 | 8.79 |
| | | SD | 0.3 | 1.6 | 1.8 | 0.3 | 0.5 |

TABLE 6B

SS-NIR compositions (fatty acid profile/weight/moisture) for segregating seed resulting from backcrosses of an Oil 119 event as described in Table 6A. This construct conferred a low stachyose/high oil phenotype in three elite female soybean lines. conferring a low stachyose/high oil phenotype into three elite female soybean lines (as in Table 6A).

| Female/Male | Plant ID | SSNIR zyg call | Oleic | Linolenic | Palmitic | Stearic | Linoleic | Weight | Moisture |
|---|---|---|---|---|---|---|---|---|---|
| 92Y51/ BC75638705 | 4 | Wild type | 22.17 | 8.02 | 11.60 | 4.25 | 53.31 | 0.19 | 6.0 |
| 92Y51/ BC75638705 | 3 | Wild type | 21.71 | 8.48 | 11.34 | 4.07 | 51.09 | 0.20 | 5.9 |
| 92Y51/ BC75638705 | 2 | TG POS | 33.05 | 2.85 | 10.66 | 5.45 | 44.21 | 0.20 | 6.9 |
| 92Y51/ BC75638705 | 5 | TG POS | 34.75 | 3.48 | 10.60 | 4.92 | 43.52 | 0.21 | 6.9 |
| 92Y51/ BC75638705 | 1 | TG POS | 36.47 | 2.73 | 9.83 | 4.56 | 42.74 | 0.21 | 5.4 |
| | Wild type | Mean | 21.94 | 8.25 | 11.47 | 4.16 | 52.20 | 0.20 | 6.0 |
| | | SD | 0.32 | 0.33 | 0.18 | 0.13 | 1.57 | 0.01 | 0.1 |
| | TG pos | Mean | 34.76 | 3.02 | 10.37 | 4.98 | 43.49 | 0.21 | 6.4 |
| | | SD | 1.71 | 0.40 | 0.46 | 0.45 | 0.74 | 0.01 | 0.8 |
| 95Y40/ BC75638779 | 2 | Wild type | 32.90 | 6.41 | 11.24 | 4.36 | 42.02 | 0.19 | 6.8 |
| 95Y40/ BC75638779 | 8 | Wild type | 34.64 | 6.11 | 11.09 | 4.43 | 41.30 | 0.18 | 6.6 |
| 95Y40/ BC75638779 | 3 | Wild type | 22.58 | 8.03 | 11.44 | 4.25 | 50.17 | 0.21 | 6.6 |
| 95Y40/ BC75638779 | 26 | Wild type | 23.73 | 7.98 | 11.58 | 4.72 | 49.01 | 0.17 | 6.7 |
| 95Y40/ BC75638779 | 9 | Wild type | 24.03 | 7.19 | 12.02 | 4.42 | 50.14 | 0.21 | 6.6 |
| 95Y40/ | 1 | Wild | 23.89 | 7.62 | 11.73 | 4.28 | 49.41 | 0.21 | 7.1 |

TABLE 6B-continued

SS-NIR compositions (fatty acid profile/weight/moisture) for segregating seed resulting from backcrosses of an Oil 119 event as described in Table 6A. This construct conferred a low stachyose/high oil phenotype in three elite female soybean lines. conferring a low stachyose/high oil phenotype into three elite female soybean lines (as in Table 6A).

| Female/Male | Plant ID | SSNIR zyg call | Oleic | Linolenic | Palmitic | Stearic | Linoleic | Weight | Moisture |
|---|---|---|---|---|---|---|---|---|---|
| BC75638779 95Y40/ | 4 | Wild type | 26.36 | 7.61 | 11.45 | 3.94 | 47.83 | 0.22 | 6.8 |
| BC75638779 95Y40/ | 19 | Wild type | 24.70 | 7.41 | 11.70 | 4.20 | 49.63 | 0.19 | 6.6 |
| BC75638779 95Y40/ | 16 | Wild type | 22.89 | 7.70 | 11.66 | 4.34 | 50.73 | 0.19 | 6.4 |
| BC75638779 95Y40/ | 12 | Wild type | 22.76 | 7.96 | 11.65 | 4.35 | 50.26 | 0.18 | 6.4 |
| BC75638779 95Y40/ | 18 | Wild type | 24.39 | 7.36 | 11.54 | 4.00 | 50.68 | 0.20 | 6.7 |
| BC75638779 95Y40/ | 11 | Wild type | 23.46 | 6.83 | 11.87 | 4.24 | 50.41 | 0.19 | 6.7 |
| 95Y40/ BC75638779 | 27 | TG POS | 41.24 | 4.01 | 10.05 | 4.75 | 36.17 | 0.22 | 6.4 |
| 95Y40/ BC75638779 | 5 | TG POS | 36.44 | 4.97 | 10.78 | 4.67 | 39.94 | 0.19 | 6.4 |
| 95Y40/ BC75638779 | 6 | TG POS | 35.61 | 4.92 | 10.92 | 5.37 | 39.35 | 0.19 | 5.8 |
| 95Y40/ BC75638779 | 14 | TG POS | 33.49 | 4.33 | 10.96 | 5.54 | 41.65 | 0.16 | 6.3 |
| 95Y40/ BC75638779 | 7 | TG POS | 32.12 | 3.92 | 11.06 | 5.46 | 43.11 | 0.16 | 5.9 |
| 95Y40/ BC75638779 | 17 | TG POS | 36.50 | 4.33 | 11.11 | 5.41 | 38.70 | 0.18 | 6.0 |
| 95Y40/ BC756387790 | 22 | TG POS | 32.24 | 4.36 | 11.59 | 5.37 | 42.55 | 0.18 | 5.7 |
| 95Y40/ BC75638779 | 13 | TG POS | 30.25 | 4.54 | 11.72 | 5.86 | 43.04 | 0.14 | 5.5 |
| 95Y40/ BC75638779 | 15 | TG POS | 34.64 | 4.11 | 10.62 | 4.51 | 42.88 | 0.19 | 5.4 |
| 95Y40/ BC75638779 | 23 | TG POS | 29.91 | 4.07 | 11.71 | 5.24 | 45.28 | 0.17 | 5.7 |
| 95Y40/ BC75638779 | 10 | TG POS | 32.52 | 5.77 | 10.92 | 5.63 | 41.43 | 0.15 | 6.0 |
| 95Y40/ BC75638779 | 20 | TG POS | 32.67 | 4.84 | 11.11 | 4.96 | 43.33 | 0.17 | 5.5 |
| 95Y40/ BC75638779 | 21 | TG POS | 30.50 | 4.41 | 11.54 | 5.02 | 44.76 | 0.17 | 5.6 |
| 95Y40/ BC75638779 | 24 | TG POS | 31.37 | 3.93 | 11.86 | 5.19 | 44.08 | 0.17 | 5.8 |
| 95Y40/ BC75638779 | 25 | TG POS | 29.02 | 5.59 | 12.42 | 5.90 | 43.35 | 0.14 | 6.2 |
| | Wild type | Mean SD | 25.53 4.00 | 7.35 0.62 | 11.58 0.25 | 4.29 0.20 | 48.47 3.28 | 0.20 0.02 | 6.7 0.2 |
| | TG POS | Mean SD | 33.24 3.21 | 4.54 0.57 | 11.22 0.59 | 5.26 0.41 | 41.98 2.48 | 0.17 0.02 | 5.9 0.3 |
| 98Y11/ BC75638838 | 16 | Wild type | 25.52 | 9.80 | 12.67 | 6.89 | 42.40 | 0.06 | 7.1 |
| 98Y11/ BC75638838 | 5 | Wild type | 18.07 | 12.28 | 11.70 | 5.24 | 50.34 | 0.15 | 7.2 |
| 98Y11/ BC75638838 | 13 | Wild type | 17.59 | 9.86 | 11.52 | 4.78 | 53.22 | 0.18 | 7.2 |
| 98Y11/ BC75638838 | 12 | Wild type | 25.24 | 8.35 | 11.07 | 4.31 | 49.12 | 0.24 | 6.4 |
| 98Y11/ BC75638838 | 6 | Wild type | 17.72 | 10.47 | 11.76 | 5.20 | 52.48 | 0.17 | 7.1 |
| 98Y11/ BC75638838 | 11 | Wild type | 16.44 | 12.58 | 12.16 | 5.28 | 51.37 | 0.08 | 7.5 |
| 98Y11/ BC75638838 | 10 | Wild type | 26.66 | 7.93 | 11.17 | 4.63 | 47.42 | 0.20 | 6.3 |
| 98Y11/ BC75638838 | 7 | Wild type | 16.02 | 11.66 | 12.24 | 4.67 | 54.64 | 0.17 | 6.4 |
| 98Y11/ BC75638838 | 4 | TG POS | 37.51 | 5.42 | 10.93 | 5.44 | 37.70 | 0.20 | 6.2 |
| 98Y11/ BC75638838 | 14 | TG POS | 32.13 | 6.46 | 11.23 | 5.66 | 40.99 | 0.19 | 6.1 |
| 98Y11/ BC75638838 | 15 | TG POS | 33.22 | 6.10 | 10.82 | 5.36 | 40.96 | 0.17 | 5.9 |
| 98Y11/ BC75638838 | 2 | TG POS | 36.06 | 5.05 | 10.69 | 5.28 | 40.20 | 0.17 | 5.6 |

TABLE 6B-continued

SS-NIR compositions (fatty acid profile/weight/moisture) for segregating seed resulting from backcrosses of an Oil 119 event as described in Table 6A. This construct conferred a low stachyose/high oil phenotype in three elite female soybean lines. conferring a low stachyose/high oil phenotype into three elite female soybean lines (as in Table 6A).

| Female/Male | Plant ID | SSNIR zyg call | Oleic | Linolenic | Palmitic | Stearic | Linoleic | Weight | Moisture |
|---|---|---|---|---|---|---|---|---|---|
| 98Y11/ BC75638838 | 1 | TG POS | 40.73 | 6.50 | 10.04 | 5.46 | 35.31 | 0.22 | 6.4 |
| 98Y11/ BC75638838 | 8 | TG POS | 35.43 | 5.14 | 10.84 | 5.21 | 40.02 | 0.21 | 5.8 |
| 98Y11/ BC75638838 | 3 | TG POS | 47.17 | 8.22 | 10.52 | 4.96 | 25.80 | 0.19 | 6.1 |
| | Wild type | Mean | 20.41 | 10.37 | 11.79 | 5.12 | 50.13 | 0.16 | 6.9 |
| | | SD | 4.54 | 1.72 | 0.55 | 0.79 | 3.88 | 0.06 | 0.5 |
| | TG POS | Mean | 37.46 | 6.13 | 10.72 | 5.34 | 37.29 | 0.19 | 6.00 |
| | | SD | 5.1 | 1.1 | 0.4 | 0.2 | 5.5 | 0.0 | 0.3 |

Example 4

In the following example FT-NIR is used to analyze seed of sample sizes of about 50 seeds to 250 seeds.

Development of NIR Models for FT-NIR

Spectral analyses and capture were performed on a Bruker Multi-Purpose Analyzer (MPA) Fourier Transformed Near Infrared (FT-NIR) spectrometer fitted with a 54 mm diameter rotating cup assembly. Sample sizes of as few as 50 seeds (approximately 10 g of seed) to a full cup load (approximately 53 g of seed) were used, with a sample size of approximately 100 seed (20 g) used where possible. The weight of each sample (to an accuracy of 0.01 g) was recorded prior to scanning. The reflected spectra were captured for each sample to a resolution of 8 cm$^{-1}$ in the wave length range between 833 and 2778 nm with the instrument in Macro-Reflectance mode. The cup was rotated over the source and detector while sixty-four full spectral scans were collected. The rotation of the cup was stopped and the beans were poured into a foil pan and then returned to the cup prior to scanning for a second time. Three full scan cycles (with complete mixing of the sample between each scan) was found to provide good data quality and sample throughput. Captured spectra were analyzed and models were developed using the Bruker OPUS 7.0 software package. Spectral regions utilized for the prediction of stachyose with the Bruker MPA after model optimization were 1157-1283 nm and 1437-2254 nm.

TABLE 7

Statistics of FT-NIR calibration curves. The number of reference chemistry measurements are shown in column n. Range (wt. %) shows the minimum and maximum reference method measured value in the samples for each constituent.

| Constituent | n | Range | R$^2$ | RMSEC | RMSECV |
|---|---|---|---|---|---|
| moisture | 811 | 0-47.2 | 0.99 | 0.40 | 0.44 |
| protein | 102 | 32.1-40.1 | 0.91 | 0.56 | 0.67 |
| oil | 114 | 15.7-23.0 | 0.96 | 0.28 | 0.39 |
| oleic | 1080 | 20.3-89.6 | 0.98 | 2.74 | 3.01 |
| linoleic | 1080 | 1.2-55.6 | 0.98 | 2.51 | 2.67 |
| linolenic | 1080 | 0.9-9.4 | 0.87 | 0.82 | 0.98 |
| stearic | 1080 | 3.1-7.1 | 0.77 | 0.35 | 0.39 |
| palmitic | 1080 | 1.9-12.4 | 0.83 | 0.84 | 0.91 |
| stachyose | 1080 | 0.1-4.9 | 0.78 | 0.66 | 0.73 |
| sucrose | 1080 | 2.15-9.57 | 0.82 | 0.61 | 0.70 |
| total soluble carbohydrates | 1080 | 5.8-12.1 | 0.85 | 0.53 | 0.58 |

TABLE 8

FT-NIR measured compositions for ~20 g batches of homozygous positive and null events of Soil 91 (Soil 91-1, Soil 91-2 and Soil 92-1) soybeans. Values presented are means and standard deviations for two positive (pos) and two null (null) replicates for each event. The delta values indicate the difference between the transgenic positive and null means for each component.

| Sample | Method | | | Stachyose | Oil | Protein | Oleic acid | Linolenic acid | Sucrose | Total soluble carbohydrate |
|---|---|---|---|---|---|---|---|---|---|---|
| Soil 91-1 | FT-NIR | Pos | Mean | 1.9 | 21.3 | 36.8 | 38.2 | 5.8 | 3.4 | 7.2 |
| | | | SD | 0.0 | 0.1 | 0.4 | 0.8 | 0.3 | 0.0 | 0.0 |
| | | Null | Mean | 4.5 | 17.5 | 33.7 | 25.1 | 8.1 | 4.9 | 11.0 |
| | | | SD | 0.3 | 0.2 | 1.6 | 0.4 | 0.2 | 0.9 | 0.5 |
| | | | Delta | −2.6 | 3.9 | 3.1 | 13.1 | −2.2 | −1.5 | −3.8 |
| | Ref Chem | Pos | Mean | 0.3 | 21.3 | 38.0 | 24.3 | 5.4 | 4.8 | 6.2 |
| | | | SD | 0.3 | 1.2 | 0.9 | 3.6 | 0.6 | 0.3 | 0.6 |
| | | Null | Mean | 3.5 | 14.9 | 34.5 | 19.1 | 9.3 | 5.4 | 10.2 |
| | | | SD | 0.1 | 1.7 | 1.6 | 0.7 | 0.0 | 1.0 | 1.2 |
| | | | Delta | −3.2 | 6.4 | 3.4 | 5.2 | −3.9 | −0.6 | −4.0 |
| Soil 91-2 | FT-NIR | Pos | Mean | 1.6 | 20.9 | 37.2 | 39.0 | 5.2 | 3.6 | 7.0 |
| | | | SD | 0.4 | 0.9 | 0.6 | 0.1 | 0.6 | 0.4 | 1.1 |

TABLE 8-continued

FT-NIR measured compositions for ~20 g batches of homozygous positive and null events of Soil 91 (Soil 91-1, Soil 91-2 and Soil 92-1) soybeans. Values presented are means and standard deviations for two positive (pos) and two null (null) replicates for each event. The delta values indicate the difference between the transgenic positive and null means for each component.

| Sample | Method | | | Stachyose | Oil | Protein | Oleic acid | Linolenic acid | Sucrose | Total soluble carbohydrate |
|---|---|---|---|---|---|---|---|---|---|---|
| | | Null | Mean | 4.7 | 17.1 | 32.6 | 26.1 | 7.8 | 4.9 | 11.5 |
| | | | SD | 0.2 | 0.7 | 0.6 | 0.1 | 0.4 | 0.4 | 0.6 |
| | | | Delta | −3.1 | 3.8 | 4.6 | 12.8 | −2.6 | −1.3 | −4.5 |
| | Ref Chem | Pos | Mean | 0.1 | 18.8 | 38.2 | 24.6 | 5.2 | 4.9 | 6.1 |
| | | | SD | 0 | 1.5 | 0.3 | 3.9 | 0.7 | 0.2 | 0.2 |
| | | Null | Mean | 3.4 | 15.7 | 34.2 | 17.9 | 9.5 | 5.2 | 9.9 |
| | | | SD | 0.1 | 2.1 | 0.5 | 0.3 | 0 | 0.1 | 0.4 |
| | | | Delta | −3.3 | 3.1 | 4.1 | 6.7 | −4.3 | −0.3 | −3.8 |
| S | | Pos | Mean | 1.84 | 23.60 | 36.39 | 43.64 | 2.47 | 3.40 | 7.64 |
| | | | SD | 0.40 | 0.58 | 2.68 | 4.07 | 1.00 | 0.12 | 0.34 |
| | | Null | Mean | 4.54 | 17.39 | 31.89 | 26.78 | 7.82 | 5.23 | 12.09 |
| | | | SD | 0.62 | 0.18 | 1.22 | 2.82 | 0.10 | 0.26 | 0.62 |
| | | | Delta | −2.7 | 6.2 | 4.5 | 16.9 | −5.3 | −1.8 | −4.5 |
| | Ref Chem | Pos | Mean | 2.78 | 20.70 | 39.28 | 30.22 | 3.78 | 1.89 | 5.70 |
| | | | SD | 0.56 | 0.73 | 2.72 | 6.96 | 0.52 | 0.85 | 0.44 |
| | | Null | Mean | 3.53 | 15.98 | 33.16 | 20.07 | 8.56 | 5.82 | 11.00 |
| | | | SD | 0.07 | 0.97 | 1.30 | 1.44 | 0.79 | 0.41 | 0.68 |
| | | | Delta | −0.8 | 4.7 | 6.1 | 10.2 | −4.8 | −3.9 | −5.3 |

The FT-NIR methods used in this example enable detection of transgenic positive material despite discrepancies between the predicted and reference chemistry measured compositions.

Further NIR Models for FT-NIR

FT-NIR measurements for stachyose and other components were taken from 13,881 field grown samples which were screened using NIT to access the compositional diversity of the sample set. Samples that represented the extreme concentrations (both high and low) were selected along with material that was evenly distributed to across the intermediate concentrations for each component. Further selections were made to maximize genetic diversity in the samples, along with samples that were clear outliers (i.e., those having measured compositions that were outside the expected ranges). A final set of approximately 400 samples resulted. Spectra were captured on the FT-NIR, as described above. The samples will be analyzed by reference chemistry to determine the concentrations of each constituent and the data will be used to refine the calibrations to facilitate accurate determinations of the sucrosyl-oligosaccharides and other constituents.

Example 5

Development of NIR Models for Near Infrared Transmittance (NIT).

NIR Spectra, from 850-1050 nm (2-nm step; 30-mm path length), for 400-500 g bulk samples of intact soybeans were acquired in transmission mode using a Foss Tecator AB model 1241 grain analyzer (commercially available from Foss Tecator AB, Höganäs, Sweden) fitted with a standard instrument hopper and sample transport mechanism. The average NIR absorption spectrum for a given sample was arrived at by duplicate analyses each using 10 subsample scans.

All data analysis was performed using InfraSoft International (ISI) chemometrics software WinISI II v.1.50e (commercially available from NIRSystems Inc., Silver Spring, Md., USA), MATLAB 7.10.0 R2010a with Neural Network Toolbox (Mathworks, 2010) and ANN Trainer v1.0a12 (Foss Tecatur AB, 2002) software. Pre-treatment of the raw NIR (log 1/Transmittance) spectral data (850-1050 nm) included multiplicative scatter correction, mean centering and unit vector scaling. Oil and protein content (corrected to a 13% moisture basis) were measured according to techniques developed by USDA-FGIS\GIPSA. Models for palmitic acid, stearic acid, oleic acid, linoleic acid, linolenic acid, sucrose, stachyose and total soluble sugars were developed using Artificial Neural Network (ANN) techniques utilizing the transformed spectrum captured from material presenting a wide compositional diversity for these components. The reference chemistry used for the calibrations was obtained, following spectral capture, using the bulk methods described in Example 2. All calibration development work was performed using standard ANN algorithms available in the software. A Levenberg-Marquardt training function was used with log-sigmoid input and pure-linear output transfer functions. Between four and nine neurons were used in one hidden node layer.

The optimum number of iterations (epochs) was chosen when the randomly selected test set error was minimized. The coefficient of determination ($R^2$) was used to describe the correlation between reference (observed) and NIR-predicted values for the calibration set. The Ratio of Performance to Deviation (RPD), defined as the ratio of the SD of the reference values to the SECV (or test set Standard Error of Prediction (SEP)), was used as a normalized indicator for comparing NIR models.

NIT wavelengths useful in the prediction of stachyose concentration in whole soybeans were 850, 866, 880, 890, 902, 910, 920, 930, 944, 952, 964, 978, 990, 1004, 1016, 1032, and 1042 nm. Measurements were taken using the spectra and reference chemistry collected from three years of field grown soybeans from multiple sites within the United States, Argentina, and Puerto Rico. The statistics for the accuracy of the non-destructive NIR methods compared with the standard methods disclosed herein are shown in Table 9.

TABLE 9

Statistics of accuracy of NIT measurements.

| Constituent | n | Range | $R^2$ | RMSEC | RMSECV |
|---|---|---|---|---|---|
| moisture (approx.) | 379 | | 0.99 | 0.30 | 0.30 |
| protein | 266 | 31.9-51.0 | 0.97 | 0.54 | 0.54 |
| oil | 103 | 16.9-25.0 | 0.96 | 0.35 | 0.35 |
| oleic | 2277 | 19.2-91.9 | 0.995 | 1.59 | 1.56 |
| linoleic | 2190 | 0.2-58.4 | 0.98 | 2.19 | 2.20 |
| linolenic | 2277 | 0.9-10.3 | 0.96 | 0.46 | 0.31 |
| stearic | 2276 | 2.6-9.5 | 0.86 | 0.41 | 0.33 |
| palmitic | 2277 | 1.79-12.5 | 0.96 | 0.52 | 0.51 |
| stachyose | 354 | 0.05-4.9 | 0.89 | 0.49 | 0.57 |
| sucrose | 354 | 2.2-9.9 | 0.90 | 0.48 | 0.39 |
| total soluble carbohydrates | 354 | 5.7-12.1 | 0.88 | 0.48 | 0.42 | n = number of reference chemistry measurements used for each constituent comparison between the NIR methods compared with the standard methods disclosed herein.

Values for stachyose measured using NIT and reference chemistry for bulk samples of transgenic positive and negative events of Soil 19 are given in Table 10.

TABLE 10

NIT predicted stachyose content of bulk samples of transgenic positive and negative events of Soil 19. The beans were harvested from plants grown at 9 independent mid-Western sites. The samples were subjected to reference chemistry after the NIT spectra had been captured.

| Event | Trait Call | 2013 EUid | Ref Chem Stachyose (wt. %) | NIT Stachyose (wt. %) |
|---|---|---|---|---|
| Soil19 1.2.1 | Pos | 242479091 | 0.45 | 0.25 |
| Soil19 1.2.1 | Neg | 242479093 | 3.62 | 3.40 |
| Δ between mean NIT measurement and the reference chem value | | | | 0.20 |
| Soil19 2.2.1 | Neg | 219154850 | 3.59 | 3.61 |
| Soil19 2.2.1 | Neg | 219154734 | 3.76 | 3.54 |
| Soil19 2.2.1 | Neg | 219154901 | 4.53 | 4.26 |
| Soil19 2.2.1 | Neg | 219154925 | 4.23 | 4.37 |
| Soil19 2.2.1 | Neg | 219154941 | 4.01 | 3.43 |
| Soil19 2.2.1 | Neg | 219154949 | 4.47 | 3.93 |
| Soil19 2.2.1 | Neg | 219154957 | 3.49 | 3.74 |
| Soil19 2.2.1 | Neg | 219154981 | 4.34 | 3.57 |
| Mean | | | 4.05 | 3.81 |
| SD | | | 0.40 | 0.35 |
| Δ between mean NIT measurement and the reference chem value | | | | 0.25 |
| Soil19 2.2.1 | Pos | 219154736 | 1.03 | 1.38 |
| Soil19 2.2.1 | Pos | 219154769 | 0.51 | 0.20 |
| Soil19 2.2.1 | Pos | 219154781 | 1.00 | 1.02 |
| Soil19 2.2.1 | Pos | 219154832 | 0.88 | 1.01 |
| Soil19 2.2.1 | Pos | 219154842 | 1.01 | 0.94 |
| Soil19 2.2.1 | Pos | 219154886 | 1.03 | 0.85 |
| Soil19 2.2.1 | Pos | 219154918 | 0.46 | 0.27 |
| Soil19 2.2.1 | Pos | 244113717 | 1.01 | 1.02 |
| Mean | | | 0.87 | 0.84 |
| SD | | | 0.24 | 0.40 |
| Δ between mean NIT measurement and the reference chem value | | | | 0.03 |
| Soil19 5.3.3 | Neg | 219154682 | 3.73 | 3.43 |
| Soil19 5.3.3 | Neg | 219154848 | 3.52 | 3.62 |
| Soil19 5.3.3 | Neg | 219154923 | 4.10 | 4.06 |
| Soil19 5.3.3 | Neg | 219154939 | 4.23 | 3.41 |
| Soil19 5.3.3 | Neg | 219154947 | 4.66 | 3.41 |
| Soil19 5.3.3 | Neg | 219154955 | 3.53 | 3.89 |
| Soil19 5.3.3 | Neg | 219154979 | 4.33 | 3.33 |
| Soil19 5.3.3 | Neg | 244113714 | 3.68 | 3.76 |
| Mean | | | 3.97 | 3.61 |
| SD | | | 0.42 | 0.27 |
| Δ between mean NIT measurement and the reference chem value | | | | 0.36 |
| Soil19 5.3.3 | Pos | 242479108 | 0.84 | 0.92 |
| Soil19 5.3.3 | Pos | 242479110 | 0.57 | 0.50 |
| Soil19 5.3.3 | Pos | 219154766 | 0.30 | 0.21 |
| Soil19 5.3.3 | Pos | 219154778 | 0.74 | 0.59 |
| Soil19 5.3.3 | Pos | 219154830 | 0.51 | 0.22 |
| Soil19 5.3.3 | Pos | 219154838 | 0.72 | 0.93 |
| Soil19 5.3.3 | Pos | 219154884 | 0.74 | 0.64 |
| Soil19 5.3.3 | Pos | 219154900 | 0.80 | 1.59 |
| Soil19 5.3.3 | Pos | 219154916 | 0.41 | 0.25 |
| Soil19 5.3.3 | Pos | 219154940 | 0.44 | 0.55 |
| Soil19 5.3.3 | Pos | 244113715 | 0.83 | 0.35 |
| Mean | | | 0.61 | 0.59 |
| SD | | | 0.19 | 0.44 |
| Δ between mean NIT measurement and the reference chem value | | | | 0.02 |

The data show that the NIT measurements of stachyose in the transgenic positive events was <1.6% whereas the minimal measured value for the transgenic negative (null) events was 3.3%, allowing distinctions between the transgenic positive and negative events to be made, based on the stachyose measurements alone. The average stachyose NIT measurements for both the transgenic positive and negative events were within 0.4% of those measured by reference chemistry (Table 10) showing a high degree of precision (ability to differentiate between transgenic positive and negative events) and accuracy (closeness to the reference chemistry determined to value).

Example 6

The Use of Near Infrared Transmittance (NIT) Spectroscopy to Identify Material for Improved Accuracy of Measurements Made with NIR or NIT The development of robust spectroscopic models for the identification of transgenic materials that have been altered in their composition is dependent on several factors:

The sample sizes used for NIT analysis in this example were large enough to be subjected to industry standard reference chemistry methods (which typically require more than 60 g of seed). Measurements taken using NIT were scalable and were transferred between NIR and NIT instruments. The sample size used for NIT (400-500 g) was compatible with growing transgenic and breeding lines in short (2 to 3 meter) field plots. Field culture allowed for the introduction of environmental variation to be accounted for i.e., representatives of the same events (such as transgenes or genetic modifications) grown in different states and under different field conditions. The sample size was sufficient to provide material to calibrate instruments with smaller sample size requirements i.e., the FT-NIR and SS-NIR, single seed reference chemistry used for SS-NIR.

NIT spectroscopy was used to analyze 3692 samples containing 400-500 g of seed grown in field plots Johnston, Iowa during the 2014 season. Compositional data for each of the 11 constituents listed in Table 11 were collected. The data was analyzed by plotting the entire ranges of composition for each component. Samples that represented the extreme concentrations (both high and low) were selected along with material that was evenly distributed across the intermediate concentrations for each component. Further selections were made to maximize genetic diversity in the samples, along with samples that were clear outliers (i.e., those having measured compositions that were outside the expected ranges). This process resulted in the selection of 183 samples for further analysis; i.e., approximately 5% of the initial set. The subset was then analyzed by SS-NIR, FT-NIR (on both a Bruker MPA and Tango FT=NIR spectrometers) prior to being ground and subjected to reference chemistry.

Another set of 2020 soybean samples containing 400-500 g of seed grown in Argentina field plots during the 2015-2016 growing season were scanned on a Foss 1241 NIT spectrometer. Compositional data for the 11 constituents in Table 11 was generated using the collected absorption spectra. A selection of 139 calibration expansion samples was made based on uniform predicted composition, and individual sample spectra compared to the model spectral database. This procedure utilized principal component analysis of the model database, and the relative similarity of the Argentina set to identify samples not currently represented in the model population. Another set of 40 samples intended to validate the model performance was selected based on wide ranging, uniform estimated concentration and the presence of similar samples in the model or currently being selected for calibration expansion.

Each sample was scanned on a Bruker MPA and then on a Bruker Tango (Fourier Transform Near Infra-Red (FT-NIR) spectrometers) each fitted with 54 mm diameter rotating cup assemblies. Twenty grams (approximately 100 seed) samples were removed from the bulk packages, after thorough mixing, and were used for analysis on one of the FT-NIR instruments. The seed samples were then returned to the bulk bags and a second sample was used for spectral capture on the second instrument. The weight of each sample (to an accuracy of 0.01 g) was recorded prior to scanning. The conditions for spectral capture on the Tango instrument were similar to those described for the Bruker MPA (Example 4) except that the wave length range was slightly narrower (867 and 2530 nm on the Tango vs 833 and 2778 nm on the MPA). Captured spectra from both instruments were analyzed and prediction models were developed using the Bruker OPUS 7.0 software package.

Twelve seeds from each sample were selected randomly from the bulk packages and were analyzed by SS-NIR. Individual seed identities were maintained during the spectral capture process. Each bean was then placed into 2 ml polypropylene tubes (Corning Inc, Corning N.Y., USA; part #430917) previously labeled with unique bar code identifiers, in preparation for single seed reference chemistry analysis (Example 2) and subsequent SS-NIR model refinement.

Seventy-five gram samples were then removed from each of the bulk samples and after grinding the samples were subjected to bulk reference chemistry analysis (see Examples 2). The mean, SD, minimum and maximum values for each component from each analytical platform are given in Table 11.

TABLE 11

Mean, SD, minimum and maximum values soybean compositional components.

| Data Source | | OIL wt. % | PROT wt. % | Palmitic acid | Stearic acid | Oleic acid | Linoleic acid | Linolenic acid | Sucrose wt. % | Raffinose wt. % | Stachyose wt. % | Total soluble carbohydrates wt. % |
|---|---|---|---|---|---|---|---|---|---|---|---|---|
| NIT 3692 | Mean | 19.5 | 36.1 | 11.0 | 4.0 | 24.0 | NA | 5.5 | 5.2 | 0.6 | 2.4 | 8.8 |
| | SD | 1.7 | 0.9 | 1.0 | 0.7 | 9.5 | NA | 2.6 | 0.6 | 0.1 | 1.0 | 0.9 |
| | Min | 16.0 | 33.1 | 4.1 | 0.8 | 12.1 | NA | 1.0 | 2.7 | 0.1 | 0.2 | 5.6 |
| | Max | 24.2 | 40.6 | 14.1 | 9.5 | 88.3 | NA | 16.5 | 7.6 | 1.2 | 4.2 | 11.3 |
| Select 183 NIT | Mean | 19.5 | 36.3 | 10.8 | 4.1 | 28.9 | NA | 5.5 | 5.3 | 0.6 | 2.3 | 8.8 |
| | SD | 1.8 | 1.1 | 1.6 | 0.9 | 18.2 | NA | 2.6 | 0.7 | 0.1 | 1.1 | 1.0 |
| | Min | 16.2 | 33.8 | 4.1 | 2.5 | 13.0 | NA | 1.1 | 2.7 | 0.1 | 0.2 | 5.7 |
| | Max | 24.2 | 40.6 | 14.1 | 9.5 | 88.3 | NA | 16.5 | 7.4 | 1.2 | 4.1 | 11.0 |
| Reference Chemistry | Mean | NA | 36.8 | 10.6 | 4.3 | 31.2 | 47.0 | 6.0 | 5.8 | 0.6 | 2.6 | 9.5 |
| | SD | NA | 1.2 | 2.7 | 0.8 | 17.4 | 14.6 | 3.0 | 1.1 | 0.2 | 1.6 | 1.3 |
| | Min | NA | 33.9 | 2.5 | 2.7 | 16.2 | 1.1 | 1.2 | 2.6 | 0.1 | 0.1 | 6.3 |
| | Max | NA | 39.7 | 19.2 | 6.8 | 86.9 | 57.4 | 9.4 | 9.7 | 1.2 | 5.2 | 13.3 |
| SS-NIR Means Only | Mean | 21.5 | 42.2 | 10.0 | 3.9 | 31.0 | 49.0 | 5.5 | 6.3 | NA | 2.5 | 10.1 |
| | SD | 2.1 | 1.7 | 1.4 | 0.9 | 16.7 | 13.9 | 2.4 | 1.0 | NA | 1.2 | 1.4 |
| | Min | 17.5 | 37.8 | 4.3 | 2.6 | 14.9 | 2.4 | 0.6 | 4.0 | NA | -0.5 | 6.8 |
| | Max | 26.1 | 46.9 | 11.9 | 6.8 | 88.4 | 62.2 | 9.8 | 9.8 | NA | 4.3 | 13.4 |
| FT-NIR MPA | Mean | 19.5 | 36.3 | 8.9 | 4.5 | 31.8 | 44.5 | 5.6 | 6.0 | NA | 2.2 | 9.5 |
| | SD | 1.9 | 1.3 | 1.7 | 0.9 | 16.2 | 13.5 | 2.2 | 0.8 | NA | 1.4 | 1.3 |
| | Min | 16.4 | 33.1 | 3.3 | 3.3 | 17.6 | -0.7 | -1.4 | 3.5 | NA | -1.1 | 5.7 |
| | Max | 23.0 | 40.1 | 11.6 | 6.5 | 86.2 | 55.8 | 8.7 | 9.2 | NA | 4.7 | 11.5 |
| FT-NIR Tango | Mean | 19.1 | 36.6 | 9.0 | 5.2 | 30.6 | 49.2 | 4.4 | 6.1 | NA | 0.8 | 8.3 |
| | SD | 1.6 | 1.4 | 1.6 | 0.9 | 16.7 | 14.2 | 2.1 | 0.7 | NA | 1.4 | 1.2 |
| | Min | 16.6 | 33.0 | 3.2 | 3.6 | 17.1 | 0.1 | -2.0 | 4.1 | NA | -2.4 | 5.1 |
| | Max | 22.4 | 40.2 | 10.5 | 7.6 | 87.2 | 60.4 | 7.3 | 9.0 | NA | 3.0 | 10.5 |

NA indicates that values were not available for these components

Comparison of the means, minimum and maximum values for the whole sample set (represented by the "Original NIT Values" which were developed for 3692 samples) and those for the selected set of 183 samples shows that the latter set covered the available dynamic range for each of the predicted components (Table 11). Further, the close agreement between the mean, minimum and maximum NIT predicted values for the selected set of 183 samples and the actual compositional contents measured for these samples by reference chemistry indicates the high degree of precision and accuracy of the measurements for most of the components. For example, the predicted mean, minimum and maximum stachyose contents for the 183 sample subset differed from the reference chemistry measured values by -0.3 wt %, 0.1 wt % and -1.1 wt %, respectively. In contrast the predicted mean, minimum and maximum palmitic acid contents for the 183 sample subset differed from the reference chemistry measured values by 0.2 relative %, 1.6 relative % and −5.0 relative %, respectively. Inclusion of the reference chemistry values into the NIT models will lead to improvements in the precision of the measurements (i.e., the ability to differentiate between unknown samples differing in their composition) and the accuracy (the ability predict compositions that are indistinguishable from those measured using standard reference chemistry methods).

Example 7

As an illustration of the precision of the reference chemistry assay for sucrose, raffinose and stachyose, bulk samples of beans from three different commodity soybean samples were subjected to analysis as blind duplicates. Six replicates for each duplicated sample were analyzed using the standard analytical methods for total soluble carbohydrate derivatization and analysis according to the methods set forth in Example 2.

Each sugar was quantified relative to its own calibration curve, after dividing each individual peak by the area of the internal standard in each sample and standard. Final carbohydrate concentrations were expressed corrected for moisture content as set forth herein. Residual sucrose, raffinose and stachyose recovered in the starch digestions were included in the total values reported for each sugar.

The average coefficient of variation (mean/standard deviation of the mean, expressed as a percentage) for sucrose, raffinose and stachyose were, 1.43%, 1.34% and 2.11%, respectively. As an illustration of the accuracy of the reference chemistry assay for sucrose, raffinose and stachyose, bulk samples of beans from three different commodity soybean samples were subjected to analysis as blind duplicates using the methods described here and at two contract research organizations. The mean values for sucrose of 4.31+/−0.22 (internal), 4.26+/−0.11, 4.26+/−0.21 were not significantly different at the 95% confidence interval. The mean values for stachyose were 3.45+/−0.13 (internal), 3.16+/−0.14 and 3.36+/−0.27 were not significantly different at the 95% confidence interval. Significant differences were observed in the raffinose values of 0.93+/−0.02 (internal), 0.73+/−0.10 and 0.47+/−0.03.

Example 8

Analysis of Soybean Meal

Rapid compositional analyses of soybean meals, including analyses reporting on the concentration of anti-nutritional factors such as the sucrosyl oligosaccharide, raffinose and stachyose and nutritionally desirable components such as protein, amino acids and sucrose can be carried out.

Defatted powders remaining after the bulk oil extraction process (Example 2.15) from soybeans are used to capture NIR reflection absorption spectra, either on a Bruker MPA or on a Foss 6500 full spectrum instrument. The integrating sphere channel of the MPA operating in macro reflectance mode is utilized to scan the powders contained within a 15×45 mm borosilicate vial (Qorpak p/n GLC-00982) in triplicate at a resolution of 8 cm-1 from 833-2778 nm. Alternately a Foss/NIRSystems 6500 near infrared reflectance instrument equipped with an autosampler attachment will be utilized to scan the powders contained within a 51 mm ring cup in duplicate at a resolution of 2 nm from 400-2500 nm. The samples are analyzed for the concentration of protein, moisture, sucrose, raffinose, stachyose and total soluble carbohydrates using reference chemistry methods described in Example 2. The resulting spectral and chemical data will enable accurate determination of each constituent's concentration.

Example 9

A diverse set of soybeans grown in the field in North America and Argentina in 2015 and North America in 2016 were selected for their compositional diversity using the methodology described in Example 6. After spectral capture on both the FT-NIR (Example 4) and the NIT (Example 5) platforms the samples were subjected to reference chemistry using the bulk sample methodologies described in Example 2. The statistical characteristics of the models obtained are described in Table 12. In generating the models raffinose and total saturated fatty acids were added as analytes. The moisture models were not updated.

TABLE 12

Statistics of accuracy of NIT measurements.

| Constituent | n | Range | $R^2$ | RMSEC | RMSECV |
|---|---|---|---|---|---|
| moisture | 379 | | 0.99 | 0.3 | 0.3 |
| protein | 1101 | 28.3-41.0 | 0.94 | 0.40 | 0.40 |
| oil | 1105 | 15.3-28.4 | 0.98 | 0.30 | 0.31 |
| oleic | 1141 | 14.6-87.3 | 1.00 | 1.40 | 1.51 |
| linoleic | 1141 | 0.8-59.2 | 1.00 | 1.24 | 1.28 |
| linolenic | 1141 | 0.8-10.2 | 0.96 | 0.49 | 0.51 |
| stearic | 1141 | 2.7-16.1 | 0.89 | 0.24 | 0.34 |
| palmitic | 1141 | 2.0-23.1 | 0.96 | 0.63 | 0.52 |
| total sats | 1141 | 4.7-28.0 | 0.98 | 0.51 | 0.52 |
| raffinose | 1200 | 0.1-1.5 | 0.56 | 0.19 | 0.26 |
| stachyose | 1200 | 0.02-5.2 | 0.95 | 0.37 | 0.44 |
| sucrose | 1200 | 1.7-9.9 | 0.72 | 0.62 | 0.67 |
| total soluble carbohydrates | 1200 | 3.7-13.3 | 0.86 | 0.62 | 0.78 | n = number of reference chemistry measurements used for each constituent comparison between the NIR methods compared with the standard methods disclosed herein.
Oil, protein and carbohydrate ranges are presented on a 13% moisture basis.
Fatty acids are presented on a relative % basis.

The performance of the stachyose model improved with the addition of the new data; $R^2$ 0.95 vs 0.89 (compare Tables 9 and 12); RMSEC 0.37 vs 0.49 (the lower value indicates an improved resolution between samples in the model); RMSECV 0.44 vs 0.57 (a lower value indicates an improved resolution between samples not in the model, i.e., unknowns). The model statistics for sucrose and total soluble carbohydrates did not improve.

Example 10

Analysis of Soybean Meals; Defatted Powder Model Derivation

Rapid compositional analyses of soybean meals, including analyses of the concentration of anti-nutritional factors such as the sucrosyl oligosaccharide, raffinose and stachyose and nutritionally desirable components such as sucrose was carried out. Defatted powder was used; defatted soybean flakes could also be used.

Defatted powders remaining after the bulk oil extraction process (Example 2.15) from soybeans were used to capture NIR reflection absorption spectra on a Bruker MPA. The integrating sphere channel of the MPA operating in macro reflectance mode was utilized to scan the powders contained within a 15×45 mm borosilicate vial (Qorpak p/n GLC-00982) in triplicate, at a resolution of 8 cm-1 from 800-2778 nm. It is expected that a Foss/NIRSystems 6500 near infrared reflectance instrument equipped with an autosampler attachment could also be utilized to scan the powders contained, for example, within a 51 mm ring cup in duplicate at a resolution of 2 nm from 400-2500 nm.

After spectral capture samples were analyzed for the concentration of protein, moisture, sucrose, raffinose, stachyose and total soluble carbohydrates using reference chemistry methods described in Example 2. The resulting spectral and chemical data were used to generate calibrations for the prediction of the meal compositions.

Captured spectra and accompanying reference chemistry were used to derive Partial Least Squares predictive models utilizing Bruker's Opus 7.0 software package. Individual triplicate spectra were averaged into a single observation prior to the model regression. Spectral regions and absorption data pre-treatment were selected to for each analyte using the OPUS optimization algorithm. Raffinose, stachyose, and total soluble carbohydrates employed first derivative and standard normal variate pre-treatment while using regions 1333-2355 nm, 1464-2355 nm, and 1063-1125 nm plus 1465-2355 nm respectively. Sucrose modeling entailed using first derivative and multiplicative scatter correction to pre-treat spectra and incorporated 1639-2355 nm wavelength regions. The resulting model statistics are displayed in Table 13.

TABLE 13

Statistics of FT-NIR calibration curves for Defatted Powders. The number of reference chemistry measurements are shown in column n. Range (wt. % corrected to 13% Moisture) shows the minimum and maximum reference method measured value in the samples for each constituent.

| Constituent | n | Range | $R^2$ | RMSEC | RMSECV |
|---|---|---|---|---|---|
| Raffinose | 231 | 0.15-1.76 | 0.73 | 0.20 | 0.22 |
| Stachyose | 238 | 0.05-5.81 | 0.97 | 0.34 | 0.39 |
| Sucrose | 230 | 3.75-8.34 | 0.85 | 0.34 | 0.38 |
| Total Carbs | 232 | 6.26-13.75 | 0.96 | 0.33 | 0.40 |

The data indicate that stachyose in soybean meals were measured to a similar degree of precision and accuracy as those achieved for whole beans using the methods described here, i.e., $R^2$ 0.97 and 0.95, RMSEC 0.34 and 0.37 for the meal and whole bean NIT models (Table 12), respectively.

All publications, patents, and patent applications mentioned in the specification are incorporated by reference herein for the purpose cited to the same extent as if each was specifically and individually indicated to be incorporated by reference herein.

The foregoing invention has been described in detail by way of illustration and example for purposes of clarity and understanding. As is readily apparent to one skilled in the art, the foregoing description represents only some of the methods and compositions that illustrate the embodiments of the foregoing invention. It will be apparent to those of ordinary skill in the art that variations, changes, modifications, and alterations may be applied to the compositions and/or methods described herein without departing from the true spirit, concept, and scope of the invention.

As used herein, the terms "comprises," "comprising," "includes," "including," "has," "having," "contains", "containing," "characterized by" or any other variation thereof, are intended to cover a non-exclusive inclusion.

Unless expressly stated to the contrary, "or" is used as an inclusive term. For example, a condition A or B is satisfied by any one of the following: A is true (or present) and B is false (or not present), A is false (or not present) and B is true (or present), and both A and B are true (or present). The indefinite articles "a" and "an" preceding an element or component are nonrestrictive regarding the number of instances (i.e., occurrences) of the element or component. Therefore "a" or "an" should be read to include one or at least one, and the singular word form of the element or component also includes the plural unless the number is obviously meant to be singular.

What is claimed is:

1. A method for measuring the amount of a sucrosyl-oligosaccharide-in a soybean seed, the method comprising:

(a) directing near infrared light from a light source onto a soybean seed to form modified light from the soybean seed;

(b) receiving the modified light in an imaging device;

(c) measuring the amount of a sucrosyl-oligosaccharide in the soybean seed based on the received modified light, the amount of the sucrosyl-oligosaccharide being measured to an accuracy that is within 1.5 wt. % of the amount measured using a standard reference analytical method; and (d) transporting the seed to a first location when the amount of sucrosyl-oligosaccharide measured is below a threshold value between 1 wt. % and 0.1 wt. % and transporting the seed to a different second location when the amount of sucrosyl-oligosaccharide measured is at or above the threshold value.

2. The method of claim 1, wherein the threshold value is between 0.5 wt. % and 0.1 wt.-%.

3. The method of claim 1, wherein a plurality of seeds are measured together in step a, and wherein the amount of a sucrosyl-oligosaccharide measured in step (c) is an average amount for the plurality of seeds.

4. The method of claim 3, wherein the plurality of seeds comprises at least 10 and less than 100 seeds.

5. The method of claim 3, wherein the plurality of seeds comprises at least 1 kg of seeds and less than 1,000 kg of seeds.

6. The method of claim 1, wherein an individual seed is measured in step (a).

7. The method of claim 6, wherein the method is an automated method, and further comprising separating the individual seed from a plurality of seeds prior to step (a).

8. The method of claim 1, wherein the seed is genetically modified to overexpress a diglyceride acyltransferase.

9. The method of claim 1, wherein the sucrosyl-oligosaccharide measured is stachyose.

10. The method of claim 9 wherein the imaging device in step (c) is calibrated using a plurality of soybean seeds having variable stachyose contents falling in a range that includes values of less than 0.3 wt. % stachyose and more than 4.5 wt. % stachyose.

11. The method of claim 1, wherein the modified light comprises transmitted light.

12. The method of claim 1, wherein the modified light comprises reflected light.

13. A method for measuring stachyose in a population of soybean seeds, the method comprising
(a) directing near infrared light from a light source onto a first and second subsample of the population of soybean seeds to form a first and second modified light from the soybean seeds;
(b) receiving the first and second modified light in an imaging device;
(c) measuring the amount of stachyose in the first and second subsamples based on the received first and second modified light, wherein (i) the first and second subsamples are separated when the amount of stachyose measured differs by at least 1 percentage point between the first and second subsamples and (ii) wherein the first and second subsamples are combined when the amount of stachyose differs by less than 0.2 percentage points.

14. The method of claim 13, wherein the population comprises genetically modified and unmodified soybean seeds.

15. The method of claim 14, wherein the modified seeds comprise a modified diacylglycerol transferase.

16. A method for processing soybean seeds genetically modified to contain high oil, high protein, modified amino acid content, or a combination thereof compared with unmodified soybean seeds in a plurality of seeds comprising the modified soybean seeds and the unmodified soybean seeds, the method comprising
(a) directing near infrared light from a light source onto a sample comprising a soybean seed to form modified light from the soybean seed;
(b) receiving the modified light in an imaging device;
(c) measuring the amount of a sucrosyl-oligosaccharide in the sample based on the received modified light, the amount of sucrosyl-oligosaccharide being measured to an accuracy that is within 1 wt. % of the amount measured using a standard reference analytical method; and
(d) repeating steps (a) to (c) for at least 10 samples, wherein an amount of sucrosyl-oligosaccharide below a threshold value indicates high oil, high protein, modified amino acid content, or a combination thereof in the soybean seed; and
(e) separating soybean seeds above the threshold value from soybean seeds below the threshold value, wherein at least 90% of the soybean seeds below the threshold value are the modified soybean seeds or wherein at least 90% of the seeds above the threshold value are the unmodified soybean seeds.

17. The method of claim 16, wherein at least one of the modified seeds separated in step (e) is grown and crossed with the same or a different soybean plant to produce progeny seed.

18. The method of claim 16, wherein the method is an automated method, and further comprising separating the sample comprising the soybean seed from the plurality of seeds prior to step (a).

19. The method of claim 16, further comprising measuring the amount of oil in the seed based on the received modified light and wherein at least 90% of the soybean seeds above the threshold value are the modified soybean seeds or wherein at least 90% of the seeds below the threshold value are the unmodified soybean seeds.

20. The method of claim 16, wherein the sucrosyl-oligosaccharide is stachyose.

* * * * *